(12) United States Patent
Hodgson et al.

(10) Patent No.: US 6,410,220 B1
(45) Date of Patent: Jun. 25, 2002

(54) SELF-ASSEMBLING GENES, VECTORS AND USES THEREOF

(75) Inventors: Clague P. Hodgson; Mary Ann Zink; Guoping Xu, all of Lincoln, NE (US)

(73) Assignee: Nature Technology Corp, Omaha, NE (US)

( * ) Notice: Subject to any disclaimer, the term of this patent is extended or adjusted under 35 U.S.C. 154(b) by 0 days.

(21) Appl. No.: 09/380,190

(22) PCT Filed: Feb. 28, 1998

(86) PCT No.: PCT/US98/03918

§ 371 (c)(1),
(2), (4) Date: Aug. 26, 1999

(87) PCT Pub. No.: WO98/38326

PCT Pub. Date: Sep. 3, 1998

Related U.S. Application Data

(60) Provisional application No. 60/070,910, filed on Feb. 28, 1997.

(51) Int. Cl.[7] ............................ C12Q 1/00; C12Q 1/68; C12N 15/63; C07H 21/04; C07H 21/02

(52) U.S. Cl. ............................ 435/4; 435/6; 435/320.1; 536/23.1; 536/24.1

(58) Field of Search ............................ 435/6, 4, 320.1; 536/23.1, 24.1

(56) References Cited

U.S. PATENT DOCUMENTS

| | | | |
|---|---|---|---|
| 4,237,224 A | 12/1980 | Cohen et al. | 435/69.1 |
| 4,293,652 A | 10/1981 | Cohen | 435/91.1 |
| 4,683,195 A | 7/1987 | Mullis et al. | 435/6 |
| 4,861,719 A | 8/1989 | Miller | 435/236 |
| 5,334,761 A | 8/1994 | Gebeyehu et al. | 564/197 |
| 5,354,674 A | 10/1994 | Hodgson | 435/6 |
| 5,366,737 A | 11/1994 | Eppstein et al. | 424/450 |
| 5,399,346 A | 3/1995 | Anderson et al. | 424/93.21 |
| 5,436,146 A | 7/1995 | Shenk et al. | 435/457 |
| 5,470,955 A | 11/1995 | Craig | 530/387.7 |
| 5,512,463 A | 4/1996 | Stemmer | 435/91.2 |
| 5,514,568 A | 5/1996 | Stemmer | 435/91.2 |
| 5,605,793 A | 2/1997 | Stemmer | 435/6 |

FOREIGN PATENT DOCUMENTS

| | | |
|---|---|---|
| WO | WO 93/25673 | 12/1993 |
| WO | WO 94/02178 | 2/1994 |
| WO | WO 94/20608 | 9/1994 |
| WO | WO 97/28282 | 8/1997 |
| WO | WO 98/38326 | 9/1998 |

OTHER PUBLICATIONS

Adams et al., "Complete Nucleotide Sequence of a Mouse VL30 Retro–Element," *Mol. Cell. Biol.*, 8(8):2989–2998 (1988).

Ausubel et al., eds., *Short Protocols in Molecular Biology, a Compendium of Methods from Current Protocols in Molecular Biology*, Third Ed., John Wiley & Sons, U.S.A., Title page, publication page and table of contents only, 22 pgs. (1995).

Beck, "High–Fidelity PCR: Enhancing the Accuracy of DNA Amplification," *The Scientist*, 12(1):16–18 (1998).

Brousseau et al., "Synthesis of a human insulin gene V. Enzymatic assembly, cloning and characterization of the human proinsulin DNA," *Gene*, 17(3):279–289 (1982).

Chakraborty et al., "Synthetic retrotransposon vectors for gene therapy," *FASEB J.*, 7(10):971–977 (1993).

Chakraborty et al., "Expression of VL30 vectors in human cells that are targets for gene therapy," *Biochem. Biophys. Res. Comm.*, 209(2):677–683 (1995).

Cook et al., "Retrotransposon Gene Engineering," *Biotechnology*, 9:748–751 (1991).

Couture et al., "Retroviral Vectors Containing Chimeric Promotor/Enhancer Elements Exhibit Cell–Type–Specific Gene Expression," *Human Gene Therapy*, 5:667–677 (1994).

Dobrynin et al., "Plasmid vectors pBBV for cloning and regeneration of DNA fragments with any terminal nucleotide sequence," Translated from *Doklady Akademii Nauk SSSR* 278 (4):1002–1005 (1984).

French et al., "Construction of a Retroviral Vector Incorporating Mouse VL30 Retrotransposon–Derived, Transcriptional Regulatory Sequences," *Anal. Biochem.*, 228(2):354–355 (1995).

Hodgson et al., "Chapter 4: Structure and Function of Mouse VL30 Sequences," *Retro–Vectors for Human Gene Therapy*, RG Landes Company, Austin, TX, pp. 73–102 (1996).

Hodgson et al., "Chapter 5: Construction, Transmission and Expression of Synthetic VL30 Vectors," *Retro–Vectors for Human Gene Therapy*, RG Landes Company, Austin, TX, pp. 103–128 (1996).

Hodgson et al., "Chapter 1: Synthetic Retrotransposon Vectors and Gene Targeting," *Artificial Self–Assembling Systems for Gene Delivery*, Felgner et al., eds., American Chemical Society Books, Washington, D.C., Publication page and pp. 2–14 (1996).

Hodgson et al., "Self–assembling genes (SAGE):construction of complex vectors and combinatorial libraries without sub–cloning," Abstract P–55, *Cancer Gene Therapy*, 4(6–conference supplement):s27 (1997).

(List continued on next page.)

*Primary Examiner*—Robert A. Schwartzman
*Assistant Examiner*—Katharine F Davis

(57) ABSTRACT

The invention relates to a method for directing the self-assembly of a gene or gene assembly having three and preferably six or more fragments in a directionally and spatially ordered fashion to produce a gene, gene vector or large nucleic acid molecule. The method can be used to create libraries, such as combinatorial libraries. In another embodiment of the invention a vector is described for the incorporation and screeming of endogenous mouse promoter elements for the identification of cell-specific promoters.

10 Claims, 8 Drawing Sheets

OTHER PUBLICATIONS

Innes et al., "Cationic Liposomes (Lipofectin) Mediate Retroviral Infection in the Absence of Specific Receptors," *J. Virol.*, 64(2):957–961 (1990).

Korobko et al., "A New Approach to Construction of DNA from Synthetic Oligonucleotides, Synthesis of DNAs Coding for Repeats of the Antigenic Determinant of Mouth and Foot Disease Virus," *Bioorganicheskaia Khimiia*, 13(1):69–81, Russian language journal article with English language abstract at p. 81 (1987).

Krieg, "An innate immune defense mechanism based on the recognition of CpG motifs in microbial DNA" Annual Meeting of the Central Society for Clinical Research, Chicago, Sep. 19–21, 1996, *J. Lab. Clin. Med.*, 128(2):128–133 (1996).

Lebedenko et al., "Method of artificial DNA splicing by directed ligation (SDL)," *Nuc. Acids Res.*, 19(24):6757–6761 (1991).

Mandecki et al., "FokI method of gene synthesis," *Gene*, 68:101–107 (1988).

Markowitz et al., "A Safe Packaging Line for Gene Transfer: Separating Viral Genes on Two Different Plasmids," *J. Virol.*, 62(4):1120–1124 (1988).

Miller et al., "Redesign of Retrovirus Packaging Cell Lines To Avoid Recombination Leading to Helper Virus Production," *Mol. Cell. Biol.*, 6(8):2895–2902 (1986).

Miller et al., "Construction and Properties of Retrovirus Packaging Cells Based on Gibbon Ape Leukemia Virus," *J. Virol.*, 65(5):2220–2224 (1991).

Moses et al., "Specific Recombination in Vitro Promoted by the Restriction Endonuclease HgaI," *J. Mol. Biol.*, 135:517–524 (1979).

Mullen et al., "Molecular Analysis of T Lymphocyte–Directed Gene Therapy for Adenosine Deaminase Deficiency: Long–Term Expression In Vivo of Genes Introduced with a Retroviral Vector," *Human Gene Therapy*, 7:1123–1129 (1996).

Narang et al., "Synthesis of the human insulin gene. Part IV. New synthetic deoxyribooligonucleotide adaptors and primers for DNA cloning and sequence analysis," *Nuc. Acids Symp. Ser.*,7:377–385 (1980).

Naviaux et al., "Retroviral vectors for persistent expression in vivo," *Curr. Opin. Biotechnol.*, 3(5):540–547 (1992).

Old et al., *Studies in Microbiology: Principles of Gene Manipulation: An Introduction to Genetic Engineering*, Carr, ed., Blackwell Sciences, Inc., Cambridge, MA, Title page, publication page and p. 24 (1994).

Padgett et al., "Creating seamless junctions independent of restriction sites in PCR cloning," *Gene*, 168(1):31–35 (1996).

Podhajska et al., "Conversion of the FokI endonuclease to a universal restriction enzyme: cleavage of phage M13mp7 DNA at predetermined sites," *Gene*, 40:175–182 (1985).

Price et al., "Lineage analysis in the vertebrate nervous system by retrovirus–mediated gene transfer," *Proc. Natl. Acad. Sci. USA*, 84(1):156–160 (1987).

Purcell et al., "An Array of Murine Leukemia Virus–Related Elements Is Transmitted and Expressed in a Primate Recipient of Retroviral Gene Transfer," *J. Virol.*, 70(2):887–897 (1996).

Shoji–Tanaka et al., "Gene Transfer Using Purified Retroviral Integrase," *Biochem. Biophys. Res. Comm.*, 203(3):1756–1764 (1994).

Stemmer et al., "Enzymatic Inverse PCR:A Restriction Site Independent, Single–Fragment Method for High–Efficiency, Site–Directed Mutagenesis," *BioTechniques*, 13(2)215–220 (1992).

Szybalski, "Universal resriction endonucleases: designing novel cleavage specificities by combining adapter oligodeoxynucleotide and enzyme moieties," *Gene*, 40:169–173 (1985).

Szybalski et al., "Class–IIS restriction enzymes—a review," *Gene*, 100:13–26 (1991).

Tomic et al., "A rapid and simple method for introducing specific mutations into any position of DNA leaving all other positions unaltered," *Nucleic Acids Res.*, 18(6):1656 (1990).

Urdea et al., "Chemical synthesis of a gene for human epidermal growth factor urogastrone and its expression in yeast," *Proc. Natl. Acad. Sci. USA*, 80(24):7461–7465 (1983).

Walther et al., "Cell type specific and inducible promoters for vectors in gene therapy as an approach for cell targeting," *J. Mol. Med.*, 74:379–392 (1996).

Wei et al., "Construction and Isolation of a Transmissible Retrovirus Containing the src Gene of Harvey Murine Sarcoma Virus and the Thymidine Kinase Gene of Herpes Simplex Virus Type I," *J. Virol.*, 39(3):935–944 (1981).

Zink et al., "Transcriptional targeting with rescued LTRs: a hepatocyte promoter," Abstract P–59, *Cancer Gene Therapy*, 4(6 conference supplement):s28 (1997).

```
                    1                                                                              90
SEQ ID NO:2  CCTCCCATCT AGAGGTTGTT CTCGGAACAC TCCTAAACTT TTCACCCCAA AACTCCTCAC CCTAAAGTTC GAAAAAACTG TTCCAAGAAC
SEQ ID NO:3  ---------- ---------- ---------- ---------- ---------- ---------- ---------- ---------- ----------

91                                                                             180
SEQ ID NO:2  ATTTTTGAGA TAAAGGCCTC CTAGAACAAC CTCAAAATGA CATTGCCAAA TGATAAGACA TGACTCCTTA GTTACGTAGG TTCCTTGATA
SEQ ID NO:3  ---------- ---------- ---------- ---------- ---CCTCCCA TCTAGAAAAC ATTTTTGAGA TAAAGCTTC CTGGAACAAC CTCAAAATGA 181                                                                             270
SEQ ID NO:2  GGACATGACT CCTTAGTTAC GTAGGTTCCT TGATAGGACA TGACTCCTTA GTTACGTAGA TTCCTTTGGT AGAACTCCCT AGTGATGTAA
SEQ ID NO:3  ACCAGTACT  CCTTAGTTAC GTAGGTTCCT TGATAGGACA TGACTCCTTA GTTACATAGA TTCCTTTGGC AGAACTCCCT AGTGATGTAA 271                           321
SEQ ID NO:2  ACTTGTACTT TCCCTGCCCA GTTCTCCCCC TTTGAGTTTT ACTATATAAG C
SEQ ID NO:3  ACTTGTACTT TCCCTGCCCA GTTCTCCCCC TTTGAGTTTT ACTATATAAG C
```

Fig. 5

|              | 1          |            |            |            |            |            |            |            | 90         |
|---|---|---|---|---|---|---|---|---|---|
| SEQ ID NO:4  | CCTCCCATCT | AGAGATTGTT | CCCAGAACAC | TCCTGAACTC | TTCACCCCAG | AATGCATGCC | TGAACTCCTC | ACCCTAGAGT | TCGAACCCTC |
| SEQ ID NO:5  | CCTCCCATCT | AGAGAGTGTT | CCCAGAACAC | TCCTGAACTC | TTCACCCCAG | AATGCATTCC | TGAACTCCTC | ACCCTAGAGT | TCGAACCCTC |
| SEQ ID NO:6  | CCTCCCATCT | AGAGAGTGTT | CCCAGAACAC | TCCTGAACTC | TTCACCCCAG | AATGCATTCC | TGAACTCCTC | ATCCTAGAGT | TCGAACCCTC |
| SEQ ID NO:7  | CCTCCCATCT | AGAGAGTGTT | CCCAGAACAC | TCCTGAACTC | TTCACCTCAA | AATGCATTCC | TGAACTCCTC | ACCCTAGAGT | TCGAACCCTC |
| SEQ ID NO:8  | CCTCCCATCT | AGAGATTGTT | CCCAGAACAC | TCCTGAACTC | TTCACCCCAG | AATGCATTCC | TGAACCCCTC | ACCCTAGAGT | TCGAACCCTC |
| SEQ ID NO:9  | CCTCCCATCT | AGAGAGTGTT | CCCAGAACAC | TCCTGAACTC | TTCATCCCAG | AATGCATTCC | TGAACTCCTC | ACCCTATAGT | TCGAACCCTC |
| SEQ ID NO:10 | CCTCCCATCT | AGAGAGTGTT | CCCAAAACAC | TCCTGAACTC | TTCACCCCAG | AATGCATTCC | TGAACTCCTC | ACCCTAAAGT | TCAAACCCTC |
| SEQ ID NO:11 | CCTCCCATCT | AGAGAGTGTT | CCCAGAACAC | TCCTGAACTC | TTCACCCCAG | AATGCATTCC | TGAACTCCTC | ACCCTAGAGT | TTGAACCCTC |
| SEQ ID NO:12 | CCTCCCATCT | AGAGAGTGTT | CCCAGAACAC | TCCTAAAACTC| TTCACCCCAG | AATGCATTCC | TGAACTCCTC | ACCCTAGAGT | TCGAACCCTT |
| SEQ ID NO:13 | CCTCCCATCT | AGAGAGTGTT | CCCAGAACAC | TCCTGAACTC | TTCACCCCAG | AATGCATTCC | TGAACTCCTC | ACCCTAGAGT | TCGAACCCTC |

|              | 91         |            |            |            |            |            |            |            | 180        |
|---|---|---|---|---|---|---|---|---|---|
| SEQ ID NO:4  | CCAACTAAAG | ACTGTTCCAA | GAACATTTTT | GAGATAAGGG | CCTCCTGGAA | CAACCTCAGA | ATCAACCGGA | TACATTGCCA | AATAATAGGA |
| SEQ ID NO:5  | CCAACTAAAG | ACTGTTCCAA | GAACATTTTT | GAGATAAGGG | CCTCCTGGAA | CAACCTCAGA | ATCAACCGGA | TACATTGCCA | AATAATAGGA |
| SEQ ID NO:6  | CCAACTAAAG | ACTGTTCCAA | GAACATTTTT | GAGATAAGGG | CCTCCTGGAA | CAACCTCAGA | ATCAACCTGG | TACATTGCCA | AATAATAGGA |
| SEQ ID NO:7  | CCAACTAAAG | ACTGTTCCAA | GAACATTTTT | GAGATAAGGG | CCTCCTGGAA | CAACCTCAGA | ATCAACCAGG | TACATTGCCA | AATAATAGGA |
| SEQ ID NO:8  | CCAACTAAAG | ACTGTTCCAA | GAACATTTTT | GAGATAAGGG | CCTCCTGGAA | CAACCTCAGA | ATCAACCAGG | TACATTGCCA | AATAATAGGA |
| SEQ ID NO:9  | CCAACTAAAG | ACTGTTCCAA | GAACATTTTT | GAGATAAGGG | CCTCCTGGAA | CAACCTCAGA | ATCAACCGGA | TACATTGCCA | AATAATAGGA |
| SEQ ID NO:10 | CCAACTAAAG | ACTGTTCCAA | GAACATTTTT | GAGATAAGGG | CCTCCTGGAA | CAACCTCAGA | ATCAACCGGG | TACATTGCCA | AATAATAGGA |
| SEQ ID NO:11 | CCAACTAAAG | ACTGTTCCAA | GAACATTTTT | GAGATAAGGG | CCTCCTGGAA | CAACCTCAGA | ATCAACCGGG | TACATTGCCA | AATAATAGGA |
| SEQ ID NO:12 | CCAACTAAAG | ACTGTTCCAA | GAACATCTTT | GAGATAAGGG | CCTCCTGGAA | CAACCTCAGA | ATCAACCGGG | TACATTGCCA | AATAATAGGA |
| SEQ ID NO:13 | CCAACTAAAG | ACTGTTCCAA | GAACATTTTT | GAGATAAGGG | CCTCCTGGAA | CAACCTCAAA | ATCAACCGGG | TACATTGCCA | AATGATAGGA |

Fig. 6

SEQUENCE LISTING (1) GENERAL INFORMATION:

(iii) NUMBER OF SEQUENCES: 74

(2) INFORMATION FOR SEQ ID NO: 1:

(i) SEQUENCE CHARACTERISTICS:
      (A) LENGTH: 6225 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
TGAAGAATAA AAAATTACTG GCCTCTTGTG AGAACATGAA CTTTCACCTC GGAGCCCACC     60

CCCTCCCATC TGGAAAACTC CAGTTATAAC TGGAGTTTTT CCTTTAAAAG CTTGTGAAAA    120

ATTTGAGTCG TCGTCGAGAC TCCTCTACCC TGTGCAAAGG TGTATGAGTT TCGACCCCAG    180
```

-continued

```
AGCTCTGTGT GCTTTCTGTT GCTGCTTTAT TTCGACCCCA GAGCTCTGGT CTGTGTGCTT      240

TCATGTCGCT GCTTTATTAA ATCTTACCTT CTACATTTTA TGTATGGTCT CAGTGTCTTC      300

TTGGGTACGC GGCTGTCCCG GGACTTGAGT GTCTGAGTGA GGGTCTTCCC TCGAGGGTCT      360

TTCATTTGGT ACATGGGCCG GGAATTCGAG AATCTTTCAT TTGGTGCATT GGCCGGGAAT      420

TCGAAAATCT TTCATTTGGT GCATTGGCCG GGAAACAGCG CGACCACCCA GAGGTCCTAG      480

ACCCACTTAG AGGTAAGATT CTTTGTTCTG TTTTGGTCTG ATGTCTGTGT TCTGATGTCT      540

GTGTTCTGTT TCTAAGTCTG GTGCGATCGC AGTTTCAGTT TGCGGACGC TCAGTGAGAC       600

CGCGCTCCGA GAGGGAGTGC GGGGTGGATA AGGATAGACG TGTCCAGGTG TCCACCGTCC      660

GTTCGCCCTG GGAGACGTCC CAGGAGGAAC AGGGGAGGAT CAGGGACGCC TGGTGGACCC      720

CTTTGAAGGC CAAGAGACCA TTTGGGGTTG CGAGATCGTG GGTTCGAGTC CCACCTCGTG      780

CCCAGTTGCG AGATCGTGGG TTCGAGTCCC ACCTCGTGTT TTGTTGCGAG ATCGTGGGTT      840

CGAGTCCCAC CTCGCGTCTG GTCACGGGAT CGTGGGTTCG AGTCCCACCT CGTGTTTTGT      900

TGCGAGATCG TGGGTTCGAG TCCCACCTCG CGTCTGGTCA CGGGATCGTG GGTTCGAGTC      960

CCACCTCGTG CAGAGGGTCT CAATTGGCCG GCCTTAGAGA GGCCATCTGA TTCTTCTGGT     1020

TTCTCTTTTT GTCTTAGTCT CGTGTCCGCT CTTGTTGTGA CTACTGTTTT TCTAAAAATG     1080

GGACAATCTG TGTCCACTCC CCTTTCTCTG ACTCTGGTTC TGTCGCTTGG TAATTTTGTT     1140

TGTTTACGTT TGTTTTTGTG AGTCGTCTAT GTTGTCTGTT ACTATCTTGT TTTTGTTTGT     1200

GGTTTACGGT TTCTGTGTGT GTCTTGTGTG TCTCTTTGTG TTCAGACTTG GACTGATGAC     1260

TGACGACTGT TTTTAAGTTA TGCCTTCTAA AATAAGCCTA AAAATCCTGT CAGATCCCTA     1320

TGCTGACCAC TTCCTTTCAG ATCAACAGCT GCCCTTACTC GAGCTCAAGC TTCGAATTCT     1380

GCAGTCGACG GTACCGCGGC CGCTAACTAA TAGCCCATTC TCCAAGGTAC GTAGCGGGGA     1440

TCAATTCCGC CCCCCCCTA ACGTTACTGG CCGAAGCCGC TTGGAATAAG GCCGGTGTGC      1500

GTTTGTCTAT ATGTTATTTT CCACCATATT GCCGTCTTTT GGCAATGTGA GGGCCCGGAA     1560

ACCTGGCCCT GTCTTCTTGA CGAGCATTCC TAGGGGTCTT TCCCCTCTCG CCAAAGGAAT     1620

GCAAGGTCTG TTGAATGTCG TGAAGGAAGC AGTTCCTCTG GAAGCTTCTT GAAGACAAAC     1680

AACGTCTGTA GCGACCCTTT GCAGGCAGCG GAACCCCCCA CCTGGCGACA GGTGCCTCTG     1740

CGGCCAAAAG CCACGTGTAT AAGATACACC TGCAAAGGCG GCACAACCCC AGTGCCACGT     1800

TGTGAGTTGG ATAGTTGTGG AAAGAGTCAA ATGGCTCTCC TCAAGCGTAT TCAACAAGGG     1860

GCTGAAGGAT GCCCAGAAGG TACCCCATTG TATGGGATCT GATCTGGGGC CTCGGTGCAC     1920

ATGCTTTACA TGTGTTTAGT CGAGGTTAAA AAAACGTCTA GGCCCCCCGA ACCACGGGGA     1980

CGTGGTTTTC CTTTGAAAAA CACGATACGG GATCCACCGG TCGCCACCAT GGGTAAAGGA     2040

GAAGAACTTT TCACAGGAGT TGTCCCAATT CTTGTTGAAT TAGATGGTGA TGTTAATGGG     2100

CACAAATTTT CTGTCAGTGG AGAGGGTGAA GGTGATGCAA CATACGGAAA ACTTACCCTT     2160

AAATTTATTT GCACTACTGG AAAACTACCT GTTCCATGGC CAACACTTGT CACTACTTTC     2220

ACTTATGGTG TTCAATGCTT TTCAAGATAC CCAGATCATA TGAAACGGCA TGACTTTTTC     2280

AAGAGTGCCA TGCCCGAAGG TTATGTACAG GAAAGAACTA TATTTTTCAA AGATGACGGG     2340

AACTACAAGA CACGTGCTGA AGTCAAGTTT GAAGGTGATA CCCTTGTTAA TAGAATCGAG     2400

TTAAAAGGTA TTGATTTTAA AGAAGATGGA ACATTCTTG GACACAAATT GGAATACAAC      2460

TATAACTCAC ACAATGTATA CATCATGGCA GACAAACAAA AGAATGGAAC CAAAGTTAAC     2520
```

```
TTCAAAATTA GACACAACAT TGAAGATGGA AGCGTTCAAC TAGCAGACCA TTATCAACAA    2580

AATACTCCAA TTGGCGATGG CCCTGTCCTT TTACCAGACA ACCATTACCT GTCCACACAA    2640

TCTGCCCTTT CGAAAGATCC CAACGAAAAG AGAGACCACA TGGTCCTTCT TGAGTTTGTA    2700

ACAGCTGCTG GGATTACACA TGGCATGGAT GAACTATACA AGTCCGGATC TAGATAACTG    2760

TATCGATGGA TCCGAAGGCG GGGACAGCAG TGCAGTGGTG GACAGAAAGC AAGTGATCTA    2820

GGCCAGCAGC CTCCCTAAAG GGACTTCAGC CCACAAAGCC AAACTTGTGG CTTTAATACA    2880

AGCTCTGTAA ATGGTAAAAA AAAAAAAGTC TACACGGACA GCAGGTATGC TCTTGCCACT    2940

GTACAGAGCA ATATACAGAC AAAGAGAACT GTTGACATCT GCAGAGAAAG ACCTAAGATG    3000

CTGTGGCTAA AAGAAATCAG ATGGCAAATC TAACCGCCCA GGCATCCTAA AGAGCAATGA    3060

TCCTGACAGT CTGAAGACTA TCAAGTTATA GACAAATTAA GACTGGTAAA AAAAACCCTG    3120

TATAAAATAG TAAAAACTGA AAAAAGAAAA CTAGTCCTCT CATGAGAAGA CAGACCTGAC    3180

ATCTACTGAA AAATAGACTT TACTGGAAAA AATATGTGTA TGAATACCTT CTAGTTTTTG    3240

TGAACGTTCT CAAGATGGAT AAAAGCTTTT CCTTGTAAAA CGAGACTGAT CAGATAGTCA    3300

TCAAGAAGAT TGTTAAAGAA AATTTTCCAA GGTTCGGAGT GCCAAAAGCA ATAGTGTCAG    3360

ATAATGGTCC TGCCTTTGTT GCCCAGGTAA GTCAGGGTGT GGCCAAGTAT TTAGAGGTCA    3420

AATGAAAATT CCATTGTGTG TACAGACCTC AGAGCTCAGG AAAGATAAAA AAGAATAAAT    3480

AAAACTCTAA ACAGACCTTG ACAAAATTAA TCCTAGAGAC TGGCACAGAC TTACTTGGTA    3540

CTCCTTCCCC TTGCCCTATT TAGAACTGAG AATACTCCCT CTTGATTCGG TTTTACTCTT    3600

TTTAAGATCC TTTATGGGGC TCCTATGCCA TCACTGTCTT AAATGATGTG TTTAAACCTA    3660

TGTTGTTATA ATAATGATCT ATATGTTAAG TTAAAAGGCT TGCAGGTGGT GCAGAAAGAA    3720

GTCTGGTCAC AACTGGCTAC AGTGAACAAG CTGGGTACCC CAAGGACATC TTACCAGTTC    3780

CAGCCAGAGA TCTGATCTAC GATCCCCGGG TCGACCCGGG TCGACCCTGT GGAATGTGTG    3840

TCAGTTAGGG TGTGGAAAGT CCCCAGGCTC CCCAGCAGGC AGAAGTATGC AAAGCATGCA    3900

TCTCAATTAG TCAGCAACCA GGTGTGGAAA GTCCCCAGGC TCCCCAGCAG GCAGAAGTAT    3960

GCAAAGCATG CATCTCAATT AGTCAGCAAC CATAGTCCCG CCCCTAACTC CGCCCATCCC    4020

GCCCCTAACT CCGCCCAGTT CCGCCCATTC TCCGCCCCAT GGCTGACTAA TTTTTTTTAT    4080

TTATGCAGAG GCCGAGGCCG CCTCGGCCTC TGAGCTATTC CAGAAGTAGT GAGGAGGCTT    4140

TTTTGGAGGC CTAGGCTTTT GCAAAAAGCT TCACGCTGCC GCAAGCACTC AGGGCGCAAG    4200

GGCTGCTAAA GGAAGCGGAA CACGTAGAAA GCCAGTCCGC AGAAACGGTG CTGACCCCGG    4260

ATGAATGTCA GCTACTGGGC TATCTGGACA AGGGAAAACG CAAGCGCAAA GAGAAAGCAG    4320

GTAGCTTGCA GTGGGCTTAC ATGGCGATAG CTAGACTGGG CGGTTTTATG GACAGCAAGC    4380

GAACCGGAAT TGCCAGCTGG GGCGCCCTCT GGTAAGGTTG GGAAGCCCTG CAAAGTAAAC    4440

TGGATGGCTT TCTTGCCGCC AAGGATCTGA TGGCGCAGGG GATCAAGATC TGATCAAGAG    4500

ACAGGATGAG GATCGTTTCG CATGATTGAA CAAGATGGAT TGCACGCAGG TTCTCCGGCC    4560

GCTTGGGTGG AGAGGCTATT CGGCTATGAC TGGGCACAAC AGACAATCGG CTGCTCTGAT    4620

GCCGCCGTGT TCCGGCTGTC AGCGCAGGGG CGCCCGGTTC TTTTTGTCAA GACCGACCTG    4680

TCCGGTGCCC TGAATGAACT GCAGGACGAG GCAGCGCGGC TATCGTGGCT GGCCACGACG    4740

GGCGTTCCTT GCGCAGCTGT GCTCGACGTT GTCACTGAAG CGGGAAGGGA CTGGCTGCTA    4800

TTGGGCGAAG TGCCGGGGCA GGATCTCCTG TCATCTCACC TTGCTCCTGC CGAGAAAGTA    4860

TCCATCATGG CTGATGCAAT GCGGCGGCTG CATACGCTTG ATCCGGCTAC CTGCCCATTC    4920
```

-continued

```
GACCACCAAG CGAAACATCG CATCGAGCGA GCACGTACTC GGATGGAAGC CGGTCTTGGG        4980

GATCAGGATG ATCTGGACGA AGAGCATCAG GGGCTCGCGC CAGCCGAACT GTTCGCCAGG        5040

CTCAAGGCGC GCATGCCCGA CGGCGAGGAT CTCGTCGTGA CCCATGGCGA TGCCTGCTTG        5100

CCGAATATCA TGGTGGAAAA TGGCCGCTTT TCTGGATTCA TCGACTGTGG CCGGCTGGGT        5160

GTGGCGGACC GCTATCAGGA CATAGCGTTG GCTACCCGTG ATATTGCTGA AGAGCTTGGC        5220

GGCGAATGGG CTGACCGCTT CCTCGTGCTT TACGGTATCG CCGCTCCCGA TTCGCAGCGC        5280

ATCGCCTTCT ATCGCCTTCT TGACGAGTTC TTCTGAGCGG GACTCTGGGG TTCGAAATGA        5340

CCGACCAAGC GACGCCCAAC CTGCCATCAC GAGATTTCGA TTCCACCGCC GCCTTCTATG        5400

AAAGGTTGGG CTTCGGAATC GTTTTCCGGG ACGGAATTCG TAATCTGCTG CTTGCAAACA        5460

AAAAAACCAC CGCTACCAGC GGTGGTTTGT TTGCCGGATC AAGAGCTACC AACTCTTTTT        5520

CCGAAGGTAA CTGGCTTCAG CAGAGCGCAG ATACCAAATA CTGTCCTTCT AGTGTAGCCG        5580

TAGTTAGGCC ACCACTTCAA GAACTCTGTA GCACCGCCTA CATACCTCGC TCTGCTAATC        5640

CTGTTACCAG TGGCTGCTGC CAGTGGCGAT AAGTCGTGTC TTACCGGGTT GGACTCAAGA        5700

CGATAGTTAC CGGATAAGGC GCAGCGGTCG GGCTGAACGG GGGGTTCGTG CACACAGCCC        5760

AGCTTGGAGC GAACGACCTA CACCGAACTG AGATACCTAC AGCGTGAGCA TTGAGAAAGC        5820

GCCACGCTTC CCGAAGGGAG AAAGGCGGAC AGGTATCCGG TAAGCGGCAG GGTCGGAACA        5880

GGAGAGCGCA CGAGGGAGCT TCCAGGGGGA AACGCCTGGT ATCTTTATAG TCCTGTCGGG        5940

TTTCGCCACC TCTGACTTGA GCGTCGATTT TTGTGATGCT CGTCAGGGGG GCGGAGCCTA        6000

TGGAAAAACG CCAGCAACGC CGAGATGCGC CGCCTCGAGT ACACCTGCGT CATGCTGAGA        6060

CCCTCAAGCC TCACTAAAAG GGTCCCTGCC TAGTTCTGTT TACTAATCTG CCTTATTCTG        6120

TTTTTGTTCC CATGTTAAAG ATAGAGTAAA TGCAGTATTC TCCACATAGA GATATAGACT        6180

TCTGAAATTC TAAGATTAGA ATTATTTACA AGAAGAAGTG GGGAA                       6225

(2) INFORMATION FOR SEQ ID NO: 2:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

CCTCCCATCT AGAGGTTGTT CTCGGAACAC TCCTAAACTT TTCACCCCAA AACTCCTCAC          60

CCTAAAGTTC GAAAAAACTG TTCCAAGAAC ATTTTTGAGA TAAAGGCCTC CTAGAACAAC         120

CTCAAAATGA CATTGCCAAA TGATAAGACA TGACTCCTTA GTTACGTAGG TTCCTTGATA         180

GGACATGACT CCTTAGTTAC GTAGGTTCCT TGATAGGACA TGACTCCTTA GTTACGTAGA         240

TTCCTTTGGT AGAACTCCCT AGTGATGTAA ACTTGTACTT TCCCTGCCCA GTTCTCCCCC         300

TTTGAGTTTT ACTATATAAG CCTGTAAAAA ATTTTTGCTG ACCGTCGAGA CTCCTCTACC         360

CTGTGCTAAG GTGTATGAGT TTCGACCCCA GAGCTCTGTG TGCTTCCATG TTGCTGCTTT         420

ATTTCGACCC CAGAGCTCTG GTCTGTGTGC TTTCATGTCG CTGCTTTATT AAATCTTGCC         480

TTCTACA                                                                  487

(2) INFORMATION FOR SEQ ID NO: 3:
```

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
CCTCCCATCT AGAAAACATT TTTGAGATAA AGGCTTCCTG GAACAACCTC AAAATGAACC      60

AGGTACTCCT TAGTTACGTA GGTTCCTTGA TAGGACATGA CTCCTTAGTT ACATAGATTC     120

CTTTGGCAGA ACTCCCTAGT GATGTAAACT TGTACTTTCC CTGCCCAGTT CTCCCCCTTT     180

GAGTTTTACT ATATAAGCCT GTGAAAAATT TTGGCTGACC GTCAGACTC CTCTACCCTG      240

TGCTAAGGTG TATGAGTTTC GACCCCAGAG CTCTGTGTGC TTCCATGTTG CTGCTTTATT     300

TCGACCCCAG AGCTCTGGTC TGTGTGCTTT CATGTTGCTG CCTTATTAAA TCTTGCCTTC     360

TACATT                                                                366
```

(2) INFORMATION FOR SEQ ID NO: 4:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CCTCCCATCT AGAGATTGTT CCCAGAACAC TCCTGAACTC TTCACCCCAG AATGCATGCC      60

TGAACTCCTC ACCCTAGAGT TCGAACCCTC CCAACTAAAG ACTGTTCCAA GAACATTTTT    120

GAGATAAGGG CCTCCTGGAA CAACCTCAGA ATGAACCGGG TACATTGCCA AATAATAGGA    180

CATGACCCCT TAGTTACGTA AAATCCCTTG GCAGAACCCC TTGTCCCTTG GCAGAACCCC    240

TTAGTTATGT AAACTTGTAC TTTCCCTACC CCGCTCTCCC CCCTTGAGTT TTTCCTATAT    300

AAGC                                                                  304
```

(2) INFORMATION FOR SEQ ID NO: 5:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
CCTCCCATCT AGAGAGTGTT CCCAGAACAC TCCTGAACTC TTCACCCCAG AATGCATTCC      60

TGAACTCCTC ACCCTAGAGT TCGAACCCTC CCAACTAAAG ACTGTTCCAA GAACATTTTT    120

GAGATAAGGG CCTCCTGGAA CAACCTCAGA ATGAACCGGA TACATTGCCA AATAATAGGA    180

CATGACCCCT TAGTTACGTA GAATCCCTTG GCAGAACCCC TTGTCCCTTG GCAGAACCCC    240

TTAGTTATGT AAACTTGTAC TTTCCCTACC CCGCTCTCCC CCCTTGAGTT TTTCCTATAT    300

AAGC                                                                  304
```

(2) INFORMATION FOR SEQ ID NO: 6:

(i) SEQUENCE CHARACTERISTICS:
        (A) LENGTH: 304 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
CCTCCCATCT AGAGAGTGTT CCCAGAACAC TCCTGAACTC TTCACCCCAG AATGCATTCC     60

TGAACTCCTC ATCCTAGAGT TCGAACCCTC CCAACTAAAG ACTGTTCCAA GAACATTTTT    120

GAGATAAGGG CCTCCTGGAA CAACCTCAGA ATGAACCTGG TACATTGCCA AATAATAGGA    180

CATGACCCTT TAGTTACGTA GAATCCCTTG GCAGAACCCC TTGTCCCTTG GCAGAACCCC    240

TTAGTTATGC AAACTTGTAC TTTCTCTGCC CCGCTCTCCC CCCTTGAGTT TTTCCTATAT    300

AAGC                                                                 304
```

(2) INFORMATION FOR SEQ ID NO: 7:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
CCTCCCATCT AGAGAGTGTT CCCAGAACAC TCCTGAACTC TTCACCTCAA AATGCATTCC     60

TGAACTCCTC ACCCTAGAGT TCGAACCCTC CCAACTAAAG ACTGTTCCAA GAACATTTTT    120

GAGATAAGGG CCTCCTGGAA CAACCTCAGA ATGAACCAGG TACATTGCCA AATAATAGGA    180

CATGACCCTT TAGTTACGTA GAATCCCTTG GCAGAACCCC TTGTCCCTTG GCAGAACCCC    240

TTAGTTATGC AAACTTGTAC TTTCTCTGCC CCGCTCTCCC CCCTTGAGTT TTTCCTATAT    300

AAGC                                                                 304
```

(2) INFORMATION FOR SEQ ID NO: 8:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
CCTCCCATCT AGAGATTGTT CCCAGAACAC TCCTGAACTC TTCACCCCAG AATGCATTCC     60

TGAACTCCTC ACCCTAGAGT TCGAACCCTC CCAACTAAAG ACTGTTCCAA GAACATTTTT    120

GAGATAAGGG CCTCCTGGAA CAACCTCAGA ATGAACCGGA TACATTGCCA AATAATAGGA    180

CATGACCCCT TAGTTACGTA GAATTCCCTT GGCAGAACCC CTTGTCCCTT GGCAGAACCC    240

CTTAGTTATG CAAACTTGTA CTTTCCCTGC CCCGCTCTCC CCCCTTGAGG TTTTCCTATA    300

TAAGC                                                                305
```

(2) INFORMATION FOR SEQ ID NO: 9:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

| | | | | | |
|---|---|---|---|---|---|
| CCTCCCATCT | AGAGAGTGTT | CCCAGAACAC | TCCTGAACTC | TTCACCCCAG | AATGCATTCC | 60
| TGAACCCCTC | ACCCTAGAGT | TCGAACCCTC | CCAACTAAAG | ACTGTTCCAA | GAACATTTTT | 120
| GAGATAAGGG | CCTCCTGGAA | CAACCTCAGA | ATGAACCAGG | TACATTGCCA | AATAATAGGA | 180
| CATGACCCCT | TAGTTACGTA | GAATTCCCTT | GGCAGAACCC | CTTGTCCCTT | GGCAGAACCC | 240
| CTTAGTTATG | CGAACTTGTA | CTTTCCCTGC | CCCGCTCTCC | CCCCTTGAGT | TTTTCCTATA | 300
| TAAGC | | | | | 305

(2) INFORMATION FOR SEQ ID NO: 10:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

| | | | | | |
|---|---|---|---|---|---|
| CCCTCCCATC | TAGAGAGTGT | TCCCAGAACA | CTCCTGAACT | CTTCATCCCA | GAATGCATTC | 60
| CTGAACTCCT | CACCCTATAG | TTCGAACCCT | CCCAACTAAA | GACTGTTCCA | AGAACATTTT | 120
| TGAGATAAGG | GCCTCCTGGA | ACAACCTCAG | AATGAACCGG | GTACATTGCC | AAATAATAGG | 180
| ACATGACCCC | TTAGTTACGT | AGAATTCCCT | TGGCAGAACC | CCTTGTCGCT | TGGCAGAACC | 240
| CCTTAGTTAT | GTAAACTTGT | ACTTTCCCTG | CCCCGCTCTC | CCCCCTTGAG | TTTTTACTAT | 300
| ATAAGC | | | | | 306

(2) INFORMATION FOR SEQ ID NO: 11:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

| | | | | | |
|---|---|---|---|---|---|
| CCTCCCATCT | AGAGAGTGTT | CCCAAAACAC | TCCTGAACTC | TTCACCCCAG | AATGCATTCC | 60
| TGAACTCCTC | ACCCTAAAGT | TCAAACCCTC | CCAACTAAAG | ACTGTTCCAA | GAACATTTTT | 120
| GAGATAAGGG | CCTCCTGGAA | CAACCTCAGA | ATGAACGGGG | TACATTGCCA | AATAATAGGA | 180
| CATGACCCCT | TAGTTACACA | GAATTCCCTT | GGCAAAACCC | CTTGTCCCTT | GGCAGAACCC | 240
| CTTAGTTATG | CAAACTTGTA | CTTTCCCTGC | CCAGCTCTCC | CCCCTTGAGT | TTTTCCTATA | 300
| TAAGC | | | | | 305

(2) INFORMATION FOR SEQ ID NO: 12:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

-continued

```
CCTCCCATCT AGAGAGTGTT CCCAGAACAC TCCTGAACTC TTCACCCCAG AATGCATTCC      60

TGAACTCCTC ACCCTAGAGT TTGAACCCTC CCAACTAAAG ACTGTTCCAA GAACATCTTT     120

GAGATAAGGG CCTCCTGGAA CAACCTCAGA ATGAACGGG TACATTGCCA AATAATAGGA     180

CATGACCCCT TAGTTACGTA GAATTCCCTT GGCAGAACCC CTTGTCGCTT GGCAGAACCC     240

CTTAGTTATG CAAACTTGTA CTTTCCCTGC CCCGCTCTCC CCCTTGAGTT TTTCCTATAA     300

AAGC                                                                 304
```

(2) INFORMATION FOR SEQ ID NO: 13:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
CCTCCCATCT AGAGAGTGTT CCCAGAACAC TCCTAAACTC TTCACCCCAG AATGCATTCC      60

TGAACTCCTC ACCCTAGAGT TCGAACCCTT CCAACTAAAG ACTGTTCCAA GAACATTTTT     120

GAGATAAGGG CCTCCTGGAA CAACCTCAAA ATGAACGGG TACATTGCCA AATGATAGGA     180

CATGACCCCT TAGTTACGTA GATTCCCTTG GCAGAACCCC TTGTCCCTTG GCAGAACCCC     240

CTAGTGATGT AAACTTGTAC TTTCCCTGCC CAGCTCTCCC CCCTTGAGTT TTCCTATATA     300

AGC                                                                  303
```

(2) INFORMATION FOR SEQ ID NO: 14:

(i) SEQUENCE CHARACTERISTICS:
        (A) LENGTH: 8657 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
TGAAGAATAA AAAATTACTG GCCTCTTGTG AGAACATGAA CTTTCACCTC GGAGCCCACC      60

CCCTCCCATC TGGAAAACAT ACTTGAGAAA AACATTTTCT GGAACAACCA CAGAATGTTT     120

CAACAGGCCA GATGTATTGC CAAACACAGG ATATGACTCT TTGGTTGAGT AAATTTGTGG     180

TTGTTAAACT TCCCCTATTC CCTCCCCATT CCCCCTCCCA GTTTGTGGTT TTTTCCTTTA     240

AAAGCTTGTG AAAAATTTGA GTCGTCGTCG AGACTCCTCT ACCCTGTGCA AAGGTGTATG     300

AGTTTCGACC CCAGAGCTCT GTGTGCTTTC TGTTGCTGCT TTATTTCGAC CCCAGAGCTC     360

TGGTCTGTGT GCTTTCATGT CGCTGCTTTA TTAAATCTTA CCTTCTACAT TTATGTATG     420

GTCTCAGTGT CTTCTTGGGT ACGCGGCTGT CCCGGGACTT GAGTGTCTGA GTGAGGGTCT     480

TCCCTCGAGG GTCTTTCATT TGGTACATGG GCCGGGAATT CGAGAATCTT TCATTTGGTG     540

CATTGGCCGG GAATTCGAAA ATCTTTCATT TGGTGCATTG GCCGGGAAAC AGCGCGACCA     600

CCCAGAGGTC CTAGACCCAC TTAGAGGTAA GATTCTTTGT TCTGTTTTGG TCTGATGTCT     660

GTGTTCTGAT GTCTGTGTTC TGTTTCTAAG TCTGGTGCGA TCGCAGTTTC AGTTTTGCGG     720

ACGCTCAGTG AGACCGCGCT CCGAGAGGGA GTGCGGGGTG GATAAGGATA GACGTGTCCA     780

GGTGTCCACC GTCCGTTCGC CCTGGGAGAC GTCCAGGAG GAACAGGGGA GGATCAGGGA     840

CGCCTGGTGG ACCCCTTTGA AGGCCAAGAG ACCATTTGGG GTTGCGAGAT CGTGGGTTCG     900
```

```
AGTCCCACCT CGTGCCCAGT TGCGAGATCG TGGGTTCGAG TCCCACCTCG TGTTTTGTTG    960

CGAGATCGTG GGTTCGAGTC CCACCTCGCG TCTGGTCACG GGATCGTGGG TTCGAGTCCC   1020

ACCTCGTGTT TTGTTGCGAG ATCGTGGGTT CGAGTCCCAC CTCGCGTCTG GTCACGGGAT   1080

CGTGGGTTCG AGTCCCACCT CGTGCAGAGG GTCTCAATTG CCGGCCTTA GAGAGGCCAT    1140

CTGATTCTTC TGGTTTCTCT TTTTGTCTTA GTCTCGTGTC CGCTCTTGTT GTGACTACTG   1200

TTTTTCTAAA AATGGGACAA TCTGTGTCCA CTCCCCTTTC TCTGACTCTG GTTCTGTCGC   1260

TTGGTAATTT TGTTTGTTTA CGTTTGTTTT TGTGAGTCGT CTATGTTGTC TGTTACTATC   1320

TTGTTTTTGT TTGTGGTTTA CGGTTTCTGT GTGTGTCTTG TGTGTCTCTT TGTGTTCAGA   1380

CTTGGACTGA TGACTGACGA CTGTTTTTAA GTTATGCCTT CTAAAATAAG CCTAAAAATC   1440

CTGTCAGATC CCTATGCTGA CCACTTCCTT TCAGATCAAC AGCTGCCCTT ACGTATCGAT   1500

GGATCCCTCG ACTAACTAAT AGCCCATTCT CCAAGGTCGA GCGGGATCAA TTCCGCCCCC   1560

CCCCTAACGT TACTGGCCGA AGCCGCTTGG AATAAGGCCG GTGTGCGTTT GTCTATATGT   1620

TATTTTCCAC CATATTGCCG TCTTTTGGCA ATGTGAGGGC CCGGAAACCT GGCCCTGTCT   1680

TCTTGACGAG CATTCCTAGG GGTCTTTCCC CTCTCGCCAA AGGAATGCAA GGTCTGTTGA   1740

ATGTCGTGAA GGAAGCAGTT CCTCTGGAAG CTTCTTGAAG ACAAACAACG TCTGTAGCGA   1800

CCCTTTGCAG GCAGCGGAAC CCCCCACCTG GCGACAGGTG CCTCTGCGGC CAAAAGCCAC   1860

GTGTATAAGA TACACCTGCA AAGGCGGCAC AACCCCAGTG CCACGTTGTG AGTTGGATAG   1920

TTGTGGAAAG AGTCAAATGG CTCTCCTCAA GCGTATTCAA CAAGGGGCTG AAGGATGCCC   1980

AGAAGGTACC CCATTGTATG GGATCTGATC TGGGGCCTCG GTGCACATGC TTTACATGTG   2040

TTTAGTCGAG GTTAAAAAAA CGTCTAGGCC CCCCGAACCA CGGGGACGTG GTTTTCCTTT   2100

GAAAAACACG ATAATAATCA TGGGCGCGGA TCCCGTCGTT TTACAACGTC GTGACTGGGA   2160

AAACCCTGGC GTTACCCAAC TTAATCGCCT TGCAGCACAT CCCCCTTTCG CCAGCTGGCG   2220

TAATAGCGAA GAGGCCCGCA CCGATCGCCC TTCCCAACAG TTGCGCAGCC TGAATGGCGA   2280

ATGGCGCTTT GCCTGGTTTC CGGCACCAGA AGCGGTGCCG GAAAGCTGGC TGGAGTGCGA   2340

TCTTCCTGAG GCCGATACTG TCGTCGTCCC CTCAAACTGG CAGATGCACG GTTACGATGC   2400

GCCCATCTAC ACCAACGTAA CCTATCCCAT TACGGTCAAT CCGCCGTTTG TTCCCACGGA   2460

GAATCCGACG GGTTGTTACT CGCTCACATT TAATGTTGAT GAAAGCTGGC TACAGGAAGG   2520

CCAGACGCGA ATTATTTTTG ATGGCGTTAA CTCGGCGTTT CATCTGTGGT GCAACGGGCG   2580

CTGGGTCGGT TACGGCCAGG ACAGTCGTTT GCCGTCTGAA TTTGACCTGA GCGCATTTTT   2640

ACGCGCCGGA GAAAACCGCC TCGCGGTGAT GGTGCTGCGT TGGAGTGACG GCAGTTATCT   2700

GGAAGATCAG GATATGTGGC GGATGAGCGG CATTTTCCGT GACGTCTCGT TGCTGCATAA   2760

ACCGACTACA CAAATCAGCG ATTTCCATGT TGCCACTCGC TTTAATGATG ATTTCAGCCG   2820

CGCTGTACTG GAGGCTGAAG TTCAGATGTG CGGCGAGTTG CGTGACTACC TACGGGTAAC   2880

AGTTTCTTTA TGGCAGGGTG AAACGCAGGT CGCCAGCGGC ACCGCCCTT TCGGCGGTGA    2940

AATTATCGAT GAGCGTGGTG GTTATGCCGA TCGCGTCACA CTACGTCTGA ACGTCGAAAA   3000

CCCGAAACTG TGGAGCGCCG AAATCCCGAA TCTCTATCGT GCGGTGGTTG AACTGCACAC   3060

CGCCGACGGC ACGCTGATTG AAGCAGAAGC CTGCGATGTC GGTTTCCGCG AGGTGCGGAT   3120

TGAAAATGGT CTGCTGCTGC TGAACGGCAA GCCGTTGCTG ATTCGAGGCG TTAACCGTCA   3180

CGAGCATCAT CCTCTGCATG GTCAGGTCAT GGATGAGCAG ACGATGGTGC AGGATATCCT   3240
```

```
GCTGATGAAG CAGAACAACT TTAACGCCGT GCGCTGTTCG CATTATCCGA ACCATCCGCT    3300

GTGGTACACG CTGTGCGACC GCTACGGCCT GTATGTGGTG GATGAAGCCA ATATTGAAAC    3360

CCACGGCATG GTGCCAATGA ATCGTCTGAC CGATGATCCG CGCTGGCTAC CGGCGATGAG    3420

CGAACGCGTA ACGCGAATGG TGCAGCGCGA TCGTAATCAC CCGAGTGTGA TCATCTGGTC    3480

GCTGGGGAAT GAATCAGGCC ACGGCGCTAA TCACGACGCG CTGTATCGCT GGATCAAATC    3540

TGTCGATCCT TCCCGCCCGG TGCAGTATGA AGGCGGCGGA GCCGACACCA CGGCCACCGA    3600

TATTATTTGC CCGATGTACG CGCGCGTGGA TGAAGACCAC CCCTTCCCGG CTGTGCCGAA    3660

ATGGTCCATC AAAAAATGGC TTTCGCTACC TGGAGAGACG CGCCCGCTGA TCCTTTGCGA    3720

ATACGCCCAC GCGATGGGTA ACAGTCTTGG CGGTTTCGCT AAATACTGGC AGGCGTTTCG    3780

TCAGTATCCC CGTTTACAGG GCGGCTTCGT CTGGGACTGG GTGGATCAGT CGCTGATTAA    3840

ATATGATGAA AACGGCAACC CGTGGTCGGC TTACGGCGGT GATTTTGGCG ATACGCCGAA    3900

CGATCGCCAG TTCTGTATGA ACGGTCTGGT CTTTGCCGAC CGCACGCCGC ATCCAGCGCT    3960

GACGGAAGCA AAACACCAGC AGCAGTTTTT CCAGTTCCGT TTATCCGGGC AAACCATCGA    4020

AGTGACCAGC GAATACCTGT TCCGTCATAG CGATAACGAG CTCCTGCACT GGATGGTGGC    4080

GCTGGATGGT AAGCCGCTGG CAAGCGGTGA AGTGCCTCTG GATGTCGCTC ACAAGGTAA    4140

ACAGTTGATT GAACTGCCTG AACTACCGCA GCCGGAGAGC GCCGGGCAAC TCTGGCTCAC    4200

AGTACGCGTA GTGCAACCGA ACGCGACCGC ATGGTCAGAA GCCGGGCACA TCAGCGCCTG    4260

GCAGCAGTGG CGTCTGGCGG AAAACCTCAG TGTGACGCTC CCCGCCGCGT CCCACGCCAT    4320

CCCGCATCTG ACCACCAGCG AAATGGATTT TTGCATCGAG CTGGGTAATA AGCGTTGGCA    4380

ATTTAACCGC CAGTCAGGCT TTCTTTCACA GATGTGGATT GGCGATAAAA AACAACTGCT    4440

GACGCCGCTG CGCGATCAGT TCACCCGTGC ACCGCTGGAT AACGACATTG GCGTAAGTGA    4500

AGCGACCCGC ATTGACCCTA ACGCCTGGGT CGAACGCTGG AAGGCGGCGG GCCATTACCA    4560

GGCCGAAGCA GCGTTGTTGC AGTGCACGGC AGATACACTT GCTGATGCGG TGCTGATTAC    4620

GACCGCTCAC GCGTGGCAGC ATCAGGGGAA AACCTTATTT ATCAGCCGGA AAACCTACCG    4680

GATTGATGGT AGTGGTCAAA TGGCGATTAC CGTTGATGTT GAAGTGGCGA GCGATACACC    4740

GCATCCGGCG CGGATTGGCC TGAACTGCCA GCTGGCGCAG GTAGCAGAGC GGGTAAACTG    4800

GCTCGGATTA GGGCCGCAAG AAAACTATCC CGACCGCCTT ACTGCCGCCT GTTTTGACCG    4860

CTGGGATCTG CCATTGTCAG ACATGTATAC CCCGTACGTC TTCCCGAGCG AAAACGGTCT    4920

GCGCTGCGGG ACGCGCGAAT TGAATTATGG CCCACACCAG TGGCGCGGCG ACTTCCAGTT    4980

CAACATCAGC CGCTACAGTC AACAGCAACT GATGGAAACC AGCCATCGCC ATCTGCTGCA    5040

CGCGGAAGAA GGCACATGGC TGAATATCGA CGGTTTCCAT ATGGGGATTG GTGGCGACGA    5100

CTCCTGGAGC CCGTCAGTAT CGGCGGAATT CCAGCTGAGC GCCGGTCGCT ACCATTACCA    5160

GTTGGTCTGG TGTCAAAAAT AATAATAACC GGGCAGGGGG GATCCGAAGG CGGGGACAGC    5220

AGTGCAGTGG TGGACAGAAA GCAAGTGATC TAGGCCAGCA GCCTCCCTAA AGGGACTTCA    5280

GCCCACAAAG CCAAACTTGT GGCTTTAATA CAAGCTCTGT AAATGGTAAA AAAAAAAAG    5340

TCTACACGGA CAGCAGGTAT GCTCTTGCCA CTGTACAGAG CAATATACAG ACAAAGAGAA    5400

CTGTTGACAT CTGCAGAGAA AGACCTAAGA TGCTGTGGCT AAAAGAAATC AGATGGCAAA    5460

TCTAACCGCC CAGGCATCCT AAAGAGCAAT GATCCTGACA GTCTGAAGAC TATCAAGTTA    5520

TAGACAAATT AAGACTGGTA AAAAAAACCC TGTATAAAAT AGTAAAAACT GAAAAAGAA    5580

AACTAGTCCT CTCATGAGAA GACAGACCTG ACATCTACTG AAAAATAGAC TTTACTGGAA    5640
```

```
AAAATATGTG TATGAATACC TTCTAGTTTT TGTGAACGTT CTCAAGATGG ATAAAAGCTT    5700

TTCCTTGTAA AACGAGACTG ATCAGATAGT CATCAAGAAG ATTGTTAAAG AAAATTTTCC    5760

AAGGTTCGGA GTGCCAAAAG CAATAGTGTC AGATAATGGT CCTGCCTTTG TTGCCCAGGT    5820

AAGTCAGGGT GTGGCCAAGT ATTTAGAGGT CAAATGAAAA TTCCATTGTG TGTACAGACC    5880

TCAGAGCTCA GGAAAGATAA AAAGAATAA ATAAAACTCT AAACAGACCT TGACAAAATT    5940

AATCCTAGAG ACTGGCACAG ACTTACTTGG TACTCCTTCC CCTTGCCCTA TTTAGAACTG    6000

AGAATACTCC CTCTTGATTC GGTTTTACTC TTTTTAAGAT CCTTTATGGG GCTCCTATGC    6060

CATCACTGTC TTAAATGATG TGTTTAAACC TATGTTGTTA TAATAATGAT CTATATGTTA    6120

AGTTAAAAGG CTTGCAGGTG GTGCAGAAAG AAGTCTGGTC ACAACTGGCT ACAGTGAACA    6180

AGCTGGGTAC CCCAAGGACA TCTTACCAGT TCCAGCCAGA GATCTGATCT ACGATCCCCG    6240

GGTCGACCCG GGTCGACCCT GTGGAATGTG TGTCAGTTAG GGTGTGGAAA GTCCCCAGGC    6300

TCCCCAGCAG GCAGAAGTAT GCAAAGCATG CATCTCAATT AGTCAGCAAC CAGGTGTGGA    6360

AAGTCCCCAG GCTCCCCAGC AGGCAGAAGT ATGCAAAGCA TGCATCTCAA TTAGTCAGCA    6420

ACCATAGTCC CGCCCCTAAC TCCGCCCATC CCGCCCCTAA CTCCGCCCAG TTCCGCCCAT    6480

TCTCCGCCCC ATGGCTGACT AATTTTTTTT ATTTATGCAG AGGCCGAGGC CGCCTCGGCC    6540

TCTGAGCTAT TCCAGAAGTA GTGAGGAGGC TTTTTTGGAG GCCTAGGCTT TTGCAAAAAG    6600

CTTCACGCTG CCGCAAGCAC TCAGGGCGCA AGGGCTGCTA AAGGAAGCGG AACACGTAGA    6660

AAGCCAGTCC GCAGAAACGG TGCTGACCCC GGATGAATGT CAGCTACTGG GCTATCTGGA    6720

CAAGGGAAAA CGCAAGCGCA AAGAGAAAGC AGGTAGCTTG CAGTGGGCTT ACATGGCGAT    6780

AGCTAGACTG GGCGGTTTTA TGGACAGCAA GCGAACCGGA ATTGCCAGCT GGGGCGCCCT    6840

CTGGTAAGGT TGGGAAGCCC TGCAAAGTAA ACTGGATGGC TTTCTTGCCG CCAAGGATCT    6900

GATGGCGCAG GGGATCAAGA TCTGATCAAG AGACAGGATG AGGATCGTTT CGCATGATTG    6960

AACAAGATGG ATTGCACGCA GGTTCTCCGG CCGCTTGGGT GGAGAGGCTA TTCGGCTATG    7020

ACTGGGCACA ACAGACAATC GGCTGCTCTG ATGCCGCCGT GTTCCGGCTG TCAGCGCAGC    7080

GGCGCCCGGT TCTTTTTGTC AAGACCGACC TGTCCGGTGC CCTGAATGAA CTGCAGGACG    7140

AGGCAGCGCG GCTATCGTGG CTGGCCACGA CGGGCGTTCC TTGCGCAGCT GTGCTCGACG    7200

TTGTCACTGA AGCGGGAAGG GACTGGCTGC TATTGGGCGA AGTGCCGGGG CAGGATCTCC    7260

TGTCATCTCA CCTTGCTCCT GCCGAGAAAG TATCCATCAT GGCTGATGCA ATGCGGCGGC    7320

TGCATACGCT TGATCCGGCT ACCTGCCCAT TCGACCACCA AGCGAAACAT CGCATCGAGC    7380

GAGCACGTAC TCGGATGGAA GCCGGTCTTG TCGATCAGGA TGATCTGGAC GAAGAGCATC    7440

AGGGGCTCGC GCCAGCCGAA CTGTTCGCCA GGCTCAAGGC GCGCATGCCC GACGGCGAGG    7500

ATCTCGTCGT GACCCATGGC GATGCCTGCT TGCCGAATAT CATGGTGGAA AATGGCCGCT    7560

TTTCTGGATT CATCGACTGT GGCCGGCTGG GTGTGGCGGA CCGCTATCAG GACATAGCGT    7620

TGGCTACCCG TGATATTGCT GAAGAGCTTG GCGGCGAATG GGCTGACCGC TTCCTCGTGC    7680

TTTACGGTAT CGCCGCTCCC GATTCGCAGC GCATCGCCTT CTATCGCCTT CTTGACGAGT    7740

TCTTCTGAGC GGGACTCTGG GGTTCGAAAT GACCGACCAA GCGACGCCCA ACCTGCCATC    7800

ACGAGATTTC GATTCCACCG CCGCCTTCTA TGAAAGGTTG GGCTTCGGAA TCGTTTTCCG    7860

GGACGGAATT CGTAATCTGC TGCTTGCAAA CAAAAAAACC ACCGCTACCA GCGGTGGTTT    7920

GTTTGCCGGA TCAAGAGCTA CCAACTCTTT TTCCGAAGGT AACTGGCTTC AGCAGAGCGC    7980
```

| | |
|---|---:|
| AGATACCAAA TACTGTCCTT CTAGTGTAGC CGTAGTTAGG CCACCACTTC AAGAACTCTG | 8040 |
| TAGCACCGCC TACATACCTC GCTCTGCTAA TCCTGTTACC AGTGGCTGCT GCCAGTGGCG | 8100 |
| ATAAGTCGTG TCTTACCGGG TTGGACTCAA GACGATAGTT ACCGGATAAG GCGCAGCGGT | 8160 |
| CGGGCTGAAC GGGGGGTTCG TGCACACAGC CCAGCTTGGA GCGAACGACC TACACCGAAC | 8220 |
| TGAGATACCT ACAGCGTGAG CATTGAGAAA GCGCCACGCT TCCCGAAGGG AGAAAGGCGG | 8280 |
| ACAGGTATCC GGTAAGCGGC AGGGTCGGAA CAGGAGAGCG CACGAGGGAG CTTCCAGGGG | 8340 |
| GAAACGCCTG GTATCTTTAT AGTCCTGTCG GGTTTCGCCA CCTCTGACTT GAGCGTCGAT | 8400 |
| TTTTGTGATG CTCGTCAGGG GGGCGGAGCC TATGGAAAAA CGCCAGCAAC GCCGAGATGC | 8460 |
| GCCGCCTCGA GTACACCTGC GTCATGCTGA GACCCTCAAG CCTCACTAAA AGGGTCCCTG | 8520 |
| CCTAGTTCTG TTTACTAATC TGCCTTATTC TGTTTTTGTT CCCATGTTAA AGATAGAGTA | 8580 |
| AATGCAGTAT TCTCCACATA GAGATATAGA CTTCTGAAAT TCTAAGATTA GAATTATTTA | 8640 |
| CAAGAAGAAG TGGGGAA | 8657 |

(2) INFORMATION FOR SEQ ID NO: 15:

(i) SEQUENCE CHARACTERISTICS:
        (A) LENGTH: 6359 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

| | |
|---|---:|
| TGAAGAATAA AAAATTACTG GCCTCTTGTG AGAACATGAA CTTTCACCTC GGAGCCCACC | 60 |
| CCCTCCCATC TGGAAAACAT ACTTGAGAAA AACATTTTCT GGAACAACCA CAGAATGTTT | 120 |
| CAACAGGCCA GATGTATTGC CAAACACAGG ATATGACTCT TTGGTTGAGT AAATTTGTGG | 180 |
| TTGTTAAACT TCCCCTATTC CCTCCCCATT CCCCCTCCCA GTTTGTGGTT TTTTCCTTTA | 240 |
| AAAGCTTGTG AAAAATTTGA GTCGTCGTCG AGACTCCTCT ACCCTGTGCA AAGGTGTATG | 300 |
| AGTTTCGACC CCAGAGCTCT GTGTGCTTTC TGTTGCTGCT TTATTTCGAC CCCAGAGCTC | 360 |
| TGGTCTGTGT GCTTTCATGT CGCTGCTTTA TTAAATCTTA CCTTCTACAT TTTATGTATG | 420 |
| GTCTCAGTGT CTTCTTGGGT ACGCGGCTGT CCCGGGACTT GAGTGTCTGA GTGAGGGTCT | 480 |
| TCCCTCGAGG GTCTTTCATT TGGTACATGG GCCGGGAATT CGAGAATCTT TCATTTGGTG | 540 |
| CATTGGCCGG GAATTCGAAA ATCTTTCATT TGGTGCATTG GCCGGGAAAC AGCGCGACCA | 600 |
| CCCAGAGGTC CTAGACCCAC TTAGAGGTAA GATTCTTTGT TCTGTTTTGG TCTGATGTCT | 660 |
| GTGTTCTGAT GTCTGTGTTC TGTTTCTAAG TCTGGTGCGA TCGCAGTTTC AGTTTTGCGG | 720 |
| ACGCTCAGTG AGACCGCGCT CCGAGAGGGA GTGCGGGGTG GATAAGGATA GACGTGTCCA | 780 |
| GGTGTCCACC GTCCGTTCGC CCTGGGAGAC GTCCAGGAG GAACAGGGGA GGATCAGGGA | 840 |
| CGCCTGGTGG ACCCCTTTGA AGGCCAAGAG ACCATTTGGG GTTGCGAGAT CGTGGGTTCG | 900 |
| AGTCCCACCT CGTGCCCAGT TGCGAGATCG TGGGTTCGAG TCCCACCTCG TGTTTTGTTG | 960 |
| CGAGATCGTG GGTTCGAGTC CCACCTCGCG TCTGGTCACG GGATCGTGGG TTCGAGTCCC | 1020 |
| ACCTCGTGTT TTGTTGCGAG ATCGTGGGTT CGAGTCCCAC CTCGCGTCTG GTCACGGGAT | 1080 |
| CGTGGGTTCG AGTCCCACCT CGTGCAGAGG GTCTCAATTG GCCGGCCTTA GAGAGGCCAT | 1140 |
| CTGATTCTTC TGGTTTCTCT TTTTGTCTTA GTCTCGTGTC CGCTCTTGTT GTGACTACTG | 1200 |
| TTTTTCTAAA AATGGGACAA TCTGTGTCCA CTCCCCTTTC TCTGACTCTG GTTCTGTCGC | 1260 |

```
TTGGTAATTT TGTTTGTTTA CGTTTGTTTT TGTGAGTCGT CTATGTTGTC TGTTACTATC    1320

TTGTTTTTGT TTGTGGTTTA CGGTTTCTGT GTGTGTCTTG TGTGTCTCTT TGTGTTCAGA    1380

CTTGGACTGA TGACTGACGA CTGTTTTTAA GTTATGCCTT CTAAAATAAG CCTAAAAATC    1440

CTGTCAGATC CCTATGCTGA CCACTTCCTT TCAGATCAAC AGCTGCCCTT ACTCGAGCTC    1500

AAGCTTCGAA TTCTGCAGTC GACGGTACCC CGGCCGCTAA CTAATAGCCC ATTCTCCAAG    1560

GTACGTAGCG GGGATCAATT CCGCCCCCCC CCTAACGTTA CTGGCCGAAG CCGCTTGGAA    1620

TAAGGCCGGT GTGCGTTTGT CTATATGTTA TTTTCCACCA TATTGCCGTC TTTTGGCAAT    1680

GTGAGGGCCC GGAAACCTGG CCCTGTCTTC TTGACGAGCA TTCCTAGGGG TCTTTCCCCT    1740

CTCGCCAAAG GAATGCAAGG TCTGTTGAAT GTCGTGAAGG AAGCAGTTCC TCTGGAAGCT    1800

TCTTGAAGAC AAACAACGTC TGTAGCGACC CTTTGCAGGC AGCGGAACCC CCCACCTGGC    1860

GACAGGTGCC TCTGCGGCCA AAAGCCACGT GTATAAGATA CACCTGCAAA GGCGGCACAA    1920

CCCCAGTGCC ACGTTGTGAG TTGGATAGTT GTGGAAAGAG TCAAATGGCT CTCCTCAAGC    1980

GTATTCAACA AGGGGCTGAA GGATGCCCAG AAGGTACCCC ATTGTATGGG ATCTGATCTG    2040

GGGCCTCGGT GCACATGCTT TACATGTGTT TAGTCGAGGT TAAAAAAACG TCTAGGCCCC    2100

CCGAACCACG GGGACGTGGT TTTCCTTTGA AAAACACGAT ACGGGATCCA CCGGTCGCCA    2160

CCATGGGTAA AGGAGAAGAA CTTTTCACAG GAGTTGTCCC AATTCTTGTT GAATTAGATG    2220

GTGATGTTAA TGGGCACAAA TTTTCTGTCA GTGGAGAGGG TGAAGGTGAT GCAACATACG    2280

GAAAACTTAC CCTTAAATTT ATTTGCACTA CTGGAAAACT ACCTGTTCCA TGGCCAACAC    2340

TTGTCACTAC TTTCACTTAT GGTGTTCAAT GCTTTTCAAG ATACCCAGAT CATATGAAAC    2400

GGCATGACTT TTTCAAGAGT GCCATGCCCG AAGGTTATGT ACAGGAAAGA ACTATATTTT    2460

TCAAAGATGA CGGGAACTAC AAGACACGTG CTGAAGTCAA GTTTGAAGGT GATACCCTTG    2520

TTAATAGAAT CGAGTTAAAA GGTATTGATT TTAAAGAAGA TGGAAACATT CTTGGACACA    2580

AATTGGAATA CAACTATAAC TCACACAATG TATACATCAT GGCAGACAAA CAAAAGAATG    2640

GAACCAAAGT TAACTTCAAA ATTAGACACA ACATTGAAGA TGGAAGCGTT CAACTAGCAG    2700

ACCATTATCA ACAAAATACT CCAATTGGCG ATGGCCCTGT CCTTTTACCA GACAACCATT    2760

ACCTGTCCAC ACAATCTGCC CTTTCGAAAG ATCCCAACGA AAAGAGAGAC CACATGGTCC    2820

TTCTTGAGTT TGTAACAGCT GCTGGGATTA CACATGGCAT GGATGAACTA TACAAGTCCG    2880

GATCTAGATA ACTGTATCGA TGGATCCGAA GGCGGGGACA GCAGTGCAGT GGTGGACAGA    2940

AAGCAAGTGA TCTAGGCCAG CAGCCTCCCT AAAGGGACTT CAGCCCACAA AGCCAAACTT    3000

GTGGCTTTAA TACAAGCTCT GTAAATGGTA AAAAAAAAAA AGTCTACACG GACAGCAGGT    3060

ATGCTCTTGC CACTGTACAG AGCAATATAC AGACAAAGAG AACTGTTGAC ATCTGCAGAG    3120

AAAGACCTAA GATGCTGTGG CTAAAAGAAA TCAGATGGCA AATCTAACCG CCCAGGCATC    3180

CTAAAGAGCA ATGATCCTGA CAGTCTGAAG ACTATCAAGT TATAGACAAA TTAAGACTGG    3240

TAAAAAAAAC CCTGTATAAA ATAGTAAAAA CTGAAAAAAG AAAACTAGTC CTCTCATGAG    3300

AAGACAGACC TGACATCTAC TGAAAAATAG ACTTTACTGG AAAAAATATG TGTATGAATA    3360

CCTTCTAGTT TTTGTGAACG TTCTCAAGAT GGATAAAAGC TTTTCCTTGT AAAACGAGAC    3420

TGATCAGATA GTCATCAAGA AGATTGTTAA AGAAAATTTT CCAAGGTTCG GAGTGCCAAA    3480

AGCAATAGTG TCAGATAATG GTCCTGCCTT TGTTGCCCAG GTAAGTCAGG GTGTGGCCAA    3540

GTATTTAGAG GTCAAATGAA AATTCCATTG TGTGTACAGA CCTCAGAGCT CAGGAAAGAT    3600

AAAAAAGAAT AAATAAAACT CTAAACAGAC CTTGACAAAA TTAATCCTAG AGACTGGCAC    3660
```

-continued

```
AGACTTACTT GGTACTCCTT CCCCTTGCCC TATTTAGAAC TGAGAATACT CCCTCTTGAT    3720

TCGGTTTTAC TCTTTTTAAG ATCCTTTATG GGGCTCCTAT GCCATCACTG TCTTAAATGA    3780

TGTGTTTAAA CCTATGTTGT TATAATAATG ATCTATATGT TAAGTTAAAA GGCTTGCAGG    3840

TGGTGCAGAA AGAAGTCTGG TCACAACTGG CTACAGTGAA CAAGCTGGGT ACCCCAAGGA    3900

CATCTTACCA GTTCCAGCCA GAGATCTGAT CTACGATCCC CGGGTCGACC CGGGTCGACC    3960

CTGTGGAATG TGTGTCAGTT AGGGTGTGGA AAGTCCCCAG GCTCCCCAGC AGGCAGAAGT    4020

ATGCAAAGCA TGCATCTCAA TTAGTCAGCA ACCAGGTGTG GAAAGTCCCC AGGCTCCCCA    4080

GCAGGCAGAA GTATGCAAAG CATGCATCTC AATTAGTCAG CAACCATAGT CCCGCCCCTA    4140

ACTCCGCCCA TCCCGCCCCT AACTCCGCCC AGTTCCGCCC ATTCTCCGCC CCATGGCTGA    4200

CTAATTTTTT TTATTTATGC AGAGGCCGAG GCCGCCTCGG CCTCTGAGCT ATTCCAGAAG    4260

TAGTGAGGAG GCTTTTTTGG AGGCCTAGGC TTTTGCAAAA AGCTTCACGC TGCCGCAAGC    4320

ACTCAGGGCG CAAGGGCTGC TAAAGGAAGC GGAACACGTA GAAAGCCAGT CCGCAGAAAC    4380

GGTGCTGACC CCGGATGAAT GTCAGCTACT GGGCTATCTG GACAAGGGAA AACGCAAGCG    4440

CAAAGAGAAA GCAGGTAGCT TGCAGTGGGC TTACATGGCG ATAGCTAGAC TGGGCGGTTT    4500

TATGGACAGC AAGCGAACCG GAATTGCCAG CTGGGGCGCC CTCTGGTAAG GTTGGGAAGC    4560

CCTGCAAAGT AAACTGGATG GCTTTCTTGC CGCCAAGGAT CTGATGGCGC AGGGGATCAA    4620

GATCTGATCA AGAGACAGGA TGAGGATCGT TTCGCATGAT TGAACAAGAT GGATTGCACG    4680

CAGGTTCTCC GGCCGCTTGG GTGGAGAGGC TATTCGGCTA TGACTGGGCA CAACAGACAA    4740

TCGGCTGCTC TGATGCCGCC GTGTTCCGGC TGTCAGCGCA GGGGCGCCCG GTTCTTTTTG    4800

TCAAGACCGA CCTGTCCGGT GCCCTGAATG AACTGCAGGA CGAGGCAGCG CGGCTATCGT    4860

GGCTGGCCAC GACGGGCGTT CCTTGCGCAG CTGTGCTCGA CGTTGTCACT GAAGCGGGAA    4920

GGGACTGGCT GCTATTGGGC GAAGTGCCGG GGCAGGATCT CCTGTCATCT CACCTTGCTC    4980

CTGCCGAGAA AGTATCCATC ATGGCTGATG CAATGCGGCG GCTGCATACG CTTGATCCGG    5040

CTACCTGCCC ATTCGACCAC CAAGCGAAAC ATCGCATCGA GCGAGCACGT ACTCGGATGG    5100

AAGCCGGTCT TGTCGATCAG GATGATCTGG ACGAAGAGCA TCAGGGGCTC GCGCCAGCCG    5160

AACTGTTCGC CAGGCTCAAG GCGCGCATGC CCGACGGCGA GGATCTCGTC GTGACCCATG    5220

GCGATGCCTG CTTGCCGAAT ATCATGGTGG AAAATGGCCG CTTTTCTGGA TTCATCGACT    5280

GTGGCCGGCT GGGTGTGGCG GACCGCTATC AGGACATAGC GTTGGCTACC CGTGATATTG    5340

CTGAAGAGCT TGGCGGCGAA TGGGCTGACC GCTTCCTCGT GCTTTACGGT ATCGCCGCTC    5400

CCGATTCGCA GCGCATCGCC TTCTATCGCC TTCTTGACGA GTTCTTCTGA GCGGGACTCT    5460

GGGGTTCGAA ATGACCGACC AAGCGACGCC CAACCTGCCA TCACGAGATT TCGATTCCAC    5520

CGCCGCCTTC TATGAAAGGT TGGGCTTCGG AATCGTTTTC CGGGACGGAA TTCGTAATCT    5580

GCTGCTTGCA AACAAAAAAA CCACCGCTAC CAGCGGTGGT TTGTTTGCCG GATCAAGAGC    5640

TACCAACTCT TTTTCCGAAG GTAACTGGCT TCAGCAGAGC GCAGATACCA AATACTGTCC    5700

TTCTAGTGTA GCCGTAGTTA GGCCACCACT TCAAGAACTC TGTAGCACCG CCTACATACC    5760

TCGCTCTGCT AATCCTGTTA CCAGTGGCTG CTGCCAGTGG CGATAAGTCG TGTCTTACCG    5820

GGTTGGACTC AAGACGATAG TTACCGGATA AGGCGCAGCG GTCGGGCTGA ACGGGGGGTT    5880

CGTGCACACA GCCCAGCTTG GAGCGAACGA CCTACACCGA ACTGAGATAC CTACAGCGTG    5940

AGCATTGAGA AAGCGCCACG CTTCCCGAAG GGAGAAAGGC GGACAGGTAT CCGGTAAGCG    6000
```

-continued

| GCAGGGTCGG | AACAGGAGAG | CGCACGAGGG | AGCTTCCAGG | GGGAAACGCC | TGGTATCTTT | 6060 |
| ATAGTCCTGT | CGGGTTTCGC | CACCTCTGAC | TTGAGCGTCG | ATTTTTGTGA | TGCTCGTCAG | 6120 |
| GGGGGCGGAG | CCTATGGAAA | AACGCCAGCA | ACGCCGAGAT | GCGCCGCCTC | GAGTACACCT | 6180 |
| GCGTCATGCT | GAGACCCTCA | AGCCTCACTA | AAAGGGTCCC | TGCCTAGTTC | TGTTTACTAA | 6240 |
| TCTGCCTTAT | TCTGTTTTTG | TTCCCATGTT | AAAGATAGAG | TAAATGCAGT | ATTCTCCACA | 6300 |
| TAGAGATATA | GACTTCTGAA | ATTCTAAGAT | TAGAATTATT | TACAAGAAGA | AGTGGGGAA  | 6359 |

(2) INFORMATION FOR SEQ ID NO: 16:

(i) SEQUENCE CHARACTERISTICS:
        (A) LENGTH: 6891 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

| TGAAGAATAA | AAAATTACTG | GCCTCTTGTG | AGAACATGAA | CTTTCACCTC | GGAGCCCACC | 60 |
| CCCTCCCATC | TGGAAAACAT | ACTTGAGAAA | AACATTTTCT | GGAACAACCA | CAGAATGTTT | 120 |
| CAACAGGCCA | GATGTATTGC | CAAACACAGG | ATATGACTCT | TTGGTTGAGT | AAATTTGTGG | 180 |
| TTGTTAAACT | TCCCCTATTC | CCTCCCCATT | CCCCCTCCCA | GTTTGTGGTT | TTTTCCTTTA | 240 |
| AAAGCTTGTG | AAAAATTTGA | GTCGTCGTCG | AGACTCCTCT | ACCCTGTGCA | AAGGTGTATG | 300 |
| AGTTTCGACC | CCAGAGCTCT | GTGTGCTTTC | TGTTGCTGCT | TTATTTCGAC | CCCAGAGCTC | 360 |
| TGGTCTGTGT | GCTTTCATGT | CGCTGCTTTA | TTAAATCTTA | CCTTCTACAT | TTTATGTATG | 420 |
| GTCTCAGTGT | CTTCTTGGGT | ACGCGGCTGT | CCCGGGACTT | GAGTGTCTGA | GTGAGGGTCT | 480 |
| TCCCTCGAGG | GTCTTTCATT | TGGTACATGG | GCCGGGAATT | CGAGAATCTT | TCATTTGGTG | 540 |
| CATTGGCCGG | GAATTCGAAA | ATCTTTCATT | TGGTGCATTG | GCCGGGAAAC | AGCGCGACCA | 600 |
| CCCAGAGGTC | CTAGACCCAC | TTAGAGGTAA | GATTCTTTGT | TCTGTTTTGG | TCTGATGTCT | 660 |
| GTGTTCTGAT | GTCTGTGTTC | TGTTTCTAAG | TCTGGTGCGA | TCGCAGTTTC | AGTTTTGCGG | 720 |
| ACGCTCAGTG | AGACCGCGCT | CCGAGAGGGA | GTGCGGGGTG | GATAAGGATA | GACGTGTCCA | 780 |
| GGTGTCCACC | GTCCGTTCGC | CCTGGGAGAC | GTCCCAGGAG | GAACAGGGGA | GGATCAGGGA | 840 |
| CGCCTGGTGG | ACCCCTTTGA | AGGCCAAGAG | ACCATTTGGG | GTTGCGAGAT | CGTGGGTTCG | 900 |
| AGTCCCACCT | CGTGCCCAGT | TGCGAGATCG | TGGGTTCGAG | TCCCACCTCG | TGTTTTGTTG | 960 |
| CGAGATCGTG | GGTTCGAGTC | CCACCTCGCG | TCTGGTCACG | GGATCGTGGG | TTCGAGTCCC | 1020 |
| ACCTCGTGTT | TTGTTGCGAG | ATCGTGGGTT | CGAGTCCCAC | CTCGCGTCTG | GTCACGGGAT | 1080 |
| CGTGGGTTCG | AGTCCCACCT | CGTGCAGAGG | GTCTCAATTG | GCCGGCCTTA | GAGAGGCCAT | 1140 |
| CTGATTCTTC | TGGTTTCTCT | TTTTGTCTTA | GTCTCGTGTC | CGCTCTTGTT | GTGACTACTG | 1200 |
| TTTTTCTAAA | AATGGGACAA | TCTGTGTCCA | CTCCCCTTTC | TCTGACTCTG | GTTCTGTCGC | 1260 |
| TTGGTAATTT | TGTTTGTTTA | CGTTTGTTTT | TGTGAGTCGT | CTATGTTGTC | TGTTACTATC | 1320 |
| TTGTTTTTGT | TTGTGGTTTA | CGGTTTCTGT | GTGTGTCTTG | TGTGTCTCTT | TGTGTTCAGA | 1380 |
| CTTGGACTGA | TGACTGACGA | CTGTTTTTAA | GTTATGCCTT | CTAAAATAAG | CCTAAAAATC | 1440 |
| CTGTCAGATC | CCTATGCTGA | CCACTTCCTT | TCAGATCAAC | AGCTGCCCTT | ACTCGAGCTC | 1500 |
| AAGCTTCGAA | TTCTGCAGTC | GACGGTACCG | CGGGGATCAA | TTCCGCCCCC | CCCTAACGT  | 1560 |
| TACTGGCCGA | AGCCGCTTGG | AATAAGGCCG | GTGTGCGTTT | GTCTATATGT | TATTTTCCAC | 1620 |

-continued

```
CATATTGCCG TCTTTTGGCA ATGTGAGGGC CCGGAAACCT GGCCCTGTCT TCTTGACGAG    1680

CATTCCTAGG GGTCTTTCCC CTCTCGCCAA AGGAATGCAA GGTCTGTTGA ATGTCGTGAA    1740

GGAAGCAGTT CCTCTGGAAG CTTCTTGAAG ACAAACAACG TCTGTAGCGA CCCTTTGCAG    1800

GCAGCGGAAC CCCCCACCTG GCGACAGGTG CCTCTGCGGC CAAAAGCCAC GTGTATAAGA    1860

TACACCTGCA AAGGCGGCAC AACCCCAGTG CCACGTTGTG AGTTGGATAG TTGTGGAAAG    1920

AGTCAAATGG CTCTCCTCAA GCGTATTCAA CAAGGGGCTG AAGGATGCCC AGAAGGTACC    1980

CCATTGTATG GGATCTGATC TGGGGCCTCG GTGCACATGC TTTACATGTG TTTAGTCGAG    2040

GTTAAAAAAC GTCTAGGCCC CCCGAACCAC GGGGACGTGG TTTTCCTTTG AAAAACACGA    2100

GCGGGATCAA TTCCGCCCCC CCCTAACGT TACTGGCCGA AGCCGCTTGG AATAAGGCCG     2160

GTGTGCGTTT GTCTATATGT TATTTTCCAC CATATTGCCG TCTTTTGGCA ATGTGAGGGC    2220

CCGGAAACCT GGCCCTGTCT TCTTGACGAG CATTCCTAGG GGTCTTTCCC CTCTCGCCAA    2280

AGGAATGCAA GGTCTGTTGA ATGTCGTGAA GGAAGCAGTT CCTCTGGAAG CTTCTTGAAG    2340

ACAAACAACG TCTGTAGCGA CCCTTTGCAG GCAGCGGAAC CCCCCACCTG GCGACAGGTG    2400

CCTCTGCGGC CAAAAGCCAC GTGTATAAGA TACACCTGCA AAGGCGGCAC AACCCCAGTG    2460

CCACGTTGTG AGTTGGATAG TTGTGGAAAG AGTCAAATGG CTCTCCTCAA GCGTATTCAA    2520

CAAGGGGCTG AAGGATGCCC AGAAGGTACC CCATTGTATG GGATCTGATC TGGGGCCTCG    2580

GTGCACATGC TTTACATGTG TTTAGTCGAG GTTAAAAAAA CGTCTAGGCC CCCCGAACCA    2640

CGGGGACGTG GTTTTCCTTT GAAAAACACG ATACGGGATC CACCGGTCGC CACCATGGGT    2700

AAAGGAGAAG AACTTTTCAC AGGAGTTGTC CCAATTCTTG TTGAATTAGA TGGTGATGTT    2760

AATGGGCACA AATTTTCTGT CAGTGGAGAG GGTGAAGGTG ATGCAACATA CGGAAAACTT    2820

ACCCTTAAAT TTATTTGCAC TACTGGAAAA CTACCTGTTC CATGGCCAAC ACTTGTCACT    2880

ACTTTCACTT ATGGTGTTCA ATGCTTTTCA AGATACCCAG ATCATATGAA ACGGCATGAC    2940

TTTTTCAAGA GTGCCATGCC CGAAGGTTAT GTACAGGAAA GAACTATATT TTTCAAAGAT    3000

GACGGGAACT ACAAGACACG TGCTGAAGTC AAGTTTGAAG GTGATACCCT TGTTAATAGA    3060

ATCGAGTTAA AAGGTATTGA TTTTAAAGAA GATGGAAACA TTCTTGGACA CAAATTGGAA    3120

TACAACTATA ACTCACACAA TGTATACATC ATGGCAGACA AACAAAAGAA TGGAACCAAA    3180

GTTAACTTCA AAATTAGACA CAACATTGAA GATGGAAGCG TTCAACTAGC AGACCATTAT    3240

CAACAAAATA CTCCAATTGG CGATGGCCCT GTCCTTTTAC CAGACAACCA TTACCTGTCC    3300

ACACAATCTG CCCTTTCGAA AGATCCCAAC GAAAAGAGAG ACCACATGGT CCTTCTTGAG    3360

TTTGTAACAG CTGCTGGGAT TACACATGGC ATGGATGAAC TATACAAGTC CGGATCTAGA    3420

TAACTGTATC GATGGATCCG AAGGCGGGA CAGCAGTGCA GTGGTGGACA GAAAGCAAGT     3480

GATCTAGGCC AGCAGCCTCC CTAAAGGGAC TTCAGCCCAC AAAGCCAAAC TTGTGGCTTT    3540

AATACAAGCT CTGTAAATGG TAAAAAAAAA AAAGTCTACA CGGACAGCAG GTATGCTCTT    3600

GCCACTGTAC AGAGCAATAT ACAGACAAAG AGAACTGTTG ACATCTGCAG AGAAAGACCT    3660

AAGATGCTGT GGCTAAAAGA AATCAGATGG CAAATCTAAC CGCCCAGGCA TCCTAAAGAG    3720

CAATGATCCT GACAGTCTGA AGACTATCAA GTTATAGACA AATTAAGACT GGTAAAAAAA    3780

ACCCTGTATA AATAGTAAA AACTGAAAAA AGAAAACTAG TCCTCTCATG AGAAGACAGA     3840

CCTGACATCT ACTGAAAAAT AGACTTTACT GGAAAAAATA TGTGTATGAA TACCTTCTAG    3900

TTTTTGTGAA CGTTCTCAAG ATGGATAAAA GCTTTTCCTT GTAAAACGAG ACTGATCAGA    3960

TAGTCATCAA GAAGATTGTT AAAGAAAATT TTCCAAGGTT CGGAGTGCCA AAAGCAATAG    4020
```

-continued

```
TGTCAGATAA TGGTCCTGCC TTTGTTGCCC AGGTAAGTCA GGGTGTGGCC AAGTATTTAG   4080
AGGTCAAATG AAAATTCCAT TGTGTGTACA GACCTCAGAG CTCAGGAAAG ATAAAAAAGA   4140
ATAAATAAAA CTCTAAACAG ACCTTGACAA AATTAATCCT AGAGACTGGC ACAGACTTAC   4200
TTGGTACTCC TTCCCCTTGC CCTATTTAGA ACTGAGAATA CTCCCTCTTG ATTCGGTTTT   4260
ACTCTTTTTA AGATCCTTTA TGGGGCTCCT ATGCCATCAC TGTCTTAAAT GATGTGTTTA   4320
AACCTATGTT GTTATAATAA TGATCTATAT GTTAAGTTAA AAGGCTTGCA GGTGGTGCAG   4380
AAAGAAGTCT GGTCACAACT GGCTACAGTG AACAAGCTGG GTACCCCAAG GACATCTTAC   4440
CAGTTCCAGC CAGAGATCTG ATCTACGATC CCCGGGTCGA CCCGGGTCGA CCCTGTGGAA   4500
TGTGTGTCAG TTAGGGTGTG GAAAGTCCCC AGGCTCCCCA GCAGGCAGAA GTATGCAAAG   4560
CATGCATCTC AATTAGTCAG CAACCAGGTG TGGAAAGTCC CCAGGCTCCC CAGCAGGCAG   4620
AAGTATGCAA AGCATGCATC TCAATTAGTC AGCAACCATA GTCCCGCCCC TAACTCCGCC   4680
CATCCCGCCC CTAACTCCGC CCAGTTCCGC CCATTCTCCG CCCCATGGCT GACTAATTTT   4740
TTTTATTTAT GCAGAGGCCG AGGCCGCCTC GGCCTCTGAG CTATTCCAGA AGTAGTGAGG   4800
AGGCTTTTTT GGAGGCCTAG GCTTTTGCAA AAAGCTTCAC GCTGCCGCAA GCACTCAGGG   4860
CGCAAGGGCT GCTAAAGGAA GCGGAACACG TAGAAAGCCA GTCCGCAGAA ACGGTGCTGA   4920
CCCCGGATGA ATGTCAGCTA CTGGGCTATC TGGACAAGGG AAAACGCAAG CGCAAAGAGA   4980
AAGCAGGTAG CTTGCAGTGG GCTTACATGG CGATAGCTAG ACTGGGCGGT TTATGGACA    5040
GCAAGCGAAC CGGAATTGCC AGCTGGGCG CCCTCTGGTA AGGTTGGGAA GCCCTGCAAA    5100
GTAAACTGGA TGGCTTTCTT GCCGCCAAGG ATCTGATGGC GCAGGGGATC AAGATCTGAT   5160
CAAGAGACAG GATGAGGATC GTTTCGCATG ATTGAACAAG ATGGATTGCA CGCAGGTTGC   5220
CCGGCCGCTT GGGTGGAGAG GCTATTCGGC TATGACTGGG CACAACAGAC AATCGGCTGC   5280
TCTGATGCCG CCGTGTTCCG GCTGTCAGCG CAGGGGCGCC CGGTTCTTTT TGTCAAGACC   5340
GACCTGTCCG GTGCCCTGAA TGAACTGCAG GACGAGGCAG CGCGGCTATC GTGGCTGGCC   5400
ACGACGGGCG TTCCTTGCGC AGCTGTGCTC GACGTTGTCA CTGAAGCGGG AAGGGACTGG   5460
CTGCTATTGG GCGAAGTGCC GGGGCAGGAT CTCCTGTCAT CTCACCTTGC TCCTGCCGAG   5520
AAAGTATCCA TCATGGCTGA TGCAATGCGG CGGCTGCATA CGCTTGATCC GGCTACCTGC   5580
CCATTCGACC ACCAAGCGAA ACATCGCATC GAGCGAGCAC GTACTCGGAT GGAAGCCGGT   5640
CTTGTCGATC AGGATGATCT GGACGAAGAG CATCAGGGGC TCGCGCCAGC CGAACTGTTC   5700
GCCAGGCTCA AGGCGCGCAT GCCCGACGGC GAGGATCTCG TCGTGACCCA TGGCGATGCC   5760
TGCTTGCCGA ATATCATGGT GGAAAATGGC CGCTTTTCTG GATTCATCGA CTGTGGCCGG   5820
CTGGGTGTGG CGGACCGCTA TCAGGACATA GCGTTGGCTA CCCGTGATAT TGCTGAAGAG   5880
CTTGGCGGCG AATGGGCTGA CCGCTTCCTC GTGCTTTACG GTATCGCCGC TCCCGATTCG   5940
CAGCGCATCG CCTTCTATCG CCTTCTTGAC GAGTTCTTCT GAGCGGGACT CTGGGGTTCG   6000
AAATGACCGA CCAAGCGACG CCCAACCTGC CATCACGAGA TTTCGATTCC ACCGCCGCCT   6060
TCTATGAAAG GTTGGGCTTC GGAATCGTTT TCCGGGACGG AATTCGTAAT CTGCTGCTTG   6120
CAAACAAAAA AACCACCGCT ACCAGCGGTG GTTTGTTTGC CGGATCAAGA GCTACCAACT   6180
CTTTTTCCGA AGGTAACTGG CTTCAGCAGA GCGCAGATAC CAAATACTGT CCTTCTAGTG   6240
TAGCCGTAGT TAGGCCACCA CTTCAAGAAC TCTGTAGCAC CGCCTACATA CCTCGCTCTG   6300
CTAATCCTGT TACCAGTGGC TGCTGCCAGT GGCGATAAGT CGTGTCTTAC CGGGTTGGAC   6360
```

-continued

```
TCAAGACGAT AGTTACCGGA TAAGGCGCAG CGGTCGGGCT GAACGGGGGG TTCGTGCACA      6420

CAGCCCAGCT TGGAGCGAAC GACCTACACC GAACTGAGAT ACCTACAGCG TGAGCATTGA      6480

GAAAGCGCCA CGCTTCCCGA AGGGAGAAAG GCGGACAGGT ATCCGGTAAG CGGCAGGGTC      6540

GGAACAGGAG AGCGCACGAG GGAGCTTCCA GGGGGAAACG CCTGGTATCT TTATAGTCCT      6600

GTCGGGTTTC GCCACCTCTG ACTTGAGCGT CGATTTTTGT GATGCTCGTC AGGGGGGCGG      6660

AGCCTATGGA AAAACGCCAG CAACGCCGAG ATGCGCCGCC TCGAGTACAC CTGCGTCATG      6720

CTGAGACCCT CAAGCCTCAC TAAAAGGGTC CCTGCCTAGT TCTGTTTACT AATCTGCCTT      6780

ATTCTGTTTT TGTTCCCATG TTAAAGATAG AGTAAATGCA GTATTCTCCA CATAGAGATA      6840

TAGACTTCTG AAATTCTAAG ATTAGAATTA TTTACAAGAA GAAGTGGGGA A              6891
```

(2) INFORMATION FOR SEQ ID NO: 17:

(i) SEQUENCE CHARACTERISTICS:
        (A) LENGTH: 6321 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
TGAAGAATAA AAAATTACTG GCCTCTTGTG AGAACATGAA CTTTCACCTC GGAGCCCACC        60

CCCTCCCATC TGGAAAACAT ACTTGAGAAA AACATTTTCT GGAACAACCA CAGAATGTTT       120

CAACAGGCCA GATGTATTGC CAAACACAGG ATATGACTCT TTGGTTGAGT AAATTTGTGG       180

TTGTTAAACT TCCCCTATTC CCTCCCCATT CCCCCTCCCA GTTTGTGGTT TTTTCCTTTA       240

AAAGCTTGTG AAAAATTTGA GTCGTCGTCG AGACTCCTCT ACCCTGTGCA AAGGTGTATG       300

AGTTTCGACC CCAGAGCTCT GTGTGCTTTC TGTTGCTGCT TTATTTCGAC CCCAGAGCTC       360

TGGTCTGTGT GCTTTCATGT CGCTGCTTTA TTAAATCTTA CCTTCTACAT TTTATGTATG       420

GTCTCAGTGT CTTCTTGGGT ACGCGGCTGT CCCGGGACTT GAGTGTCTGA GTGAGGGTCT       480

TCCCTCGAGG GTCTTTCATT TGGTACATGG GCCGGGAATT CGAGAATCTT TCATTTGGTG       540

CATTGGCCGG GAATTCGAAA ATCTTTCATT TGGTGCATTG GCCGGGAAAC AGCGCGACCA       600

CCCAGAGGTC CTAGACCCAC TTAGAGGTAA GATTCTTTGT TCTGTTTTGG TCTGATGTCT       660

GTGTTCTGAT GTCTGTGTTC TGTTTCTAAG TCTGGTGCGA TCGCAGTTTC AGTTTTGCGG       720

ACGCTCAGTG AGACCGCGCT CCGAGAGGGA GTGCGGGGTG GATAAGGATA GACGTGTCCA       780

GGTGTCCACC GTCCGTTCGC CCTGGGAGAC GTCCCAGGAG GAACAGGGGA GGATCAGGGA       840

CGCCTGGTGG ACCCCTTTGA AGGCCAAGAG ACCATTTGGG GTTGCGAGAT CGTGGGTTCG       900

AGTCCCACCT CGTGCCCAGT TGCGAGATCG TGGGTTCGAG TCCCACCTCG TGTTTTGTTG       960

CGAGATCGTG GGTTCGAGTC CCACCTCGCG TCTGGTCACG GGATCGTGGG TTCGAGTCCC      1020

ACCTCGTGTT TTGTTGCGAG ATCGTGGGTT CGAGTCCCAC CTCGCGTCTG GTCACGGGAT      1080

CGTGGGTTCG AGTCCCACCT CGTGCAGAGG GTCTCAATTG GCCGGCCTTA GAGAGGCCAT      1140

CTGATTCTTC TGGTTTCTCT TTTTGTCTTA GTCTCGTGTC CGCTCTTGTT GTGACTACTG      1200

TTTTTCTAAA AATGGGACAA TCTGTGTCCA CTCCCCTTTC TCTGACTCTG GTTCTGTCGC      1260

TTGGTAATTT TGTTTGTTTA CGTTTGTTTT TGTGAGTCGT CTATGTTGTC TGTTACTATC      1320

TTGTTTTTGT TTGTGGTTTA CGGTTTCTGT GTGTGTCTTG TGTGTCTCTT TGTGTTCAGA      1380

CTTGGACTGA TGACTGACGA CTGTTTTTAA GTTATGCCTT CTAAAATAAG CCTAAAAATC      1440
```

```
CTGTCAGATC CCTATGCTGA CCACTTCCTT TCAGATCAAC AGCTGCCCTT ACTCGAGCTC    1500

AAGCTTCGAA TTCTGCAGTC GACGGTACCG CGGGGATCAA TTCCGCCCCC CCCCTAACGT    1560

TACTGGCCGA AGCCGCTTGG AATAAGGCCG GTGTGCGTTT GTCTATATGT TATTTTCCAC    1620

CATATTGCCG TCTTTTGGCA ATGTGAGGGC CCGGAAACCT GGCCCTGTCT TCTTGACGAG    1680

CATTCCTAGG GGTCTTTCCC CTCTCGCCAA AGGAATGCAA GGTCTGTTGA ATGTCGTGAA    1740

GGAAGCAGTT CCTCTGGAAG CTTCTTGAAG ACAAACAACG TCTGTAGCGA CCCTTTGCAG    1800

GCAGCGGAAC CCCCCACCTG GCGACAGGTG CCTCTGCGGC CAAAAGCCAC GTGTATAAGA    1860

TACACCTGCA AAGGCGGCAC AACCCCAGTG CCACGTTGTG AGTTGGATAG TTGTGGAAAG    1920

AGTCAAATGG CTCTCCTCAA GCGTATTCAA CAAGGGGCTG AAGGATGCCC AGAAGGTACC    1980

CCATTGTATG GGATCTGATC TGGGGCCTCG GTGCACATGC TTTACATGTG TTTAGTCGAG    2040

GTTAAAAAAA CGTCTAGGCC CCCCGAACCA CGGGGACGTG GTTTTCCTTT GAAAAACACG    2100

ATACGGGATC CACCGGTCGC CACCATGGGT AAAGGAGAAG AACTTTTCAC AGGAGTTGTC    2160

CCAATTCTTG TTGAATTAGA TGGTGATGTT AATGGGCACA AATTTTCTGT CAGTGGAGAG    2220

GGTGAAGGTG ATGCAACATA CGGAAAACTT ACCCTTAAAT TTATTTGCAC TACTGGAAAA    2280

CTACCTGTTC CATGGCCAAC ACTTGTCACT ACTTTCACTT ATGGTGTTCA ATGCTTTTCA    2340

AGATACCCAG ATCATATGAA ACGGCATGAC TTTTTCAAGA GTGCCATGCC CGAAGGTTAT    2400

GTACAGGAAA GAACTATATT TTTCAAAGAT GACGGGAACT ACAAGACACG TGCTGAAGTC    2460

AAGTTTGAAG GTGATACCCT TGTTAATAGA ATCGAGTTAA AAGGTATTGA TTTTAAAGAA    2520

GATGGAAACA TTCTTGGACA CAAATTGGAA TACAACTATA ACTCACACAA TGTATACATC    2580

ATGGCAGACA AACAAAAGAA TGGAACCAAA GTTAACTTCA AAATTAGACA CAACATTGAA    2640

GATGGAAGCG TTCAACTAGC AGACCATTAT CAACAAAATA CTCCAATTGG CGATGGCCCT    2700

GTCCTTTTAC CAGACAACCA TTACCTGTCC ACACAATCTG CCCTTTCGAA AGATCCCAAC    2760

GAAAAGAGAG ACCACATGGT CCTTCTTGAG TTTGTAACAG CTGCTGGGAT TACACATGGC    2820

ATGGATGAAC TATACAAGTC CGGATCTAGA TAACTGTATC GATGGATCCG AAGGCGGGGA    2880

CAGCAGTGCA GTGGTGGACA GAAAGCAAGT GATCTAGGCC AGCAGCCTCC CTAAAGGGAC    2940

TTCAGCCCAC AAAGCCAAAC TTGTGGCTTT AATACAAGCT CTGTAAATGG TAAAAAAAA    3000

AAAGTCTACA CGGACAGCAG GTATGCTCTT GCCACTGTAC AGAGCAATAT ACAGACAAAG    3060

AGAACTGTTG ACATCTGCAG AGAAAGACCT AAGATGCTGT GGCTAAAAGA AATCAGATGG    3120

CAAATCTAAC CGCCCAGGCA TCCTAAAGAG CAATGATCCT GACAGTCTGA AGACTATCAA    3180

GTTATAGACA AATTAAGACT GGTAAAAAAA ACCCTGTATA AAATAGTAAA AACTGAAAAA    3240

AGAAAACTAG TCCTCTCATG AGAAGACAGA CCTGACATCT ACTGAAAAAT AGACTTTACT    3300

GGAAAAAATA TGTGTATGAA TACCTTCTAG TTTTTGTGAA CGTTCTCAAG ATGGATAATT    3360

GCTTTTCCTT GTAAAACGAG ACTGATCAGA TAGTCATCAA GAAGATTGTT AAAGAAAACC    3420

TTCCAAGGTT CGGAGTGCCA AAAGCAATAG TGTCAGATAA TGGTCCTGCC TTTGTTGCCC    3480

AGGTAAGTCA GGGTGTGGCC AAGTATTTAG AGGTCAAATG AAAATTCCAT TGTGTGTACA    3540

GACCTCAGAG CTCAGGAAAG ATAAAAAAGA ATAAATAAAA CTCTAAACAG ACCTTGACAA    3600

AATTAATCCT AGAGACTGGC ACAGACTTAC TTGGTACTCC TTCCCCTTGC CCTATTTAGA    3660

ACTGAGAATA CTCCCTCTTG ATTCGGTTTT ACTCTTTTTA AGATCCTTTA TGGGCTCCT    3720

ATGCCATCAC TGTCTTAAAT GATGTGTTTA AACCTATGTT GTTATAATAA TGATCTATAT    3780

GTTAAGTTAA AAGGCTTGCA GGTGGTGCAG AAAGAAGTCT GGTCACAACT GGCTACAGTG    3840
```

-continued

```
AACAAGCTGG GTACCCCAAG GACATCTTAC CAGTTCCAGC CAGAGATCTG ATCTACGATC    3900

CCCGGGTCGA CCCGGGTCGA CCCTGTGGAA TGTGTGTCAG TTAGGGTGTG AAAAGTCCCC    3960

AGGCTCCCCA GCAGGCAGAA GTATGCAAAG CATGCATCTC AATTAGTCAG CAACCAGGTG    4020

TGGAAAGTCC CCAGGCTCCC CAGCAGGCAG AAGTATGCAA AGCATGCATC TCAATTAGTC    4080

AGCAACCATA GTCCCGCCCC TAACTCCGCC CATCCCGCCC CTAACTCCGC CCAGTTCCGC    4140

CCATTCTCCG CCCCATGGCT GACTAATTTT TTTTATTTAT GCAGAGGCCG AGGCCGCCTC    4200

GGCCTCTGAG CTATTCCAGA AGTAGTGAGG AGGCTTTTTT GGAGGCCTAG GCTTTTGCAA    4260

AAAGCTTCAC GCTGCCGCAA GCACTCAGGG CGCAAGGGCT GCTAAAGGAA GCGGAACACG    4320

TAGAAAGCCA GTCCGCAGAA ACGGTGCTGA CCCCGGATGA ATGTCAGCTA CTGGGCTATC    4380

TGGACAAGGG AAAACGCAAG CGCAAAGAGA AAGCAGGTAG CTTGCAGTGG GCTTACATGG    4440

CGATAGCTAG ACTGGGCGGT TTTATGGACA GCAAGCGAAC CGGAATTGCC AGCTGGGGCG    4500

CCCTCTGGTA AGGTTGGGAA GCCCTGCAAA GTAAACTGGA TGGCTTTCTT GCCGCCAAGG    4560

ATCTGATGGC GCAGGGGATC AAGATCTGAT CAAGAGACAG GATGAGGATC GTTTCGCATG    4620

ATTGAACAAG ATGGATTGCA CGCAGGTTCT CCGGCCGCTT GGGTGGAGAG GCTATTCGGC    4680

TATGACTGGG CACAACAGAC AATCGGCTGC TCTGATGCCG CCGTGTTCCG GCTGTCAGCG    4740

CAGGGGCGCC CGGTTCTTTT TGTCAAGACC GACCTGTCCG GTGCCCTGAA TGAACTGCAG    4800

GACGAGGCAG CGCGGCTATC GTGGCTGGCC ACGACGGGCG TTCCTTGCGC AGCTGTGCTC    4860

GACGTTGTCA CTGAAGCGGG AAGGGACTGG CTGCTATTGG GCGAAGTGCC GGGGCAGGAT    4920

CTCCTGTCAT CTCACCTTGC TCCTGCCGAG AAAGTATCCA TCATGGCTGA TGCAATGCGG    4980

CGGCTGCATA CGCTTGATCC GGCTACCTGC CCATTCGACC ACCAAGCGAA ACATCGCATC    5040

GAGCGAGCAC GTACTCGGAT GGAAGCCGGT CTTGTCGATC AGGATGATCT GGACGAAGAG    5100

CATCAGGGGC TCGCGCCAGC CGAACTGTTC GCCAGGCTCA AGGCGCGCAT GCCCGACGGC    5160

GAGGATCTCG TCGTGACCCA TGGCGATGCC TGCTTGCCGA ATATCATGGT GGAAAATGGC    5220

CGCTTTTCTG GATTCATCGA CTGTGGCCGG CTGGGTGTGG CGGACCGCTA TCAGGACATA    5280

GCGTTGGCTA CCCGTGATAT TGCTGAAGAG CTTGGCGGCG AATGGGCTGA CCGCTTCCTC    5340

GTGCTTTACG GTATCGCCGC TCCCGATTCG CAGCGCATCG CCTTCTATCG CCTTCTTGAC    5400

GAGTTCTTCT GAGCGGGACT CTGGGGTTCG AAATGACCGA CCAAGCGACG CCCAACCTGC    5460

CATCACGAGA TTTCGATTCC ACCGCCGCCT TCTATGAAAG GTTGGGCTTC GGAATCGTTT    5520

TCCGGGACGG AATTCGTAAT CTGCTGCTTG CAAACAAAAA AACCACCGCT ACCAGCGGTG    5580

GTTTGTTTGC CGGATCAAGA GCTACCAACT CTTTTTCCGA AGGTAACTGG CTTCAGCAGA    5640

GCGCAGATAC CAAATACTGT CCTTCTAGTG TAGCCGTAGT TAGGCCACCA CTTCAAGAAC    5700

TCTGTAGCAC CGCCTACATA CCTCGCTCTG CTAATCCTGT TACCAGTGGC TGCTGCCAGT    5760

GGCGATAAGT CGTGTCTTAC CGGGTTGGAC TCAAGACGAT AGTTACCGGA TAAGGCGCAG    5820

CGGTCGGGCT GAACGGGGGG TTCGTGCACA CAGCCCAGCT TGGAGCGAAC GACCTACACC    5880

GAACTGAGAT ACCTACAGCG TGAGCATTGA GAAAGCGCCA CGCTTCCCGA AGGGAGAAAG    5940

GCGGACAGGT ATCCGGTAAG CGGCAGGGTC GGAACAGGAG AGCGCACGAG GGAGCTTCCA    6000

GGGGGAAACG CCTGGTATCT TTATAGTCCT GTCGGGTTTC GCCACCTCTG ACTTGAGCGT    6060

CGATTTTTGT GATGCTCGTC AGGGGGGCGG AGCCTATGGA AAAACGCCAG CAACGCCGAG    6120

ATGCGCCGCC TCGAGTACAC CTGCGTCATG CTGAGACCCT CAAGCCTCAC TAAAAGGGTC    6180
```

-continued

| | |
|---|---|
| CCTGCCTAGT TCTGTTTACT AATCTGCCTT ATTCTGTTTT TGTTCCCATG TTAAAGATAG | 6240 |
| AGTAAATGCA GTATTCTCCA CATAGAGATA TAGACTTCTG AAATTCTAAG ATTAGAATTA | 6300 |
| TTTACAAGAA GAAGTGGGGA A | 6321 |

(2) INFORMATION FOR SEQ ID NO: 18:

(i) SEQUENCE CHARACTERISTICS:
        (A) LENGTH: 5754 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

| | |
|---|---|
| TGAAGAATAA AAAATTACTG GCCTCTTGTG AGAACATGAA CTTTCACCTC GGAGCCCACC | 60 |
| CCCTCCCATC TGGAAAACAT ACTTGAGAAA AACATTTTCT GGAACAACCA CAGAATGTTT | 120 |
| CAACAGGCCA GATGTATTGC CAAACACAGG ATATGACTCT TTGGTTGAGT AAATTTGTGG | 180 |
| TTGTTAAACT TCCCCTATTC CCTCCCCATT CCCCCTCCCA GTTTGTGGTT TTTTCCTTTA | 240 |
| AAAGCTTGTG AAAAATTTGA GTCGTCGTCG AGACTCCTCT ACCCTGTGCA AAGGTGTATG | 300 |
| AGTTTCGACC CCAGAGCTCT GTGTGCTTTC TGTTGCTGCT TTATTTCGAC CCCAGAGCTC | 360 |
| TGGTCTGTGT GCTTTCATGT CGCTGCTTTA TTAAATCTTA CCTTCTACAT TTTATGTATG | 420 |
| GTCTCAGTGT CTTCTTGGGT ACGCGGCTGT CCCGGGACTT GAGTGTCTGA GTGAGGGTCT | 480 |
| TCCCTCGAGG GTCTTTCATT TGGTACATGG GCCGGGAATT CGAGAATCTT TCATTTGGTG | 540 |
| CATTGGCCGG GAATTCGAAA ATCTTTCATT TGGTGCATTG GCCGGGAAAC AGCGCGACCA | 600 |
| CCCAGAGGTC CTAGACCCAC TTAGAGGTAA GATTCTTTGT TCTGTTTTGG TCTGATGTCT | 660 |
| GTGTTCTGAT GTCTGTGTTC TGTTTCTAAG TCTGGTGCGA TCGCAGTTTC AGTTTTGCGG | 720 |
| ACGCTCAGTG AGACCGCGCT CCGAGAGGGA GTGCGGGGTG GATAAGGATA GACGTGTCCA | 780 |
| GGTGTCCACC GTCCGTTCGC CCTGGGAGAC GTCCCAGGAG GAACAGGGGA GGATCAGGGA | 840 |
| CGCCTGGTGG ACCCCTTTGA AGGCCAAGAG ACCATTTGGG GTTGCGAGAT CGTGGGTTCG | 900 |
| AGTCCCACCT CGTGCCCAGT TGCGAGATCG TGGGTTCGAG TCCCACCTCG TGTTTTGTTG | 960 |
| CGAGATCGTG GGTTCGAGTC CCACCTCGCG TCTGGTCACG GGATCGTGGG TTCGAGTCCC | 1020 |
| ACCTCGTGTT TTGTTGCGAG ATCGTGGGTT CGAGTCCCAC CTCGCGTCTG GTCACGGGAT | 1080 |
| CGTGGGTTCG AGTCCCACCT CGTGCAGAGG GTCTCAATTG GCCGGCCTTA GAGAGGCCAT | 1140 |
| CTGATTCTTC TGGTTTCTCT TTTTGTCTTA GTCTCGTGTC CGCTCTTGTT GTGACTACTG | 1200 |
| TTTTTCTAAA AATGGGACAA TCTGTGTCCA CTCCCCTTTC TCTGACTCTG GTTCTGTCGC | 1260 |
| TTGGTAATTT TGTTTGTTTA CGTTTGTTTT TGTGAGTCGT CTATGTTGTC TGTTACTATC | 1320 |
| TTGTTTTTGT TTGTGGTTTA CGGTTTCTGT GTGTGTCTTG TGTGTCTCTT TGTGTTCAGA | 1380 |
| CTTGGACTGA TGACTGACGA CTGTTTTTAA GTTATGCCTT CTAAAATAAG CCTAAAAATC | 1440 |
| CTGTCAGATC CCTATGCTGA CCACTTCCTT TCAGATCAAC AGCTGCCCTT ACTCGAGCTC | 1500 |
| AAGCTTCGAA TTCTGCAGTC GACGGTACCG CGGGCCCGGG ATCCACCGGT CGCCACCATG | 1560 |
| GGTAAAGGAG AAGAACTTTT CACAGGAGTT GTCCCAATTC TTGTTGAATT AGATGGTGAT | 1620 |
| GTTAATGGGC ACAAATTTTC TGTCAGTGGA GAGGGTGAAG GTGATGCAAC ATACGGAAAA | 1680 |
| CTTACCCTTA AATTTATTTG CACTACTGGA AAACTACCTG TTCCATGGCC AACACTTGTC | 1740 |
| ACTACTTTCA CTTATGGTGT TCAATGCTTT TCAAGATACC CAGATCATAT GAAACGGCAT | 1800 |

-continued

```
GACTTTTTCA AGAGTGCCAT GCCCGAAGGT TATGTACAGG AAAGAACTAT ATTTTTCAAA    1860

GATGACGGGA ACTACAAGAC ACGTGCTGAA GTCAAGTTTG AAGGTGATAC CCTTGTTAAT    1920

AGAATCGAGT TAAAAGGTAT TGATTTTAAA GAAGATGGAA ACATTCTTGG ACACAAATTG    1980

GAATACAACT ATAACTCACA CAATGTATAC ATCATGGCAG ACAAACAAAA GAATGGAACC    2040

AAAGTTAACT TCAAAATTAG ACACAACATT GAAGATGGAA GCGTTCAACT AGCAGACCAT    2100

TATCAACAAA ATACTCCAAT TGGCGATGGC CCTGTCCTTT TACCAGACAA CCATTACCTG    2160

TCCACACAAT CTGCCCTTTC GAAAGATCCC AACGAAAGA GAGACCACAT GGTCCTTCTT    2220

GAGTTTGTAA CAGCTGCTGG GATTACACAT GGCATGGATG AACTATACAA GTCCGGATCT    2280

AGATAACTGT ATCGATGGAT CCGAAGGCGG GGACAGCAGT GCAGTGGTGG ACAGAAAGCA    2340

AGTGATCTAG GCCAGCAGCC TCCCTAAAGG GACTTCAGCC CACAAAGCCA AACTTGTGGC    2400

TTTAATACAA GCTCTGTAAA TGGTAAAAAA AAAAAGTCT ACACGGACAG CAGGTATGCT    2460

CTTGCCACTG TACAGAGCAA TATACAGACA AAGAGAACTG TTGACATCTG CAGAGAAAGA    2520

CCTAAGATGC TGTGGCTAAA AGAAATCAGA TGGCAAATCT AACCGCCCAG GCATCCTAAA    2580

GAGCAATGAT CCTGACAGTC TGAAGACTAT CAAGTTATAG ACAAATTAAG ACTGGTAAAA    2640

AAAACCCTGT ATAAAATAGT AAAAACTGAA AAAGAAAAC TAGTCCTCTC ATGAGAAGAC    2700

AGACCTGACA TCTACTGAAA AATAGACTTT ACTGGAAAAA ATATGTGTAT GAATACCTTC    2760

TAGTTTTTGT GAACGTTCTC AAGATGGATA AAAGCTTTTC CTTGTAAAAC GAGACTGATC    2820

AGATAGTCAT CAAGAAGATT GTTAAAGAAA ATTTTCCAAG GTTCGGAGTG CCAAAAGCAA    2880

TAGTGTCAGA TAATGGTCCT GCCTTTGTTG CCCAGGTAAG TCAGGGTGTG GCCAAGTATT    2940

TAGAGGTCAA ATGAAAATTC CATTGTGTGT ACAGACCTCA GAGCTCAGGA AAGATAAAAA    3000

AGAATAAATA AAACTCTAAA CAGACCTTGA CAAAATTAAT CCTAGAGACT GGCACAGACT    3060

TACTTGGTAC TCCTTCCCCT TGCCCTATTT AGAACTGAGA ATACTCCCTC TTGATTCGGT    3120

TTTACTCTTT TTAAGATCCT TTATGGGCT CCTATGCCAT CACTGTCTTA AATGATGTGT    3180

TTAAACCTAT GTTGTTATAA TAATGATCTA TATGTTAAGT TAAAAGGCTT GCAGGTGGTG    3240

CAGAAAGAAG TCTGGTCACA ACTGGCTACA GTGAACAAGC TGGGTACCCC AAGGACATCT    3300

TACCAGTTCC AGCCAGAGAT CTGATCTACG ATCCCCGGGT CGACCCGGGT CGACCCTGTG    3360

GAATGTGTGT CAGTTAGGGT GTGGAAAGTC CCCAGGCTCC CCAGCAGGCA GAAGTATGCA    3420

AAGCATGCAT CTCAATTAGT CAGCAACCAG GTGTGGAAAG TCCCCAGGCT CCCCAGCAGG    3480

CAGAAGTATG CAAAGCATGC ATCTCAATTA GTCAGCAACC ATAGTCCCGC CCCTAACTCC    3540

GCCCATCCCG CCCCTAACTC CGCCCAGTTC CGCCCATTCT CCGCCCCATG CTGACTAAT    3600

TTTTTTTATT TATGCAGAGG CCGAGGCCGC CTCGGCCTCT GAGCTATTCC AGAAGTAGTG    3660

AGGAGGCTTT TTTGGAGGCC TAGGCTTTTG CAAAAAGCTT CACGCTGCCG CAAGCACTCA    3720

GGGCGCAAGG GCTGCTAAAG GAAGCGGAAC ACGTAGAAAG CCAGTCCGCA GAAACGGTGC    3780

TGACCCCGGA TGAATGTCAG CTACTGGGCT ATCTGGACAA GGGAAAACGC AAGCGCAAAG    3840

AGAAAGCAGG TAGCTTGCAG TGGGCTTACA TGGCGATAGC TAGACTGGGC GGTTTTATGG    3900

ACAGCAAGCG AACCGGAATT GCCAGCTGGG GCGCCCTCTG GTAAGGTTGG AAGCCCTGC    3960

AAAGTAAACT GGATGGCTTT CTTGCCGCCA AGGATCTGAT GGCGCAGGGG ATCAAGATCT    4020

GATCAAGAGA CAGGATGAGG ATCGTTTCGC ATGATTGAAC AAGATGGATT GCACGCAGGT    4080

TCTCCGGCCG CTTGGGTGGA GAGGCTATTC GGCTATGACT GGGCACAACA GACAATCGGC    4140

TGCTCTGATG CCGCCGTGTT CCGGCTGTCA GCGCAGGGGC GCCCGGTTCT TTTTGTCAAG    4200
```

```
ACCGACCTGT CCGGTGCCCT GAATGAACTG CAGGACGAGG CAGCGCGGCT ATCGTGGCTG    4260

GCCACGACGG GCGTTCCTTG CGCAGCTGTG CTCGACGTTG TCACTGAAGC GGGAAGGGAC    4320

TGGCTGCTAT TGGGCGAAGT GCCGGGGCAG GATCTCCTGT CATCTCACCT TGCTCCTGCC    4380

GAGAAAGTAT CCATCATGGC TGATGCAATG CGGCGGCTGC ATACGCTTGA TCCGGCTACC    4440

TGCCCATTCG ACCACCAAGC GAAACATCGC ATCGAGCGAG CACGTACTCG GATGGAAGCC    4500

GGTCTTGTCG ATCAGGATGA TCTGGACGAA GAGCATCAGG GGCTCGCGCC AGCCGAACTG    4560

TTCGCCAGGC TCAAGGCGCG CATGCCCGAC GGCGAGGATC TCGTCGTGAC CCATGGCGAT    4620

GCCTGCTTGC CGAATATCAT GGTGGAAAAT GGCCGCTTTT CTGGATTCAT CGACTGTGGC    4680

CGGCTGGGTG TGGCGGACCG CTATCAGGAC ATAGCGTTGG CTACCCGTGA TATTGCTGAA    4740

GAGCTTGGCG GCGAATGGGC TGACCGCTTC CTCGTGCTTT ACGGTATCGC CGCTCCCGAT    4800

TCGCAGCGCA TCGCCTTCTA TCGCCTTCTT GACGAGTTCT TCTGAGCGGG ACTCTGGGGT    4860

TCGAAATGAC CGACCAAGCG ACGCCCAACC TGCCATCACG AGATTTCGAT TCCACCGCCG    4920

CCTTCTATGA AAGGTTGGGC TTCGGAATCG TTTTCCGGGA CGGAATTCGT AATCTGCTGC    4980

TTGCAAACAA AAAACCACC GCTACCAGCG GTGGTTTGTT TGCCGGATCA AGAGCTACCA    5040

ACTCTTTTTC CGAAGGTAAC TGGCTTCAGC AGAGCGCAGA TACCAAATAC TGTCCTTCTA    5100

GTGTAGCCGT AGTTAGGCCA CCACTTCAAG AACTCTGTAG CACCGCCTAC ATACCTCGCT    5160

CTGCTAATCC TGTTACCAGT GGCTGCTGCC AGTGGCGATA AGTCGTGTCT TACCGGGTTG    5220

GACTCAAGAC GATAGTTACC GGATAAGGCG CAGCGGTCGG GCTGAACGGG GGGTTCGTGC    5280

ACACAGCCCA GCTTGGAGCG AACGACCTAC ACCGAACTGA GATACCTACA GCGTGAGCAT    5340

TGAGAAAGCG CCACGCTTCC CGAAGGGAGA AAGGCGGACA GGTATCCGGT AAGCGGCAGG    5400

GTCGGAACAG GAGAGCGCAC GAGGGAGCTT CCAGGGGGAA ACGCCTGGTA TCTTTATAGT    5460

CCTGTCGGGT TTCGCCACCT CTGACTTGAG CGTCGATTTT TGTGATGCTC GTCAGGGGGG    5520

CGGAGCCTAT GGAAAAACGC CAGCAACGCC GAGATGCGCC GCCTCGAGTA CACCTGCGTC    5580

ATGCTGAGAC CCTCAAGCCT CACTAAAAGG GTCCCTGCCT AGTTCTGTTT ACTAATCTGC    5640

CTTATTCTGT TTTTGTTCCC ATGTTAAAGA TAGAGTAAAT GCAGTATTCT CCACATAGAG    5700

ATATAGACTT CTGAAATTCT AAGATTAGAA TTATTTACAA GAAGAAGTGG GGAA          5754
```

(2) INFORMATION FOR SEQ ID NO: 19:

(i) SEQUENCE CHARACTERISTICS:
        (A) LENGTH: 5754 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
TGAAGAATAA AAAATTACTG GCCTCTTGTG AGAACATGAA CTTTCACCTC GGAGCCCACC      60

CCCTCCCATC TGGAAAACAT ACTTGAGAAA AACATTTTCT GGAACAACCA CAGAATGTTT     120

CAACAGGCCA GATGTATTGC CAAACACAGG ATATGACTCT TGGTTGAGT AAATTTGTGG      180

TTGTTAAACT TCCCCTATTC CCTCCCCATT CCCCCTCCCA GTTTGTGGTT TTTTCCTTTA     240

AAAGCTTGTG AAAATTTGA GTCGTCGTCG AGACTCCTCT ACCCTGTGCA AAGGTGTATG      300

AGTTTCGACC CCAGAGCTCT GTGTGCTTTC TGTTGCTGCT TTATTTCGAC CCCAGAGCTC     360

TGGTCTGTGT GCTTTCATGT CGCTGCTTTA TTAAATCTTA CCTTCTACAT TTATGTATG     420
```

-continued

```
GTCTCAGTGT CTTCTTGGGT ACGCGGCTGT CCCGGGACTT GAGTGTCTGA GTGAGGGTCT      480

TCCCTCGAGG GTCTTTCATT TGGTACATGG GCCGGGAATT CGAGAATCTT TCATTTGGTG      540

CATTGGCCGG GAATTCGAAA ATCTTTCATT TGGTGCATTG GCCGGGAAAC AGCGCGACCA      600

CCCAGAGGTC CTAGACCCAC TTAGAGGTAA GATTCTTTGT TCTGTTTTGG TCTGATGTCT      660

GTGTTCTGAT GTCTGTGTTC TGTTTCTAAG TCTGGTGCGA TCGCAGTTTC AGTTTTGCGG      720

ACGCTCAGTG AGACCGCGCT CCGAGAGGGA GTGCGGGGTG GATAAGGATA GACGTGTCCA      780

GGTGTCCACC GTCCGTTCGC CCTGGGAGAC GTCCAGGAG GAACAGGGGA GGATCAGGGA       840

CGCCTGGTGG ACCCCTTTGA AGGCCAAGAG ACCATTTGGG GTTGCGAGAT CGTGGGTTCG      900

AGTCCCACCT CGTGCCCAGT TGCGAGATCG TGGGTTCGAG TCCCACCTCG TGTTTTGTTG      960

CGAGATCGTG GGTTCGAGTC CCACCTCGCG TCTGGTCACG GGATCGTGGG TTCGAGTCCC     1020

ACCTCGTGTT TTGTTGCGAG ATCGTGGGTT CGAGTCCCAC CTCGCGTCTG GTCACGGGAT     1080

CGTGGGTTCG AGTCCCACCT CGTGCAGAGG GTCTCAATTG GCCGGCCTTA GAGAGGCCAT     1140

CTGATTCTTC TGGTTTCTCT TTTTGTCTTA GTCTCGTGTC CGCTCTTGTT GTGACTACTG     1200

TTTTTCTAAA AATGGGACAA TCTGTGTCCA CTCCCCTTTC TCTGACTCTG GTTCTGTCGC     1260

TTGGTAATTT TGTTTGTTTA CGTTTGTTTT TGTGAGTCGT CTATGTTGTC TGTTACTATC     1320

TTGTTTTTGT TTGTGGTTTA CGGTTTCTGT GTGTGTCTTG TGTGTCTCTT TGTGTTCAGA     1380

CTTGGACTGA TGACTGACGA CTGTTTTTAA GTTATGCCTT CTAAAATAAG CCTAAAAATC     1440

CTGTCAGATC CCTATGCTGA CCACTTCCTT TCAGATCAAC AGCTGCCCTT ACTCGAGCTC     1500

AAGCTTCGAA TTCTGCAGTC GACGGTACCG CGGGCCCGGG ATCCACCGGT CGCCACCATG     1560

GGTAAAGGAG AAGAACTTTT CACTGGAGTT GTCCCAATTC TTGTTGAATT AGATGGTGAT     1620

GTTAATGGGC ACAAATTTTC TGTCAGTGGA GAGGGTGAAG GTGATGCAAC ATACGGAAAA     1680

CTTACCCTTA AATTTATTTG CACTACTGGA AAACTACCTG TTCCATGGCC AACACTTGTC     1740

ACTACTTTCT CTTATGGTGT TCAATGCTTT TCAAGATACC CAGATCATAT GAAACGGCAT     1800

GACTTTTTCA AGAGTGCCAT GCCCGAAGGT TATGTACAGG AAAGAACTAT ATTTTTCAAA     1860

GATGACGGGA ACTACAAGAC ACGTGCTGAA GTCAAGTTTG AAGGTGATAC CCTTGTTAAT     1920

AGAATCGAGT TAAAAGGTAT TGATTTTAAA GAAGATGGAA ACATTCTTGG ACACAAATTG     1980

GAATACAACT ATAACTCACA CAATGTATAC ATCATGGCAG ACAAACAAAA GAATGGAACC     2040

AAAGTTAACT TCAAAATTAG ACACAACATT GAAGATGGAA GCGTTCAACT AGCAGACCAT     2100

TATCAACAAA ATACTCCAAT TGGCGATGGC CCTGTCCTTT TACCAGACAA CCATTACCTG     2160

TCCACACAAT CTGCCCTTTC GAAAGATCCC AACGAAAAGA GAGACCACAT GGTCCTTCTT     2220

GAGTTTGTAA CAGCTGCTGG GATTACACAT GGCATGGATG AACTATACAA GTCCGGATCT     2280

AGATAACTGT ATCGATGGAT CCGAAGGCGG GGACAGCAGT GCAGTGGTGG ACAGAAAGCA     2340

AGTGATCTAG GCCAGCAGCC TCCCTAAAGG GACTTCAGCC CACAAAGCCA AACTTGTGGC     2400

TTTAATACAA GCTCTGTAAA TGGTAAAAAA AAAAAGTCT ACACGGACAG CAGGTATGCT      2460

CTTGCCACTG TACAGAGCAA TATACAGACA AAGAGAACTG TTGACATCTG CAGAGAAAGA     2520

CCTAAGATGC TGTGGCTAAA AGAAATCAGA TGGCAAATCT AACCGCCCAG GCATCCTAAA     2580

GAGCAATGAT CCTGACAGTC TGAAGACTAT CAAGTTATAG ACAAATTAAG ACTGGTAAAA     2640

AAACCCTGT ATAAAATAGT AAAAACTGAA AAAAGAAAAC TAGTCCTCTC ATGAGAAGAC      2700

AGACCTGACA TCTACTGAAA AATAGACTTT ACTGGAAAAA ATATGTGTAT GAATACCTTC     2760
```

-continued

```
TAGTTTTTGT GAACGTTCTC AAGATGGATA AAAGCTTTTC CTTGTAAAAC GAGACTGATC    2820

AGATAGTCAT CAAGAAGATT GTTAAAGAAA ATTTTCCAAG GTTCGGAGTG CCAAAAGCAA    2880

TAGTGTCAGA TAATGGTCCT GCCTTTGTTG CCCAGGTAAG TCAGGGTGTG GCCAAGTATT    2940

TAGAGGTCAA ATGAAAATTC CATTGTGTGT ACAGACCTCA GAGCTCAGGA AGATAAAAA     3000

AGAATAAATA AAACTCTAAA CAGACCTTGA CAAAATTAAT CCTAGAGACT GGCACAGACT    3060

TACTTGGTAC TCCTTCCCCT TGCCCTATTT AGAACTGAGA ATACTCCCTC TTGATTCGGT    3120

TTTACTCTTT TTAAGATCCT TTATGGGGCT CCTATGCCAT CACTGTCTTA AATGATGTGT    3180

TTAAACCTAT GTTGTTATAA TAATGATCTA TATGTTAAGT TAAAAGGCTT GCAGGTGGTG    3240

CAGAAAGAAG TCTGGTCACA ACTGGCTACA GTGAACAAGC TGGGTACCCC AAGGACATCT    3300

TACCAGTTCC AGCCAGAGAT CTGATCTACG ATCCCCGGGT CGACCCGGGT CGACCCTGTG    3360

GAATGTGTGT CAGTTAGGGT GTGGAAAGTC CCCAGGCTCC CCAGCAGGCA GAAGTATGCA    3420

AAGCATGCAT CTCAATTAGT CAGCAACCAG GTGTGGAAAG TCCCCAGGCT CCCCAGCAGG    3480

CAGAAGTATG CAAAGCATGC ATCTCAATTA GTCAGCAACC ATAGTCCCGC CCCTAACTCC    3540

GCCCATCCCG CCCCTAACTC CGCCCAGTTC CGCCCATTCT CCGCCCCATG GCTGACTAAT    3600

TTTTTTTATT TATGCAGAGG CCGAGGCCGC CTCGGCCTCT GAGCTATTCC AGAAGTAGTG    3660

AGGAGGCTTT TTTGGAGGCC TAGGCTTTTG CAAAAAGCTT CACGCTGCCG CAAGCACTCA    3720

GGGCGCAAGG GCTGCTAAAG GAAGCGGAAC ACGTAGAAAG CCAGTCCGCA GAAACGGTGC    3780

TGACCCCGGA TGAATGTCAG CTACTGGGCT ATCTGGACAA GGGAAAACGC AAGCGCAAAG    3840

AGAAAGCAGG TAGCTTGCAG TGGGCTTACA TGGCGATAGC TAGACTGGGC GGTTTTATGG    3900

ACAGCAAGCG AACCGGAATT GCCAGCTGGG GCGCCCTCTG GTAAGGTTGG GAAGCCCTGC    3960

AAAGTAAACT GGATGGCTTT CTTGCCGCCA AGGATCTGAT GGCGCAGGGG ATCAAGATCT    4020

GATCAAGAGA CAGGATGAGG ATCGTTTCGC ATGATTGAAC AAGATGGATT GCACGCAGGT    4080

TCTCCGGCCG CTTGGGTGGA GAGGCTATTC GGCTATGACT GGGCACAACA GACAATCGGC    4140

TGCTCTGATG CCGCCGTGTT CCGGCTGTCA GCGCAGGGGC GCCCGGTTCT TTTTGTCAAG    4200

ACCGACCTGT CCGGTGCCCT GAATGAACTG CAGGACGAGG CAGCGCGGCT ATCGTGGCAC    4260

GCCACGACGG GCGTTCCTTG CGCAGCTGTG CTCGACGTTG TCACTGAAGC GGGAAGGGCC    4320

TGGCTGCTAT TGGGCGAAGT GCCGGGGCAG GATCTCCTGT CATCTCACCT TGCTCCTGCC    4380

GAGAAAGTAT CCATCATGGC TGATGCAATG CGGCGGCTGC ATACGCTTGA TCCGGCTACC    4440

TGCCCATTCG ACCACCAAGC GAAACATCGC ATCGAGCGAG CACGTACTCG GATGGAAGCC    4500

GGTCTTGTCG ATCAGGATGA TCTGGACGAA GAGCATCAGG GGCTCGCGCC AGCCGAACTG    4560

TTCGCCAGGC TCAAGGCGCG CATGCCCGAC GGCGAGGATC TCGTCGTGAC CCATGGCGAT    4620

GCCTGCTTGC CGAATATCAT GGTGGAAAAT GGCCGCTTTT CTGGATTCAT CGACTGTGGC    4680

CGGCTGGGTG TGGCGGACCG CTATCAGGAC ATAGCGTTGG CTACCCGTGA TATTGCTGAA    4740

GAGCTTGGCG GCGAATGGGC TGACCGCTTC CTCGTGCTTT ACGGTATCGC CGCTCCCGAT    4800

TCGCAGCGCA TCGCCTTCTA TCGCCTTCTT GACGAGTTCT TCTGAGCGGG ACTCTGGGGT    4860

TCGAAATGAC CGACCAAGCG ACGCCCAACC TGCCATCACG AGATTTCGAT TCCACCGCCG    4920

CCTTCTATGA AAGGTTGGGC TTCGGAATCG TTTTCCGGGA CGGAATTCGT AATCTGCTGC    4980

TTGCAAACAA AAAACCACC GCTACCAGCG GTGGTTTGTT TGCCGGATCA AGAGCTACCA     5040

ACTCTTTTTC CGAAGGTAAC TGGCTTCAGC AGAGCGCAGA TACCAAATAC TGTCCTTCTA    5100

GTGTAGCCGT AGTTAGGCCA CCACTTCAAG AACTCTGTAG CACCGCCTAC ATACCTCGCT    5160
```

```
CTGCTAATCC TGTTACCAGT GGCTGCTGCC AGTGGCGATA AGTCGTGTCT TACCGGGTTG      5220

GACTCAAGAC GATAGTTACC GGATAAGGCG CAGCGGTCGG GCTGAACGGG GGGTTCGTGC      5280

ACACAGCCCA GCTTGGAGCG AACGACCTAC ACCGAACTGA GATACCTACA GCGTGAGCAT      5340

TGAGAAAGCG CCACGCTTCC CGAAGGGAGA AAGGCGGACA GGTATCCGGT AAGCGGCAGG      5400

GTCGGAACAG GAGAGCGCAC GAGGGAGCTT CCAGGGGGAA ACGCCTGGTA TCTTTATAGT      5460

CCTGTCGGGT TTCGCCACCT CTGACTTGAG CGTCGATTTT TGTGATGCTC GTCAGGGGG       5520

CGGAGCCTAT GGAAAAACGC CAGCAACGCC GAGATGCGCC GCCTCGAGTA CACCTGCGTC      5580

ATGCTGAGAC CCTCAAGCCT CACTAAAAGG GTCCCTGCCT AGTTCTGTTT ACTAATCTGC      5640

CTTATTCTGT TTTTGTTCCC ATGTTAAAGA TAGAGTAAAT GCAGTATTCT CCACATAGAG      5700

ATATAGACTT CTGAAATTCT AAGATTAGAA TTATTTACAA GAAGAAGTGG GGAA            5754

(2) INFORMATION FOR SEQ ID NO: 20:

(i) SEQUENCE CHARACTERISTICS:
          (A) LENGTH: 4958 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 20:

AGGCGGGGAC AGCAGTGCAG TGGTGGACAG AAAGCAAGTG ATCTAGGCCA GCAGCCTCCC        60

TAAAGGGACT TCAGCCCACA AAGCCAAACT TGTGGCTTTA ATACAAGCTC TGTAAATGGT       120

AAAAAAAAAA AAGTCTACAC GGACAGCAGG TATGCTCTTG CCACTGTACA GAGCAATATA       180

CAGACAAAGA GAACTGTTGA CATCTGCAGA GAAAGACCTA AGATGCTGTG GCTAAAAGAA       240

ATCAGATGGC AAATCTAACC GCCCAGGCAT CCTAAAGAGC AATGATCCTG ACAGTCTGAA       300

GACTATCAAG TTATAGACAA ATTAAGACTG GTAAAAAAAA CCCTGTATAA AATAGTAAAA       360

ACTGAAAAAA GAAAACTAGT CCTCTCATGA GAAGACAGAC CTGACATCTA CTGAAAAATA       420

GACTTTACTG GAAAAAATAT GTGTATGAAT ACCTTCTAGT TTTTGTGAAC GTTCTCAAGA       480

TGGATAAAAG CTTTTCCTTG TAAAACGAGA CTGATCAGAT AGTCATCAAG AAGATTGTTA       540

AAGAAAATTT TCCAAGGTTC GGAGTGCCAA AAGCAATAGT GTCAGATAAT GGTCCTGCCT       600

TTGTTGCCCA GGTAAGTCAG GGTGTGGCCA AGTATTTAGA GGTCAAATGA AAATTCCATT       660

GTGTGTACAG ACCTCAGAGC TCAGGAAAGA TAAAAAAGAA TAAATAAAAC TCTAAACAGA       720

CCTTGACAAA ATTAATCCTA GAGACTGGCA CAGACTTACT TGGTACTCCT TCCCCTTGCC       780

CTATTTAGAA CTGAGAATAC TCCCTCTTGA TTCGGTTTTA CTCTTTTTAA GATCCTTTAT       840

GGGGCTCCTA TGCCATCACT GTCTTAAATG ATGTGTTTAA ACCTATGTTG TTATAATAAT       900

GATCTATATG TTAAGTTAAA AGGCTTGCAG GTGGTGCAGA AAGAAGTCTG GTCACAACTG       960

GCTACAGTGA ACAAGCTGGG TACCCCAAGG ACATCTTACC AGTTCCAGCC AGAGATCTGA      1020

TCTACGATCC CCGGGTCGAC CCGGGTCGAC CCTGTGGAAT GTGTGTCAGT TAGGGTGTGG      1080

AAAGTCCCCA GGCTCCCCAG CAGGCAGAAG TATGCAAAGC ATGCATCTCA ATTAGTCAGC      1140

AACCAGGTGT GGAAAGTCCC CAGGCTCCCC AGCAGGCAGA AGTATGCAAA GCATGCATCT      1200

CAATTAGTCA GCAACCATAG TCCCGCCCCT AACTCCGCCC ATCCCGCCCC TAACTCCGCC      1260

CAGTTCCGCC CATTCTCCGC CCCATGGCTG ACTAATTTTT TTATTTATG CAGAGGCCGA       1320

GGCCGCCTCG GCCTCTGAGC TATTCCAGAA GTAGTGAGGA GGCTTTTTTG GAGGCCTAGG      1380
```

```
CTTTTGCAAA AAGCTTCACG CTGCCGCAAG CACTCAGGGC GCAAGGGCTG CTAAAGGAAG    1440

CGGAACACGT AGAAAGCCAG TCCGCAGAAA CGGTGCTGAC CCCGGATGAA TGTCAGCTAC    1500

TGGGCTATCT GGACAAGGGA AAACGCAAGC GCAAAGAGAA AGCAGGTAGC TTGCAGTGGG    1560

CTTACATGGC GATAGCTAGA CTGGGCGGTT TTATGGACAG CAAGCGAACC GGAATTGCCA    1620

GCTGGGGCGC CCTCTGGTAA GGTTGGGAAG CCCTGCAAAG TAAACTGGAT GGCTTTCTTG    1680

CCGCCAAGGA TCTGATGGCG CAGGGGATCA AGATCTGATC AAGAGACAGG ATGAGGATCG    1740

TTTCGCATGA TTGAACAAGA TGGATTGCAC GCAGGTTCTC CGGCCGCTTG GGTGGAGAGG    1800

CTATTCGGCT ATGACTGGGC ACAACAGACA ATCGGCTGCT CTGATGCCGC CGTGTTCCGG    1860

CTGTCAGCGC AGGGGCGCCC GGTTCTTTTT GTCAAGACCG ACCTGTCCGG TGCCCTGAAT    1920

GAACTGCAGG ACGAGGCAGC GCGGCTATCG TGGCTGGCCA CGACGGGCGT TCCTTGCGCA    1980

GCTGTGCTCG ACGTTGTCAC TGAAGCGGGA AGGGACTGGC TGCTATTGGG CGAAGTGCCG    2040

GGGCAGGATC TCCTGTCATC TCACCTTGCT CCTGCCGAGA AAGTATCCAT CATGGCTGAT    2100

GCAATGCGGC GGCTGCATAC GCTTGATCCG GCTACCTGCC CATTCGACCA CCAAGCGAAA    2160

CATCGCATCG AGCGAGCACG TACTCGGATG GAAGCCGGTC TTGTCGATCA GGATGATCTG    2220

GACGAAGAGC ATCAGGGGCT CGCGCCAGCC GAACTGTTCG CCAGGCTCAA GGCGCGCATG    2280

CCCGACGGCG AGGATCTCGT CGTGACCCAT GGCGATGCCT GCTTGCCGAA TATCATGGTG    2340

GAAAATGGCC GCTTTTCTGG ATTCATCGAC TGTGGCCGGC TGGGTGTGGC GGACCGCTAT    2400

CAGGACATAG CGTTGGCTAC CCGTGATATT GCTGAAGAGC TTGGCGGCGA ATGGGCTGAC    2460

CGCTTCCTCG TGCTTTACGG TATCGCCGCT CCCGATTCGC AGCGCATCGC CTTCTATCGC    2520

CTTCTTGACG AGTTCTTCTG AGCGGGACTC TGGGGTTCGA AATGACCGAC CAAGCGACGC    2580

CCAACCTGCC ATCACGAGAT TTCGATTCCA CCGCCGCCTT CTATGAAAGG TTGGGCTTCG    2640

GAATCGTTTT CCGGGACGGA ATTCGTAATC TGCTGCTTGC AAACAAAAAA ACCACCGCTA    2700

CCAGCGGTGG TTTGTTTGCC GGATCAAGAG CTACCAACTC TTTTTCCGAA GGTAACTGGC    2760

TTCAGCAGAG CGCAGATACC AAATACTGTC CTTCTAGTGT AGCCGTAGTT AGGCCACCAC    2820

TTCAAGAACT CTGTAGCACC GCCTACATAC CTCGCTCTGC TAATCCTGTT ACCAGTGGCT    2880

GCTGCCAGTG GCGATAAGTC GTGTCTTACC GGGTTGGACT CAAGACGATA GTTACCGGAT    2940

AAGGCGCAGC GGTCGGGCTG AACGGGGGGT TCGTGCACAC AGCCCAGCTT GGAGCGAACG    3000

ACCTACACCG AACTGAGATA CCTACAGCGT GAGCATTGAG AAAGCGCCAC GCTTCCCGAA    3060

GGGAGAAAGG CGGACAGGTA TCCGGTAAGC GGCAGGGTCG GAACAGGAGA GCGCACGAGG    3120

GAGCTTCCAG GGGGAAACGC CTGGTATCTT TATAGTCCTG TCGGGTTTCG CCACCTCTGA    3180

CTTGAGCGTC GATTTTTGTG ATGCTCGTCA GGGGGGCGGA GCCTATGGAA AAACGCCAGC    3240

AACGCCGAGA TGCGCCGCCT CGAGTACACC TGCGTCATGC TGAGACCCTC AAGCCTCACT    3300

AAAAGGGTCC CTGCCTAGTT CTGTTTACTA ATCTGCCTTA TTCTGTTTTT GTTCCCATGT    3360

TAAAGATAGA GTAAATGCAG TATTCTCCAC ATAGAGATAT AGACTTCTGA AATTCTAAGA    3420

TTAGAATTAT TTACAAGAAG AAGTGGGAA TGAAGAATAA AAAATTACTG GCCTCTTGTG    3480

AGAACATGAA CTTTCACCTC GGAGCCCACC CCCTCCCATC TGGAAAACAT ACTTGAGAAA    3540

AACATTTTCT GGAACAACCA CAGAATGTTT CAACAGGCCA GATGTATTGC CAAACACAGG    3600

ATATGACTCT TTGGTTGAGT AAATTTGTGG TTGTTAAACT TCCCCTATTC CCTCCCCATT    3660

CCCCCTCCCA GTTTGTGGTT TTTTCCTTTA AAAGCTTGTG AAAAATTTGA GTCGTCGTCG    3720
```

-continued

```
AGACTCCTCT ACCCTGTGCA AAGGTGTATG AGTTTCGACC CCAGAGCTCT GTGTGCTTTC    3780

TGTTGCTGCT TTATTTCGAC CCCAGAGCTC TGGTCTGTGT GCTTTCATGT CGCTGCTTTA    3840

TTAAATCTTA CCTTCTACAT TTTATGTATG GTCTCAGTGT CTTCTTGGGT ACGCGGCTGT    3900

CCCGGGACTT GAGTGTCTGA GTGAGGGTCT TCCCTCGAGG GTCTTTCATT TGGTACATGG    3960

GCCGGGAATT CGAGAATCTT TCATTTGGTG CATTGGCCGG GAATTCGAAA ATCTTTCATT    4020

TGGTGCATTG GCCGGGAAAC AGCGCGACCA CCCAGAGGTC CTAGACCCAC TTAGAGGTAA    4080

GATTCTTTGT TCTGTTTTGG TCTGATGTCT GTGTTCTGAT GTCTGTGTTC TGTTTCTAAG    4140

TCTGGTGCGA TCGCAGTTTC AGTTTTGCGG ACGCTCAGTG AGACCGCGCT CCGAGAGGGA    4200

GTGCGGGGTG GATAAGGATA GACGTGTCCA GGTGTCCACC GTCCGTTCGC CCTGGGAGAC    4260

GTCCCAGGAG GAACAGGGGA GGATCAGGGA CGCCTGGTGG ACCCCTTTGA AGGCCAAGAG    4320

ACCATTTGGG GTTGCGAGAT CGTGGGTTCG AGTCCCACCT CGTGCCCAGT TGCGAGATCG    4380

TGGGTTCGAG TCCCACCTCG TGTTTTGTTG CGAGATCGTG GGTTCGAGTC CCACCTCGCG    4440

TCTGGTCACG GGATCGTGGG TTCGAGTCCC ACCTCGTGTT TTGTTGCGAG ATCGTGGGTT    4500

CGAGTCCCAC CTCGCGTCTG GTCACGGGAT CGTGGGTTCG AGTCCCACCT CGTGCAGAGG    4560

GTCTCAATTG GCCGGCCTTA GAGAGGCCAT CTGATTCTTC TGGTTTCTCT TTTTGTCTTA    4620

GTCTCGTGTC CGCTCTTGTT GTGACTACTG TTTTTCTAAA AATGGGACAA TCTGTGTCCA    4680

CTCCCCTTTC TCTGACTCTG GTTCTGTCGC TTGGTAATTT TGTTTGTTTA CGTTTGTTTT    4740

TGTGAGTCGT CTATGTTGTC TGTTACTATC TTGTTTTTGT TTGTGGTTTA CGGTTTCTGT    4800

GTGTGTCTTG TGTGTCTCTT TGTGTTCAGA CTTGGACTGA TGACTGACGA CTGTTTTTAA    4860

GTTATGCCTT CTAAAATAAG CCTAAAAATC CTGTCAGATC CCTATGCTGA CCACTTCCTT    4920

TCAGATCAAC AGCTGCCCTT ACGTATCGAT GGATCCGA                             4958
```

(2) INFORMATION FOR SEQ ID NO: 21:

(i) SEQUENCE CHARACTERISTICS:
        (A) LENGTH: 7080 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
GAATACAAGC TTGCATGCCT GCAGGTCGAC TCTAGAGGAT CTTGAAGAAT AAAAAATTAC      60

TGGCCTCTTG TGAGAACATG AACTTTCACC TCGGAGCCCA CCCCCTCCCA TCTGAAAAAC     120

ATACTTGAGA AAAACATTTT CTGGAACAAC CACAGAATGT TCAACAGGC CAGATGTATT      180

GCCAAACACA GGATATGACT CTTTGGTTGA GTAAATTTGT GGTTGTTAAA CTTCCCCTAT     240

TCCCTCCCCA TTCCCCCTCC CAGTTTGTGG TTTTTTCCTT TAAAAGCTTG TGAAAAATTT     300

GAGTCGTCGT CGAGACTCCT CTACCCTGTG CAAAGGTGTA TGAGTTTCGA CCCCAGAGCT     360

CTGTGTGCTT TCTGTTGCTG CTTTATTTCG ACCCCAGAGC TCTGGTCTGT GTGCTTTCAT     420

GTCGCTGCTT TATTAAATCT TACCTTCTAC ATTTTATGTA TGGTCTCAGT GTCTTCTTGG     480

GTACGCGGCT GTCCCGGGAC TTGAGTGTCT GAGTGAGGGT CTTCCCTCGA GGGTCTTTCA     540

TTTGGTACAT GGGCCGGGAA TTCGAGAATC TTTCATTTGG TGCATTGGCC GGGAATTCGA     600

AAATCTTTCA TTTGGTGCAT TGGCCGGGAA ACAGCGCGAC CACCCAGAGG TCCTAGACCC     660

ACTTAGAGGT AAGATTCTTT GTTCTGTTTT GGTCTGATGT CTGTGTTCTG ATGTCTGTGT     720
```

```
TCTGTTTCTA AGTCTGGTGC GATCGCAGTT TCAGTTTTGC GGACGCTCAG TGAGACCGCG      780

CTCCGAGAGG GAGTGCGGGG TGGATAAGGA TAGACGTGTC CAGGTGTCCA CCGTCCGTTC      840

GCCCTGGGAG ACGTCCCAGG AGGAACAGGG GAGGATCAGG GACGCCTGGT GGACCCCTTT      900

GAAGGCCAAG AGACCATTTG GGGTTGCGAG ATCGTGGGTT CGAGTCCCAC CATCGATGGT      960

GCAGAGGGTC TCAATTGGCC GGCCTTAGAA TTACGGATCT AGCATGATTG AACAAGATGG     1020

ATTGCACGCA GGTTCTCCGG CCGCTTGGGT GGAGAGGCTA TTCGGCTATG ACTGGGCACA     1080

ACAGACAATC GGCTGCTCTG ATGCCGCCGT GTTCCGGCTG TCAGCGCAGG GCGCCCGGT      1140

TCTTTTTGTC AAGACCGACC TGTCCGGTGC CCTGAATGAA CTGCAGGACG AGGCAGCGCG     1200

GCTATCGTGG CTGGCCACGA CGGGCGTTCC TTGCGCAGCT GTGCTCGACG TTGTCACTGA     1260

AGCGGGAAGG GACTGGCTGC TATTGGGCGA AGTGCCGGGG CAGGATCTCC TGTCATCTCA     1320

CCTTGCTCCT GCCGAGAAAG TATCCATCAT GGCTGATGCA ATGCGGCGGC TGCATACGCT     1380

TGATCCGGCT ACCTGCCCAT TCGACCACCA AGCGAAACAT CGCATCGAGC GAGCACGTGC     1440

TCGGATGGAA GCCGGTCTTG TCGATCAGGA TGATCTGGAC GAAGAGCATC AGGGGCTCGC     1500

GCCAGCCGAA CTGTTCGCCA GGCTCAAGGC GCGCATGCCC GACGGCGAGG ATCTCGTCGT     1560

GACCCATGGC GATGCCTGCT TGCCGAATAT CATGGTGGAA AATGGCCGCT TTTCTGGATT     1620

CATCGACTGT GGCCGGCTGG GTGTGGCGGA CCGCTATCAG GACATAGCGT TGGCTACCCG     1680

TGATATTGCT GAAGAGCTTG GCGGCGAATG GGCTGACCGC TTCCTCGTGC TTTACGGTAT     1740

CGCCGCTCCC GATTCGCAGC GCATCGCCTT CTATCGCCTT CTTGACGAGT TCTTCTGAGC     1800

GGGACTCTGG GGTTCGTAAT GACCGACCAA GCGACGCCCA ACCTGCCATC ACGAGATTTC     1860

GATTCCACCG CCGCCTTCTA TGAAAGGTTG GGCTTCGGAG TTAGCTTGTT TCTTTACTGT     1920

TTGTCAATTC TATTATTTCA ATACAGAACA ATAGCTTCTA TAACTGAAAT ATATTTGCTA     1980

TTGTATATTA TGATTGTCCC TCGAACCATG AACACTCCTC CAGCTGAATT TCACAATTCC     2040

TCTGTCATCT GCCAGGCCAT TAAGTTATTC ATGGAAGATC TTTGAGGAAC ACTGCAAGTT     2100

CATATCATAA ACACATTTGA AATTGAGTAT TGTTTTGCAT TGTATGGAGC TATGTTTTGC     2160

TGTATCCTCA GAAAAAAAGT TTGTTATAAA GCATTCACAC CCATAAAAAG ATAGATTTAA     2220

ATATTCCAGC TATAGGAAAG AAAGTGCGTC TGCTCTTCAC TCTAGTCTCA GTTGGCTCCT     2280

TCACATGCAT GCTTCTTTAT TTCTCCTATT TTGTCAAGAA AATAATAGGT CACGTCTTGT     2340

TCTCACTTAT GTCCTGCCTA GCATGGCTCA GATGCACGTT GTAGATACAA GAAGGATCAA     2400

ATGAAACAGA CTTCTGGTCT GTTACTACAA CCATAGTAAT AAGCACACTA ACTAATAATT     2460

GCTAATTATG TTTTCCATCT CTAAGGTTCC CACATTTTTC TGTTTTCTTA AAGATCCCAT     2520

TATCTGGTTG TAACTGAAGC TCAATGGAAC ATGAGCAATA TTTCCCAGTC TTCTCTCCCA     2580

TCCAACAGTC CTGATGGATT AGCAGAACAG GCAGAAAACA CATTGTTACC CAGAATTAAA     2640

AACTAATATT TGCTCTCCAT TCAATCCAAA ATGGACCTAT TGAAACTAAA ATCTAACCCA     2700

ATCCATTAAA ATGATTTCTA TGGCGTCAAA GGTCAAACTT CTGAAGGGAA CCTGTGGGTG     2760

GGTCACAATT CAGGCTATAT ATTCCCCAGG GCTCAGCCAG TGTCTGTACA TACACAACGG     2820

ATCCTGTGGA CAGCTCACCT AGCTGCAATG GCTACAGGCT CCCGGACGTC CCTGCTCCTG     2880

GCTTTTGGCC TGCTCTGCCT GCCCTGGCTT CAAGAGGGCA GTGCCTTCCC AACCATTCCC     2940

TTATCCAGGC TTTTTGACAA CGCTATGCTC CGCGCCCATC GTCTGCACCA GCTGGCCTTT     3000

GACACCTACC AGGAGTTTGA AGAAGCCTAT ATCCCAAAGG AACAGAAGTA TTCATTCCTG     3060

CAGAACCCCC AGACCTCCCT CTGTTTCTCA GAGTCTATTC CGACACCCTC AACAGGGAG     3120
```

```
GAAACACAAC AGAAATCCAA CCTAGAGCTG CTCCGCATCT CCCTGCTGCT CATCCAGTCG    3180

TGGCTGGAGC CCGTGCAGTT CCTCAGGAGT GTCTTCGCCA ACAGCCTGGT GTACGGCGCC    3240

TCTGACAGCA ACGTCTATGA CCTCCTAAAG GACCTAGAGG AAGGCATCCA AACGCTGATG    3300

GGGAGGCTGG AAGATGGCAG CCCCCGGACT GGGCAGATCT TCAAGCAGAC CTACAGCAAG    3360

TTCGACACAA ACTCACACAA CGATGACGCA CTACTCAAGA ACTACGGGCT GCTCTACTGC    3420

TTCAGGAAGG ACATGGACAA GGTCGAGACA TTCCTGCGCA TCGTGCAGTG CCGCTCTGTG    3480

GAGGGCAGCT GTGGCTTCTA GCTGCCCGGG TGGCATCCTG TGACCCCTCC CCAGTGCCTC    3540

TCCTGGCCCT GGAAGTTGCC ACTCCAGTGC CCACCAGCCT TGTCCTAATA AAATTAAGTT    3600

GCATCAAAAA AAAAAAAAAG CTAGCGGCCG CTAGACTTCT GAAATTCTAA GATTAGAATT    3660

ATTTACAAGA AGAAGTGGGG AATGAAGAAT AAAAAATTAC TGGCCTCTTG TGAGAACATG    3720

AACTTTCACC TCGGAGCCCA CCCCCTCCCA TCTGGAAAAA ATACTTGAGA AAAACATTTT    3780

CTGGAACAAC CACAGAATGT TTCAACAGGC CAGATGTATT GCCAAACACA GGATATGACT    3840

CTTTGGTTGA GTAAATTTGT GGTTGTTAAA CTTCCCCTAT TCCCTCCCCA TTCCCCCTCC    3900

CAGTTTGTGG TTTTTTCCTT TAAAAGCTTG TGAAAAATTT GAGTCGTCGT CGAGACTCCT    3960

CTACCCTGTG CAAAGGTGTA TGAGTTTCGA CCCCAGAGCT CTGTGTGCTT TCTGTTGCTG    4020

CTTTATTTCG ACCCCAGAGC TCTGGTCTGT GTGCTTTCAT GTCGCTGCTT TATTAAATCT    4080

TACCTTCTAC ATTTTATGTA TGGTCTCAGT GTCTTCTTGG GTACGCGGCT GTCCCGGGAC    4140

TTGAGTGTCT GAGTGAGGGT CTTCCCTCGA GGGTCTTTCA TTTGGTACAT GGGCCGGGAA    4200

TTCGAGAATC TTTCATTTGG TGCATTGGCC GGGAATTCGA AAATCTTTCA GATCCCCGGG    4260

TACCGAGCTC GAATTCCGGT CTCCCTATAG TGAGTCGTAT TAATTTCGAT AAGCCAGCTG    4320

CATTAATGAA TCGGCCAACG CGCGGGGAGA GGCGGTTTGC GTATTGGGCG CTCTTCCGCT    4380

TCCTCGCTCA CTGACTCGCT GCGCTCGGTC GTTCGGCTGC GGCGAGCGGT ATCAGCTCAC    4440

TCAAAGGCGG TAATACGGTT ATCCACAGAA TCAGGGGATA ACGCAGGAAA GAACATGTGA    4500

GCAAAAGGCC AGCAAAAGGC CAGGAACCGT AAAAAGGCCG CGTTGCTGGC GTTTTTCCAT    4560

AGGCTCCGCC CCCCTGACGA GCATCACAAA AATCGACGCT CAAGTCAGAG GTGGCGAAAC    4620

CCGACAGGAC TATAAAGATA CCAGGCGTTT CCCCCTGGAA GCTCCCTCGT GCGCTCTCCT    4680

GTTCCGACCC TGCCGCTTAC CGGATACCTG TCCGCCTTTC TCCCTTCGGG AAGCGTGGCG    4740

CTTTCTCATA GCTCACGCTG TAGGTATCTC AGTTCGGTGT AGGTCGTTCG CTCCAAGCTG    4800

GGCTGTGTGC ACGAACCCCC CGTTCAGCCC GACCGCTGCG CCTTATCCGG TAACTATCGT    4860

CTTGAGTCCA ACCCGGTAAG ACACGACTTA TCGCCACTGG CAGCAGCCAC TGGTAACAGG    4920

ATTAGCAGAG CGAGGTATGT AGGCGGTGCT ACAGAGTTCT TGAAGTGGTG GCCTAACTAC    4980

GGCTACACTA GAAGGACAGT ATTTGGTATC TGCGCTCTGC TGAAGCCAGT TACCTTCGGA    5040

AAAAGAGTTG GTAGCTCTTG ATCCGGCAAA CAAACCACCG CTGGTAGCGG TGGTTTTTTT    5100

GTTTGCAAGC AGCAGATTAC GCGCAGAAAA AAAGGATCTC AAGAAGATCC TTTGATCTTT    5160

TCTACGGGGT CTGACGCTCA GTGGAACGAA AACTCACGTT AAGGGATTTT GGTCATGAGA    5220

TTATCAAAAA GGATCTTCAC CTAGATCCTT TTAAATTAAA AATGAAGTTT TAAATCAATC    5280

TAAAGTATAT ATGAGTAAAC TTGGTCTGAC AGTTACCAAT GCTTAATCAG TGAGGCACCT    5340

ATCTCAGCGA TCTGTCTATT TCGTTCATCC ATAGTTGCCT GACTCCCCGT CGTGTAGATA    5400

ACTACGATAC GGGAGGGCTT ACCATCTGGC CCCAGTGCTG CAATGATACC GCGAGACCCA    5460
```

```
CGCTCACCGG CTCCAGATTT ATCAGCAATA AACCAGCCAG CCGGAAGGGC CGAGCGCAGA    5520

AGTGGTCCTG CAACTTTATC CGCCTCCATC CAGTCTATTA ATTGTTGCCG GGAAGCTAGA    5580

GTAAGTAGTT CGCCAGTTAA TAGTTTGCGC AACGTTGTTG CCATTGCTAC AGGCATCGTG    5640

GTGTCACGCT CGTCGTTTGG TATGGCTTCA TTCAGCTCCG GTTCCCAACG ATCAAGGCGA    5700

GTTACATGAT CCCCCATGTT GTGCAAAAAA GCGGTTAGCT CCTTCGGTCC TCCGATCGTT    5760

GTCAGAAGTA AGTTGGCCGC AGTGTTATCA CTCATGGTTA TGGCAGCACT GCATAATTCT    5820

CTTACTGTCA TGCCATCCGT AAGATGCTTT TCTGTGACTG GTGAGTACTC AACCAAGTCA    5880

TTCTGAGAAT AGTGTATGCG GCGACCGAGT TGCTCTTGCC CGGCGTCAAT ACGGGATAAT    5940

ACCGCGCCAC ATAGCAGAAC TTTAAAAGTG CTCATCATTG GAAAACGTTC TTCGGGGCGA    6000

AAACTCTCAA GGATCTTACC GCTGTTGAGA TCCAGTTCGA TGTAACCCAC TCGTGCACCC    6060

AACTGATCTT CAGCATCTTT TACTTTCACC AGCGTTTCTG GGTGAGCAAA ACAGGAAGG    6120

CAAAATGCCG CAAAAAAGGG AATAAGGGCG ACACGGAAAT GTTGAATACT CATACTCTTC    6180

CTTTTTCAAT ATTATTGAAG CATTTATCAG GGTTATTGTC TCATGAGCGG ATACATATTT    6240

GAATGTATTT AGAAAAATAA ACAAATAGGG GTTCCGCGCA CATTTCCCCG AAAAGTGCCA    6300

CCTGACGTCT AAGAAACCAT TATTATCATG ACATTAACCT ATAAAAATAG GCGTATCACG    6360

AGGCCCTTTC GTCTCGCGCG TTTCGGTGAT GACGGTGAAA ACCTCTGACA CATGCAGCTC    6420

CCGGAGACGG TCACAGCTTG TCTGTAAGCG GATGCCGGGA GCAGACAAGC CCGTCAGGGC    6480

GCGTCAGCGG GTGTTGGCGG GTGTCGGGGC TGGCTTAACT ATGCGGCATC AGAGCAGATT    6540

GTACTGAGAG TGCACCATAT CGACGCTCTC CCTTATGCGA CTCCTGCATT AGGAAGCAGC    6600

CCAGTAGTAG GTTGAGGCCG TTGAGCACCG CCGCCGCAAG GAATGGTGCA AGGAGATGGC    6660

GCCCAACAGT CCCCCGGCCA CGGGGCCTGC CACCATACCC ACGCCGAAAC AAGCGCTCAT    6720

GAGCCCGAAG TGGCGAGCCC GATCTTCCCC ATCGGTGATG TCGGCGATAT AGGCGCCAGC    6780

AACCGCACCT GTGGCGCCGG TGATGCCGGC CACGATGCGT CCGGCGTAGA GGATCTGGCT    6840

AGCGATGACC CTGCTGATTG GTTCGCTGAC CATTTCCGGG GTGCGGAACG GCGTTACCAG    6900

AAACTCAGAA GGTTCGTCCA ACCAAACCGA CTCTGACGGC AGTTTACGAG AGAGATGATA    6960

GGGTCTGCTT CAGTAAGCCA GATGCTACAC AATTAGGCTT GTACATATTG TCGTTAGAAC    7020

GCGGCTACAA TTAATACATA ACCTTATGTA TCATACACAT ACGATTTAGG TGACACTATA    7080

(2) INFORMATION FOR SEQ ID NO: 22:

(i) SEQUENCE CHARACTERISTICS:
            (A) LENGTH: 6795 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 22:

AATGAAAGAC CCCACCTGTA GGTTTGGCAA GCTAGCTTAA GTAACGCCAT TTTGCAAGGC      60

ATGGAAAAAT ACATAACTGA GAATAGAGAA GTTCAGATCA AGGTCAGGAA CAGATGGAAC     120

AGCTGAATAT GGGCCAAACA GGATATCTGT GGTAAGCAGT TCCTGCCCCG GCTCAGGGCC     180

AAGAACAGAT GGAACAGCTG AATATGGGCC AAACAGGATA TCTGTGGTAA GCAGTTCCTG     240

CCCCGGCTCA GGGCCAAGAA CAGATGGTCC CCAGATGCGG TCCAGCCCTC AGCAGTTTCT     300

AGAGAACCAT CAGATGTTTC CAGGGTGCCC CAAGGACCTG AAATGACCCT GTGCCTTATT     360
```

-continued

```
TGAACTAACC AATCAGTTCG CTTCTCGCTT CTGTTCGCGC GCTTCTGCTC CCCGAGCTCA    420
ATAAAAGAGC CCACAACCCC TCACTCGGGG CGCCAGTCCT CCGATTGACT GAGTCGCCCG    480
GGTACCCGTG TATCCAATAA ACCCTCTTGC AGTTGCATCC GACTTGTGGT CTCGCTGTTC    540
CTTGGGAGGG TCTCCTCTGA GTGATTGACT ACCCGTCAGC GGGGGTCTTT CATTTGGGGG    600
CTCGTCCGGG ATCGGGAGAC CCCTGCCCAG GGACCACCGA CCCACCACCG GGAGGTAAGC    660
TGGCCAGCAA CTTATCTGTG TCTGTCCGAT TGTCTAGTGT CTATGACTGA TTTTATGCGC    720
CTGCGTCGGT ACTAGTTAGC TAACTAGCTC TGTATCTGGC GGACCCGTGG TGGAACTGAC    780
GAGTTCGGAA CACCCGGCCG CAACCCTGGG AGACGTCCCA GGAGGAACAG GGGAGGATCA    840
GGGACGCCTG GTGGACCCCT TTGAAGGCCA AGAGACCATT TGGGGTTGCG AGATCGTGGG    900
TTCGAGTCCC ACCTCGTGCC CAGTTGCGAG ATCGTGGGTT CGAGTCCCAC CTCGTGTTTT    960
GTTGCGAGAT CGTGGGTTCG AGTCCCACCT CGCGTCTGGT CACGGGATCG TGGGTTCGAG   1020
TCCCACCTCG TGTTTTGTTG CGAGATCGTG GGTTCGAGTC CCACCTCGCG TCTGGTCACG   1080
GGATCGTGGG TTCGAGTCCC ACCTCGTGCA GAGGGTCTCA ATTGGCCGGC CTTAGAGAGG   1140
CCATCTGATT CTTCTGGTTT CTCTTTTTGT CTTAGTCTCG TGTCCGCTCT TGTTGTGACT   1200
ACTGTTTTTC TAAAAATGGG ACAATCTGTG TCCACTCCCC TTTCTCTGAC TCTGGTTCTG   1260
TCGCTTGGTA ATTTTGTTTG TTTACGTTTG TTTTTGTGAG TCGTCTATGT TGTCTGTTAC   1320
TATCTTGTTT TTGTTTGTGG TTTACGGTTT CTGTGTGTGT CTTGTGTGTC TCTTTGTGTT   1380
CAGACTTGGA CTGATGACTG ACGACTGTTT TTAAGTTATG CCTTCAAAA TAAGCCTAAA   1440
AATCCTGTCA GATCCCTATG CTGACCACTT CCTTTCAGAT CAACAGCTGC CCTTACTCGA   1500
GCTCAAGCTT CGAATTCTGC AGTCGACGGT ACCGCGGCCG CTAACTAATA GCCCATTCTC   1560
CAAGGTACGT AGCGGGGATC AATTCCGCCC CCCCCCTAAC GTTACTGGCC GAAGCCGCTT   1620
GGAATAAGGC CGGTGTGCGT TTGTCTATAT GTTATTTTCC ACCATATTGC CGTCTTTTGG   1680
CAATGTGAGG GCCCGGAAAC CTGGCCCTGT CTTCTTGACG AGCATTCCTA GGGGTCTTTC   1740
CCCTCTCGCC AAAGGAATGC AAGGTCTGTT GAATGTCGTG AAGGAAGCAG TTCCTCTGGA   1800
AGCTTCTTGA AGACAAACAA CGTCTGTAGC GACCCTTTGC AGGCAGCGGA ACCCCCCACC   1860
TGGCGACAGG TGCCTCTGCG GCCAAAAGCC ACGTGTATAA GATACACCTG CAAAGGCGGC   1920
ACAACCCCAG TGCCACGTTG TGAGTTGGAT AGTTGTGGAA AGAGTCAAAT GGCTCTCCTC   1980
AAGCGTATTC AACAAGGGGC TGAAGGATGC CCAGAAGGTA CCCCATTGTA TGGGATCTGA   2040
TCTGGGGCCT CGGTGCACAT GCTTTACATG TGTTTAGTCG AGGTTAAAAA AACGTCTAGG   2100
CCCCCCGAAC CACGGGGACG TGGTTTTCCT TTGAAAAACA CGATACGGGA TCCACCGGTC   2160
GCCACCATGG GTAAAGGAGA AGAACTTTTC ACAGGAGTTG TCCCAATTCT TGTTGAATTA   2220
GATGGTGATG TTAATGGGCA CAAATTTTCT GTCAGTGGAG AGGGTGAAGG TGATGCAACA   2280
TACGGAAAAC TTACCCTTAA ATTTATTTGC ACTACTGGAA AACTACCTGT TCCATGGCCA   2340
ACACTTGTCA CTACTTTCAC TTATGGTGTT CAATGCTTTT CAAGATACCC AGATCATATG   2400
AAACGGCATG ACTTTTTCAA GAGTGCCATG CCCGAAGGTT ATGTACAGGA AGAACTATA   2460
TTTTTCAAAG ATGACGGGAA CTACAAGACA CGTGCTGAAG TCAAGTTTGA AGGTGATACC   2520
CTTGTTAATA GAATCGAGTT AAAAGGTATT GATTTTAAAG AAGATGGAAA CATTCTTGGA   2580
CACAAATTGG AATACAACTA TAACTCACAC AATGTATACA TCATGGCAGA CAAACAAAAG   2640
AATGGAACCA AAGTTAACTT CAAAATTAGA CACAACATTG AAGATGGAAG CGTTCAACTA   2700
GCAGACCATT ATCAACAAAA TACTCCAATT GGCGATGGCC CTGTCCTTTT ACCAGACAAC   2760
```

-continued

```
CATTACCTGT CCACACAATC TGCCCTTTCG AAAGATCCCA ACGAAAAGAG AGACCACATG    2820

GTCCTTCTTG AGTTTGTAAC AGCTGCTGGG ATTACACATG GCATGGATGA ACTATACAAG    2880

TCCGGATCTA GATAACTGTA TCGATGGATC CGAAGGCGGG GACAGCAGTG CAGTGGTGGA    2940

CAGAAAGCAA GTGATCTAGG CCAGCAGCCT CCCTAAAGGG ACTTCAGCCC ACAAAGCCAA    3000

ACTTGTGGCT TTAATACAAG CTCTGTAAAT GGTAAAAAAA AAAAAGTCTA CACGGACAGC    3060

AGGTATGCTC TTGCCACTGT ACAGAGCAAT ATACAGACAA AGAGAACTGT TGACATCTGC    3120

AGAGAAAGAC CTAAGATGCT GTGGCTAAAA GAAATCAGAT GGCAAATCTA ACCGCCCAGG    3180

CATCCTAAAG AGCAATGATC CTGACAGTCT GAAGACTATC AAGTTATAGA CAAATTAAGA    3240

CTGGTAAAAA AAACCCTGTA TAAAATAGTA AAAACTGAAA AAAGAAAACT AGTCCTCTCA    3300

TGAGAAGACA GACCTGACAT CTACTGAAAA ATAGACTTTA CTGGAAAAAA TATGTGTATG    3360

AATACCTTCT AGTTTTTGTG AACGTTCTCA AGATGGATAA AAGCTTTTCC TTGTAAAACG    3420

AGACTGATCA GATAGTCATC AAGAAGATTG TTAAAGAAAA TTTTCCAAGG TTCGGAGTGC    3480

CAAAAGCAAT AGTGTCAGAT AATGGTCCTG CCTTTGTTGC CCAGGTAAGT CAGGGTGTGG    3540

CCAAGTATTT AGAGGTCAAA TGAAAATTCC ATTGTGTGTA CAGACCTCAG AGCTCAGGAA    3600

AGATAAAAAA GAATAAATAA AACTCTAAAC AGACCTTGAC AAAATTAATC CTAGAGACTG    3660

GCACAGACTT ACTTGGTACT CCTTCCCCTT GCCCTATTTA GAACTGAGAA TACTCCCTCT    3720

TGATTCGGTT TTACTCTTTT TAAGATCCTT TATGGGCTC CTATGCCATC ACTGTCTTAA    3780

ATGATGTGTT TAAACCTATG TTGTTATAAT AATGATCTAT ATGTTAAGTT AAAAGGCTTG    3840

CAGGTGGTGC AGAAAGAAGT CTGGTCACAA CTGGCTACAG TGAACAAGCT GGGTACCCCA    3900

AGGACATCTT ACCAGTTCCA GCCAGAGATC TGATCTACGA TCCCCGGGTC GACCCGGGTC    3960

GACCCTGTGG AATGTGTGTC AGTTAGGGTG TGGAAAGTCC CCAGGCTCCC CAGCAGGCAG    4020

AAGTATGCAA AGCATGCATC TCAATTAGTC AGCAACCAGG TGTGGAAAGT CCCCAGGCTC    4080

CCCAGCAGGC AGAAGTATGC AAAGCATGCA TCTCAATTAG TCAGCAACCA TAGTCCCGCC    4140

CCTAACTCCG CCCATCCCGC CCCTAACTCC GCCCAGTTCC GCCCATTCTC CGCCCCATGG    4200

CTGACTAATT TTTTTTATTT ATGCAGAGGC CGAGGCCGCC TCGGCCTCTG AGCTATTCCA    4260

GAAGTAGTGA GGAGGCTTTT TTGGAGGCCT AGGCTTTTGC AAAAAGCTTC ACGCTGCCGC    4320

AAGCACTCAG GGCGCAAGGG CTGCTAAAGG AAGCGGAACA CGTAGAAAGC CAGTCCGCAG    4380

AAACGGTGCT GACCCCGGAT GAATGTCAGC TACTGGGCTA TCTGGACAAG GGAAAACGCA    4440

AGCGCAAAGA GAAAGCAGGT AGCTTGCAGT GGGCTTACAT GGCGATAGCT AGACTGGGCG    4500

GTTTTATGGA CAGCAAGCGA ACCGGAATTG CCAGCTGGGG CGCCCTCTGG TAAGGTTGGG    4560

AAGCCCTGCA AAGTAAACTG GATGGCTTTC TTGCCGCCAA GGATCTGATG GCGCAGGGGA    4620

TCAAGATCTG ATCAAGAGAC AGGATGAGGA TCGTTTCGCA TGATTGAACA AGATGGATTG    4680

CACGCAGGTT CTCCGGCCGC TTGGGTGGAG AGGCTATTCG GCTATGACTG GGCACAACAG    4740

ACAATCGGCT GCTCTGATGC CGCCGTGTTC CGGCTGTCAG CGCAGGGGCG CCCGGTTCTT    4800

TTTGTCAAGA CCGACCTGTC CGGTGCCCTG AATGAACTGC AGGACGAGGC AGCGCGGCTA    4860

TCGTGGCTGG CCACGACGGG CGTTCCTTGC GCAGCTGTGC TCGACGTTGT CACTGAAGCG    4920

GGAAGGGACT GGCTGCTATT GGGCGAAGTG CCGGGGCAGG ATCTCCTGTC ATCTCACCTT    4980

GCTCCTGCCG AGAAAGTATC CATCATGGCT GATGCAATGC GGCGGCTGCA TACGCTTGAT    5040

CCGGCTACCT GCCCATTCGA CCACCAAGCG AAACATCGCA TCGAGCGAGC ACGTACTCGG    5100
```

-continued

| | |
|---|---|
| ATGGAAGCCG GTCTTGTCGA TCAGGATGAT CTGGACGAAG AGCATCAGGG GCTCGCGCCA | 5160 |
| GCCGAACTGT TCGCCAGGCT CAAGGCGCGC ATGCCCGACG GCGAGGATCT CGTCGTGACC | 5220 |
| CATGGCGATG CCTGCTTGCC GAATATCATG GTGGAAAATG GCCGCTTTTC TGGATTCATC | 5280 |
| GACTGTGGCC GGCTGGGTGT GGCGGACCGC TATCAGGACA TAGCGTTGGC TACCCGTGAT | 5340 |
| ATTGCTGAAG AGCTTGGCGG CGAATGGGCT GACCGCTTCC TCGTGCTTTA CGGTATCGCC | 5400 |
| GCTCCCGATT CGCAGCGCAT CGCCTTCTAT CGCCTTCTTG ACGAGTTCTT CTGAGCGGGA | 5460 |
| CTCTGGGGTT CGAAATGACC GACCAAGCGA CGCCCAACCT GCCATCACGA GATTTCGATT | 5520 |
| CCACCGCCGC CTTCTATGAA AGGTTGGGCT TCGGAATCGT TTTCCGGGAC GGAATTCGTA | 5580 |
| ATCTGCTGCT TGCAAACAAA AAACCACCG CTACCAGCGG TGGTTTGTTT GCCGGATCAA | 5640 |
| GAGCTACCAA CTCTTTTTCC GAAGGTAACT GGCTTCAGCA GAGCGCAGAT ACCAAATACT | 5700 |
| GTCCTTCTAG TGTAGCCGTA GTTAGGCCAC CACTTCAAGA ACTCTGTAGC ACCGCCTACA | 5760 |
| TACCTCGCTC TGCTAATCCT GTTACCAGTG GCTGCTGCCA GTGGCGATAA GTCGTGTCTT | 5820 |
| ACCGGGTTGG ACTCAAGACG ATAGTTACCG GATAAGGCGC AGCGGTCGGG CTGAACGGGG | 5880 |
| GGTTCGTGCA CACAGCCCAG CTTGGAGCGA ACGACCTACA CCGAACTGAG ATACCTACAG | 5940 |
| CGTGAGCATT GAGAAAGCGC CACGCTTCCC GAAGGGAGAA AGGCGGACAG GTATCCGGTA | 6000 |
| AGCGGCAGGG TCGGAACAGG AGAGCGCACG AGGGAGCTTC CAGGGGGAAA CGCCTGGTAT | 6060 |
| CTTTATAGTC CTGTCGGGTT TCGCCACCTC TGACTTGAGC GTCGATTTTT GTGATGCTCG | 6120 |
| TCAGGGGGGC GGAGCCTATG GAAAAACGCC AGCAACGCCG AGATGCGCCG CCTCGAGAAC | 6180 |
| CCTGGCCCTA TTATTGGGTG GACTAACCAT GGGGGGAATT GCCGCTGGAA TAGGAACAGG | 6240 |
| GACTACTGCT CTAATGGCCA CTCAGCAATT CCAGCAGCTC CAAGCCGCAG TACAGGATGA | 6300 |
| TCTCAGGGAG GTTGAAAAAT CAATCTCTAA CCTAGAAAAG TCTCTCACTT CCCTGTCTGA | 6360 |
| AGTTGTCCTA CAGAATCGAA GGGGCCTAGA CTTGTTATTT CTAAAAGAAG GAGGGCTGTG | 6420 |
| TGCTGCTCTA AAAGAAGAAT GTTGCTTCTA TGCGGACCAC ACAGGACTAG TGAGAGACAG | 6480 |
| CATGGCCAAA TTGAGAGAGA GGCTTAATCA GAGACAGAAA CTGTTTGAGT CAACTCAAGG | 6540 |
| ATGGTTTGAG GGACTGTTTA ACAGATCCCC TTGGTTTACC ACCTTGATAT CTACCATTAT | 6600 |
| GGGACCCCTC ATTGTACTCC TAATGATTTT GCTCTTCGGA CCCTGCATTC TTAATCGATT | 6660 |
| AGTCCAATTT GTTAAAGACA GGATATCAGT GGTCCAGGCT CTAGTTTTGA CTCAACAATA | 6720 |
| TCACCAGCTG AAGCCTATAG AGTACAGAGCC ATAGATAAAA TAAAAGATTT TATTTAGTCT | 6780 |
| CCAGAAAAAG GGGGG | 6795 |

(2) INFORMATION FOR SEQ ID NO: 23:

(i) SEQUENCE CHARACTERISTICS:
  (A) LENGTH: 9093 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 23:

| | |
|---|---|
| AATGAAAGAC CCCACCTGTA GGTTTGGCAA GCTAGCTTAA GTAACGCCAT TTTGCAAGGC | 60 |
| ATGGAAAAAT ACATAACTGA GAATAGAGAA GTTCAGATCA AGGTCAGGAA CAGATGGAAC | 120 |
| AGCTGAATAT GGGCCAAACA GGATATCTGT GGTAAGCAGT TCCTGCCCCG GCTCAGGGCC | 180 |
| AAGAACAGAT GGAACAGCTG AATATGGGCC AAACAGGATA TCTGTGGTAA GCAGTTCCTG | 240 |

-continued

```
CCCCGGCTCA GGGCCAAGAA CAGATGGTCC CCAGATGCGG TCCAGCCCTC AGCAGTTTCT    300

AGAGAACCAT CAGATGTTTC CAGGGTGCCC CAAGGACCTG AAATGACCCT GTGCCTTATT    360

TGAACTAACC AATCAGTTCG CTTCTCGCTT CTGTTCGCGC GCTTCTGCTC CCCGAGCTCA    420

ATAAAAGAGC CCACAACCCC TCACTCGGGG CGCCAGTCCT CCGATTGACT GAGTCGCCCG    480

GGTACCCGTG TATCCAATAA ACCCTCTTGC AGTTGCATCC GACTTGTGGT CTCGCTGTTC    540

CTTGGGAGGG TCTCCTCTGA GTGATTGACT ACCCGTCAGC GGGGGTCTTT CATTTGGGGG    600

CTCGTCCGGG ATCGGGAGAC CCCTGCCCAG GGACCACCGA CCCACCACCG GGAGGTAAGC    660

TGGCCAGCAA CTTATCTGTG TCTGTCCGAT TGTCTAGTGT CTATGACTGA TTTTATGCGC    720

CTGCGTCGGT ACTAGTTAGC TAACTAGCTC TGTATCTGGC GGACCCGTGG TGGAACTGAC    780

GAGTTCGGAA CACCCGGCCG CAACCCTGGG AGACGTCCCA GGAGGAACAG GGGAGGATCA    840

GGGACGCCTG GTGGACCCCT TTGAAGGCCA AGAGACCATT TGGGGTTGCG AGATCGTGGG    900

TTCGAGTCCC ACCTCGTGCC CAGTTGCGAG ATCGTGGGTT CGAGTCCCAC CTCGTGTTTT    960

GTTGCGAGAT CGTGGGTTCG AGTCCCACCT CGCGTCTGGT CACGGGATCG TGGGTTCGAG   1020

TCCCACCTCG TGTTTTGTTG CGAGATCGTG GGTTCGAGTC CCACCTCGCG TCTGGTCACG   1080

GGATCGTGGG TTCGAGTCCC ACCTCGTGCA GAGGGTCTCA ATTGGCCGGC CTTAGAGAGG   1140

CCATCTGATT CTTCTGGTTT CTCTTTTTGT CTTAGTCTCG TGTCCGCTCT TGTTGTGATG   1200

ACTGTTTTTC TAAAAATGGG ACAATCTGTG TCCACTCCCC TTTCTCTGAC TCTGGTTCGT   1260

TCGCTTGGTA ATTTTGTTTG TTTACGTTTG TTTTTGTGAG TCGTCTATGT TGTCTGTTAC   1320

TATCTTGTTT TTGTTTGTGG TTTACGGTTT CTGTGTGTGT CTTGTGTGTC TCTTTGTGTT   1380

CAGACTTGGA CTGATGACTG ACGACTGTTT TTAAGTTATG CCTTCTAAAA TAAGCCTAAA   1440

AATCCTGTCA GATCCCTATG CTGACCACTT CCTTTCAGAT CAACAGCTGC CCTTACGTAT   1500

CGATGGATCC CTCGACTAAC TAATAGCCCA TTCTCCAAGG TCGAGCGGGA TCAATTCCGC   1560

CCCCCCCCTA ACGTTACTGG CCGAAGCCGC TTGGAATAAG GCCGGTGTGC GTTTGTCTAT   1620

ATGTTATTTT CCACCATATT GCCGTCTTTT GGCAATGTGA GGGCCCGGAA ACCTGGCCCT   1680

GTCTTCTTGA CGAGCATTCC TAGGGGTCTT TCCCCTCTCG CCAAAGGAAT GCAAGGTCTG   1740

TTGAATGTCG TGAAGGAAGC AGTTCCTCTG GAAGCTTCTT GAAGACAAAC AACGTCTGTA   1800

GCGACCCTTT GCAGGCAGCG GAACCCCCCA CCTGGCGACA GGTGCCTCTG CGGCCAAAAG   1860

CCACGTGTAT AAGATACACC TGCAAAGGCG GCACAACCCC AGTGCCACGT TGTGAGTTGG   1920

ATAGTTGTGG AAAGAGTCAA ATGGCTCTCC TCAAGCGTAT TCAACAAGGG GCTGAAGGAT   1980

GCCCAGAAGG TACCCCATTG TATGGGATCT GATCTGGGGC CTCGGTGCAC ATGCTTTACA   2040

TGTGTTTAGT CGAGGTTAAA AAAACGTCTA GGCCCCCCGA ACCACGGGGA CGTGGTTTTC   2100

CTTTGAAAAA CACGATAATA ATCATGGGCG CGGATCCCGT CGTTTTACAA CGTCGTGACT   2160

GGGAAAACCC TGGCGTTACC CAACTTAATC GCCTTGCAGC ACATCCCCCT TTCGCCAGCT   2220

GGCGTAATAG CGAAGAGGCC CGCACCGATC GCCCTTCCCA ACAGTTGCGC AGCCTGAATG   2280

GCGAATGGCG CTTTGCCTGG TTTCCGGCAC CAGAAGCGGT GCCGGAAAGC TGGCTGGAGT   2340

GCGATCTTCC TGAGGCCGAT ACTGTCGTCG TCCCCTCAAA CTGGCAGATG CACGGTTACG   2400

ATGCGCCCAT CTACACCAAC GTAACCTATC CCATTACGGT CAATCCGCCG TTTGTTCCCA   2460

CGGAGAATCC GACGGGTTGT TACTCGCTCA CATTTAATGT TGATGAAAGC TGGCTACAGG   2520

AAGGCCAGAC GCGAATTATT TTTGATGGCG TTAACTCGGC GTTTCATCTG TGGTGCAACG   2580

GGCGCTGGGT CGGTTACGGC CAGGACAGTC GTTTGCCGTC TGAATTTGAC CTGAGCGCAT   2640
```

```
TTTTACGCGC CGGAGAAAAC CGCCTCGCGG TGATGGTGCT GCGTTGGAGT GACGGCAGTT    2700

ATCTGGAAGA TCAGGATATG TGGCGGATGA GCGGCATTTT CCGTGACGTC TCGTTGCTGC    2760

ATAAACCGAC TACACAAATC AGCGATTTCC ATGTTGCCAC TCGCTTTAAT GATGATTTCA    2820

GCCGCGCTGT ACTGGAGGCT GAAGTTCAGA TGTGCGGCGA GTTGCGTGAC TACCTACGGG    2880

TAACAGTTTC TTTATGGCAG GGTGAAACGC AGGTCGCCAG CGGCACCGCG CCTTTCGGCG    2940

GTGAAATTAT CGATGAGCGT GGTGGTTATG CCGATCGCGT CACACTACGT CTGAACGTCG    3000

AAAACCCGAA ACTGTGGAGC GCCGAAATCC CGAATCTCTA TCGTGCGGTG GTTGAACTGC    3060

ACACCGCCGA CGGCACGCTG ATTGAAGCAG AAGCCTGCGA TGTCGGTTTC CGCGAGGTGC    3120

GGATTGAAAA TGGTCTGCTG CTGCTGAACG GCAAGCCGTT GCTGATTCGA GGCGTTAACC    3180

GTCACGAGCA TCATCCTCTG CATGGTCAGG TCATGGATGA GCAGACGATG GTGCAGGATA    3240

TCCTGCTGAT GAAGCAGAAC AACTTTAACG CCGTGCGCTG TTCGCATTAT CCGAACCATC    3300

CGCTGTGGTA CACGCTGTGC GACCGCTACG GCCTGTATGT GGTGGATGAA GCCAATATTG    3360

AAACCCACGG CATGGTGCCA ATGAATCGTC TGACCGATGA TCCGCGCTGG CTACCGGCGA    3420

TGAGCGAACG CGTAACGCGA ATGGTGCAGC GCGATCGTAA TCACCCGAGT GTGATCATCT    3480

GGTCGCTGGG GAATGAATCA GGCCACGGCG CTAATCACGA CGCGCTGTAT CGCTGGATCA    3540

AATCTGTCGA TCCTTCCCGC CCGGTGCAGT ATGAAGGCGG CGGAGCCGAC ACCACGGCCA    3600

CCGATATTAT TTGCCCGATG TACGCGCGCG TGGATGAAGA CCAGCCCTTC CCGGCTGTGC    3660

CGAAATGGTC CATCAAAAAA TGGCTTTCGC TACCTGGAGA GACGCGCCCG CTGATCCTTT    3720

GCGAATACGC CCACGCGATG GGTAACAGTC TTGGCGGTTT CGCTAAATAC TGGCAGGCGT    3780

TTCGTCAGTA TCCCCGTTTA CAGGGCGGCT TCGTCTGGGA CTGGGTGGAT CAGTCGCTGA    3840

TTAAATATGA TGAAAACGGC AACCCGTGGT CGGCTTACGG CGGTGATTTT GGCGATACGC    3900

CGAACGATCG CCAGTTCTGT ATGAACGGTC TGGTCTTTGC CGACCGCACG CCGCATCCAG    3960

CGCTGACGGA AGCAAAACAC CAGCAGCAGT TTTTCCAGTT CCGTTTATCC GGGCAAACCA    4020

TCGAAGTGAC CAGCGAATAC CTGTTCCGTC ATAGCGATAA CGAGCTCCTG CACTGGATGG    4080

TGGCGCTGGA TGGTAAGCCG CTGGCAAGCG GTGAAGTGCC TCTGGATGTC GCTCCACAAG    4140

GTAAACAGTT GATTGAACTG CCTGAACTAC CGCAGCCGGA GAGCGCCGGG CAACTCTGGC    4200

TCACAGTACG CGTAGTGCAA CCGAACGCGA CCGCATGGTC AGAAGCCGGG CACATCAGCG    4260

CCTGGCAGCA GTGGCGTCTG GCGGAAAACC TCAGTGTGAC GCTCCCCGCC GCGTCCCACG    4320

CCATCCCGCA TCTGACCACC AGCGAAATGG ATTTTTGCAT CGAGCTGGGT AATAAGCGTT    4380

GGCAATTTAA CCGCCAGTCA GGCTTTCTTT CACAGATGTG GATTGGCGAT AAAAAACAAC    4440

TGCTGACGCC GCTGCGCGAT CAGTTCACCC GTGCACCGCT GGATAACGAC ATTGGCGTAA    4500

GTGAAGCGAC CCGCATTGAC CCTAACGCCT GGGTCGAACG CTGGAAGGCG GCGGGCCATT    4560

ACCAGGCCGA AGCAGCGTTG TTGCAGTGCA CGGCAGATAC ACTTGCTGAT GCGGTGCTGA    4620

TTACGACCGC TCACGCGTGG CAGCATCAGG GGAAAACCTT ATTTATCAGC CGGAAAACCT    4680

ACCGGATTGA TGGTAGTGGT CAAATGGCGA TTACCGTTGA TGTTGAAGTG GCGAGCGATA    4740

CACCGCATCC GGCGCGGATT GGCCTGAACT GCCAGCTGGC GCAGGTAGCA GAGCGGGTAA    4800

ACTGGCTCGG ATTAGGGCCG CAAGAAAACT ATCCCGACCG CCTTACTGCC GCCTGTTTTG    4860

ACCGCTGGGA TCTGCCATTG TCAGACATGT ATACCCCGTA CGTCTTCCCG AGCGAAAACG    4920

GTCTGCGCTG CGGGACGCGC GAATTGAATT ATGGCCCACA CCAGTGGCGC GGCGACTTCC    4980
```

```
AGTTCAACAT CAGCCGCTAC AGTCAACAGC AACTGATGGA AACCAGCCAT CGCCATCTGC    5040

TGCACGCGGA AGAAGGCACA TGGCTGAATA TCGACGGTTT CCATATGGGG ATTGGTGGCG    5100

ACGACTCCTG GAGCCCGTCA GTATCGGCGG AATTCCAGCT GAGCGCCGGT CGCTACCATT    5160

ACCAGTTGGT CTGGTGTCAA AAATAATAAT AACCGGGCAG GGGGGATCCG AAGGCGGGGA    5220

CAGCAGTGCA GTGGTGGACA GAAAGCAAGT GATCTAGGCC AGCAGCCTCC CTAAAGGGAC    5280

TTCAGCCCAC AAAGCCAAAC TTGTGGCTTT AATACAAGCT CTGTAAATGG TAAAAAAAAA    5340

AAAGTCTACA CGGACAGCAG GTATGCTCTT GCCACTGTAC AGAGCAATAT ACAGACAAAG    5400

AGAACTGTTG ACATCTGCAG AGAAAGACCT AAGATGCTGT GGCTAAAAGA AATCAGATGG    5460

CAAATCTAAC CGCCCAGGCA TCCTAAAGAG CAATGATCCT GACAGTCTGA AGACTATCAA    5520

GTTATAGACA AATTAAGACT GGTAAAAAAA ACCCTGTATA AAATAGTAAA AACTGAAAAA    5580

AGAAAACTAG TCCTCTCATG AGAAGACAGA CCTGACATCT ACTGAAAAAT AGACTTTACT    5640

GGAAAAAATA TGTGTATGAA TACCTTCTAG TTTTTGTGAA CGTTCTCAAG ATGGATAAAA    5700

GCTTTTCCTT GTAAAACGAG ACTGATCAGA TAGTCATCAA GAAGATTGTT AAAGAAAATT    5760

TTCCAAGGTT CGGAGTGCCA AAAGCAATAG TGTCAGATAA TGGTCCTGCC TTTGTTGCCC    5820

AGGTAAGTCA GGGTGTGGCC AAGTATTTAG AGGTCAAATG AAAATTCCAT TGTGTGTACA    5880

GACCTCAGAG CTCAGGAAAG ATAAAAAAGA ATAAATAAAA CTCTAAACAG ACCTTGACAA    5940

AATTAATCCT AGAGACTGGC ACAGACTTAC TTGGTACTCC TTCCCCTTGC CCTATTTAGA    6000

ACTGAGAATA CTCCCTCTTG ATTCGGTTTT ACTCTTTTTA AGATCCTTTA TGGGGCTCCT    6060

ATGCCATCAC TGTCTTAAAT GATGTGTTTA AACCTATGTT GTTATAATAA TGATCTATAT    6120

GTTAAGTTAA AAGGCTTGCA GGTGGTGCAG AAAGAAGTCT GGTCACAACT GGCTACAGTG    6180

AACAAGCTGG GTACCCCAAG GACATCTTAC CAGTTCCAGC CAGAGATCTG ATCTACGATC    6240

CCCGGGTCGA CCCGGGTCGA CCCTGTGGAA TGTGTGTCAG TTAGGGTGTG GAAAGTCCCC    6300

AGGCTCCCCA GCAGGCAGAA GTATGCAAAG CATGCATCTC AATTAGTCAG CAACCAGGTG    6360

TGGAAAGTCC CCAGGCTCCC CAGCAGGCAG AAGTATGCAA AGCATGCATC TCAATTAGTC    6420

AGCAACCATA GTCCCGCCCC TAACTCCGCC CATCCCGCCC CTAACTCCGC CCAGTTCCGC    6480

CCATTCTCCG CCCCATGGCT GACTAATTTT TTTTATTTAT GCAGAGGCCG AGGCCGCCTC    6540

GGCCTCTGAG CTATTCCAGA AGTAGTGAGG AGGCTTTTTT GGAGGCCTAG CTTTTGCAA    6600

AAAGCTTCAC GCTGCCGCAA GCACTCAGGG CGCAAGGGCT GCTAAAGGAA GCGGAACACG    6660

TAGAAAGCCA GTCCGCAGAA ACGGTGCTGA CCCCGGATGA ATGTCAGCTA CTGGGCTATC    6720

TGGACAAGGG AAAACGCAAG CGCAAAGAGA AGCAGGTAG CTTGCAGTGG GCTTACATGG    6780

CGATAGCTAG ACTGGGCGGT TTTATGGACA GCAAGCGAAC CGGAATTGCC AGCTGGGGCG    6840

CCCTCTGGTA AGGTTGGGAA GCCCTGCAAA GTAAACTGGA TGGCTTTCTT GCCGCCAAGG    6900

ATCTGATGGC GCAGGGGATC AAGATCTGAT CAAGAGACAG GATGAGGATC GTTTCGCATG    6960

ATTGAACAAG ATGGATTGCA CGCAGGTTCT CCGGCCGCTT GGGTGGAGAG GCTATTCGGC    7020

TATGACTGGG CACAACAGAC AATCGGCTGC TCTGATGCCG CCGTGTTCCG GCTGTCAGCG    7080

CAGGGGCGCC CGGTTCTTTT TGTCAAGACC GACCTGTCCG GTGCCCTGAA TGAACTGCAG    7140

GACGAGGCAG CGCGGCTATC GTGGCTGGCC ACGACGGGCG TTCCTTGCGC AGCTGTGCTC    7200

GACGTTGTCA CTGAAGCGGG AAGGGACTGG CTGCTATTGG GCGAAGTGCC GGGGCAGGAT    7260

CTCCTGTCAT CTCACCTTGC TCCTGCCGAG AAAGTATCCA TCATGGCTGA TGCAATGCGG    7320

CGGCTGCATA CGCTTGATCC GGCTACCTGC CCATTCGACC ACCAAGCGAA ACATCGCATC    7380
```

```
GAGCGAGCAC GTACTCGGAT GGAAGCCGGT CTTGTCGATC AGGATGATCT GGACGAAGAG    7440

CATCAGGGGC TCGCGCCAGC CGAACTGTTC GCCAGGCTCA AGGCGCGCAT GCCCGACGGC    7500

GAGGATCTCG TCGTGACCCA TGGCGATGCC TGCTTGCCGA ATATCATGGT GGAAAATGGC    7560

CGCTTTTCTG GATTCATCGA CTGTGGCCGG CTGGGTGTGG CGGACCGCTA TCAGGACATA    7620

GCGTTGGCTA CCCGTGATAT TGCTGAAGAG CTTGGCGGCG AATGGGCTGA CCGCTTCCTC    7680

GTGCTTTACG GTATCGCCGC TCCCGATTCG CAGCGCATCG CCTTCTATCG CCTTCTTGAC    7740

GAGTTCTTCT GAGCGGGACT CTGGGGTTCG AAATGACCGA CCAAGCGACG CCCAACCTGC    7800

CATCACGAGA TTTCGATTCC ACCGCCGCCT TCTATGAAAG GTTGGGCTTC GGAATCGTTT    7860

TCCGGGACGG AATTCGTAAT CTGCTGCTTG CAAACAAAAA AACCACCGCT ACCAGCGGGA    7920

GTTTGTTTGC CGGATCAAGA GCTACCAACT CTTTTTCCGA AGGTAACTGG CTTCAGCAGA    7980

GCGCAGATAC CAAATACTGT CCTTCTAGTG TAGCCGTAGT TAGGCCACCA CTTCAAGAAC    8040

TCTGTAGCAC CGCCTACATA CCTCGCTCTG CTAATCCTGT TACCAGTGGC TGCTGCCAGT    8100

GGCGATAAGT CGTGTCTTAC CGGGTTGGAC TCAAGACGAT AGTTACCGGA TAAGGCGCAG    8160

CGGTCGGGCT GAACGGGGGG TTCGTGCACA CAGCCCAGCT TGGAGCGAAC GACCTACACC    8220

GAACTGAGAT ACCTACAGCG TGAGCATTGA GAAAGCGCCA CGCTTCCCGA AGGGAGAAAG    8280

GCGGACAGGT ATCCGGTAAG CGGCAGGGTC GGAACAGGAG AGCGCACGAG GGAGCTTCCA    8340

GGGGGAAACG CCTGGTATCT TTATAGTCCT GTCGGGTTTC GCCACCTCTG ACTTGAGCGT    8400

CGATTTTTGT GATGCTCGTC AGGGGGGCGG AGCCTATGGA AAAACGCCAG CAACGCCGAG    8460

ATGCGCCGCC TCGAGAACCC TGGCCCTATT ATTGGGTGGA CTAACCATGG GGGGAATTGC    8520

CGCTGGAATA GGAACAGGGA CTACTGCTCT AATGGCCACT CAGCAATTCC AGCAGCTCCA    8580

AGCCGCAGTA CAGGATGATC TCAGGGAGGT TGAAAAATCA ATCTCTAACC TAGAAAAGTC    8640

TCTCACTTCC CTGTCTGAAG TTGTCCTACA GAATCGAAGG GGCCTAGACT TGTTATTTCT    8700

AAAAGAAGGA GGGCTGTGTG CTGCTCTAAA AGAAGAATGT TGCTTCTATG CGGACCACAC    8760

AGGACTAGTG AGAGACAGCA TGGCCAAATT GAGAGAGAGG CTTAATCAGA GACAGAAACT    8820

GTTTGAGTCA ACTCAAGGAT GGTTTGAGGG ACTGTTTAAC AGATCCCCTT GGTTTACCAC    8880

CTTGATATCT ACCATTATGG GACCCCTCAT TGTACTCCTA ATGATTTTGC TCTTCGGACC    8940

CTGCATTCTT AATCGATTAG TCCAATTTGT TAAAGACAGG ATATCAGTGG TCCAGGCTCT    9000

AGTTTTGACT CAACAATATC ACCAGCTGAA GCCTATAGAG TACGAGCCAT AGATAAAATA    9060

AAAGATTTTA TTTAGTCTCC AGAAAAAGGG GGG                                 9093
```

(2) INFORMATION FOR SEQ ID NO: 24:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
GACTAACCTT GATTCCCTGG AGGCGGGGGT CTTTCATTTG GGGGCT                    46
```

(2) INFORMATION FOR SEQ ID NO: 25:

(i) SEQUENCE CHARACTERISTICS:
        (A) LENGTH: 4834 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 25:

```
TGAAGAATAA AAAATTACTG GCCTCTTGTG AGAACATGAA CTTTCACCTC GGAGCCCACC      60
CCCTCCCATC TGGAAAACAT ACTTGAGAAA ACATTTTCT GGAACAACCA CAGAATGTTT      120
CAACAGGCCA GATGTATTGC CAAACACAGG ATATGACTCT TTGGTTGAGT AAATTTGTGG     180
TTGTTAAACT TCCCCTATTC CCTCCCCATT CCCCCTCCCA GTTTGTGGTT TTTTCCTTTA     240
AAAGCTTGTG AAAAATTTGA GTCGTCGTCG AGACTCCTCT ACCCTGTGCA AAGGTGTATG     300
AGTTTCGACC CCAGAGCTCT GTGTGCTTTC TGTTGCTGCT TTATTTCGAC CCCAGAGCTC     360
TGGTCTGTGT GCTTTCATGT CGCTGCTTTA TTAAATCTTA CCTTCTACAT TTATGTATG     420
GTCTCAGTGT CTTCTTGGGT ACGCGGCTGT CCCGGGACTT GAGTGTCTGA GTGAGGGTCT     480
TCCCTCGAGG GTCTTTCATT TGGTACATGG GCCGGGAATT CGAGAATCTT TCATTTGGTG     540
CATTGGCCGG GAATTCGAAA ATCTTTCATT TGGTGCATTG GCCGGGAAAC AGCGCGACCA     600
CCCAGAGGTC CTAGACCCAC TTAGAGGTAA GATTCTTTGT TCTGTTTTGG TCTGATGTCT     660
GTGTTCTGAT GTCTGTGTTC TGTTTCTAAG TCTGGTGCGA TCGCAGTTTC AGTTTTGCGG     720
ACGCTCAGTG AGACCGCGCT CCGAGAGGGA GTGCGGGGTG GATAAGGATA GACGTGTCCA     780
GGTGTCCACC GTCCGTTCGC CCTGGGAGAC GTCCAGGAG GAACAGGGGA GGATCAGGGA     840
CGCCTGGTGG ACCCCTTTGA AGGCAAGAG ACCATTTGGG GTTGCGAGAT CGTGGGTTCG      900
AGTCCCACCT CGTGCCCAGT TGCGAGATCG TGGGTTCGAG TCCCACCTCG TGTTTTGTTG     960
CGAGATCGTG GGTTCGAGTC CCACCTCGCG TCTGGTCACG GGATCGTGGG TTCGAGTCCC    1020
ACCTCGTGTT TTGTTGCGAG ATCGTGGGTT CGAGTCCCAC CTCGCGTCTG GTCACGGGAT    1080
CGTGGGTTCG AGTCCCACCT CGTGCAGAGG GTCTCAATTG GCCGGCCTTA GAGAGGCCAT    1140
CTGATTCTTC TGGTTTCTCT TTTTGTCTTA GTCTCGTGTC CGCTCTTGTT GTGACTACTG    1200
TTTTTCTAAA AATGGGACAA TCTGTGTCCA CTCCCCTTTC TCTGACTCTG GTTCTGTCGC    1260
TTGGTAATTT TGTTTGTTTA CGTTTGTTTT TGTGAGTCGT CTATGTTGTC TGTTACTATC    1320
TTGTTTTTGT TTGTGGTTTA CGGTTTCTGT GTGTGTCTTG TGTGTCTCTT TGTGTTCAGA    1380
CTTGGACTGA TGACTGACGA CTGTTTTTAA GTTATGCCTT CTAAAATAAG CCTAAAAATC    1440
CTGTCAGATC CCTATGCTGA CCACTTCCTT TCAGATCAAC AGCTGCCCTG CCTCCCACTC    1500
CAACTCCAGA GAGCAGCCAG CGGGTCACAG TGGTCCCGCC CATGAACCTG GAGCCTAGGG    1560
AAAAATGAGC TCGGAAATCC GGAGCAAATG AGGAGTGGTC CCTGAGAAGT CAGTGGCCTA    1620
AATGTTGTGG CTGCTGAAGC AAAAGAAGAG GAGGCTGTTC GAGTAGCCGG CCAAGAGCGC    1680
CGCGGGTTCC CAGGCAGCTT CTCATTCCCC TGTCCCTCCC ATCCCGTCTC TTGTTAACAG    1740
AAAAACTGCT TTCACTTTGA GATATGAGTG GCCCGATACA GCCAGCTGTG AGAGCTGTAC    1800
TCCCTTCCCT GCCCCACGTG TTTTCTCTTC TCAGGCGACC CCTCCCTGAG CTGCTGGCAG    1860
TGAGTCTGTT CTAAGCTCCA GTGAGGGAGG CATCCGCCCA CTTGGGGCTT CTGTCCAAGG    1920
TAAGGAGCAC CTGTGAGTCT AACTGCCAGG CTCTGATGGG GGTCTCGTCT CTGTGGGACT    1980
AGAAAGTGTC CCAACAATCT GACCAAGGTA ACAGGAAGTT AAGACAAAGA CAGAGACCAA    2040
AGTCAGAATC AGAGCTGTGC TGTGAGACAA AAAGATAAAA AAATAAAAT GCTGGCCACA     2100
AAAGTCAGGA AAACTAGAAA ACTTAGATAG TACCTGGCAA CAAAAGAAAG CTTTTGGCTA    2160
```

```
AAGATCAACG TGTATACTGT AAAGAAAATG AGCACTGGGT GAGAGACTGC CCCAACAAAA    2220

AGAAGAGGAG CCCCCCTCAT GACCAAACCC TTCACCTGTT CGTGGCTAAA AGTAAAGAGA    2280

TAACAAAAGG GGTGCTAACA CAGAAGCTGA GTCCTTAAAA GAGTCCGGTG GCCTACCTGT    2340

TGAAGCAGCT AAAAAAGAGA CTGTGTTTCA TACTCCTCCA CTGACCAGTG CAAAACAAGC    2400

TAAAAAGTTC CTGGGCACTG CGGGCTTTTG CAGATTGTGG ATTCCAGGTT TTGCTGAGTT    2460

AAAGAGATAA ACAGCCCTTC GTATAGAAAA ATAAAAAACA ACCTTGGATG TCCTTGGATG    2520

CTATTGAGAC TGCCCTAATG TTGTCCCCAG CTATGGGACT CCTAGATGTG ACTGAGAACA    2580

AAGGTATTGC CAAAGAAGTT CTTACTCAGA GATTGGGACC CTGAAAAAGA CCTGTGGCAT    2640

ACTTGTAAGA AATTAGACCT GGTGGCTGTA AGATGGCCTG CTTGTCTGCA CATAGTGGCT    2700

TCTGGTCAAG GACGCAGATA AATTGACTCT GAGACAAAAC TTGGCACATG TCCTAGAAAG    2760

TGTGGTTCAG CCCCCATGAC CGATGGCTGA CTAACGCTCT TGAAAACATT ATCCAACTGT    2820

TCCCCTGACC GATGGACACA TTGTCAGAGC TTTTTTTGAC TGAACGAGTG ACCTTCGCTC    2880

CCCCTGCTAT CCTCGATCTC ACTACTGCCT GAGACTTCAC CTACTCATCA TTGTGCTGAC    2940

ATTCTGGCAG AAGAAACTCA TACTCGAAAT GATCTGAAGG ATCAGATCAG CCTTGGCCTG    3000

AGAGTTTGAG CTGGTACACG GATGGCAGTA GCCTGGAGGT TAAGGGTAAG CGGAAGGCGG    3060

GGACAGCAGT GCAGTGGTGG ACAGAAAGCA AGTGATCTAG GCCAGCAGCC TCCCTAAAGG    3120

GACTTCAGCC CACAAAGCCA AACTTGTGGC TTTAATACAA GCTCTGTAAA TGGTAAAAAA    3180

AAAAAAGTCT ACACGGACAG CAGGTATGCT CTTGCCACTG TACAGAGCAA TATACAGACA    3240

AAGAGAACTG TTGACATCTG CAGAGAAAGA CCTAAGATGC TGTGGCTAAA AGAAATCAGA    3300

TGGCAAATCT AACCGCCCAG GCATCCTAAA GAGCAATGAT CCTGACAGTC TGAAGACTAT    3360

CAAGTTATAG ACAAATTAAG ACTGGTAAAA AAACCCTGT ATAAAATAGT AAAAACTGAA     3420

AAAAGAAAAC TAGTCCTCTC ATGAGAAGAC AGACCTGACA TCTACTGAAA AATAGACTTT    3480

ACTGGAAAAA ATATGTGTAT GAATACCTTC TAGTTTTTGT GAACGTTCTC AAGATGGATA    3540

AAAGCTTTTC CTTGTAAAAC GAGACTGATC AGATAGTCAT CAAGAAGATT GTTAAAGAAA    3600

ATTTTCCAAG GTTCGGAGTG CCAAAAGCAA TAGTGTCAGA TAATGGTCCT GCCTTTGTTG    3660

CCCAGGTAAG TCAGGGTGTG GCCAAGTATT TAGAGGTCAA ATGAAAATTC CATTGTGTGT    3720

ACAGACCTCA GAGCTCAGGA AAGATAAAAA AGAATAAATA AAACTCTAAA CAGACCTTGA    3780

CAAAATTAAT CCTAGAGACT GGCACAGACT TACTTGGTAC TCCTTCCCCT TGCCCTATTT    3840

AGAACTGAGA ATACTCCCTC TTGATTCGGT TTTACTCTTT TTAAGATCCT TTATGGGGCT    3900

CCTATGCCAT CACTGTCTTA AATGATGTGT TTAAACCTAT GTTGTTATAA TAATGATCTA    3960

TATGTTAAGT TAAAAGGCTT GCAGGTGGTG CAGAAAGAAG TCTGGTCACA ACTGGCTACA    4020

GTGAACAAGC TGGGTACCCC AAGGACATCT TACCAGTTCC AGCCAGAGAT CTGATCTACG    4080

TACACCTGCG TCATGCTGAG ACCCTCAAGC CTCACTAAAA GGGTCCCTGC CTAGTTCTGT    4140

TTACTAATCT GCCTTATTCT GTTTTGTTC CCATGTTAAA GATAGAGTAA ATGCAGTATT     4200

CTCCACATAG AGATATAGAC TTCTGAAATT CTAAGATTAG AATTATTTAC AAGAAGAAGT    4260

GGGGAATGAA GAATAAAAAA TTACTGGCCT CTTGTGAGAA CATGAACTTT CACCTCGGAG    4320

CCCACCCCCT CCCATCTGGA AAACATACTT GAGAAAAACA TTTTCTGGAA CAACCACAGA    4380

ATGTTTCAAC AGGCCAGATG TATTGCCAAA CACAGGATAT GACTCTTTGG TTGAGTAAAT    4440

TTGTGGTTGT TAAACTTCCC CTATTCCCTC CCCATTCCCC CTCCCAGTTT GTGGTTTTTT    4500
```

```
CCTTTAAAAG CTTGTGAAAA ATTTGAGTCG TCGTCGAGAC TCCTCTACCC TGTGCAAAGG    4560

TGTATGAGTT TCGACCCCAG AGCTCTGTGT GCTTTCTGTT GCTGCTTTAT TTCGACCCCA    4620

GAGCTCTGGT CTGTGTGCTT TCATGTCGCT GCTTTATTAA ATCTTACCTT CTACATTTTA    4680

TGTATGGTCT CAGTGTCTTC TTGGGTACGC GGCTGTCCCG GGACTTGAGT GTCTGAGTGA    4740

GGGTCTTCCC TCGAGGGTCT TTCATTTGGT ACATGGGCCG GGAATTCGAG AATCTTTCAT    4800

TTGGTGCATT GGCCGGGAAT TCGAAAATCT TTCA                                4834
```

(2) INFORMATION FOR SEQ ID NO: 26:

(i) SEQUENCE CHARACTERISTICS:
        (A) LENGTH: 4518 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

```
CACCTGACGC GCCCTGTAGC GGCGCATTAA GCGCGGCGGG TGTGGTGGTT ACGCGCAGCG      60

TGACCGCTAC ACTTGCCAGC GCCCTAGCGC CCGCTCCTTT CGCTTTCTTC CCTTCCTTTC     120

TCGCCACGTT CGCCGGCTTT CCCCGTCAAG CTCTAAATCG GGGGCTCCCT TTAGGGTTCC     180

GATTTAGTGC TTTACGGCAC CTCGACCCCA AAAAACTTGA TTAGGGTGAT GGTTCACGTA     240

GTGGGCCATC GCCCTGATAG ACGGTTTTTC GCCCTTTGAC GTTGGAGTCC ACGTTCTTTA     300

ATAGTGGACT CTTGTTCCAA ACTGGAACAA CACTCAACCC TATCTCGGTC TATTCTTTTG     360

ATTTATAAGG GATTTTGCCG ATTTCGGCCT ATTGGTTAAA AAATGAGCTG ATTTAACAAA     420

AATTTAACGC GAATTTTAAC AAAATATTAA CGCTTACAAT TTACGCGTTA AGATACATTG     480

ATGAGTTTGG ACAAACCACA ACTAGAATGC AGTGAAAAAA ATGCTTTATT TGTGAAATTT     540

GTGATGCTAT TGCTTTATTT GTAACCATTA TAAGCTGCAA TAAACAAGTT AACAACAACA     600

ATTGCATTCA TTTTATGTTT CAGGTTCAGG GGGAGGTGTG GGAGGTTTTT TAAAGCAAGT     660

AAAACCTCTA CAAATGTGGT ATGGCTGATT ATGATCATGA ACAGACTGTG AGGACTGAGG     720

GGCCTGAAAT GAGCCTTGGG ACTGTGAATC TAAAATACAC AAACAATTAG AATCAGTAGT     780

TTAACACATT ATACACTTAA AAATTGGATC TCCATTCGCC ATTCAGGCTG CGCAACTGTT     840

GGGAAGGGCG ATCGGTGCGG GCCTCTTCGC TATTACGCCA GCTGGCGAAA GGGGGATGTG     900

CTGCAAGGCG ATTAAGTTGG GTAACGCCAG GGTTTTCCCA GTCACGACGT TGTAAAACGA     960

CGGCCAGTGA ATTGTAATAC GACTCACTAT AGGGCGAATT GGGTACACTT ACCTGGTACC    1020

CCACCCGGGT GGAAAATCGA TGGGCCCGCG GCCGCTCTAG AAGTACTCTC GAGAAGCTTT    1080

TTGAATTCTT TGGATCCACT AGTGTCGACC TGCAGGCGCG CGAGCTCCAG CTTTTGTTCC    1140

CTTTAGTGAG GGTTAATTTC GAGCTTGGCG TAATCAAGGT CATAGCTGTT TCCTGTGTGA    1200

AATTGTTATC CGCTCACAAT TCCACACAAT ATACGAGCCG GAAGTATAAA GTGTAAAGCC    1260

TGGGGTGCCT AATGAGTGAG CTAACTCACA GTAATTGCGG CTAGCGGATC TGACGGTTCA    1320

CTAAACCAGC TCTGCTTATA TAGACCTCCC ACCGTACACG CCTACCGCCC ATTTGCGTCA    1380

ATGGGCGGA GTTGTTACGA CATTTTGGAA AGTCCCGTTG ATTTTGGTGC CAAAACAAAC    1440

TCCCATTGAC GTCAATGGGG TGGAGACTTG GAAATCCCCG TGAGTCAAAC CGCTATCCAC    1500

GCCCATTGAT GTACTGCCAA AACCGCATCA CCATGGTAAT AGCGATGACT AATACGTAGA    1560

TGTACTGCCA AGTAGGAAAG TCCCATAAGG TCATGTACTG GGCATAATGC CAGGCGGGCC    1620
```

-continued

```
ATTTACCGTC ATTGACGTCA ATAGGGGGCG TACTTGGCAT ATGATACACT TGATGTACTG    1680

CCAAGTGGGC AGTTTACCGT AAATACTCCA CCCATTGACG TCAATGGAAA GTCCCTATTG    1740

GCGTTACTAT GGGAACATAC GTCATTATTG ACGTCAATGG GCGGGGGTCG TTGGGCGGTC    1800

AGCCAGGCGG GCCATTTACC GTAAGTTATG TAACGCGGAA CTCCATATAT GGGCTATGAA    1860

CTAATGACCC CGTAATTGAT TACTATTAAT AACTAATGCA TGGCGGTAAT ACGGTTATCC    1920

ACAGAATCAG GGGATAACGC AGGAAAGAAC ATGTGAGCAA AAGGCCAGCA AAAGGCCAGG    1980

AACCGTAAAA AGGCCGCGTT GCTGGCGTTT TTCCATAGGC TCCGCCCCCC TGACGAGCAT    2040

CACAAAAATC GACGCTCAAG TCAGAGGTGG CGAAACCCGA CAGGACTATA AGATACCAG    2100

GCGTTTCCCC CTGGAAGCTC CCTCGTGCGC TCTCCTGTTC CGACCCTGCC GCTTACCGGA    2160

TACCTGTCCG CCTTTCTCCC TTCGGAAGC GTGGCGCTTT CTCATAGCTC ACGCTGTAGG    2220

TATCTCAGTT CGGTGTAGGT CGTTCGCTCC AAGCTGGGCT GTGTGCACGA ACCCCCCGTT    2280

CAGCCCGACC GCTGCGCCTT ATCCGGTAAC TATCGTCTTG AGTCCAACCC GGTAAGACAC    2340

GACTTATCGC CACTGGCAGC AGCCACTGGT AACAGGATTA GCAGAGCGAG GTATGTAGGC    2400

GGTGCTACAG AGTTCTTGAA GTGGTGGCCT AACTACGGCT ACACTAGAAG GACAGTATTT    2460

GGTATCTGCG CTCTGCTGAA GCCAGTTACC TTCGGAAAAA GAGTTGGTAG CTCTTGATCC    2520

GGCAAACAAA CCACCGCTGG TAGCGGTGGT TTTTTTGTTT GCAAGCAGCA GATTACGCGC    2580

AGAAAAAAAG GATCTCAAGA AGATCCTTTG ATCTTTTCTA CGGGGTCTGA CGCTCAGTGG    2640

AACGAAAACT CACGTTAAGG GATTTTGGTC ATGAGATTAT CAAAAAGGAT CTTCACCTAG    2700

ATCCTTTTAA ATTAAAAATG AAGTTTTAAA TCAATCTAAA GTATATATGA GTAACCTGAG    2760

GCTATGGCAG GGCCTGCCGC CCCGACGTTG GCTGCGAGCC CTGGGCCTTC ACCCGAACTT    2820

GGGGGGTGGG GTGGGAAAA GGAAGAAACG CGGGCGTATT GGCCCCAATG GGGTCTCGGT    2880

GGGGTATCGA CAGAGTGCCA GCCCTGGGAC CGAACCCCGC GTTTATGAAC AAACGACCCA    2940

ACACCGTGCG TTTTATTCTG TCTTTTTATT GCCGTCATAG CGCGGGTTCC TTCCGGTATT    3000

GTCTCCTTCC GTGTTTCAGT TAGCCTCCCC CTAGGGTGGG CGAAGAACTC CAGCATGAGA    3060

TCCCCGCGCT GGAGGATCAT CCAGCCGGCG TCCCGGAAAA CGATTCCGAA GCCCAACCTT    3120

TCATAGAAGG CGGCGGTGGA ATCGAAATCT CGTGATGGCA GGTTGGGCGT CGCTTGGTCG    3180

GTCATTTCGA ACCCCAGAGT CCCGCTCAGA AGAACTCGTC AAGAAGGCGA TAGAAGGCGA    3240

TGCGCTGCGA ATCGGGAGCG GCGATACCGT AAAGCACGAG GAAGCGGTCA GCCCATTCGC    3300

CGCCAAGCTC TTCAGCAATA TCACGGGTAG CCAACGCTAT GTCCTGATAG CGGTCCGCCA    3360

CACCCAGCCG GCCACAGTCG ATGAATCCAG AAAAGCGGCC ATTTTCCACC ATGATATTCG    3420

GCAAGCAGGC ATCGCCATGG GTCACGACGA GATCCTCGCC GTCGGGCATG CTCGCCTTGA    3480

GCCTGGCGAA CAGTTCGGCT GGCGCGAGCC CCTGATGCTC TTCGTCCAGA TCATCCTGAT    3540

CGACAAGACC GGCTTCCATC CGAGTACGTG CTCGCTCGAT GCGATGTTTC GCTTGGTGGT    3600

CGAATGGGCA GGTAGCCGGA TCAAGCGTAT GCAGCCGCCG CATTGCATCA GCCATGATGG    3660

ATACTTTCTC GGCAGGAGCA AGGTGAGATG ACAGGAGATC CTGCCCCGGC ACTTCGCCCA    3720

ATAGCAGCCA GTCCCTTCCC GCTTCAGTGA CAACGTCGAG CACAGCTGCG CAAGGAACGC    3780

CCGTCGTGGC CAGCCACGAT AGCCGCGCTG CCTCGTCTTG CAGTTCATTC AGGGCACCGG    3840

ACAGGTCGGT CTTGACAAAA AGAACCGGGC GCCCCTGCGC TGACAGCCGG AACACGCGG    3900

CATCAGAGCA GCCGATTGTC TGTTGTGCCC AGTCATAGCC GAATAGCCTC TCCACCCAAG    3960

CGGCCGGAGA ACCTGCGTGC AATCCATCTT GTTCAATCAT GCGAAACGAT CCTCATCCTG    4020
```

```
TCTCTTGATC GATCTTTGCA AAAGCCTAGG CCTCCAAAAA AGCCTCCTCA CTACTTCTGG      4080

AATAGCTCAG AGGCCGAGGC GGCCTCGGCC TCTGCATAAA TAAAAAAAAT TAGTCAGCCA      4140

TGGGGCGGAG AATGGGCGGA ACTGGGCGGA GTTAGGGGCG GGATGGGCGG AGTTAGGGGC      4200

GGGACTATGG TTGCTGACTA ATTGAGATGC ATGCTTTGCA TACTTCTGCC TGCTGGGGAG      4260

CCTGGGGACT TTCCACACCT GGTTGCTGAC TAATTGAGAT GCATGCTTTG CATACTTCTG      4320

CCTGCTGGGG AGCCTGGGGA CTTTCCACAC CCTAACTGAC ACACATTCCA CAGCTGGTTC      4380

TTTCCGCCTC AGGACTCTTC CTTTTTCAAT ATTATTGAAG CATTTATCAG GGTTATTGTC      4440

TCATGAGCGG ATACATATTT GAATGTATTT AGAAAAATAA ACAAATAGGG GTTCCGCGCA      4500

CATTTCCCCG AAAAGTGC                                                   4518

(2) INFORMATION FOR SEQ ID NO: 27:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 27:

CTCCACATAG AGATATAGAC TTCTG                                             25

(2) INFORMATION FOR SEQ ID NO: 28:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 28:

CGATCTTATT AATTAACTGG AGTTTTGAGC CCRMCCCCTC CCATC                       45

(2) INFORMATION FOR SEQ ID NO: 29:

(i) SEQUENCE CHARACTERISTICS:
         (A) LENGTH: 5594 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 29:

TGCATTAGTT ATTAATAGTA ATCAATTACG GGGTCATTAG TTCATAGCCC ATATATGGAG        60

TTCCGCGTTA CATAACTTAC GGTAAATGGC CCGCCTGGCT GACCGCCCAA CGACCCCCGC      120

CCATTGACGT CAATAATGAC GTATGTTCCC ATAGTAACGC CAATAGGGAC TTTCCATTGA      180

CGTCAATGGG TGGAGTATTT ACGGTAAACT GCCCACTTGG CAGTACATCA AGTGTATCAT      240

ATGCCAAGTA CGCCCCCTAT TGACGTCAAT GACGGTAAAT GGCCCGCCTG GCATTATGCC      300

CAGTACATGA CCTTATGGGA CTTTCCTACT TGGCAGTACA TCTACGTATT AGTCATCGCT      360

ATTACCATGG TGATGCGGTT TTGGCAGTAC ATCAATGGGC GTGGATAGCG GTTTGACTCA      420

CGGGGATTTC CAAGTCTCCA CCCCATTGAC GTCAATGGGA GTTTGTTTTG GCACCAAAAT      480

CAACGGGACT TTCCAAAATG TCGTAACAAC TCCGCCCCAT TGACGCAAAT GGGCGGTAGG      540
```

```
CGTGTACGGT GGGAGGTCTA TATAAGCAGA GCTGGTTTAG TGAACCGTCA GATCCGCGCC    600

AGTCCTCCGA TTGACTGAGT CGCCCGGGTA CCCGTGTATC CAATAAACCC TCTTGCAGTT    660

GCATCCGACT TGTGGTCTCG CTGTTCCTTG GGAGGGTCTC CTCTGAGTGA TTGACTACCC    720

GTCAGCGGGG GTCTTTCATT TGGGGGCTCG TCCGGGATCG GGAGACCCCT GCCCAGGGAC    780

CACCGACCCA CCACCGGGAG GTAAGCTGGC CAGCAACTTA TCTGTGTCTG TCCGATTGTC    840

TAGTGTCTAT GACTGATTTT ATGCGCCTGC GTCGGTACTA GTTAGCTAAC TAGCTCTGTA    900

TCTGGCGGAC CCGTGGTGGA ACTGACGAGT TCGGAACACC CGGCCGCAAC CCTGGGAGAC    960

GTCCCAGGAG GAACAGGGGA GGATCAGGGA CGCCTGGTGG ACCCCTTTGA AGGCCAAGAG   1020

ACCATTTGGG GTTGCGAGAT CGTGGGTTCG AGTCCCACCT CGTGCCCAGT TGCGAGATCG   1080

TGGGTTCGAG TCCCACCTCG TGTTTTGTTG CGAGATCGTG GGTTCGAGTC CCACCTCGTT   1140

TCTGGTCACG GGATCGTGGG TTCGAGTCCC ACCTCGTGTT TTGTTGCGAG ATCGTGGGTT   1200

CGAGTCCCAC CTCGCGTCTG GTCACGGGAT CGTGGGTTCG AGTCCCACCT CGTGCAGAGG   1260

GTCTCAATTG GCCGGCCTTA GAGAGGCCAT CTGATTCTTC TGGTTTCTCT TTTTGTCTTA   1320

GTCTCGTGTC CGCTCTTGTT GTGACTACTG TTTTTCTAAA AATGGGACAA TCTGTGTCCA   1380

CTCCCCTTTC TCTGACTCTG GTTCTGTCGC TTGGTAATTT TGTTTGTTTA CGTTTGTTTT   1440

TGTGAGTCGT CTATGTTGTC TGTTACTATC TTGTTTTTGT TTGTGGTTTA CGGTTTCTGT   1500

GTGTGTCTTG TGTGTCTCTT TGTGTTCAGA CTTGGACTGA TGACTGACGA CTGTTTTTAA   1560

GTTATGCCTT CTAAAATAAG CCTAAAAATC CTGTCAGATC CCTATGCTGA CCACTTCCTT   1620

TCAGATCAAC AGCTGCCCTT ACGTATCGAT GGATCCCTCG ACTAACTAAT AGCCCATTCT   1680

CCAAGGTCGA GCGGGATCAA TTCCGCCCCC CCCTAACGT TACTGGCCGA AGCCGCTTGG    1740

AATAAGGCCG GTGTGCGTTT GTCTATATGT TATTTTCCAC CATATTGCCG TCTTTTGGCA   1800

ATGTGAGGGC CCGGAAACCT GGCCCTGTCT TCTTGACGAG CATTCCTAGG GGTCTTTCCC   1860

CTCTCGCCAA AGGAATGCAA GGTCTGTTGA ATGTCGTGAA GGAAGCAGTT CCTCTGGAAG   1920

CTTCTTGAAG ACAAACAACG TCTGTAGCGA CCCTTTGCAG GCAGCGGAAC CCCCCACCTG   1980

GCGACAGGTG CCTCTGCGGC CAAAAGCCAC GTGTATAAGA TACACCTGCA AAGGCGGCAC   2040

AACCCCAGTG CCACGTTGTG AGTTGGATAG TTGTGGAAAG AGTCAAATGG CTCTCCTCAA   2100

GCGTATTCAA CAAGGGGCTG AAGGATGCCC AGAAGGTACC CCATTGTATG GGATCTGATC   2160

TGGGGCCTCG GTGCACATGC TTTACATGTG TTTAGTCGAG GTTAAAAAAA CGTCTAGGCC   2220

CCCCGAACCA CGGGGACGTG GTTTTCCTTT GAAAAACACG ATAATAATCA TGGCTACAGG   2280

CTCCCGGACG TCCCTGCTCC TGGCTTTTGG CCTGCTCTGC CTGCCCTGGC TTCAAGAGGG   2340

CAGTGCCTTC CCAACCATTC CCTTATCCAG GCTTTTTGAC AACGCTATGC TCCGCGCCCA   2400

TCGTCTGCAC CAGCTGGCCT TTGACACCTA CCAGGAGTTT GAAGAAGCCT ATATCCCAAA   2460

GGAACAGAAG TATTCATTCC TGCAGAACCC CCAGACCTCC CTCTGTTTCT CAGAGTCTAT   2520

TCCGACACCC TCCAACAGGG AGGAAACACA ACAGAAATCC AACCTAGAGC TGCTCCGCAT   2580

CTCCCTGCTG CTCATCCAGT CGTGGCTGGA GCCCGTGCAG TTCCTCAGGA GTGTCTTCGC   2640

CAACAGCCTG GTGTACGGCG CCTCTGACAG CAACGTCTAT GACCTCCTAA AGGACCTAGA   2700

GGAAGGCATC CAAACGCTGA TGGGGAGGCT GGAAGATGGC AGCCCCCGGA CTGGGCAGAT   2760

CTTCAAGCAG ACCTACAGCA AGTTCGACAC AAACTCACAC AACGATGACG CACTACTCAA   2820

GAACTACGGG CTGCTCTACT GCTTCAGGAA GGACATGGAC AAGGTCGAGA CATTCCTGCG   2880
```

-continued

```
CATCGTGCAG TGCCGCTCTG TGGAGGGCAG CTGTGGCTTC TAGCTGCCCG GGTGGCATCC    2940
TGTGACCCCT CCCCAGTGCC TCTCCTGGCC CTGGAAGTTG CCACTCCAGT GCCCACCAGC    3000
CTTGTCCTAA TGTGTGTCAG TTAGGGTGTG GAAAGTCCCC AGGCTCCCA GCAGGCAGAA     3060
GTATGCAAAG CATGCATCTC AATTAGTCAG CAACCAGGTG TGGAAAGTCC CCAGGCTCCC    3120
CAGCAGGCAG AAGTATGCAA AGCATGCATC TCAATTAGTC AGCAACCATA GTCCCGCCCC    3180
TAACTCCGCC CATCCCGCCC CTAACTCCGC CCAGTTCCGC CCATTCTCCG CCCCATGGCT    3240
GACTAATTTT TTTTATTTAT GCAGAGGCCG AGGCCGCCTC GGCCTCTGAG CTATTCCAGA    3300
AGTAGTGAGG AGGCTTTTTT GGAGGCCTAG GCTTTTGCAA AAAGCTTCAC GCTGCCGCAA    3360
GCACTCAGGG CGCAAGGGCT GCTAAAGGAA GCGGAACACG TAGAAAGCCA GTCCGCAGAA    3420
ACGGTGCTGA CCCCGGATGA ATGTCAGCTA CTGGGCTATC TGGACAAGGG AAAACGCAAG    3480
CGCAAAGAGA AAGCAGGTAG CTTGCAGTGG GCTTACATGG CGATAGCTAG ACTGGGCGGT    3540
TTTATGGACA GCAAGCGAAC CGGAATTGCC AGCTGGGGCG CCCTCTGGTA AGGTTGGGAA    3600
GCCCTGCAAA GTAAACTGGA TGGCTTTCTT GCCGCCAAGG ATCTGATGGC GCAGGGGATC    3660
AAGATCTGAT CAAGAGACAG GATGAGGATC GTTTCGCATG ATTGAACAAG ATGGATTGCA    3720
CGCAGGTTCT CCGGCCGCTT GGGTGGAGAG GCTATTCGGC TATGACTGGG CACAACAGAC    3780
AATCGGCTGC TCTGATGCCG CCGTGTTCCG GCTGTCAGCG CAGGGGCGCC CGGTTCTTTT    3840
TGTCAAGACC GACCTGTCCG GTGCCCTGAA TGAACTGCAG GACGAGGCAG CGCGGCTATC    3900
GTGGCTGGCC ACGACGGGCG TTCCTTGCGC AGCTGTGCTC GACGTTGTCA CTGAAGCGGG    3960
AAGGGACTGG CTGCTATTGG GCGAAGTGCC GGGGCAGGAT CTCCTGTCAT CTCACCTTGC    4020
TCCTGCCGAG AAAGTATCCA TCATGGCTGA TGCAATGCGG CGGCTGCATA CGCTTGATCC    4080
GGCTACCTGC CCATTCGACC ACCAAGCGAA ACATCGCATC GAGCGAGCAC GTACTCGGAT    4140
GGAAGCCGGT CTTGTCGATC AGGATGATCT GGACGAAGAG CATCAGGGGC TCGCGCCAGC    4200
CGAACTGTTC GCCAGGCTCA AGGCGCGCAT GCCCGACGGC GAGGATCTCG TCGTGACCCA    4260
TGGCGATGCC TGCTTGCCGA ATATCATGGT GGAAAATGGC CGCTTTTCTG GATTCATCGA    4320
CTGTGGCCGG CTGGGTGTGG CGGACCGCTA TCAGGACATA GCGTTGGCTA CCCGTGATAT    4380
TGCTGAAGAG CTTGGCGGCG AATGGGCTGA CCGCTTCCTC GTGCTTTACG GTATCGCCGC    4440
TCCCGATTCG CAGCGCATCG CCTTCTATCG CCTTCTTGAC GAGTTCTTCT GAGCGGGACT    4500
CTGGGGTTCG AAATGACCGA CCAAGCGACG CCCAACCTCC AGAAAAAGGG GGGAATGAAA    4560
GACCCCACCT GTAGGTTTGG CAAGCTAGCT TAAGTAACGC CATTTTGCAA GGCATGGAAA    4620
AATACATAAC TGAAATAGA GAAGTTCAGA TCAAGGTCAG GAACAGATGG AACAGCTGAA     4680
TATGGGCCAA ACAGGATATC TGTGGTAAGC AGTTCCTGCC CCGGCTCAGG GCCAAGAACA    4740
GATGGAACAG CTGAATATGG GCCAAACAGG ATATCTGTGG TAAGCAGTTC CTGCCCCGGC    4800
TCAGGGCCAA GAACAGATGG TCCCCAGATG CGGTCCAGCC CTCAGCAGTT CTAGAGAAC     4860
CATCAGATGT TTCCAGGGTG CCCCAAGGAC CTGAAATGAC CCTGTGCCTT ATTTGAACTA    4920
ACCAATCAGT TCGCTTCTCG CTTCTGTTCG CGCGCTTCTG CTCCCCGAGC TCAATAAAAG    4980
AGCCCACAAC CCCTCACTCG GGGCGCCAGT AATCTGCTGC TTGCAAACAA AAAAACCACC    5040
GCTACCAGCG GTGGTTTGTT TGCCGGATCA AGAGCTACCA ACTCTTTTTC CGAAGGTAAC    5100
TGGCTTCAGC AGAGCGCAGA TACCAAATAC TGTCCTTCTA GTGTAGCCGT AGTTAGGCCA    5160
CCACTTCAAG AACTCTGTAG CACCGCCTAC ATACCTCGCT CTGCTAATCC TGTTACCAGT    5220
GGCTGCTGCC AGTGGCGATA AGTCGTGTCT TACCGGGTTG GACTCAAGAC GATAGTTACC    5280
```

```
GGATAAGGCG CAGCGGTCGG GCTGAACGGG GGGTTCGTGC ACACAGCCCA GCTTGGAGCG    5340

AACGACCTAC ACCGAACTGA GATACCTACA GCGTGAGCAT TGAGAAAGCG CCACGCTTCC    5400

CGAAGGGAGA AAGGCGGACA GGTATCCGGT AAGCGGCAGG GTCGGAACAG GAGAGCGCAC    5460

GAGGGAGCTT CCAGGGGGAA ACGCCTGGTA TCTTTATAGT CCTGTCGGGT TTCGCCACCT    5520

CTGACTTGAG CGTCGATTTT TGTGATGCTC GTCAGGGGGG CGGAGCCTAT GGAAAAACGC    5580

CAGCAACGCC GAGA                                                     5594
```

(2) INFORMATION FOR SEQ ID NO: 30:

(i) SEQUENCE CHARACTERISTICS:
        (A) LENGTH: 6561 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

```
GATCCCCGGG TCGACCCGGG TCGACCCTGT GGAATGTGTG TCAGTTAGGG TGTGGAAAGT      60

CCCCAGGCTC CCCAGCAGGC AGAAGTATGC AAAGCATGCA TCTCAATTAG TCAGCAACCA     120

GGTGTGGAAA GTCCCCAGGC TCCCCAGCAG GCAGAAGTAT GCAAAGCATG CATCTCAATT     180

AGTCAGCAAC CATAGTCCCG CCCCTAACTC CGCCCATCCC GCCCCTAACT CCGCCCAGTT     240

CCGCCCATTC TCCGCCCCAT GGCTGACTAA TTTTTTTTAT TTATGCAGAG GCCGAGGCCG     300

CCTCGGCCTC TGAGCTATTC CAGAAGTAGT GAGGAGGCTT TTTTGGAGGC CTAGGCTTTT     360

GCAAAAAGCT TCACGCTGCC GCAAGCACTC AGGGCGCAAG GGCTGCTAAA GGAAGCGGAA     420

CACGTAGAAA GCCAGTCCGC AGAAACGGTG CTGACCCCGG ATGAATGTCA GCTACTGGGC     480

TATCTGGACA AGGGAAAACG CAAGCGCAAA GAGAAAGCAG GTAGCTTGCA GTGGGCTTAC     540

ATGGCGATAG CTAGACTGGG CGGTTTTATG GACAGCAAGC GAACCGGAAT TGCCAGCTGG     600

GGCGCCCTCT GGTAAGGTTG GGAAGCCCTG CAAAGTAAAC TGGATGGCTT TCTTGCCGCC     660

AAGGATCTGA TGGCGCAGGG GATCAAGATC TGATCAAGAG ACAGGATGAG GATCGTTTCG     720

CATGATTGAA CAAGATGGAT TGCACGCAGG TTCTCCGGCC GCTTGGGTGG AGAGGCTATT     780

CGGCTATGAC TGGGCACAAC AGACAATCGG CTGCTCTGAT GCCGCCGTGT TCCGGCTGTC     840

AGCGCAGGGG CGCCCGGTTC TTTTTGTCAA GACCGACCTG TCCGGTGCCC TGAATGAACT     900

GCAGGACGAG GCAGCGCGGC TATCGTGGCT GGCCACGACG GGCGTTCCTT GCGCAGCTGT     960

GCTCGACGTT GTCACTGAAG CGGGAAGGGA CTGGCTGCTA TTGGGCGAAG TGCCGGGGCA    1020

GGATCTCCTG TCATCTCACC TTGCTCCTGC CGAGAAAGTA TCCATCATGG CTGATGCAAT    1080

GCGGCGGCTG CATACGCTTG ATCCGGCTAC CTGCCCATTC GACCACCAAG CGAAACATCG    1140

CATCGAGCGA GCACGTACTC GGATGGAAGC CGGTCTTGTC GATCAGGATG ATCTGGACGA    1200

AGAGCATCAG GGGCTCGCGC CAGCCGAACT GTTCGCCAGG CTCAAGGCGC GCATGCCCGA    1260

CGGCGAGGAT CTCGTCGTGA CCCATGGCGA TGCCTGCTTG CCGAATATCA TGGTGGAAAA    1320

TGGCCGCTTT TCTGGATTCA TCGACTGTGG CCGGCTGGGT GTGGCGGACC GCTATCAGGA    1380

CATAGCGTTG GCTACCCGTG ATATTGCTGA AGAGCTTGGC GGCGAATGGG CTGACCGCTT    1440

CCTCGTGCTT TACGGTATCG CCGCTCCCGA TTCGCAGCGC ATCGCCTTCT ATCGCCTTCT    1500

TGACGAGTTC TTCTGAGCGG GACTCTGGGG TTCGAAATGA CCGACCAAGC GACGCCCAAC    1560

CTGCCATCAC GAGATTTCGA TTCCACCGCC GCCTTCTATG AAAGGTTGGG CTTCGGAATC    1620
```

```
GTTTTCCGGG ACGCCGGCTG GATGATCCTC CAGCGCGGGG ATCTCATGCT GGAGTTCTTC    1680

GCCCACCCCG GAATTCGTAA TCTGCTGCTT GCAAACAAAA AAACCACCGC TACCAGCGGT    1740

GGTTTGTTTG CCGGATCAAG AGCTACCAAC TCTTTTTCCG AAGGTAACTG GCTTCAGCAG    1800

AGCGCAGATA CCAAATACTG TCCTTCTAGT GTAGCCGTAG TTAGGCCACC ACTTCAAGAA    1860

CTCTGTAGCA CCGCCTACAT ACCTCGCTCT GCTAATCCTG TTACCAGTGG CTGCTGCCAG    1920

TGGCGATAAG TCGTGTCTTA CCGGGTTGGA CTCAAGACGA TAGTTACCGG ATAAGGCGCA    1980

GCGGTCGGGC TGAACGGGGG GTTCGTGCAC ACAGCCCAGC TTGGAGCGAA CGACCTACAC    2040

CGAACTGAGA TACCTACAGC GTGAGCATTG AGAAAGCGCC ACGCTTCCCG AAGGGAGAAA    2100

GGCGGACAGG TATCCGGTAA GCGGCAGGGT CGGAACAGGA GAGCGCACGA GGGAGCTTCC    2160

AGGGGGAAAC GCCTGGTATC TTTATAGTCC TGTCGGGTTT CGCCACCTCT GACTTGAGCG    2220

TCGATTTTTG TGATGCTCGT CAGGGGGGCG GAGCCTATGG AAAAACGCCA GCAACGCCGA    2280

GATGCGCCGC CTCGAGTACA CCTGCGTCAT GCTGAGACCC TCAAGCCTCA CTAAAAGGGT    2340

CCCTGCCTAG TTCTGTTTAC TAATCTGCCT TATTCTGTTT TTGTTCCCAT GTTAAAGATA    2400

GAGTAAATGC AGTATTCTCC ACATAGAGAT ATAGACTTCT GAAATTCTAA GATTAGAATT    2460

ATTTACAAGA AGAAGTGGGG AATGAAGAAT AAAAAATTAC TGGCCTCTTG TGAGAACATG    2520

AACTTTCACC TCGGAGCCCA CCCCCTCCCA TCTGGAAAAC ATACTTGAGA AAAACATTTT    2580

CTGGAACAAC CACAGAATGT TCAACAGGCA CAGATGTATT GCCAAACACA GGATATGACT    2640

CTTTGGTTGA GTAAATTTGT GGTTGTTAAA CTTCCCCTAT TCCCTCCCCA TTCCCCCTCC    2700

CAGTTTGTGG TTTTTTCCTT TAAAAGCTTG TGAAAAATTT GAGTCGTCGT CGAGACTCCT    2760

CTACCCTGTG CAAAGGTGTA TGAGTTTCGA CCCCAGAGCT CTGTGTGCTT TCTGTTGCTG    2820

CTTTATTTCG ACCCCAGAGC TCTGGTCTGT GTGCTTTCAT GTCGCTGCTT TATTAAATCT    2880

TACCTTCTAC ATTTTATGTA TGGTCTCAGT GTCTTCTTGG GTACGCGGCT GTCCCGGGAC    2940

TTGAGTGTCT GAGTGAGGGT CTTCCCTCGA GGGTCTTTCA TTTGGTACAT GGGCCGGGAA    3000

TTCGAGAATC TTTCATTTGG TGCATTGGCC GGGAATTCGA AAATCTTTCA TTTGGTGCAT    3060

TGGCCGGGAA ACAGCGCGAC CACCCAGAGG TCCTAGACCC ACTTAGAGGT AAGATTCTTT    3120

GTTCTGTTTT GGTCTGATGT CTGTGTTCTG ATGTCTGTGT TCTGTTTCTA AGTCTGGTGC    3180

GATCGCAGTT TCAGTTTTGC GGACGCTCAG TGAGACCGCG CTCCGAGAGG GAGTGCGGGG    3240

TGGATAAGGA TAGACGTGTC CAGGTGTCCA CCGTCCGTTC GCCCTGGGAG ACGTCCCAGG    3300

AGGAACAGGG GAGGATCAGG GACGCCTGGT GGACCCCTTT GAAGGCCAAG AGACCATTTG    3360

GGGTTGCGAG ATCGTGGGTT CGAGTCCCAC CTCGTGCCCA GTTGCGAGAT CGTGGGTTCG    3420

AGTCCCACCT CGTGTTTTGT TGCGAGATCG TGGGTTCGAG TCCCACCTCG CGTCTGGTCA    3480

CGGGATCGTG GGTTCGAGTC CCACCTCGTG TTTTGTTGCG AGATCGTGGG TTCGAGTCCC    3540

ACCTCGCGTC TGGTCACGGG ATCGTGGGTT CGAGTCCCAC CTCGTGCAGA GGGTCTCAAT    3600

TGGCCGGCCT TAGAGAGGCC ATCTGATTCT TCTGGTTTCT CTTTTTGTCT TAGTCTCGTG    3660

TCCGCTCTTG TTGTGACTAC TGTTTTTCTA AAAATGGGAC AATCTGTGTC CACTCCCCTT    3720

TCTCTGACTC TGGTTCTGTC GCTTGGTAAT TTTGTTTGTT TACGTTTGTT TTTGTGAGTC    3780

GTCTATGTTG TCTGTTACTA TCTTGTTTTT GTTTGTGGTT TACGGTTTCT GTGTGTGTCT    3840

TGTGTGTCTC TTTGTGTTCA GACTTGGACT GATGACTGAC GACTGTTTTT AAGTTATGCC    3900

TTCTAAAATA AGCCTAAAAA TCCTGTCAGA TCCCTATGCT GACCACTTCC TTTCAGATCA    3960
```

-continued

```
ACAGCTGCCC TGCCTCCCAC TCCAACTCCA GAGAGCAGCC AGCGGGTCAC AGTGGTCCCG    4020

CCCATGAACC TGGAGCCTAG GGAAAAATGA GCTCGGAAAT CCGGAGCAAA TGAGGAGTGG    4080

TCCCTGAGAA GTCAGTGGCC TAAATGTTGT GGCTGCTGAA GCAAAAGAAG AGGAGGCTGT    4140

TCGAGTAGCC GGCCAAGAGC GCCGCGGGTT CCCAGGCAGC TTCTCATTCC CCTGTCCCTC    4200

CCATCCCGTC TCTTGTTAAC AGAAAAACTG CTTTCACTTT GAGATATGAG TGGCCCGATA    4260

CAGCCAGCTG TGAGAGCTGT ACTCCCTTCC CTGCCCCACG TGTTTTCTCT TCTCAGGCGA    4320

CCCCTCCCTG AGCTGCTGGC AGTGAGTCTG TTCTAAGCTC CAGTGAGGGA GGCATCCGCC    4380

CACTTGGGGC TTCTGTCCAA GGTAAGGAGC ACCTGTGAGT CTAACTGCCA GGCTCTGATG    4440

GGGGTCTCGT CTCTGTGGGA CTAGAAAGTG TCCCAACAAT CTGACCAAGG TAACAGGAAG    4500

TTAAGACAAA GACAGAGACC AAAGTCAGAA TCAGAGCTGT GCTGTGAGAC AAAAAGATAA    4560

AAAAAATAAA ATGCTGGCCA CAAAAGTCAG GAAAACTAGA AAACTTAGAT AGTACCTGGC    4620

AACAAAAGAA AGCTTTTGGC TAAAGATCAA CGTGTATACT GTAAAGAAAA TGAGCACTGG    4680

GTGAGAGACT GCCCCAACAA AAAGAAGAGG AGCCCCCTC ATGACCAAAC CCTTCACCTG     4740

TTCGTGGCTA AAAGTAAAGA GATAACAAAA GGGGTGCTAA CACAGAAGCT GAGTCCTTAA    4800

AAGAGTCCGG TGGCCTACCT GTTGAAGCAG CTAAAAAAGA GACTGTGTTT CATACTCCTC    4860

CACTGACCAG TGCAAAACAA GCTAAAAAGT TCCTGGGCAC TGCGGGCTTT TGCAGATTGT    4920

GGATTCCAGG TTTTGCTGAG TTAAAGAGAT AAACAGCCCT TCGTATAGAA AAATAAAAAA    4980

CAACCTTGGA TGTCCTTGGA TGCTATTGAG ACTGCCCTAA TGTTGTCCCC AGCTATGGGA    5040

CTCCTAGATG TGACTGAGAA CAAAGGTATT GCCAAAGAAG TTCTTACTCA GAGATTGGGA    5100

CCCTGAAAAA GACCTGTGGC ATACTTGTAA GAAATTAGAC CTGGTGGCTG TAAGATGGCC    5160

TGCTTGTCTG CACATAGTGG CTTCTGGTCA AGGACGCAGA TAAATTGACT CTGAGACAAA    5220

ACTTGGCACA TGTCCTAGAA AGTGTGGTTC AGCCCCCATG ACCGATGGCT GACTAACGCT    5280

CTTGAAAACA TTATCCAACT GTTCCCCTGA CCGATGGACA CATTGTCAGA GCTTTTTTTG    5340

ACTGAACGAG TGACCTTCGC TCCCCCTGCT ATCCTCGATC TCACTACTGC CTGAGACTTC    5400

ACCTACTCAT CATTGTGCTG ACATTCTGGC AGAAGAAACT CATACTCGAA ATGATCTGAA    5460

GGATCAGATC AGCCTTGGCC TGAGAGTTTG AGCTGGTACA CGGATGGCAG TAGCCTGGAG    5520

GTTAAGGGTA AGCGGAAGGC GGGGACAGCA GTGCAGTGGT GGACAGAAAG CAAGTGATCT    5580

AGGCCAGCAG CCTCCCTAAA GGGACTTCAG CCCACAAAGC CAAACTTGTG GCTTTAATAC    5640

AAGCTCTGTA AATGGTAAAA AAAAAAAAGT CTACACGGAC AGCAGGTATG CTCTTGCCAC    5700

TGTACAGAGC AATATACAGA CAAAGAGAAC TGTTGACATC TGCAGAGAAA GACCTAAGAT    5760

GCTGTGGCTA AAAGAAATCA GATGGCAAAT CTAACCGCCC AGGCATCCTA AAGAGCAATG    5820

ATCCTGACAG TCTGAAGACT ATCAAGTTAT AGACAAATTA AGACTGGTAA AAAAAACCCT    5880

GTATAAAATA GTAAAAACTG AAAAAGAAA ACTAGTCCTC TCATGAGAAG ACAGACCTGA    5940

CATCTACTGA AAAATAGACT TTACTGGAAA AAATATGTGT ATGAATACCT TCTAGTTTTT    6000

GTGAACGTTC TCAAGATGGA TAAAAGCTTT TCCTTGTAAA ACGAGACTGA TCAGATAGTC    6060

ATCAAGAAGA TTGTTAAAGA AAATTTTCCA AGGTTCGGAG TGCCAAAAGC AATAGTGTCA    6120

GATAATGGTC CTGCCTTTGT TGCCCAGGTA AGTCAGGGTG TGGCCAAGTA TTTAGAGGTC    6180

AAATGAAAAT TCCATTGTGT GTACAGACCT CAGAGCTCAG GAAAGATAAA AAAGAATAAA    6240

TAAAACTCTA AACAGACCTT GACAAAATTA ATCCTAGAGA CTGGCACAGA CTTACTTGGT    6300

ACTCCTTCCC CTTGCCCTAT TTAGAACTGA GAATACTCCC TCTTGATTCG GTTTTACTCT    6360
```

```
TTTTAAGATC CTTTATGGGG CTCCTATGCC ATCACTGTCT TAAATGATGT GTTTAAACCT      6420

ATGTTGTTAT AATAATGATC TATATGTTAA GTTAAAAGGC TTGCAGGTGG TGCAGAAAGA      6480

AGTCTGGTCA CAACTGGCTA CAGTGAACAA GCTGGGTACC CCAAGGACAT CTTACCAGTT      6540

CCAGCCAGAG ATCTGATCTA C                                                6561
```

(2) INFORMATION FOR SEQ ID NO: 31:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

```
GACTAACCTT GATTCCACTG GAGCCGTATT ACCGCCATGC ATTAGTTATT AATAG          55
```

(2) INFORMATION FOR SEQ ID NO: 32:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

```
GACTAACCTT GATTCCACTG GAGTAATTGC GGCTAGCGGA TCTGACG                   47
```

(2) INFORMATION FOR SEQ ID NO: 33:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

```
GACTAACCTT GATTCCACTG GAGACACTTG ACCTCTACCG CGCCAGTCCT CCGATTGACT     60

GAGTCG                                                                 66
```

(2) INFORMATION FOR SEQ ID NO: 34:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

```
GACTAACCTT GATTCCACTG GAGGGATCCG CGCCCATGAT TATTATCG                  48
```

(2) INFORMATION FOR SEQ ID NO: 35:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

GACTAACCTT GATTCCAGCA ATGTCATGGC TACAGGCTCC CGGACGTCCC TGCTC            55

(2) INFORMATION FOR SEQ ID NO: 36:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

GACTAACCTT GATTCCAGCA ATGTTAGGAC AAGGCTGGTG GGCACTGG                    48

(2) INFORMATION FOR SEQ ID NO: 37:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

GACTAACCTT GATTCCACTG GAGGGTCGAC CCTGTGGAAT GTGTGTCAG                   49

(2) INFORMATION FOR SEQ ID NO: 38:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

GACTAACCTT GATTCCACTG GAGAATCTCG TGATGGCAGG TTGGGCGT                    48

(2) INFORMATION FOR SEQ ID NO: 39:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

GACTAACCTT GATTCCACTG AAGAGATTTT ATTTAGTCTC CAGAAAAAGG GGGG             54

(2) INFORMATION FOR SEQ ID NO: 40:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

GACTAACCTT GATTCCACTG AAGCCCCCAA ATGAAAGACC CCCGCTGACG       50

(2) INFORMATION FOR SEQ ID NO: 41:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

GACTAACCTT GATTCCACTG GAGCCGGGAC GGAATTCGTA ATCTGCTGC        49

(2) INFORMATION FOR SEQ ID NO: 42:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

GACTAACCTT GATTCCACTG GAGTTCTCGA GGCGGCGCAT CTCGGCG         47

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

CGCTCTAGAA CTAGTGGATC                                       20

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

GTAATACGAC TCACTATAGG G                                     21

(2) INFORMATION FOR SEQ ID NO: 45:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

CGATCCACTG GAGCTCGGAG CCCACCCCCT CCCATCTAGA GGT             43

(2) INFORMATION FOR SEQ ID NO: 46:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

```
CGTCCTCCTG GAGAGCACAG GGTAGAGGAG TCTCGACGGT CAG          43
```

(2) INFORMATION FOR SEQ ID NO: 47:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

```
CGCAACCCTG GAGACCTCTA GATGGGAGGG GGTGGGCTCC GAG          43
```

(2) INFORMATION FOR SEQ ID NO: 48:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

```
GCAGGACCTG GAGCTGACCG TCGAGACTCC TCTACCCTGT GCT          43
```

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

```
CGCTCTAGAA CTAGTGGATC                                    20
```

(2) INFORMATION FOR SEQ ID NO: 50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

```
GTAATACGAC TCACTATAGG G                                  21
```

(2) INFORMATION FOR SEQ ID NO: 51:

(i) SEQUENCE CHARACTERISTICS:
        (A) LENGTH: 19 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

TACGTATCGA TGGATCCGA                                                19

(2) INFORMATION FOR SEQ ID NO: 52:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

GGATCCATCG ATACGTAAG                                                19

(2) INFORMATION FOR SEQ ID NO: 53:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

GGCCGCTAAC TAATAGCCCA TTCTCCAAGG TACGTAGC                            38

(2) INFORMATION FOR SEQ ID NO: 54:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

TACGTACCTT GGAGAATGGG CTATTAGTTA GCGGCCGC                            38

(2) INFORMATION FOR SEQ ID NO: 55:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

GACTAACCTT GATTCCACTG GAGTTTTCTC TATTCTTCAT TCCCCACTTC TTCTT         55

(2) INFORMATION FOR SEQ ID NO: 56:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

GACTAACCTT GATTCCACTG GAGAATCTGG ACCAATTCTA TATAAGCCTG TGAAAAATTT      60

(2) INFORMATION FOR SEQ ID NO: 57:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

GACTAACCTT GATTCCACTG GAGAAGAAGA AGTGGGGAAT GAAGAA      46

(2) INFORMATION FOR SEQ ID NO: 58:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

GACTAACCTT GATTCCACTG GAGATCTCTA GATGGGAGGG GGTCTGGGCT C      51

(2) INFORMATION FOR SEQ ID NO: 59:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

GACTAACCTT GATTCCACTG GAGCTCGGAG CCCACCCCCT CCCATCT      47

(2) INFORMATION FOR SEQ ID NO: 60:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

GACTAACCTT GATTCCACTG GAGGGAGGCC CTTATCTCAA AAATGTT      47

(2) INFORMATION FOR SEQ ID NO: 61:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

```
GACTAACCTT GATTCCACTG GAGTCTAAGA ACATTTTTGA GATAAGGGCC T                51
```

(2) INFORMATION FOR SEQ ID NO: 62:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

```
GACTAACCTT GATTCCACTG GAGTCACAGG CTTATATAGT GAAA                       44
```

(2) INFORMATION FOR SEQ ID NO: 63:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

```
GACTAACCTT GATTCCCTGG AGACTGCACT GCTGTCCCCG CCTTCG                     46
```

(2) INFORMATION FOR SEQ ID NO: 64:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

```
GAGTAACCTT GATTCCCTGG AGATTTCTCA GACCCGGGTC GACCCTGTGG AAT             53
```

(2) INFORMATION FOR SEQ ID NO: 65:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

```
GACTAACCTT GATTCCCTGG AGCTCGAGGC GGCGCATCTC GGCG                       44
```

(2) INFORMATION FOR SEQ ID NO: 66:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

```
GACTAACCTT GATTCCCTGA AGACCTGCGT CATGCTGAGA CCCTCAA                    47
```

(2) INFORMATION FOR SEQ ID NO: 67:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 67:

GACTAACCTT GATTCCCTGA AGCGGCCAAT GCACCAAATG AAAGATTTTC         50

(2) INFORMATION FOR SEQ ID NO: 68:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 68:

CGCATCTTTT AATTAACTGG AGARAATTTT TYACAGGCTT ATATAGKAAA         50

(2) INFORMATION FOR SEQ ID NO: 69:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 69:

NNNNNNNNNN NNNNNNCTGG AGTTTTGAGC CCACCCCCTC CCATCTGGA          49

(2) INFORMATION FOR SEQ ID NO: 70:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

TGAACTTTCA CCTCGGAGCC CACCCCTCC CATCTGGAAA A                   41

(2) INFORMATION FOR SEQ ID NO: 71:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

TTTTTCCTTT AAAAGCTTGT GAAAAATTTG AG                            32

(2) INFORMATION FOR SEQ ID NO: 72:

(i) SEQUENCE CHARACTERISTICS:
        (A) LENGTH: 32 base pairs
        (B) TYPE: nucleic acid -continued

```
        (C) STRANDEDNESS: single
        (D) TOPOLOGY: linear (ii) MOLECULE TYPE: DNA (genomic)

(xi) SEQUENCE DESCRIPTION: SEQ ID NO: 72:

CTCAAATTTT TCACAAGCTT TTAAAGGAAA AA                                    32

(2) INFORMATION FOR SEQ ID NO: 73:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

ACTTGAAAGT GGAGCCTCGG GTGGGGAGG GTAGACCTTT T                            41

(2) INFORMATION FOR SEQ ID NO: 74:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 74:

NNNNNNNNNN NNNNNNCTGG AGAAAATTTT TCACAGGCTT ATATAGGAAA                  50
```

SELF-ASSEMBLING GENES, VECTORS AND USES THEREOF

This application claims the benefit of a provisional application U.S. Ser. No. 60/070,910, filed on Feb. 28, 1997, entitled "Self-Assembling Genes."

FIELD OF THE INVENTION

This invention relates to the construction and usage of synthetic genes for genetic engineering and gene therapy.

BACKGROUND OF THE INVENTION

Recombination at the genetic level is important for generating diversity and adaptive change within genomes of virtually all organisms. Recombinant DNA technology is based upon simple 'cut-and-paste' methods for manipulating nucleic acid molecules in vitro. The pieces of genetic material, or DNA are first digested with a restriction endonuclease enzyme which recognizes specific sequences within the DNA. After preparation of two or more pieces of DNA, the ends of the DNA are further manipulated, if necessary, to make them compatible for ligation or joining together. DNA ligase, together with adenosine triphosphate (ATP) is added to the genes, ligating them back together. The genetic assembly containing an origin of DNA replication and a selectable gene is then inserted into a living cell, is grown up, and is positively selected to yield a pure culture capable of providing high yields of individual recombinant DNA molecules, or their products such as RNA or protein.

Significant improvements have been made to this technology over the last two and a half decades. Numerous enzymes, end-linkers and adapter molecules have been made commercially available, which facilitate in the construction of recombinant DNA molecules. By using two restriction enzymes with different single-stranded termini or blunt ends, it is possible to directionally assemble genes (forced cloning). This reduces the amount of screening required to determine orientation. Procedures have been automated for synthesis of single-stranded gene fragments up to 200 or more nucleotides in length by means of phosphoramidite chemistry, and the instrumentation is readily available through Applied Biosystems, Inc., Foster City, Calif. Such single-stranded fragments can be joined by annealing overlapping complimentary phosphorylated strands, and by enzymatically filling in the ends with DNA polymerase and DNA precursors In this way, multiple, overlapping, single-stranded fragments can be assembled into a larger, double-stranded superstructure. Whole genes have been synthesized by similar methods. However, it becomes increasingly difficult to use synthetic DNA strands when making genes larger than approximately one kilobase. Using gene amplification methods (e.g. polymerase chain reaction (PCR), Mullis et al., U.S. Pat. No. 4,683,195), together with synthetic oligonucleotides, it is possible to make biologically active, synthetic retro-vectors that are capable of RNA transcription, reverse-transcription, viral packaging, and integration into genomic DNA (see for example, Hodgson, WO94/20608). Hodgson, supra, also disclosed methods for cloning of transcriptional promoters into such a vector using traditional recombinant DNA technology.

Modified restriction enzyme sites, linkers, and adapters can change the primary or secondary structure of complex nucleic acid sequences thereby altering or obliterating a desired biological activity. For example, small mutations can drastically modify transcriptional promoters or change the reading frame of coding DNA. A logical goal of vectorology is to make exact constructs, without need of fortuitous restriction sites, adapters, or linkers.

Restriction endonucleases can be grouped based on similar characteristics In general there are three major types or classes: I, II (including IIS) and III. Class I enzymes cuts at a somewhat random site from the enzyme recognition sites (see Old and Primrose, 1994. *Principles of Gene Manipulation*. Blackwell Sciences, Inc., Cambridge, Mass., p.24). Most enzymes used in molecular biology are type II enzymes. These enzymes recognize a particular target sequence (i.e., restriction endonuclease recognition site) and break the polynucleotide chains within or near to the recognition site. The type II recognition sequences are continuous or interrupted. Class IIS enzymes (i.e., type IIS enzymes) have asymmetric recognition sequences. Cleavage occurs at a distance from the recognition site.

These enzymes have been reviewed by Szybalski et al. *Gene* 100:13–26, 1991. Class III restriction enzymes are rare and are not commonly used in molecular biology.

U.S. Pat. No. 4,293,652 employed a linker with a class IIS enzyme recognition sequence to permit synthesized DNA to be inserted into a vector without disturbing a recognition sequence. Brousseau et al. (*Gene* 17:279–289, 1982) and Urdea et al. (*Proc. Natl. Acad. Sci. USA* 80:7461–7465, 1983) disclose the use of class IIS enzymes for the production of vectors to produce recombinant insulin and epidermal growth factor respectively. Mandecki et al. described a method for making synthetic genes by cloning small oligonucleotides using a vector (*Gene* 68:101–107, 1988). Expansion of a population of oligonucleotides required synthesis, cloning excision and fragment purification. The oligonucleotides were used to create a complete plasmid.

Lebedenko et al. (*Nucl. Acids Res.* 19(24):6757–6761) illustrated the class IIS enzymes and PCR for precisely joining 3 nucleic acid molecules for convention sub-cloning using BamHI. Tomic et al. (*Nucleic Acids Res.*, 18:1656, 1990), reported a method for site-directed mutagenesis using the polymerase chain reaction and class IIS enzymes to join two nucleic acid molecules. Two overlapping PCR primers were used where the primers included class IIS recognition sites. The primers included a region of complementarity to the template DNA and include one to a few site-directed mutations. Stemmer (U.S. Pat. No. 5,514,568) employed overlapping primers with class IIS enzymes to amplify a plasmid and to introduce specific mutations into DNA leaving all other positions unaltered.

There remains a need for the ordering and assembly of complex genes to overcome the problems associated with sequential sub-cloning such as multiple purification steps, the potential for sample loss, and the like. Moreover there is a need for eliminating the use of prokaryotic hosts and for minimizing or avoiding the risks associated with bacterial contamination resulting from the use of bacteria as intermediaries in the cloning process. Further, there remains a need for efficient methods to assemble large nucleic acid molecules or many-fragmented nucleic acid assemblies with precision.

BRIEF DESCRIPTION OF THE FIGURES

FIG. 3B is an illustration of an LTR with the insertion of a U3 (transcriptional promoter) region rescued by reverse transcriptase-polymerase chain reaction (RT-PCR). The promoter is amplified from the RNA of a cell expressing the VL30 U3 region. Complementary overhanging ends are created using class IIS restriction endonuclease digestion sites within the LTR and within the promoter. FIG. 3C provides the linear structure of a VL30 RNA transcript from a mouse cell with a U3 region near the 3'-terminus of the RNA molecule. PCR primers include a class IIS enzyme recognition site to amplify the U3 region from the RNA resulting in a double stranded DNA molecule. Cleavage with a class IIS enzyme (here BpmI), results in a double-stranded DNA molecule with end complementary to a site in the vector of FIG. 3A.

FIG. 4b is a diagram of a U3 (transcriptional enhancer and promoter region of an LTR illustrating several sub-divisions of the transcriptional control region, including a distal enhancer region, an enhancer repeat region, a medial promoter and a aproximal promoter. These regions have been described for other vectors in Hodgson et al. (1996. "Construction, Transmission and Expression of Synthetic VL30 Vectors" in Hodgson ed. *Retro-vectors for Human Gene Therapy.* R G Landes Company, Austin Tex.). Segments of these regions are amplified using primers for highly conserved sequences. Highly conserved sequences are determine based on a comparison of known VL30 sequences such as provided in FIG. 4.2 of Hodgson, 1996, infra). The parts are joined by annealing and ligation to provide an ordered assembly. Each construct is an allele or a representative of allelic variation in the combinatorial library.

FIG. 5 discloses two transcriptional promoters that have been rescued from mouse VL30 RNA sequences isolated from a mouse T-helper cell library. These promoters were assembled into a vector and introduced into ritroviral helper cells and packaged into recombinant retrovirus for introduction into human T-cells. After transduction to human T cells, a β-galactosidase reporter gene was expressed from the T cell-derived promoters. (SEQ ID NOS:2 and 3).

FIG. 6 discloses 10 biologically active mouse VL30 promoters obtained from mouse liver RNA. These promoters were introduced into the vector of SEQ ID NO:1. The vectors were introduced into retroviral helper cells and then packaged into retrovirus where they were introduced into human liver cells. The cells expressed the green fluorescent protein. (SEQ ID NOS:4–13).

BRIEF SUMMARY OF THE INVENTION

Figure 1A:
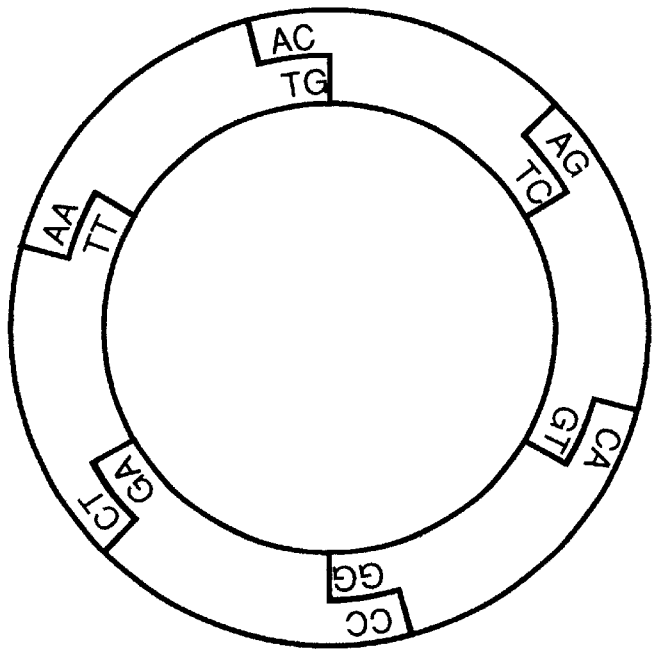
FIG. 1A. provides one schematic of six double stranded DNA fragments, each terminus comprising a unique overhanging two-nucleotide sequence complementary to only one other terminus FIG. 1B. illustrates a three-piece ligation where 100% of the clones tested contained the predicted fragment order and desired fragment orientation.

The invention described herein provides seamless, directional, ordered construction of complex DNA molecules, vectors and libraries. More particularly, it enables gene constructs to be assembled with greater efficiency and precision, and it enables multiple gene fragments to be assembled in the correct order and orientation without disturbing the internal structure of the gene. The method utilizes in vitro assembly of nucleic acid fragments and relies upon the unusual ability of certain enzymes to digest nucleic acid molecules at pre-determined sites without disrupting the structure of the gene. It is especially useful for the construction of genetic vectors for gene therapy or genetic engineering of cells and organisms. A particular application of the invention is in combinatorial, or evolutionary genetics, where it enables a large number of non-random, self-assembled constructs to be screened simultaneously for function.

In a preferred embodiment of this invention, the invention relates to a method method for assembling a gene or gene vector comprising the steps of: a) designing at least 6 primers to produce to amplify at least three fragments in at least three separate polymerase chain reactions wherein each primer comprises at least one predetermined restriction endonuclease recognition site that recognizes a restriction endonuclease that cleaves at a distance from the recognition site, a sequence complementary to a template nucleic acid for amplification, and bases positioned at the restriction endonuclease cleavage site that are selected to be complementary to only one other overhanging created from enzymatic cleavage of the fragments; b) combining the primers with template nucleic acid and performing the polymerase chain reaction to produce multiple copies of an amplified template fragment incorporating the restriction endonuclease recognition site; c) digesting the amplified template fragments with one or more restriction endonucleases that recognize the restriction endonuclease recognition site of the primers to create overhanging termini wherein each overhanging termini is complementary to only one other overhanging termini on another fragment; and d) combining the amplified and digested template fragments in a ligation reaction to produce a directionally ordered gene, nucleic acid fragment or gene vector.

In a preferred aspect of this embodiment, the restriction endonuclease is at least one class IIS restriction endonuclease and preferably, the class IIS restriction endonuclease is selected from the group consisting of: AlwI, Alw26I, BbsI, BbvI, BbvII, BpmI, BsmAI, BsmI, BsmBI, BspMI, BsrI, BsrDI, Eco57I, EarI, FokI, GsuI, HgaI, HphI, MboII, MnlI, PleI, SapI, SfaNI, TaqII, Tth111II. Still more preferably, class II restriction endonuclease recognition sites (to be distinguished from class IIS restriction endonuclease recognition sites), linkers, or adapters are not used to create the gene or gene vector. In one embodiment, the product of the ligation reaction is introduced into prokaryotic or eukaryotic cells. Preferably, at least one template nucleic acid sequence is chosen from the group consisting of: transcriptional regulatory sequences; genetic vectors; introns and/or exons; viral encapsidation sequences; integration signals intended for introducing nucleic acid molecules into other nucleic acid molecules; retrotransposon(s); VL30 elements; or multiple allelic forms of a sequence.

In another preferred aspect of this embodiment, the method is used to generate combinatorial libraries of a target sequence. Preferably, the target sequence is part or all of a gene. In one embodiment, the gene encodes a protein. In one embodiment, the primers amplify allelic variants of part or all of a gene.

In still another preferred aspect of this embodiment, the product of the ligation reaction is passed between eukaryotic cells using a virus particle, by cell fusion, or by transfection. Preferably the product of the ligation reaction is not introduced into prokaryotic cells. Moreover, the method further comprises combining at least one screening or selection step to select the products of the ligation reaction. In one embodiment, the product of the ligation reaction is mutated during passage in cells in order to generate genetic diversity and preferably the product of the ligation reaction is mutated by homologous recombination during passage in cells.

In another aspect of this embodiment, the method is used to isolate and identify regulatory sequences from a cell. In anther aspect of this embodiment, cells containing the product of the ligation reaction are selected for enhanced biological activity. Preferably, the cells containing the product of the ligation reaction are selected for tissue-specific, hormone-specific or developmental-specific gene expression. Also preferably, the ligation reaction is a circularized gene vector.

In another embodiment of this invention, the invention relates to a nucleic acid primer having a 5' and a 3' end to amplify a nucleic acid fragment for the ligation of at least two fragments comprising: a restriction endonuclease recognition site that recognizes a restriction endonuclease, wherein the restriction endonuclease cleaves at a distance from the recognition site and creates overhanging termini; a sequence complementary to a template sequence to be amplified to produce the nucleic acid fragment; at least two nucleic acid bases positioned at the restriction endonuclease cleavage site and that form an overhanging terminus after cleavage by the restriction endonuclease, wherein the at least two nucleic acid bases are selected to be complementary to only one other overhanging terminus on another fragment of the ligation; and an affinity handle on the 5' end of the primer. Preferably the primer further comprises an anchor to provide stability to the restriction enzyme at the restriction enzyme recognition site.

In yet another embodiment of this invention, the invention relates to a method for isolating and identifying promoters comprising the steps of: a) obtaining a vector comprising at least a portion of a promoter region from a retrovirus transposon LTR and having two non-complementary overhanging termini; b) designing at least two PCR primers to amplify at least one region of a retrovirus transposon LTR from template nucleic acid to produce at least one nucleic acid fragment wherein each primer comprises at least one predetermined restriction endonuclease recognition site that recognizes a restriction endonuclease that cleaves at a distance from the recognition site, a sequence complementary to a template sequence from a retrovirus transposon, and bases positioned at the restriction endonuclease cleavage site that are selected to be complementary to only one other overhanging terminus of the vector wherein the restriction endonuclease cleavage site is created from enzymatic cleavage of the fragments; b) combining the primers with template nucleic acid and performing a polymerase chain reaction to produce multiple copies of an amplified template fragment incorporating the restriction endonuclease recognition site; c) digesting the amplified template fragments with one or more restriction endonuclease that recognize the restriction endonuclease recognition site of the primer to create overhanging termini; and combining the amplified and digested template fragment in a ligation reaction with the vector to produce a gene vector with an intact LTR sequence. In one embodiment of this aspect of the invention, the template nucleic acid is DNA or RNA. In another embodiment of this aspect of the invention, the method further comprises the step of sequencing the insert to identify the promoter sequence. In one embodiment promoter sequences of SEQ ID NOS:1–13 identified using the methods of claim.

DETAILED DESCRIPTION OF THE INVENTION

In one embodiment of this invention, the invention relates to the seamless, oriented self-assembly of at least three DNA fragments having overlapping unique cohesive ends generated by the enzymatic cleavage of at least one restriction endonuclease that is capable of cleaving at a site distant to the restriction enzyme recognition site. Preferably the restriction endonucleases employed in this invention are class IIS restriction endonucleases. These enzymes recognize a predetermined group of nucleotides and cleave at a distance characteristic of the particular endonuclease from the recognition site. The term "unique cohesive ends" is used herein to refer to the notion that the cleavage site for the endonucleases of this invention can be manipulated to produce overhanging ends with unique termini selected by the investigator. The term "complementary" as used herein in reference to the overhanging ends of the fragments of this invention refers to standard complementarity recognized in the field of molecular biology. For example, the nucleotides sequence 5'-TAG-3' is said to be complementary to the nucleotide sequence 5'-CTA-3'. The term "PCR" is used generally to refer to the polymerase chain reaction and its variations, including RT-PCR as well as other gene amplification techniques employing primers.

In a first step for practicing one embodiment of this invention, a series of at least three overlapping fragments are created trough the selection and creation of primers incorporating at least one class IIS restriction enzyme recognition sequence. The oligonucleotide primers of this invention are designed to amplify one or more nucleic acid fragments and comprise a sequence complementary to a target sequence for gene amplification, a recognition sequence for a restriction endonuclease that cleaves DNA at a distance from the recognition sequence (such as a class IIS restriction enzyme) and bases positioned at the restriction endonuclease cleavage site that are preferably unique and complementary to only one other overhanging termini in the annealing/ligation reaction that generates the complex nucleic acid molecules. Optionally, the primers of this invention can include an "affinity handle for cleanup" at the 5' end. These sequences can be of any length, preferably at least about 6 bp and the sequences extend the primer in the 5' direction from the restriction enzyme recognition site. This extra length gives many enzymes greater stability and improved activity. In addition, the sequence can be used for recognition and removal of the ends of the primers (either undigested fragments or digested ends of primers) using complementary nucleotide sequences bound to a solid support (such as cellulose, nitrocellulose or silica). Incubation with, or passage over a column or support containing the complementary sequences can be used to remote the tags by allowing them to anneal or hybridize. The nucleic acid can then be eluted from the column. Adapters can also be used in this invention. For purposes of this invention, adapters refer to double stranded fragments containing an enzyme recognition site, according to this invention. The adapters are ligated to double stranded DNA molecules, creating a Fragment analogous to a PCR fragment with similar sites derived from a primer. The primers or adapters can be prepared using a number of methods for synthesizing oligonucleotides known in the art. For example instruments for producing oligonucleotides are available from Applied Biosystems, Inc., Foster City, Calif.

In one example, for the design of an oligonucleotide primer for use in this invention, the particular complementary bases that will form the site for hybridization of the primer to template (i.e., target DNA or RNA) are selected. A restriction endonuclease recognition site is selected followed by a number of nucleotides to be positioned between the recognition site and the cleavage site. The nucleotides of the cleavage site are selected to include overhanging regions formed from the restriction endonuclease cleavage that are complementary to the overhanging regions of an adjacent fragment in the annealing/ligation reaction.

The length of the primer used in this invention can vary, but preferably the primer length is up to about 80 bases and preferably up to about 50 bases. In addition the primers are preferably at least about 15 bases in length and preferably at least about 25 bases in length. The 5' region of the primer contains preferably at least about 6, preferably at least about 10 and still more preferably at least about 16–18 bases that are not complementary to the template DNA or RNA. Further, the primer incorporates a restriction endonuclease recognition site preferably 5' to the region of complementarity and a restriction endonuclease digestion site preferably 5' to the region of complementarity or within the region of complementarity. There are a variety of restriction endonucleases that cleave at a distance from the restriction endonuclease recognition site of a DNA strand and a variety of enzymes that are commercially available from New England Biolabs are provided in Table 1.

TABLE 1

Restriction endonucleases useful in the construction of self-assembling genes

| Enzyme | Site size (bp) | Distance to overlap | Size of overlap | Overlap type |
|---|---|---|---|---|
| Alw26I | 5 | 1–5 bp | 4 bp | 5'-Overhang |
| BbsI | 6 | 2–6 bp | 4 bp | 5'-overhang |
| BpmI | 6 | 16–14 bp | 2 bp | 3'-overhang |
| BsmBI | 6 | 1–5 bp | 4 bp | 5'-overhang |
| BspMI | 6 | 4–8 bp | 4 bp | 5'-overhang |
| BsrDI | 6 | 0–2 bp | 2 bp | 3'-overhang |
| Eco57I | 6 | 16–14 bp | 2 bp | 3'-overhang |
| FokI | 5 | 9–13 bp | 4 bp | 5'-overhang |
| HgaI | 5 | 5–10 bp | 5 bp | 5'-overhang |
| HphI | 5 | 8–7 bp | 1 bp | 3'-overhang |
| MnlI | 5 | 7–6 bp | 1 bp | 3'-overhang |
| PleI | 5 | 4–5 bp | 1 bp | 5'-overhang |
| SapI | 7 | 1–4 bp | 3 bp | 5'-overhang |
| SfaNI | 5 | 5–9 bp | 4 bp | 5'-overhang |

In addition to the enzymes provided in Table 1, other restriction endonucleases that cleave at a distance from their restriction endonuclease recognition site include, but are not limited to, AlwI, BbsI, BbvI, BbvII, BsmAI, BsmI, BsrI, EarI, GsuI, MboII, TaqII, Tth111II and their respective isoschizomers. These and other enzymes are known in the art and many are available from other manufacturers. The primers can be prepared to produce either 5'-overlapping ends or 3'-overlapping ends, as long as they are both are either 5'-overlapping ends or 3'-overlapping ends and are complementary to one other set of overlapping ends.

In the case of Bpm1 (see Example 1), the enzyme digests asymmetrically, 14–16 bp from the 3'-nucleotide of the recognition site. The resulting cleavage has a 3'-overhanging end of 2 bp. A second primer is then designed with a complementary overhanging end, and it is used to generate the adjoining fragment terminus. At the opposite ends of the two fragments that are to be joined, similar complementary, overhanging ends are designed.

The oligonucleotides are then combined with template nucleic acid (either DNA or RNA, e.g., such as for reverse transcriptase polymerase chain reaction (RT-PCR)) containing bases complementary to at least a 3' portion of the primers (also referred to herein as "templates"). In one embodiment, the fragments are gene-amplified by PCR, RT-PCR or another gene amplification process using established PCR protocols such as those provided with PCR amplification kits, including those available from Perkin-Elmer Corp. (Emeryville, Calif.). Preferably, the PCR products are Analyzed by electrophoresis on a gel, such as an agarose gel and still more preferably the fragments of the predicted size are purified free of excess primers and small byproducts (such as by purification through a small column, such as a Qiagen™ column (Qiagen, Valencia, Calif.)). Following amplification or purification, the fragments are digested with the restriction endonuclease recognizing the restriction endonuclease recognition site in the primers. The digested fragments are then purified from the digested ends of the primers, preferably by preparative agarose gel electrophoresis. The fragments are combined, annealed and are ligated using standard hybridization and ligation conditions known for cloning (see Ausubel et al., *Current Protocols in Molecular Biology,* John Wiley & Sons, 1994).

FIG. 1A illustrates an example of a self-assembling gene construct (SEQ ID NO:1) comprising six fragments, each having unique overhanging dinucleotide ends. In this example, the ends of the fragments prepared by the methods of this invention are constructed using primers that include BpmI restriction endonuclease recognition sites It will be understood by those of ordinary skill in the art that one or more other restriction endonucleases (such as those of Table 1) could similarly be used for the self-assembling product of FIG. 1A. In a preferred embodiment, the primers were created as described above and preferably the 3'ends of the primers are non-palindromic (i.e., non self-complementary) to prevent self-annealing of such fragments. Each fragment in this example preferably joins to only one other dinucleotide overhang in the annealing/ligation mixture, assuring ligation only to the intended fragment partner. An advantage of this strategy is that the formation of concatamers or multimers is minimal. The restriction endonuclease site is removed by digestion with the restriction endonuclease, leaving the junction free of the extra DNA sequences associated with the site.

Using a single restriction endonuclease with a dinucleotide overhang (for example, using the enzyme BpmI) up to six pieces of genetic material can be joined together in a linear or circular form (such as a vector) without the need to perform sub-cloning procedures or detailed analysis of individual products because six unique combinations of dinucleotide overhangs create a directional clone with extremely high fidelity. With enzymes digesting single-base overlaps, only two fragments can be joined with positional and directional precision. With enzymes digesting three-base overlaps, $4^3/2$, or 32 fragments can be so joined in the correct order and orientation. Therefore, this invention also relates to the use of restriction endonuclease recognition sites that facilitate cleavage by restriction endonucleases with three-base overlaps and self-assembly gene constructs including 32 fragments. Alternatively, a combination of restriction endonuclease recognition sites for use with a combination of restriction enzymes that create two-base or three-base overlaps can be used. Each enzyme has its characteristic limits to self-assembly imposed by the size of the overlap. For example, there are sixteen dinucleotides, therefore BpmI fragments (which have two dinucleotide ends each) are limited to eight for the purpose of self-assembly; therefore in another embodiment of this invention an assembly comprising eight fragments is contemplated. However, four of the sixteen dinucleotides are palindromes. Use of these palindromic dinucleotides can create some infidelity in the annealing/ligation reaction. The enzyme HgaI has a five base overlap, and there are 1,024 pentanucleotide combinations, permitting 512 fragments to be ligated together directionally and in order (no palindromes). The fragments to be joined at a particular place are designed to have their cut sites aligned, so that the overlapping region fits together. In some cases, the target sequences will contain natural restriction endonuclease recognition sites for the enzyme that is being used, such as one or more internal BpmI sites. These sites have the potential to self-religate during vector or gene construction or they can be by passed by using a substitute enzyme in the primers (for example, Eco 571 can substitute for BpmI). Alternatively, these sites can be removed by site-directed mutagenesis after consideration to the, consequences of the mutagenized sequence to the gene or vector.

In addition to class IIS enzymes, class II restriction endonucleases can be used. These enzymes have intrinsic methylation activity that affects the outcome in either a negative or a positive way, depending on the purpose for which it is used. In a preferred embodiment, the methylation activity of class II enzymes is ablated by mutation or by genetic engineering to convert the enzyme to an effective class IIS enzyme to expand the repertoire of useful enzymes for this invention.

In another aspect of this invention, the primer design and target fragment sequence selection can be automated (see Example 5) using a computer to assist in the selection of unique overhanging ends that have complementarity only to the overhanging end of an adjacent fragment.

Therefore, this invention permits high-fidelity annealing and ligation of six or more fragments with unique overhanging termini complementary to a single other overhanging termini. Any multitude of combinations can be created by combining the type of overhanging termini that can be created. Moreover, if one is willing to sacrifice the fidelity of the reaction, a variety of combinations can be used to anneal a variety of fragment numbers. In these cases, some selection may be necessary, such as size selection of the resulting fragment based on electrophoretic migration or restriction endonuclease profiling, both methods well known to those of ordinary skill in the art It is also necessary to have a high per-step efficiency (e.g., each step in the precess is performed with an efficiency of at least 80%) to effectively ligate large numbers of fragments without error. Where large numbers of fragments are used, the purity of the fragments becomes important. This means that for large numbers of fragments, the digested DNA fragments for annealing and ligation should be substantially pure. If undigested fragments, digested ends of primers, degraded or partially degraded molecules are present they can decrease the purity and affect the fidelity of the product. Therefore, it is particularly desirable to ensure complete digestion of both ends of each fragment and to remove al of the digested ends from the fragments prior to including the fragments in an annealing and ligation reaction. The use of Qiagen columns for oligonucleotide removal prior to digestion is generally sufficient to permit efficient digestion of the fragments. Agarose gel isolation is desirable after digestion particularly where the product contains some fragments that do not appear to be full length. The use of an analytical gel before and after digestion helps in determining whether both oligonucleotide tags have been removed. The isolation of fragments from agarose gels preferably avoids the use of ultraviolet light and exposure of the DNA to ethidium bromide is also preferably avoided. These methods can be avoided by running replicate lanes and staining only a portion of the gel.

The fragments and vector are then digested to yield fully complementary ends, and the fragments are preferably again purified, as described above (such as through a Qiagen column or by gel isolation). The purified fragments are ligated together in a test tube, under standard conditions, such as using bacteriophage T4 DNA ligase and ATP. Preferred ligations include at least 20 $\mu$g/ml total DNA concentration in the ligation mix to favor intermolecular interactions, and an equimolar ratio of fragments to be ligated. Where a prokaryotic intermediary is used, the ligated assemblage is transformed into a bacterium, such as an *E. coli* host, and the colonies are: selected with a drug (such as an ampicillin, tetracycline, or kanamycin marker). The colonies can then be selected either by individually selecting colonies or growing a mass culture, such as where a vector library has been created. Restriction enzyme analysis can be used to determine the identity of individual constructs or to assess the validation of the combination of plasmids. The plasmids can then be grown up and used as needed.

In one embodiment of this invention, at least a portion of a vector is used as one of the fragments for the ligation of at least three fragments according to this invention. In one example, where a vector is used as one of the starting fragments, two restriction endonuclease recognition sites recognizing an enzyme that cleaves at a distance from the recognition site, such as at least one BpmI site, can also be introduced into the vector. This permits the vector to be digested with the restriction endonuclease to produce a product having ends complementary to two ends of the insert DNA fragments. The vector can be made by amplifying a plasmid or portion thereof using the primers of this invention. Thus, the vector can also be constructed to include a variety of restriction endonuclease recognition sites using a variety of restriction endonucleases, including a variety of class II restriction endonucleases. In some cases, the target fragments for amplification will contain natural restriction endonuclease recognition sites for the enzyme that is being used for the self-assembly, such as for example, a fragment that includes one or more internal BpmI sites. Care should be taken either to utilize the complementarity of the naturally occurring site to reform the fragment as it originally existed or to eliminate the restriction endonuclease recognition site using, for example, site-directed mutagenesis. Preferably, the restriction endonuclease recognition site is be substituted for a different enzyme (in the case of BpmI. substituting Eco57I or BsrDI) that has an equivalent structure at its ends. Two or more fragments of insert or two or more fragments of vector with at least one insert are amplified using primers according to this invention.

Figure 1B:
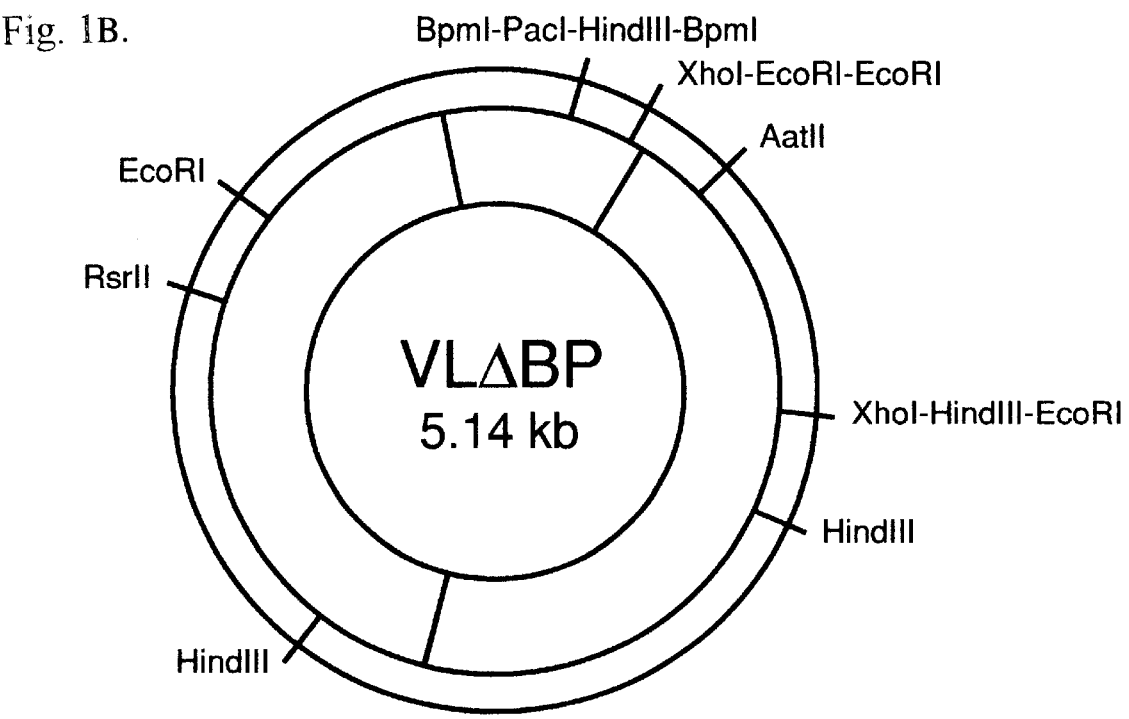

The exemplary enzyme, BpmI digests DNA 14–16 base pairs (bp) from the 3'-nucleotide of the recognition sequence (RS). Thus, by placing the RS exactly 14–16 bp from the desired dinucleotide cut site, the practitioner tags the dinucleotide for ligation with another dinucleotide that is exactly complementary to it. Such a complementary dinucleotide can be inserted by using the same enzyme and RS to make another fragment which fits the first exactly, as illustrated in FIG. 1. Because there are sixteen possible dinucleotide combinations (including twelve combinations that do not have palindromic ends), it is possible to create up to six fragments with unique dinucleotides, and it is also possible to join them all together in a predetermined order and orientation (FIG. 1A). In addition, the palindromic sequences (such as AT, CG, TA, and GC) could also be used, although inefficiency and incorrect ligation will result from the self-complimentarity of these sequences. It is furthermore possible and desirable to have three or more fragments joined in this way, such that the construct is circular as in FIG. 1, comprising a vector that may be grown in a bacterial and/or eukaryotic host cell. If the genetic construct is to be used as a vector, the vector should be designed to include a proper origin of replication to enable it to replicate in a particular cell. For example, a prokaryotic origin of replication such as a coliform plasmid origin of replication enables circular DNAs to be propagated in $E.$ $coli$ host cells. It is desirable to have at least one selectable marker, such as a neomycin marker that enables recovery of the clone through a selection process. It is also desirable, but not essential, to have two or more selectable genetic elements, to permit dual selection. For example, if one of the fragments contains a prokaryotic plasmid origin of replication, and another fragment contains a selectable marker, then the two fragments are both selectable, since the construct will grow in prokaryotic cells in the presence of a selection drug (such as ampicillin) only when both fragments are present. Drug selection can be combined with the methods of directed self-assembly to assure a high percentage of correct products. Because of the unique complementarity of the fragments, each contributes a selectable element that leads to recovery of a high percentage of correct products.

For prokaryotic vector construction, at least one fragment should contain a prokaryotic origin of replication and one fragment should contain a drug resistance marker gene. However, an advantage of the methods of this invention is that the construct can be introduced directly into eukaryotic cells. Here no plasmid origin of replication is necessary and no prokaryotic selectable marker or other prokaryotic nucleic acid sequence is necessary. In cases where the vector is subject to regulatory approval or where optimal gene function is necessary, it may be undesirable to include prokaryotic sequences, such as extraneous plasmids or expressed prokaryotic fragments particularly if the sequences contain inmmunostimulatory sites that can lead to activation of the intracellular immune system and inactivation of a gene product (see Kreig, $J.$ $Lab.$ $Clin.$ $Med.,$ 128:128–133, 1996) or to avoid risks of endotoxin contamination. Moreover, the use of self-assembled product, according to the methods of this invention saves labor and time involved in the screening process.

Thus, in a preferred embodiment of the invention, the nucleic acid fragments are self-assembled in vitro, and are transferred directly into eukaryotic cells, by transfection, injection, or other methods known in the art. In one embodiment the cells receiving the assembled product of this invention are helper cells for recombinant virus assembly (including, but not limited to retroviral helper cells for retroviral or retrotransposon vectors, adenovirus helper cells for adenovirus vectors or herpes simplex virus helper cells for herpes simplex vectors). Alternatively, the assembled product can be introduced into cells along with a helper virus or the assembled product can be introduced into target cells for direct expression. The assembled product can be a vector, a minichromosome vector, a portion of a chromosome, or the like. In the preferred case of a retroviral vector, the genes are first transfected into a first helper cell line (such as ecotropic helper cells, GP+E86 (Markowitz et al. $J.$ $Virol.$ 62:1120–1124, 1988). The retrovirus-containing supernatant from these cells is then filtered (0.45 mm Nalgene filters) preferably 48–72 hours after transfection and the filtrate is transferred to a second complementation retroviral helper cell line (such as PA317 retroviral helper cells, Miller et al., $Mol.$ $Cell.$ $Biol.$ 6:2895–2902, 1986). After an additional 48 h, the second helper cell line is selected with the marker drug (such as the drug G418 for the selectable neomycin (neo) marker gene), until only drug-resistant cells remain. These cells contain stably integrated vectors that can be used to repeatedly transduce human cells. Advantageously, in the case of adenovirus vectors or other large eukaryotic-derived vectors including eukaryotic virus-derived vectors, it may be impossible to propagate them in prokaryotic hosts. The gene self-assembly method of the instant invention provides an alternative to in vitro recombination method of gene construction by permitting large constructs to be constructed.

One advantage of introducing the assembled product of this invention into a helper cell line to produce recombinant virus for the introduction of a gene or nucleic acid complex into a cell is that the assembled product will be auto-selected by the cells during the packaging process. Therefore, even where the overhanging termini have palindromic sequences, where there is more than one (but preferably less than four) unique complementary matches for a particular overhanging termini, or where concatamers have formed, only the correct or functional assembled products are expressed, transmitted, and assembled into virus. When the virus is then introduced into cells, the use of a reporter gene or another selectable marker provides yet a second layer of security for the selection of cells containing a properly assembled construct. For example, where a retrovirus helper cell line is used to produce a recombinant retrovirus containing the product of this invention (for retrovirus, RNA transcribed from the DNA product of the invention becomes packaged into the virus particle), a retrovirus-derived vector is transcribed as RNA and transmitted by packaging the RNA in a retrovirus particle. In order to be properly transmitted as a virus, the construct must be: 1) transcribed as RNA in a vector producer cell; 2) packaged into viral particles; 3) reverse transcribed into double-stranded DNA (in the recipient cell); and 4) integrated into the host chromosome. Each of these steps requires specific cis-acting sequences that must be correctly positioned within the vector. Thus, passage via retrovirus (or by other virus) is a means of auto-selection for the essential sequences.

In one application of the methods of this invention, the methods are used to rescue expressed sequences from RNA, or genomic sequences from cell DNA without disrupting the promoter sequences. Cellular transcriptional promoters are typically difficult to identify and isolate because they are generally not included in the RNA molecule and often extend over a considerable distance in a chromosome. One application of this invention relates to a promoter rescue technique that permits the entire promoter, or a fragment of a promoter to be isolated and cloned directly in to an expression vector without disruption of the flanking sequences. Promoter rescue techniques are known and include WO 94/20608 to Hodgson.

In a preferred embodiment of the invention, transcriptional promoters are cloned in a transcriptionally active manner for the selection and identification of new and/or of tissue or cell-specific promoters enabling them to be used, selected, or screened for activity directly. For example, FIG. 3 illustrates one example of the formation of a vector for the incorporation of promoter sequences and the ultimate identification of those sequences using an exemplary plasmid VLBPGN (SEQ ID NO:1) as provided in Example 3, with Bpm1 sites located within the locus of a retrotransposon (VL30) long terminal repeat (LTR). These methods preserve the structure and functionality of transcription factor response elements. The characteristic secondary structure of the LTR RNA remains very similar to the original LTR from which the promoter was rescued, thus preserving the important features of the original RNA/DNA molecule. Those of ordinary skill in the art will recognize that any of a variety of primers can be used with a variety of vectors and that the constructs of FIGS. 2 and 3 are exemplary and not limiting.

Figure 2:
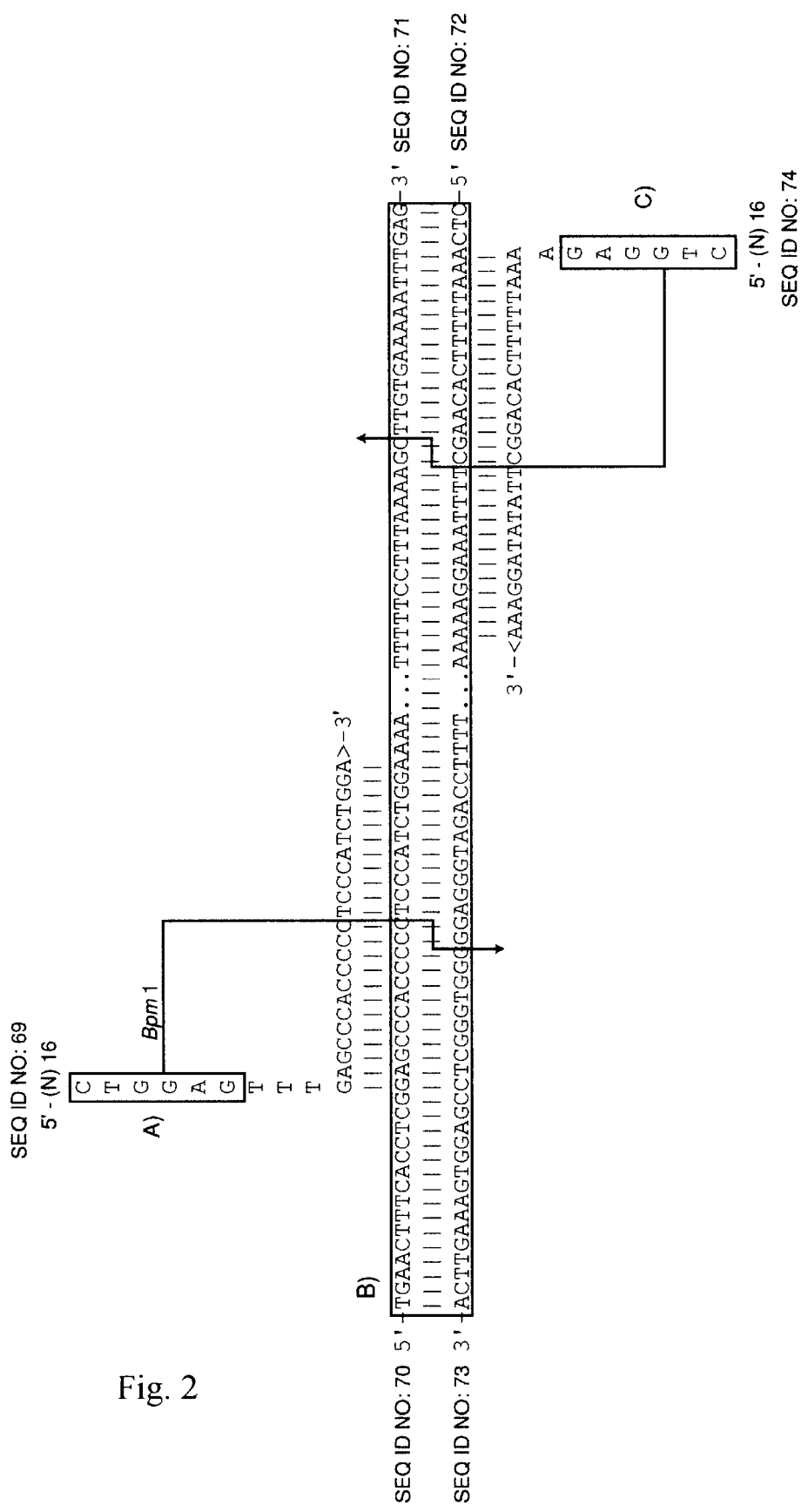
FIG. 2. illustrates the use of a class IIS restriction endonuclease (as one example, Bpm 1), restriction endonuclease recognition site and the selection of cohesive overhanging ends (SEQ ID NOS:69–74).

FIG. 2 illustrates the primers used to amplify the promoter insert (identified at a and c in FIG. 2), and the insert region of the LTR (boxed), both of which can be digested at the same nucleotide position with Bpm1, to ensure a proper and seamless fit. In this example, after digestion of the vector, the two Bpm1 sites leave non-complementary ends (a 3'-CC overhang on one end, and a 3'-GC overhang on the other). Thus, the ends will not efficiently anneal or ligate to one another. However, the complementary termini of the insert serves as linkage, enabling the plasmid to be completed by ligation.

In the example illustrated in FIG. 2, the terminus on the 3'-side (GC) is palindromic. Palindromic termini are self-complementary and can therefore ligate to themselves or to an identical terminus facing the opposite way (forming concatamers in the opposite direction). Despite the presence of palindromic termini and despite the potential for reduced fidelity in the self-assembling process, a large percentage of clones obtained by inserting promoter sequences into VLBPGN were assembled correctly (20/23). These levels are reduced somewhat when three or more fragments are combined for self-assembly, according to this invention and preferably, the use of palindromic termini are avoided when even numbers of nucleotides are exposed as overhanging termini because with even numbers of nucleotides there is an axis of symmetry. As noted above, where five base overhangs are used there are 1024 possible combinations of five nucleotides [$(4)^5$], yet none of them is palindromic.

The vector of FIG. 3 is an example of a particular type of vector that is known as a retrotransposon vector. Retrotransposon vectors are described and reviewed in Hodgson et al., 1996 *Retro-Vectors for Human Gene Therapy.* R G Landes Company, Austin Tex., chapter 5 and see U.S. Pat. No. 5,354,674 to Hodgson. This type of vector is derived from a mouse cellular retro-transposon element that has no essential viral or cellular genes, and that has little sequence similarity to a retrovirus. However, this RNA (known as VL30 [virus-like, 30S]) has all the necessary cis-acting structural elements (such as LTRs and primer binding sites) required for efficient transmission by a type C murine or primate retrovirus. Thus, it is a parasite transmitted by retroviruses that is also expressed as a cellular RNA in most mouse cells and tissues. This RNA becomes packaged into retroviral particles when the mouse cells become infected by a retrovirus. The retrovirus then transmits the VL30 (or a VL30 vector) to the next infected cell (which can be a human cell). The RNA is then reverse transcribed and integrated into the DNA of the host cell.

Some advantages of VL30 vectors (over retrovirus-derived vectors) are: 1) lack of viral genes and other sequence homology that could lead to replication competent retrovirus (RCR); 2) ability to be expressed long-term in vivo; 3) a variety of LTR transcriptional promoters that can be expressed in various tissues and under the influence of various hormones and other stimuli; and 4) the ability to express genes in a number of cell types that are targets of gene therapy. An additional advantage is that VL30 parts can be switched with those of classical retrovirus-derived vectors. For example, the LTR or packaging signal of VL30 can be used in place of the equivalent retroviral signal. The ability to make mixed, or chimeric retro-vectors is a special application of gene self assembly technology.

Using a specific primer set, such as that shown in FIG. 2, or others, as taught in this invention, it is possible to amplify the U3 sequences expressed in the RNA of many different types of mouse cells. This is done using standard RNA isolation methods (Ausubel et al., supra), coupled with extensive digestion with ribonuclease-free dexoyribonuclease, to eliminate residual DNA. Thus, to obtain a promoter that is expressed in the liver, one isolates RNA from liver and uses an RT-PCR procedure, such as those known in the art, with the primers to amplify the desired promoters. FIG. 6 illustrates liver RNA-derived promoters obtained using the methods of this invention. However, the promoters can also be derived by conventional PCR from cDNA libraries (FIG. 5 illustrates T cell-derived promoters that were obtained in this manner). It is also possible to use the well-known hormonal and pharmacological inducibility of VL30 LTRs to find LTRs that are responsive to peptides, hormones, and cytokines (for a table and description of VL30 pharmacologic responses (see Hodgson et al., 1996 *Retro-Vectors for Human Gene Therapy.* R G Landes Company, Austin Tex., chapter 4, and FIG. 4.2). Examples of substances inducing various VL30 promoters to high levels include: epidermal growth factor, basic fibroblast growth factor, insulin, erythropoietin, glucocorticoid hormones, activators of cyclic 3'–5' AMP, and others. To rescue promoters with pharmacological responsiveness, cells or animals stimulated with the desired pharmacological agent are subjected to the RT-PCR procedure and the resulting U3 regions are cloned into a vector, (such as the exemplary VLBPGN) and are tested for inducibility. Standard RNA blotting procedures can be used before isolating VL30 promoters, to determine whether a particular drug or hormone causes induction of VL30 RNA expression in a particular mouse cell or tissue. After the promoter has been rescued, the vector is transmitted via retrovirus to the target cell (possibly a human equivalent of the mouse cell from which the promoter was rescued). After selection with the drug G418 (400–700 µg/ml, for 7–10 days) to select against cells not containing the vector, the target cell population is challenged with the pharmacological agent of choice. Reporter gene expression (in the example, GFP) or RNA expression, as determined by RNA blotting, can be used as an assay of gene inducibility by the agent (for exemplary gene expression methods, see Chakraborty et al., *Biochem. Biophys Res. Commun.* 209:677–683, 1995).

Using any specific primer set designed for use with VL30 retro-elements and using total cellular RNA from a particular mouse cell type as a template for RT-PCR, (using commercially available kits and methods therein) candidate promoter elements can be amplified. This method is useful for the identification of mouse-derived promoters and in particular the method is useful for the identification of cell-type specific or tissue-specific promoters from a mouse and for the selection of these promoters and the identification of tissue-specific or cell-specific promoters that function in human cells. Thus, these types of vectors and the methods for using these vectors permits the identification of promoters to permit controlled transcription of a foreign gene. The promoters, originally obtained from the mouse, can be used to effect tissue-specific or cell-specific expression in a human or animal liver cell such as a hepatocyte, or in a human blood cell such as a T-helper cell or in an erythrocyte (red blood cell). Methods are disclosed in Example 2 for the screening and selection of the promoters from a library of amplified promoter sequences. Other methods are well known to those of ordinary skill in the art. The specificity of the selected promoter can be assessed, for example, by introducing a selectable marker under the control of the test promoter in question and introducing this construct into various cells to assess the ability of the promoter to selectively regulate expression.

The amplified fragments represent U3 promoter regions from any RNA species expressed in the originating cells and their abundance will be in approximate proportion to the number of expressed copies of RNA in the original mixture. Example 3 illustrates one example using a mouse T-helper cell cDNA library to produce amplified fragments representing U3 regions expressed in T cells. The vectors were efficiently expressed as RNA and protein in PA317 helper cells, and were transmitted by retrovirus into human T-helper cells, where they were integrated and expressed as protein in the form of a β-galactosidase reporter gene, as visualized by X-gal staining. The products of this experiment are provided in FIG. 5 and as SEQ ID NOS: 2 and 3 from T-helper RNA. The products of another experiment are shown in FIG. 6 as SEQ ID NOS: 4–13 from mouse liver RNA (by RT-PCR).

Examination of the different U3 sequences isolated from T cells and from liver revealed several things. First, the T cell U3 sequences were related to each other, as were the liver sequences. However, the two types of U3 sequences were quite different between the two sources (T-cell, FIG. 5 and liver, FIG. 6). Specifically, the liver sequences (FIG. 6) appeared to be a closely related group, differing mostly by single point mutations, some of which may affect transcription factor binding sites. Some of the polymorphic sites included: a phorbol ester response element (VLTRE); a Rel/NFκb binding region, and a possible glucocorticoid response element (GRE). Some of these polymorphisms are illustrated in FIG. 6. The T cell-derived sequences (FIG. 5, SEQ ID NO:2 and 3), on the other hand, differed significantly in length, with SEQ ID NO:3 missing more than 120 bases (compared with SEQ ID NO:2) including putative binding sites for retinoids (RAR/RXR) and several elements contained within the enhancer repeat region (including a cAMP response element (VLCRE, or CREB/jun binding site), and putative serum response element (SRE, CARG, and NF1/IL6). SEQ ID NO:3 represented one out of five clones sequenced, while SEQ ID NO:2 represented four out of five. Possible sites of interactions between transcription factors and DNA can be observed by comparing the experimentally derived U3 sequences with those in Hodgson et al.,(Retro-Vectors for Human Gene Therapy, 1996 FIG. 4.2 supra). In addition to the deleted sequences of SEQ ID NO:2, there: are a number of single base differences within the conserved regions of the two T cell-derived sequences.

Advantageously, a number of new VL30 promoter sequences (SEQ ID NOS: 2–13, supra) were identified using these methods despite the fact that VL30 RNA comprises only about 0.3% of cell mRNA represented in a cDNA library. Moreover, in each case, the cloned insert was isolated without the need to use linkers, adapters, or multiple cloning sequences such as those that are typically use for other library construction methods. The promoter sequences can be used in the vectors disclosed here to express inserted foreign genes or the promoter sequences can be substituted into other retroviral vectors, such as MoMLV-derived vectors or other VL30-derived vectors. Further, vectors containing the promoter sequences can be propagated in retroviral helper cells, such as PA317 (U.S. Pat. No. 4,861,719 to Miller) or introduced into cells by chemical or physical transfection.

In another application of the methods of this invention, libraries of amplified sequences can be incorporated into vectors using two or more fragments and using the restriction endonucleases cleaving at a distance from their recognition sites. Preferably the vectors are created using six or more fragments and preferably greater than 10 or more fragments. For example, as applied to VL30 promoter sequences, because there are over a hundred VL30 retroelements in the mouse genome, it is possible to amplify all of the promoter sequences en masse, and propagate them en masse, enabling screening by serial passage through helper cells (such as the PA317 helper cell line) or by means of a replication competent retrovirus, as illustrated in Examples 3 and 4. Conversely, the promoter region may be broken down into several sub-domains and permutations of each could be combined and screened to enhance the chances of generating a superior construct (FIG. 4B).

Figure 7:
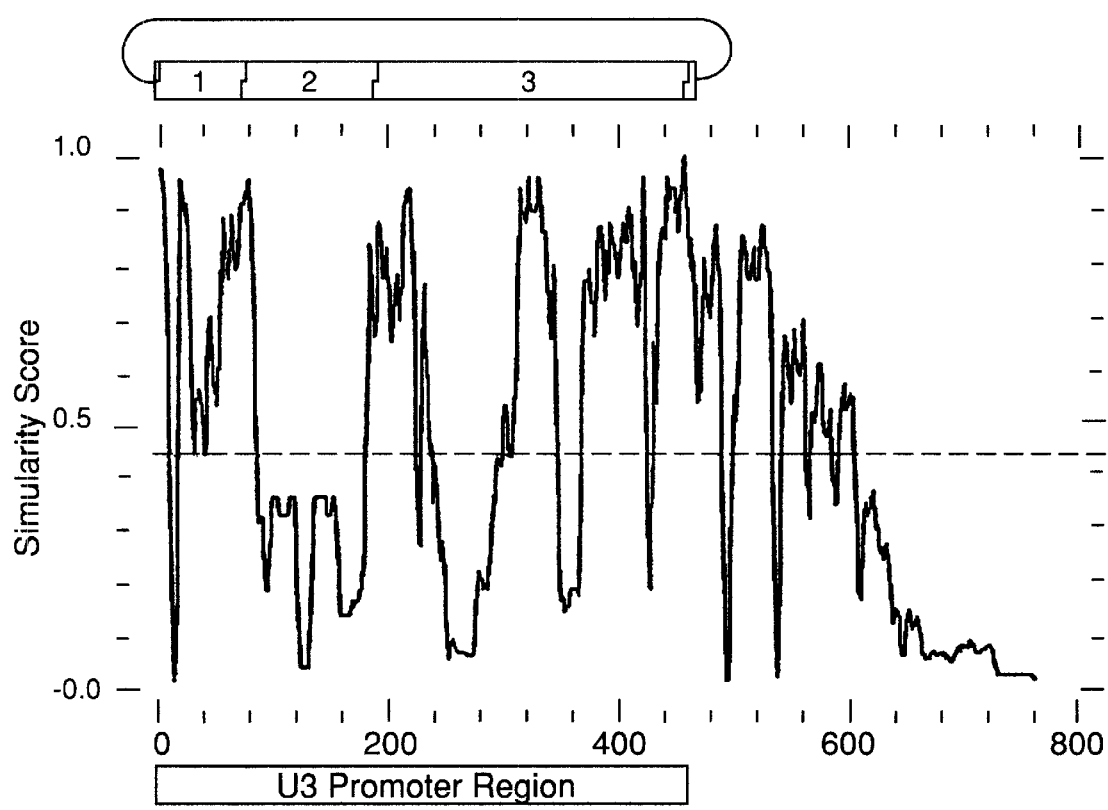
FIG. 7 illustrates a similarity plot of nucleotide sequences found in VL30 U3 regions.

As an example of breaking a promoter region down into several sub-domains, FIG. 7 illustrates a similarity plot of nucleotide sequences found in VL30 U3 regions. Plot similarity was performed using the Plot Similarity program (Wisconsin Sequence Analysis Package, release 8.1, Genetics Computer Grout, Madison, Wis.). This program plots the running average of the similarity among the sequences in a multiple sequence alignment. The sequences compared were those found in FIG. 4.2 of Hodgson, 1996, chapter 4 (infra). That is, the plot discloses the degree of conservation of VL30 promoter sequences among known VL30 promoters. From the figure, it can be seen that conserved sequences (close to 100% conserved) can be used as primer binding sites to amplify the adjacent sequences by PCR. An allelic mixture of three fragment sets is then created to make a combinatorial library of promoters that can be positively selected, such by using retroviral amplification of the active sequences. This, used in combination with the FIG. 4.2 (Hodgson, 1996, chapter 4 supra) can be used to determine regions of high similarity. Regions of high similarity within the U3 region can be replaced with one another. Therefore, a library of permutations of these sections can be made by combining allelic pools obtained by amplifying the sequences from individual subsections, followed by ligating the subsections in the correct order using the methods of the instant invention for gene self-assembly. For example, subsection 1 can include the distal enhancer (from the LTR 5'-end to the site of insert primer 2, see for example the region defined by the insert primers 1 and 2 (SEQ ID NOS 55 and 56 of Example 4). In this way, using a plot similarity (such as FIG. 7), within each sub-section, the primers position fragments within a region of nearly 100% identity. Degenerate primers can also be used in these experiments to account for multiple nucleic acid base combinations along a particular sequence. In each case, the primers preferably are designed to have a melting temperature that is compatible with the RT-PCR conditions being used, and the conditions should be those recommended by the manufacturer (preferably Perkin Elmer Corp., Emeryville, Calif.). In Example 4, a set of primers is given that can be used to amplify different U3 subsections, together with directions for assembling a combinatorial library.

It will be appreciated by persons of ordinary skill in the art that the methods of the instant invention can thus be used to make allelic libraries of a variety of genes. For example, different allelic portions of a gene can be combined in a predetermined order and orientation to produce combinatorial libraries, without the need for fortuitous restriction sites separating the parts in the original construct, and without perturbing the important sequences joining the parts using the methods of this invention.

In this invention primers are constructed as described above. However, for the generation of allelic libraries or more complex library constructs it may be helpful to include 5'tags into the 5' end of the primer. The purposes of the tag sequence are: 1) to provide extra nucleotides on both sides of the restriction endonuclease recognition sites (for more efficient digestion); and 2) to enable recovery of sequence tags or undigested fragments by means of an affinity reagent (such as silica, magnetic beads, or nitro-cellulose containing the complementary sequences) for purification. The use of an affinity reagent permits the digested ends to be purified away from the digested fragments. Furthermore, if any undigested ends remain after thorough digestion, the affinity reagent will remove them, further aiding in the purification. In one embodiment, affinity purification of the digested fragments is used in place of gel isolation, eliminating possible damage caused by ultraviolet light as well as possible damage caused by dye (e.g., ethidium bromide) binding to the DNA.

It will also be appreciated that a number of other variations to the primer sequences can be employed. For example, as discussed above, the enzyme recognition site for an enzyme that digests outside of its recognition sequence is included in the primer, so that the DNA digest creates an overlapping end that is complementary to one other terminus to which it will be joined. The enzyme recognition site can be moved to any location within the primer so as to digest the DNA at the exact location desired. The primer can also be programmed with a novel enzyme recognition sequence to add any desired sequences between the two sequences to be joined or to incorporate a linker or adapter if desired. If the sequences to be amplified contain the enzyme recognition site of the primers, it may be necessary to switch to a different enzyme usage. The use of several different enzymes is possible and has been discussed above. As with other PCR procedures, after the initial primer selections have been made the primers are assessed for their ability to fold back on themselves or to create internal secondary structure. The primers are preferably modified to avoid palindromic sequences or the potential for self folding within a primer. Nucleic acid analytical software (such as the Wisconsin GCG package, Oxford Biomolecular, Oxford, UK) is available to perform this analysis and aid in the selection of alternative primers.

In addition, as with all PCR processes, it is necessary to determine the melting temperatures ($T_m$), and to adjust the annealing temperature of the PCR reactions to compensate for such temperatures. Finally, it is important to perform a sequence redundancy search, to determine whether the target sequence (the sequence complementary to the primer) is found more than once in the region to be amplified. If the sequence is repeated, it will be necessary to use a different primer in order to establish the single, correct priming site. Preferably, no more than 6–8 bases of incorrect target complementarity at the 3'-end of the complementary region is used and to allow a difference of at least 10° C. between the $T_m$s of the correct and the incorrect target. The annealing temperature should always be at least 5° C. lower than the $T_m$ of the correct target and 5° C. above the $T_m$ of the incorrect target. Again, the necessary software and instructions are readily available from the cited sources (Wisconsin Gene Computer Group and Oxford Biomolecular, supra)

Next, a vector is constructed to include the appropriate elements for expression in the desired cell type. For example, the plasmid of FIG. 3A can be used for the creation of a promoter library or a vector can be created using a commercially available vector and primers to create a three or more fragment annealing and ligation reaction as provided above. Preferably, the inclusion of a dominant negative selectable marker on the vector (e.g., the neomycin phosphotransferase gene, conferring G418 drug resistance) can be used to reduce the likelihood that cells without the vector are being maintained in culture.

Multiple allelic copies of DNA (cell derived or cDNA) can be amplified in separate reactions as a set of potential inserts with each set having its own unique overlap sequence following digestion with a restriction endonuclease, according to this invention. The fragments can then be ligated into an existing vector or in a single reaction of three or more fragments to form a combinatorial collection of potential alleles. For example, if six adjacent regions are amplified from five separate alleles, the number of combinations would be $5^6$, or 15,625 potential combinations. The combinations can then be grown en masse, and selected in vitro or in vivo. A variety of screening strategies can be used in this invention and those of ordinary skill in the art will appreciate that the type of screen will match the type of library being generation. Therefore, for the promoter library, introducing members of the library into particular cell types to assess for expression in one or more cell types versus the absence of expression in another cell type is evidence of tissue-specific or cell-specific expression. For screening purposes, the libraries of this invention function like other libraries created through other methods. A variety of screening methods for a variety of libraries have been described in the art. For example, selective screens are reviewed by Hodgson et al. (1996, RG Landes Company, supra). Reporter protein production is well known in the art as is dominant selectable marker (e.g. drug) selection and selection by fluorescence activated cell sorting, antibody affinity selection, phage display selection (such as commercially available from Amersham, Milwaukee, Wis.), and the like can be used without detracting from this invention.

In this way, it is possible to isolate multiple forms of genes, gene fragments or regulatory regions such as transcriptional promoters or packaging signals (for example, in a retro-vector system). The individual constructs may then be tested in vitro or in vivo to further characterize a particular phenotype.

In one example the method is used to create a library of complementarity determining regions (e.g., allelic variations that give rise to antibody diversity) of antibodies or from receptors, including T-cell receptors, epitopes, antigens, ligands and the like. For example, where a library of T-cell receptors is created, the introduction of a vector designed to create a functioning T-cell receptor can be introduced into T cells or T-cell progenitors and the cells can be tested for their ability to bind to a particular test ligand. The ligand-recognizing cells can then be isolated from the ligand and grown in the presence of cytokines to produce specialized T cell clones. Where a library of antibodies or antibody fragments is created, the antigen reactive portions, for example, can be recombined in a vector containing the remaining portions of an antibody molecule to generate antibodies or antibody fragments in a cell. In other examples, the methods of this invention can be used to create allelic domains of receptor families (such as the steroid receptor super-family); libraries with related regions from peptide hormones; cytochromes P450; or other protein families that have shared domains or sub-sections with similar structures. The methods of the instant invention allow the joining of allelic sub-sections in an ordered fashion. In each case, it will be necessary to design primers, and to keep track of the uniqueness of joining overlaps and the presence of internal restriction sites as described above. While these will be different in each case, here are listed some general guidelines that are incorporated into the method of the instant invention.

As discussed above, although described as it relates to promoter libraries, libraries of other nucleic acid sequences can be created using the methods of this invention. These libraries include, introns and/or exons and/or functional domains libraries, libraries of potential alleles for a particular gene sequence, and the like. These sequences can be amplified from cell DNA or RNA using the primers of this invention and incorporated into a variety of vectors. For example, one vector of this invention, VLBPGN, has a portion of LTR removed and can be used to create a variety of libraries following digestion with Bpm1.

Selected or screened products of the combinatorial library can be used for gene expression, such as the promoters of FIGS. 5 and 6. In addition, the exploitation of these sequences for the expression of a variety of genes, the LTR fragment containing the promoter can be joined to one or more functional retroviral packaging signals, internal ribosome entry sites, additional promoters, coding regions, processing sites, and the like.

Advantageously, there are almost no spatial constraints upon the joining of molecules by the method of the instant invention and other methods have not taken advantage of the combination of PCR to isolate genes or gene fragments; enzymes cleaving at a site distant from their restriction endonuclease recognition site to combine three or more fragments with precision; and, the use of unique overlapping non-palindromic termini to ensure fidelity of multi-fragment ligations. This combination permits the artisan to prepare complex gene constructions in one ligation step and does not require sequential sub-cloning into a vector or propagation in a prokaryotic host. Added to this the combination by these methods of fragment pools facilitates recombinatorial genetics.

The ability to recombine (in the correct order and direction) and screen a large number of allelic variants (whether as a simple library or as a combinatorial library), resulting in increased abundance (by amplification in the RNA, and subsequently in the DNA) is a special characterisitic of this invention. Particular advantages of this system are obtained when the methods of this invention are combined with retrovirus vector technology or other virus vector technology. For example, the combination provides a form of in vitro evolution whereby the passage of the library through virus and through cells selects functioning sequences and increases the abundance of the surviving RNA and DNA molecules.

For example, consider the consequences of screening several different promoters expressing RNA in a donor cell (i.e. a cell producing virus particles), but at differing levels of RNA abundance. In the following example, the least abundant RNA species is expressed at 0.1 copy of RNA per cell, while six others are expressed at 1 copy, 10 copies, 100 copies 1,000 copies, or 10,000 copies, or 100,000 copies/cell, respectively. After a single passage, the DNA copy number in the recipient cells now reflects the approximate RNA copy number in the donor cells. These numbers are further amplified in the relative abundance of RNA species produced in the recipient cells. Disallowing for factors such as position effects, transcription factor depletion, etc., (which may be considerable), the same relative ratios of expression would be expected. Taking into consideration position effects, the disparity between abundance caused by changing insertion loci should average out. The most abundant RNA species after two passages is then many orders of magnitude more abundant than the least abundant.

TABLE 2

Enhancement of DNA and RNA copy number as a result of different RNA expression levels, after retroviral passage. P = (no. of passages). Numbers are interpreted as relative ratios within a column.

| Species | RNA abundance P = 0 | DNA copy no. P = 1 | RNA abun. P = 1 | DNA copy no. P = 2 | RNA abun. P = 2 |
|---|---|---|---|---|---|
| A | 0.1 copy/cell | 0.1 | 0.01 | 0.01 | 0.001 |
| B | 1 | 1 | 1 | 1 | 1 |
| C | 10 | 10 | 100 | 100 | 1,000 |
| D | 100 | 100 | 10,000 | 10,000 | $10^6$ |
| E | 1,000 | 1,000 | $10^6$ | $10^6$ | $10^9$ |
| F | 10,000 | 10,000 | $10^8$ | $10^8$ | $10^{12}$ |
| G | 100,000 | 100,000 | $10^{10}$ | $10^{10}$ | $10^{15}$ |

The present invention is able to efficiently create a library of RNA or DNA sequences whether or not they are in low abundance. The kinetics of screening for RNA abundance of a promoter can be appreciated best in the following discussion. For the purposes of this discussion, position effects have been ignored. An equation describing the kinetics of screening for RNA abundancy is:

$$R_{rel\chi} = A\chi / \Sigma A_{a\infty} \tag{1}$$

The above equation (1) can be stated in plain English: The relative abundance of an RNA species $\chi$ ($[R_{rel\chi}]$ within a population of RNA molecules expressed in a single cell or within a population of cells) is equal to the RNA copy number of RNA species $\chi$ ($A_\chi$) divided by the sum of the RNA copies of all RNA species present, including $\chi$.

The relative abundance number of any given species changes as the number of passages change, according to the following approximation:

$$R_{\chi py} = D_{\chi p0} R^{p+1} \tag{2}$$

In the simplest of terms, equation two (2) can be expressed as: The abundance of RNA species $\chi$ after Y passages ($R_{\chi py}$) is equal to the initial abundance of the DNA for species $\chi$ at passage=0 ($D_{\chi p0}$), multiplied by the RNA abundance/DNA copy, raised to the power of the number of passages plus one. Thus, a typical RNA species that starts out as a single copy of DNA, after zero passages (i.e., in the donor cell) expresses 10 copies of RNA/cell. After one passage it is amplified at the DNA level to a relative ten copies (the same as the RNA abundance at P=0), and at the RNA level to 100 copies (10 copies per DNA copy). The reason for the amplification is that viral packaging and passage is based upon the number of RNA copies present in the donor cell. These calculations can be used to arrive at approximate abundance determinations for any given passage. The actual results of any given experiment, of course, will be biological rather than physical or mathematical. This means that other variables such as RNA efficiency of transmission and longevity, availability of transcription factors, experimental variation, etc. also come into play. The underlying purpose of the approximating equations, however, is to illustrate that RNA is amplified in DNA in proportion to the abundance of the template (RNA) within the cell.

The abundance of mRNA in cells can vary continuously from less than a copy per cell to nearly 100,000 copies/cell in actively transcribing, highly-specialized cells such as reticulocytes, the chicken oviduct, the silk mote silk gland, etc. Therefore, the spectrum of RNA abundance from $0–10^5$/cell is within the biological window of interest. For most practical purposes, such as biotechnological expression of genes in specific cells, only the higher end of this abundance range is desired. Therefore, using a viral selection system, as disclosed in this invention, it may be possible to disregard those species with less than a threshold level, such as <0.1 copies per cell. The selection through virus will lead to the recovery of the more abundant species. Furthermore, because the vector is likely to be the only considered sequence, it may be considered as a proportion of the whole of RNAs expressed in the target cell. The situation is more complex when a large number of permutations and combinations is generated, for example by self-assembling thousands or millions of fragments in a predetermined order using the self-assembly technique of the instant invention. Consider the assembly of allelic variants of four promoter subregions: distal enhancer, proximal enhancer, distal promoter and proximal promoter. If 100 varieties of each of the four groups were amplified and combined using the instant process along with a single vector, $10^8$ resultant combinations could occur. However, a sufficient number of molecules to start out a combinatorial screening program might be a million. The problem can be simplified by considering these in groups as follows:

expressed RNA sequences in two passages. Using similar procedures in combination with drug and/or hormonal stimulation, and after consideration of the possible transcription factor binding sites within the sequence family (FIGS. 5 & 6), it is within the intended scope of the invention to select for hormonal or pharmacological controls of transcription such as have been described herein. The factors contributing to the outcome are not only the input constructs, but recombinants and mutants as well. These secondary contributors to molecular diversity will be enhanced if multiple rounds of infections are allowed to occur, as oftentimes the difference between a particular transcription factor being able to bind (or not) may depend upon a single base change. Because viral infection is progressive and competitive, molecular evolution can be used to generate gene constructs de novo in the tissue culture dish in short time periods. Advantageously, the use primers to generate amplified fragments with uniquely complementary cohesive ends (i.e., that the ends will preferably only hybridize with the intended 5' and 3' fragments) to ligate three or more fragments as taught in this invention improves the potential for obtaining a diverse library.

Although the examples particularly point out a transcriptional promoter as the product of the process, the skilled artisan can appreciate that a particular selection technique can be applied to other cis- and trans-acting genetic sequences as well. Although a virus is used to propagate the selective advantage of a preferred embodiment, it can also be appreciated that any selective screen, such as drug selection, cell survival, phenotypic selection, cell sorting, antibody selection, and the like (see Ausubel et al., supra) could be substituted without changing the intended scope of the invention. Likewise, transfection or cell fusion could be used in place of viral infection. Furthermore, substitution of different viruses, retrotransposons, or functional groups are likewise within the intended scope of the invention. The described embodiments are to be considered only as illustrative and not restrictive, and the scope of the invention is indicated by the claims rather than by the narrative description. All references and publications, cited herein, are incorporated by reference into this disclosure.

Like the embodiments detailed above, the method of library production is also conducive to assembly and transfer of genetic material directly into eukaryotic cells, saving the step of propagation in bacteria that is standard in bacteria. An advantage of direct transfer of the libraries of this invention to eukaryotic cells, including the exemplary ret-

TABLE 3

Grouped abundance of RNA molecules derived from combinations.

| No. of species in group: | RNA abundance: | Total No. RNA molec. at P = 0: | RNA at P = 1 | RNA at P = 2 | RNA at P = 3 |
|---|---|---|---|---|---|
| $9 \times 10^5$ | 1 | $9 \times 10^5$ | $9 \times 10^5$ | $9 \times 10^5$ | $9 \times 10^5$ |
| $2 \times 10^5$ | 10 | $2 \times 10^6$ | $2 \times 10^7$ | $2 \times 10^8$ | $2 \times 10^9$ |
| $2 \times 10^4$ | 1,00 | $2 \times 10^6$ | $2 \times 10^8$ | $2 \times 10^{10}$ | $2 \times 10^{12}$ |
| $1 \times 10^3$ | 1000 | $1 \times 10^6$ | $1 \times 10^9$ | $2 \times 10^{12}$ | $2 \times 10^{15}$ |
| $1 \times 10^1$ | 10,000 | $1 \times 10^5$ | $1 \times 10^9$ | $1 \times 10^{13}$ | $1 \times 10^{17}$ |
| 1 | 100,000 | $1 \times 10^5$ | $1 \times 10^{10}$ | $1 \times 10^{15}$ | $1 \times 10^{20}$ |
| Sum Total: | | $6.6 \times 10^6$ | $1.11 \times 10^{10}$ | $1.01 \times 10^{15}$ | $1 \times 10^{20}$ |

Thus, it follows that in the example population (Table 3) of over a million constructs (equally represented in the DNA), a single construct expressing 105 copies of RNA per DNA copy will increase to approximately 99% of the total roviral vector producer cells, is that certain essential cis-acting structural features will be under positive selection (i.e., if they are not present, the molecule will be lost due to its non-functionality). As discussed above, it is often advantageous to eliminate bacterial and plasmid DNA sequences, endotoxin, and other bacterial contaminants by introducing the constructs directly into eukaryotic cells.

In addition to providing a method for constructing complex DNA molecules efficiently (as in the examples of three piece and six piece constructs), the methods of this invention permit the assembly of constructs that are larger than those conventionally propagated in *E. coli*. Examples of these types of vectors include adenovirus vectors, herpes simplex vectors and artificial minichromosomes. In order to insert genes into such vectors that are too large for conventional molecular cloning procedures, in the past it was often necessary to resort to in vivo recombination, wherein the genes of interest are cloned into a suitable vector and the flanking homologous regions are used to target the foreign genes to a homologous site within the larger viral or minichromosome vector. However, the methods of this invention permit PCR fragments of any size (up to the limits of PCR capability, 20–30 kb per fragment) to be joined together. Thus, it is feasible to precisely construct adenovirus vectors by amplifying larger sequences, and combining them by ligation. For example, several sections of adenovirus (5–10 kb each) can be ligated using the methods of this invention, up to for example, about 37 kb, and then transformed directly into human cells. Only the correctly recombined vectors are capable of replicating. Hence, the DNA is autoselecting. A similar procedure is used for, generating herpes virus vectors, which are approximately 150 kb. The precision of the methods of this invention permit nonessential viral genes to be more easily eliminated from the construct. After transfection into appropriate cells, the DNA replicates and virus particles are formed.

Some special considerations apply to larger vectors, however. First, it is desirable to use enzymes that do not cut within the large DNA fragments. To prevent excessive fragmentation of the DNA by internal sites, it is desirable to use enzymes that cut rarely or infrequently, such as CpG-containing enzymes recognizing six bases, or enzymes such as Sap1, recognizing seven bases and digesting a three bp overhang (thus permitting up to 32 fragments to be joined in order). It is also desirable to avoid shearing the DNA once large segments have been joined by ligation. One method of avoiding shear is to add the transfection agent, such as Superfect™ reagent (dendrimers, Qiagen) or Lipofectamine™ (liposomes, Life Technologies, Gaithersburg, Md.) directly to the ligation reaction, and then add the cells to be transfected to the mixture. This, or a similar method avoids the need to physically move the ligated DNA, and thus prevents shearing. Another method is to add a DNA condensing reagent (dendrimers, polycations [such as polyethyleneamine] histones or liposomes) directly to the DNA ligation reaction, and then move the DNA by pipette after it has condensed (thus reducing shearing of the DNA). Once inside the cell, viral DNA can replicate (as in the examples of partially replication-competent adenovirus and herpes simplex virus vectors).

Artificial minichromosomes have been under development for years. True artificial chromosomes require a centromere, at least one origin of DNA replication, and in the case of linear molecules, telomeric repeats at the chromosomal termini. In addition, to be very effective it is desirable to have a selectable marker gene, one or more therapeutic genes, and/or reporter genes.

In reality, the use of minichromosomes has been delayed by the inability to effectively manipulate the larger DNA molecules in vitro. Yeast and bacterial artificial chromosomes have been used with little success in mammals, and the addition of telomeres to the ends of linear chromosomes is also a special problem, as there is no prokaryotic host that can tolerate large linear DNA. The methods of this invention offers the opportunity to assemble human or mammalian minichromosomes in vitro, by using large segments (10–30 kb) of synthetic, gene-amplified DNA as ligation starting materials. For example, up to 32 Sap1 fragments (up to 30 kb each, containing the essential cis- and trans-acting sequences), or 512 shorter Hga1 fragments can be combined using these methods. As with the other examples, several enzymes suitable for this invention (e.g., such as class IIS enzymes) can be combined (possibly with different termini lengths) to simplify the task. The methods of this invention also facilitate construction of telomeric repeats, because the constructs of this invention do not need to be circular. Thus, the methods of this invention can be used to make telomeres of any length, by adding additional segments onto the ends of molecules. One way to do this is using self assembling genes that employ a repeating overhang sequence (self-complementary molecule, such as AG-3' at one end, and CT-3' at the other end), permitting the telomeres to be lengthened to the extent desired by adding the required molar excess of the telomeric repeat-containing fragment. This technique gives the investigator some control over the relative length of the telomeres, although the self-complementarity indicates that many repeats will be lost due to self-ligation. This can be alleviated by using higher starting concentrations of DNA to favor inter-molecular ligations over intra-molecular ligations (e.g., >20 µg/ml starting concentration of DNA).

A two fold molar excess of telomeric fragments gives approximately twice the average length of telomere as a strictly 1:1 molar ratio of all fragments. By using a higher molar ratio of shorter telomeric repeats it is possible to give greater uniformity to the overall length of the molecules, which will vary from one terminus to the other. Thus, in addition to providing a way to build large molecules with precision, the methods of this invention provides for a way to control the telomere length (or potential life-span) of the artificial chromosome. To prevent damage during handling, the minichromosome DNA can be condensed with polycations, adenovirus particles, dendrimers, histones, or liposomes prior to transfection, similar to larger viral vectors.

The methods of this invention can be used to create recombinant virus. One example of this is an adenovirus vector self-assembling gene system. This system can include three parts: 1) vector: 2) helper virus; and 3) helper cells. The vector part is a self-assembling fragment set of at least three fragments comprising the essential cis-acting sequences (left and right inverted terminal repeats, which are the 103 bp at both ends of the genome that are required for replication [ITRs] and packaging sequences [Y, base pairs 194–358) and central 'baggage' area, comprising one or more self-assembling fragments including therapeutic genes, marker genes, and reporter genes. The baggage area is thus flanked by the cis-acting sequences in the vector. Because the synthetic oligonucleotide sequences comprising the 5' and 3' termini of the helper virus are not phosphorylated, they will not ligate together creating multimers. Thus, the Ad5 vector region will assemble only into monomers. The helper virus part comprises all Ad5 trans-acting genes except for the E1A and E1B genes. The helper virus part has no cis-acting sequences, and it is amplified in several sections. In this preferred embodiment, the virus is amplified using primers that exclude the ITRs, packaging region and E1A&B genes. The helper virus is digested by Sap1 digestion, creating seven uniquely terminated fragments comprising the trans-acting viral genome, with dephosphorylated, blunt 5' and 3' ends on the terminating fragments. The primers are designed so as to amplify the internal virus sequences without changing them, except for the 5' and 3' ends of the virus. The PCR-amplified fragments are digested with Sap1 and are religated in their natural order after gel isolation and Qiagen column purification. The 5' end of the helper virus genome starts at 3.2 kb (in the E1A gene) so as not to overlap the vector sequences, which could otherwise cause replication competent adenovirus (RCA). Because the 5' and 3' ends of the helper virus do not contain Sap1 sites, they remain intact after digestion with Sap1. Because the synthetic oligonucleotide sequences comprising the 5' and 3' termini of the helper virus are not phosphorylated, they will not ligate. Thus, the Ad5 helper virus genome assembles only into preferred monomers during ligation.

In a preferred embodiment, non-essential genes are deleted from the Ad5 genome by means of the method of self-assembling genes. In another preferred embodiment, the helper virus genome is approximately 30 kb after deletion of E1A, E1B and E3 gene sequences from the helper virus, and it is amplified as a single long fragment using the eLONGase Amplification System (Life Technologies or a similar strategy for creating long PCR fragments with high fidelity). It is not of great importance that occasional PCR errors may occur, because multiple copies of the Ad5 helper virus are transfected into target cells, thus providing trans-complementation. The helper cells are preferably 293 cells, a human kidney cell line expressing E1A and E1B genes: (ATCC). The vector part and the helper virus part are combined in equimolar ratios after ligation has been performed separately on each fragment set. The Superfect protocol (Qiagen) Iis used to transfect the vector part and the helper part into the helper cells. The helper cells lyse, releasing high-titer adenovirus particles that are capable of infecting a variety of human cells. The resulting defective virus is incapable of forming RCA, and it transmits up to 34 kb of foreign genes in the baggage area. Unlike conventional Ad5 vectors that require separate constructs for *E. coli* propagation of insert genes, and recombination in vivo, the present vectors are relatively easy to make and provide a precise, safe alternative to first generation and second generation adenovirus vectors.

Exemplary methods for producing self-assembling vectors and genes are provided below. Further, the Examples provide methods for producing libraries of nucleic acid sequences using the methods of this invention. A number of nucleic acid sequences identified using the methods of this invention are described. The examples provided below are exemplary and not limiting. All references and publications provided herein are incorporated by reference into this disclosure.

EXAMPLE 1

Three-Piece Gene Self-Assembly with 100% Efficiency

Using 6 primers (SEQ ID NOS:24 and 63–67), three PCR fragments were amplified from templates VLMG (SEQ ID NO:22) and VLBPGN (SEQ ID NO: 1). PCR reactions were carried out using the hot start technique, according to the manufacturer's instructions (Perkin Elmer) using Pfu DNA polymerase (Stratagene). To amplify specific portions of the above templates, each primer contained a class IIS enzyme site capable of digesting a unique overhanging end that was complementary to only one other terminus in the subsequent ligation. The class IIS enzymes used were Bpm1 and Eco 57I (the latter was used to copy a fragment that contained an internal Bpm1 site). The reactions were carried out as follows: 1) the lower reaction was assembled according to the protocol for PCR Gems (Perkin Elmer); 2) the lower reaction was heated to 80° C., 5 min, then cooled to 4° C. for 5 min; 3) the upper reaction was prepared according to PCR Gems protocol and was added to the lower reaction (separated by cooled wax). The primer concentration was 0.3 $\mu$M (final). The dNTP concentration was 200 $\mu$M (final). 5 Units of Pfu polymerase was used. All fragments were amplified using the following conditions: 96° C.; 45 sec; (then followed by 30 cycles of the following) 96° C. 45 sec, 52° C. 45 sec, 72° C., 6 min; then followed by a single incubation at 72° C. for 10 min; then hold at 4° C. All fragments were successfully amplified. The PCR fragments were purified using the Qiaquick PCR purification protocol (Qiagen). The fragments were digested with an excess of the appropriate restriction enzyme (Bpm1 or Eco57I). The digested fragments were run on a 1% agarose gel and were excised using minimal irradiation from a hand-held 365 nm ultraviolet light. The fragments were purified using the Qiagen Qiaquick Gel Purification Protocol. The fragments were ligated at an equimolar ratio at a concentration of >20 $\mu$g/ml with T4 DNA ligase (Boehringer Mannheim) overnight at 4° C. Competent *E. coli* SCS110 cells (Stratagene) were transformed with the ligated DNA. Eight colonies were characterized by restriction enzyme analysis, and all eight contained the correct order and orientation of the three fragments. The experiment was repeated independently by another investigator, and the same result was obtained (8/8=100%). Thus, the procedure resulted in a high percentage of correctly assembled vectors.

This three-piece vector was VLΔBP. The deletion extended from the distal enhancer region to the TATA box near the start of transcription. The deletion region was a pair of Bpm1 sites that permitted U3 sequences to be cloned into the insert.

One validated *E. coli* clone of VLΔBP was transfected into retroviral helper cells. After 48 h, the vector was transduced into amphotropic helper cells. After selection for two weeks with the drug G418, drug resistant colonies were grown up in a mass culture and the vector was transduced from the amphotropic helper cells into a human HT1080 cell line (ATCC, Rockville, Md.). Surprisingly, even with a large deletion in the LTR promoter, the basal TATA box-containing VLΔBP was transmitted as a retrovector and was permanently inserted into the human cell line, thus establishing the validity of the self-assembly technique for the construction of functional eukaryotic vectors.

EXAMPLE 2

Production of a Six Piece Self-Assembling Expression Vector

Due to the high efficiency of the gene self assembly process for the three piece assembly, a complex vector containing six fragments was constructed. The results here were extended to determine whether such a self-assembled vector would also have biological activity in human cells without being cloned and grown in a prokaryotic cell.

Figure 8:
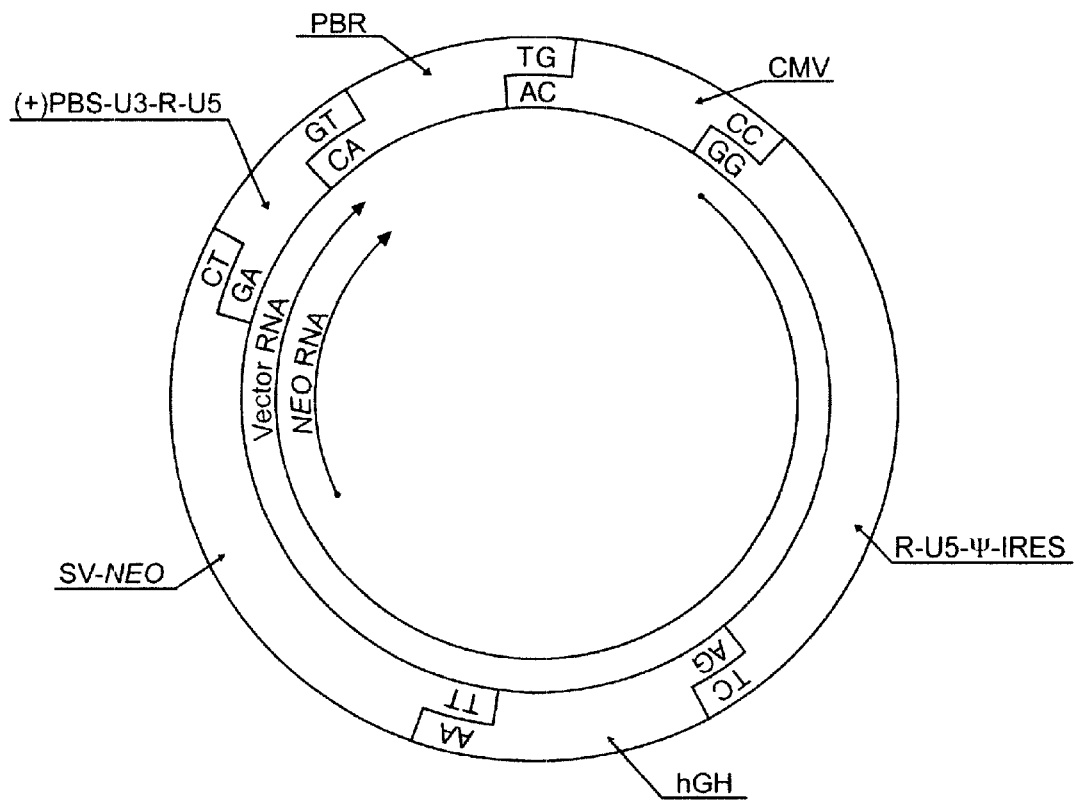
FIG. 8 illustrates a retro-vector comprising six double-stranded DNA fragments that were self-assembled into a circular structure using unique overlapping termini created using class IIS restriction endonucleases. Three templates and twelve primers were used in conjunction with three class IIS enzymes to make the six fragments that were ligated in a single step. The vector was efficiently self-assembled and was effectively transmitted by both DNA transfection as well as by retroviral transduction of the self-assembled DNA, without molecular cloning through a prokaryotic host (see Example 2).

Six fragments were individually constructed by PCR using three different templates and twelve primers (as illustrated in FIG. 8). The primers used three different class IIS enzymes. The enzymes were chosen so as to give 2 base pair, 3'-overhanging ends. Three enzymes were used in order to avoid the use of enzymes that had additional sites internal to the fragments being amplified. Thus, Bpm1 was used unless there was an internal Bpm1 site. If such a site existed, Eco57I was used. If there was also an internal Eco57I site, then BsrD1 was used. However, it is alternatively possible to use an enzyme such as Eam11041, where the Eam11041 sites in the primers are unmethylated (therefore susceptible to digestion by the enzyme), and wherein the $^{m5}$dCTP analog of dCTP is used in the PCR reaction, methylating all internal sites (and protecting them from digestion by Eam11041), as suggested by Padgett and Sorge, Gene, 168(1):31–35, 1996, and incorporated herein by reference.

Using 12 primers, 6 fragments were amplified from 3 templates: pBK-CMV (SEQ ID NO:26), pVLMB (SEQ ID NO:23) and pVLOVhGH-900 (SEQ ID NO:21). Fragment 1 was amplified from pBK-CMV using primers 1 and 2 (SEQ ID NOS:31 and 32). Fragment 2 was amplified from pVLMB using primers 3 and 4 (SEQ ID NOS:33 and 34). Fragment 3 was amplified from pVLOVhGH-900 using primers 5 and 6 (SEQ ID NOS:35 and 36). Fragment 4 was amplified from pVLMB using primers 7 and 8 (SEQ ID NOS:37 and 38). Fragment 5 was amplified from pVLMB using primers 9 and 10 (SEQ ID NOS:39 and 40). Fragment 6 was amplified from pVLMB using primers 11 and 12 (SEQ ID NOS:41 and 42). PCR reactions were carried out using the hot start technique, according to the manufacturer's instructions (Perkin Elmer Ampliwax PCR GEMS 100). The lower reaction was heated to 80° C. for 5 min, then cooled to 20° C. for 5 min. The upper reaction was prepared according to PCR gems protocol and was added to the lower reaction (separated by cooled wax). The primer concentration was 0.3 micromolar (final). The dNTP concentration was 200 µM (final). 5 U of Pfu polymerase (Stratagene) was used per reaction. 100 ng of template was used for each reaction 14 rounds of PCR amplification were used to reduce mutagenesis of the templates. The PCR cycling protocol was 96° C. 45 sec; then two cycles of (96° C. 45 sec, 52° C. 45 sec, 72° C. 6 min); then 12 cycles of (96° C. 45 sec, 58° C. 45 sec, 72° C. 6 min) followed by a 72° C. soak for 10 min, then to 4° C. hold.

The six PCR fragments were designed to self-assemble into a retro-vector after digestion with the correct class IIS restriction enzyme (FIG. 8). After transfection into retroviral helper cells, the vector DNA is transcribed as RNA by means of the cytomegalovirus immediate early promoter (fragment 1). This promoter replaces the retroviral or VL30 LTR in this vector. The RNA transcript region begins with the R and U5 regions of the Moloney murine leukemia virus (MoMLV) LTR, the viral packaging signals (Ψ) region of MoMLV, the packaging enhance (Ψ+) region of mouse VL30 and the IRES region of EMCV fragment 2. Fragment 3 consists of the human growth hormone (hGH) cDNA sequence. Fragment 4 consists of the SV40 virus early region promoter driving expression of the neomycin phosphotransferase (neo) gene. Fragment five consists of the (+)-strand primer binding site of the MoMLV LTR, the U3 region of the MoMLV LTR, the repeat (or R) region, and a portion of the U5 region Fragment 6 consists of the PBR322 plasmid origin of replication.

```
Fragment 1: CMV early region promoter
Template: pBK-CMV plasmid DNA (Stratagene, LaJolla, CA) Bpml    (SEQ ID NO:26)
PCR primer 1                                                    (SEQ ID NO:31)
GACTAACCTTGATTCCACTGGAGCCGTATTACCGCCATGCATTAGTTATTAATAG
PCR primer 2                                                    (SEQ ID NO:32)
GACTAACCTTGATTCCACTGGAGTAATTGCGGCTAGCGGATCTGACG Fragment 2: R-U5-Psi-Psi(+)-IRES Bpml
Template: pVLMB plasmid DNA                                     (SEQ ID NO:23)
PCR primer 3:                                                   SEQ ID NO:33
GACTAACCTTGATTCCACTGGAGACACTTGACCTCTACCGCGCCAGTCCTCCGAT
TGACTGAGTCG
PCR primer 4:                                                   SEQ ID NO:34
GACTAACCTTGATTCCACTGGAGGGATCCGCGCCCATGATTATTATCG Fragment 3: human growth hormone (hGH) Bsr DI
Template: pVLCNOVhGH plasmid DNA                                (SEQ ID NO:21)
PCR primer 5:                                                   SEQ ID NO:35
GACTAACCTTGATTCCAGCAATGTCGGTTAGCTTGTTTCTTTACTGTTTGTC
PCR primer 6:                                                   SEQ ID NO:36
GACTAACCTTGATTCCAGCAATGTTAGGACAAGGCTGGTGGGCACTGG Fragment 4: SV40 early promoter-neomycin phosphotransferase
Template: VLMB plasmid                                          (SEQ ID NQ:23)
PCR primer 7:                                                   SEQ ID NO:37
GACTAACCTTGATTCCACTGGAGGGTCGACCCTGTGGAATGTGTGTCAG
PCR primer 8:                                                   SEQ ID NO:38
GACTAACCTTGATTCCACTGGAGAATCTCGTGATGGCAGGTTGGGCGT Fragment 5: MLV(+)PBS-U3-R-U5
Template: VLMB plasmid                                          (SEQ ID NO:23)
PCR primer 9:                                                   SEQ ID NO:39
GACTAACCTTGATTCCACTGAAGAGATTTTATTTAGTCTCCAGAAAAAGGGGGG
PCR primer 10:                                                  SEQ ID NO:40
GACTAACCTTGATTCCACTGAAGCCCCCAAATGAAAGACCCCCGCTGACG
```

-continued

Fragment 6: PBR322 origin of replication
Template: VLMB plasmid                                            (SEQ ID NO:23)
PCR primer 11:                                                    SEQ ID NO:41
GACTAACCTTGATTCCACTGGAGCCGGGACGGAATTCGTAATCTGCTGC
PCR primer 12:                                                    SEQ ID NO:42
GACTAACCTTGATTCCACTGGAGTTCTCGAGGCGGCGCATCTCGGCG Procedure: The twelve primers were prepared by the following procedure: 1) oligonucleotides were synthesized with trityls off. After deprotection and lyophilization, the samples were resuspended in 5 microliters deionized formamide and loaded onto a polyacrylamide gel (12% polyacrylamide, 250V). The samples were excised under short wave UV irradiation and eluted overnight in 600 microliters of sample elution buffer (0.5 M ammonium acetate, 10 mM Mg acetate, 1 mM EDTA, 0.1% SDS). The contents were loaded onto a BioRad Chromatography column (Cat. # 732-6008) and centrifuged into an Eppendorf tube at low speed (2000 RPM, 5 min). After washing the column with 500 microliters TE buffer (10 mM Tris, 1 mM EDTA), pH 8.0 and recentrifugation (2000 RPM, 5 min), the pooled eluate was ethanol precipitated, washed with 100% ethanol, resuspended in TE buffer and quantitated by spectrophotometry of a small sample, which was then discarded.

Fragments were cleaned using the Qiaquick PCR cleanup procedure. The fragments were digested with their respective class IIS restriction enzyme. The digested fragments were run on 1% agarose gels, and the fragments were excised and cleaned using the Qiaquick gel cleanup procedure. Fragments were combined in an equimolar mixture and ligated overnight at 4° C. with T4 ligase and ATP. An analytical gel was run with the ligated DNA, as well as with controls including unligated fragments and ligated fragments with a single fragment missing. As opposed to the controls, the complete ligation included bands equivalent to the full-length supercoiled monomer (refered to as GENSA 981, SEQ ID NO:29), as well as bands possibly representing multimers (up to six bands were observed).

In order to assess the efficiency of the method, eleven nanograms of DNA were transfected into SCS1 supercompetent cells. Thirteen kanamycin resistant colonies were harvested, and plasmid DNA preps indicated 10 out of thirteen that appeared to be the correct length. All ten gave the expected bands when digested with Pst1, SnaB1, and Bam HI. 1.35 µg of the ligated DNA was purified by phenol-chloroform-isoamyl alcohol extraction, followed by two extractions with chloroform-isoamyl alcohol, and was precipitated in ethanol. The DNA was washed in 70% ethanol and re-suspended in 50 µl of sterile phosphate buffered saline (for transfection). The DNA was transfected (using the Qiagen Superfect protocol) into HTam1 (amphotropic human helper cells). 24 h after transfection, the target cells were washed and fresh culture media was added. 48 h after transfection, the supernatant from the vector producer cells was filtered (0.45 µm, Nalgene) and transferred to PG13 helper cells (ATCC) and HT1080 human fibrosarcoma cells. This procedure was repeated after 72 h. 48 h after transduction, recipient cells were started on G418 drug selection (500 µg/ml). The appearance of G418 drug-resistant colonies on transduced PG13 and HT 1080 cells after 6 days of selection indicated successful transmission via retrovirus particles. The transfect HTam cells were also selected with G418. After six days of drug treatment, 45 colonies of resistant cells were counted. Thus, the six fragment gene assembly was effectively transmitted and expressed as either a DNA (transfection) vector or a retrovector.

EXAMPLE 3

Design and Construction of Single LTR Vectors

Figures 3A, 3B, 3C:
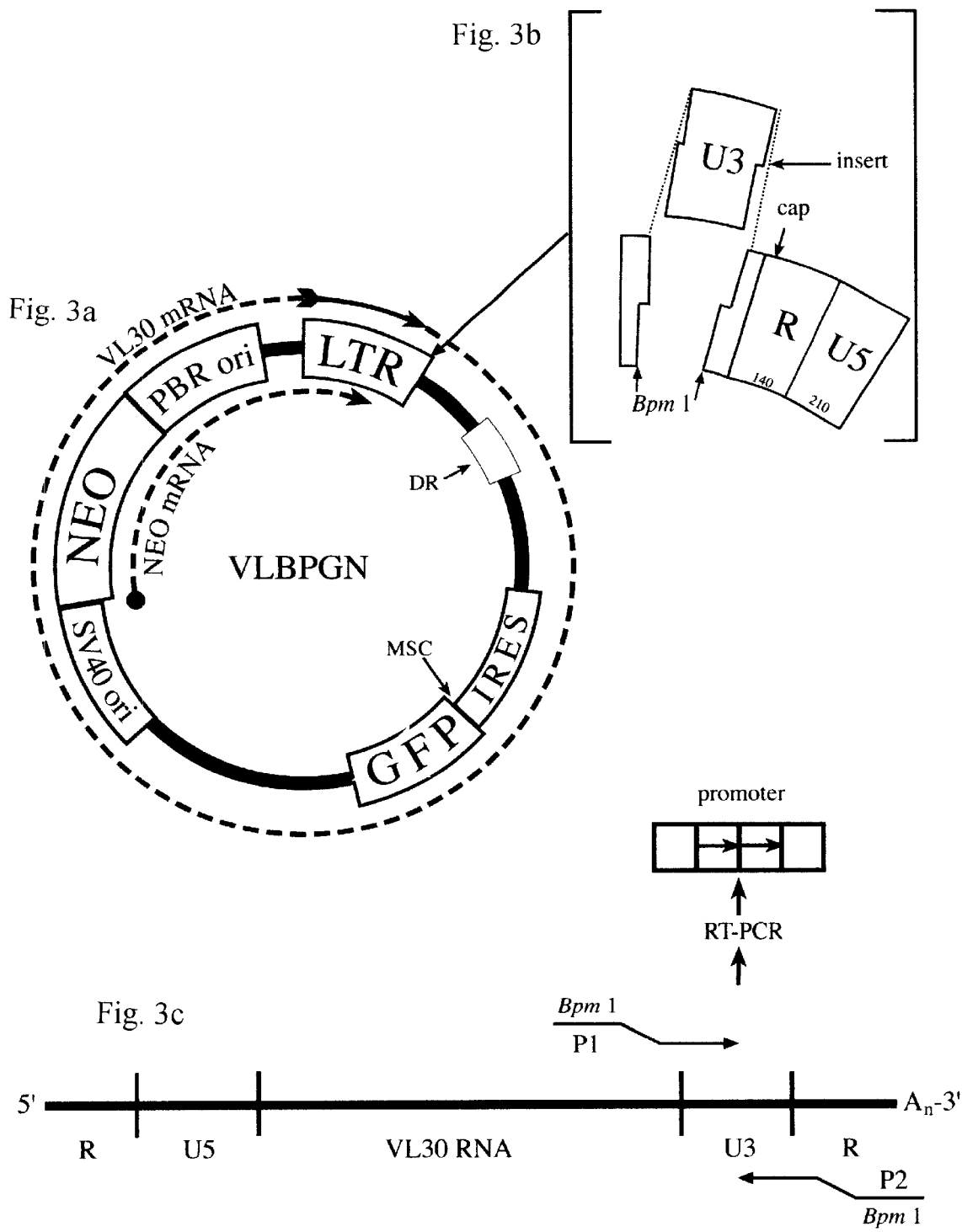
FIGS. 3A–C illustrates an exemplary refrotransposon-derived vector including a murine VL30 LTR (NLV-3) and packaging signal, an internal ribosome entry site (IRES) from encephalomyocarditis virus (EMCV), a gene encoding a green fluorescent protein (GFP), additional internal VL30 sequences (solid bar), SV40 early region promoter and Tn5 aminoglycosidase phosphotransferase (neo) gene PBR322 plasmid origin of replication and a plus-strand primer binding site (VL30). An exemplary vector sequence is provided as VLBPGN (SEQ ID NO:1).

Background: In order to manipulate the interior of the VL30 LTR sequences using a promoter rescue technique, single LTR vectors were constructed. The mouse VL30 element NVL-3 was used as the starting material as it is constitutively and abundantly expressed in most mouse tissues. Single LTR vectors are circular and behave as if they contained two LTRs. Thus, in these vectors RNA transcription begins at the start of the R region (see FIG. 3B), and continues through the polyadenylation site after completing the second round of transcription of the R sequences (FIG. 3A). In previous studies, these vectors were expressed transiently in vector producer cells and the DNA did not integrate into cell DNA as a standard two LTR vector. Therefore, the vectors were usually passed to a second complementation helper cell line via retroviral transduction of the vector RNA transcribed in the first helper cell. This process resulted in the vector regenerating a correct (two LTR) structure upon integration into the recipient cell DNA. Experimental method: The plasmid pNVL-3 (SEQ ID NO:25, kindly provided by Dr. J. Nortonm Manchester, UK), containing a complete copy of the NVL-3 (mouse VL30) genome (Adams et al., Mol. Cell. Biol., 8:2989–2998, 1988), was digested with Xho1 (which cuts in the LTRs), releasing the 4.27 kb VL30 genome with one copy of the LTR. This fragment was circularized using T4 DNA ligase and ATP. The circular DNA was linearized by digestion with SnaB1, 187 bp from the 3'-LTR. A 2.3 kb fragment containing the SV40 virus early region promoter and the aminoglycoside phosphotransferase (neo) gene, together with the PBR322 plasmid origin of replication, was excised from the BAG retrovirus vector (Price et al., Proc. Natl. Acad. Sci. 84:156–160, 1987, kindly provided by C. Cepko, Cambridge, Mass.). BAG is also obtainable in a retrovirus helper cell line from American Type Culture Collection (ATCC), Rockville. Md. by digestion with Xho1 and BamHI. This fragment was blunted with T4 DNA polymerase and dephosphorylated with calf intestinal alkaline phosphatase (CIP). The fragment was then ligated to the linearized SnaBI fragment of NVL-3 . The resulting plasmid (containing a circularly permuted NVL-3 genome with the SV-neo-ori region) was designated VLSNO2 (SEQ ID NO:30).

In order to facilitate the switching of LTR sequences by means of the class IIS enzyme Bpm1, VLSNO2 was digested with Bpm1 (six sites). The region containing four Bpm1 sites was removed and replaced with a 19 bp linker (SEQ ID NOS: 1 and 52, see below), 921 bp beyond the LTR. The linker contained Sna BI, Cla1 and Bam HI cloning sites.

Linker (top strand): 5'-TACGTATCGATGGATCCGA-3' (SEQ ID NO:51)

Linker (bottom strand): 5'-GGATCCATCGATACGTAAG-3' (SEQ ID NO:52)

The remaining two of the Bpm1 stes had complementary ends, which permitted their ligation and resulted in eradication of all Bpm1 sites within the resulting vector VLSNO3 (SEQ ID NO:20).

In order to facilitate reporter/therapeutic gene function, a 3.7 kb fragment containing the internal ribosome entry site (IRES) from encephalocyocarditis virus, together with the β-galactosidase reporter gene, was excised from the plasmid pVLSAIBAG (kindly provided by Mr. James Grunkemeyer, Omaha, Nebr.) by means of a partial digestion of the plasmid with Bam HI. This region was inserted into the Bam HI site of VLSNO3, resulting in the vector VLSNOSIB (SEQ ID NO:14).

A second reporter construct, pVLSNOG (5774 bp, SEQ ID NO:19) contained the green fluorescent protein (GFP, Clontech, Palo Alto, Calif.) gene was constructed by inserting a Bgl2-Bcl1 fragment (800 bp) from plasmid pGFP-N1. This sequence, containing the GFP gene, was treated with mung bean exonuclease and inserted into the unique Sna B1 site of pVLSNO3.

In order to enhance GFP fluorescence from the reporter plasmid pVLSNOG, the serine-65 codon in the GFP gene was mutated into threonine by a site-directed mutagenesis procedure with the Transformert™ Site-Directed Mutagenesis kit from Clontech. A Bpm1 site in the GFP gene (threonine-9) was mutated at the same time without changing the amino acid (ACT to ACA). The resulting plasmid was pVLSNOGM (SEQ ID NO:18).

An Nco1-Xho1 fragment (585 bp) from plasmid pG1IL2EN (kindly provided by Dr. Steven Rosenberg, Bethesda, Md.), containing the internal ribosome entry site (IRES) from encephalomyocarditis virus (EMCV) was inserted into the Apa1 site upstream of the GFP gene in pVLSNOGM, resulting in pVLSNOGMI (SEQ ID NO:17). Both insert and plasmid fragments were blunted with mung bean exonuclease. One variant version of pVLSNOGMI with an IRES tandem dimer was also constructed and designated pVLSNOGMI2 (SEQ ID NO:16).

Oligonucleotides (SEQ ID NO:53 and 54) containing a splice acceptor (SA) of AKV virus (in bold) was inserted into pVLSNOGMI at the unique Sac 2 site just before the IRES, resulting in pVLSNOGMIS (SEQ ID NO:15).

Oligo: (SEQ ID NO:53) 5'-GGCCGCTAACTAATAGCCCATTCTCCAAGGTACGTAGC-3'
3'-CGCCGGCGATTGATTATCGGGTAAGAGGTTCCATGCAT-5' (SEQ ID NO:54, bottom Oligo)

Recovery of LTR Promoter Sequences from Mouse CD4+ T-helper Cells

In order to facilitate the recovery of VL30 promoter sequences expressed in mouse T-helper cells, a mouse CD4+ T-helper cell cDNA library (Stratagene, San Diego, Calif., Catalog #937311) was screened by plaque hybridization. Approximately $2 \times 10^4$ bacteriophage λ-ZAP clones were plated on a lawn of *E. coli* cells according to the manufacturer's instructions. Two nylon filters were sequentially layered onto the lawn of *E. coli* cells and bacteriophage. The filters were hybridized to a $^{32}$P-labelled (Prime-It RmT Random Primer Labeling Kit, Stratagene), 4.2 kb internal Xho1 fragment of NVL-3 (containing the NVL-3 genome). 55 plaques (of approximately 0.3% of the total phage) reacted positively on both filters. 18 VL30 cDNA sequences were cloned from the plate, which was used to identify U3 promoters that at actively expressed in the RNA of mouse T-cells. Five of the 18 clones contained intact U3 sequences, representing four of one molecular species, named TH1 (SEQ ID NO: 2) and one of another species, named TH2 (SEQ ID NO: 3) also provided in FIG. 5. TH1 contained approximately 120 bp more DNA than did TH2. Because TH1 was more abundant (4 out of 5 clones), the additional sequences in the enhancer region were implicated to be a possible reason for the stronger expression in mouse T cells. Examination of the known and putative transcription factor binding sites in the VL30 LTR (Hodgson, 1996, chapter 4, FIG. 4.2 supra) revealed several interesting features of TH1 and TH2. First, the extra sequences of TH1 that were missing in TH2 included an extra copy of the enhancer repeat region as well as a potential retinoid (RAR/RXR) binding site. Several transcription factor binding sites in the enhancer repeat region that differed between the two elements included: a cyclic 3'–5' AMP response element (VLCRE, a potential CREB/jun binding site), a serur response element (SRE), and a potential NF1/IL6 binding site (although there were additional sites for these factors in other enhancer repeats). These factors could possibly explain why VLTH1 appeared to be expressed at higher levels, both in the source cells and into transduced cells. Together, the VL30 sequences represented 0.3% of the mRNA expressed in the T cells, and TH1 appeared to be most abundant VL30.

Sequencing Primers
(SK, SEQ ID NO:49) 5'-CGCTCTAGAACTAGTGGATC (20 mers, Tm 60° C.).
(T7, SEQ ID NO:50) 5'-GTAATACGACTCACTATAGGG (21 mers, Tm 60° C.).

Seamless Rescue of T Cell Promoters Using Class IIS Restriction Enzymes

Two sets of primers containing offset Bpm1 restriction sites were designed and synthesized. One set was for amplification of the plasmid sequences, and another was for the amplification of the inserts.

Insert Primers: (Bpm1 Site Bold)
ITA (43 mer, Tm: 67.2° C., SEQ ID NO:45) CGATC-CACTGGAGCTCGGAGCCCACCCCTC-CCATCTAGAGGT
ITB (43 mers, Tm: 66.3° C., SEQ ID NO:46) CGTCCTC-CTGGAGAGCACAGGGTAGAGGAGTCTC-GACGGTCAG Vector Primers: (Bpm1 Site Bold)
VLA (43 mers, Tm: 68.2° C., SEQ ID NO:47) CGCAAC-CCTGGAGACCTCTAGATGG-GAGGGGGTGGGCTCCGAG
VLB (43 mers, Tm: 66.3° C., SEQ ID NO:48) GCAGGAC-CTGGAGCTGACCGTCGAGACTCCTCAC-CCTGTGCT To amplify vector sequences more efficiently, vector templates were shortened by deleting marker genes from vectors. pVLSNOSIB (SEQ ID NO:14) was cut with Kpn 1 and a 4201 bp fragment containing β-gal gene was removed. The remaining vector has 3923 bp.

The U3-promoter inserts (357 bp for TH1 and 240 bp for TH2) were PCR-amplified from TH1 and TH2 promoters with primers ITA and ITB. The vector cassettes (~4.2 kb for pVLSNOSIB and ~3.7 kb for pVLSNOGMIS) were PCR-amplified from the shortened vector templates using primers VLA and VLB, (supra). The PCR-amplification was done with high-fidelity Pfu DNA polymerase from Stratagene (La Jolla, Calif.). The amplified products were gel-purified (1% agarose gel). The inserts were then cut with Bpm 1 to produce complementary ends. The vector cassette products were phosphorylated with PNK, then circularized with T4 ligase, and transformed into SCS 110 cells. Recovered plasmids were then digested with Bpm 1 and treated with CIP to produce complementary ends. Bpm 1 treated inserts and vector cassettes were ligated, and T-cell tissue-specific VL 30 vectors VLTH1 and VLTH2 were produced. The marker β-gal gene and GFP gene were put back into those vectors at the original unique sites Kpn 1 and Sal 1 respectively.

Transmission and Expression of Single LTR Vectors and T Cell U3 Sequences

Vector DNA constructs were transfected into GP+E86 retroviral helper cells (Markowitz et al, 1988, supra) using the Lipofectamine protocol (Life Technologies, Gaithersburg, Md.). The culture media from these cells (supernatant), containing defective transducing particles (72 h post-transfection), was transmitted to PA317 Miller, U.S. Pat. No. 4,861,719 amphotropic helper cells, using ectamine to enhance transduction efficiency (Hodgson et al., 1996. Synthetic Retrotransposon Vectors and Gene Targetings pp. 2–14, in: Felgner et al., eds. *Artificial Self-Assembling Systems for Gene Delivery.* American Chemical Soc. Books, Washington, D.C.). A similar procedure was used to transmit VLTH1 and VLTH2 to the PG13 helper cell line (Miller et al., 1991. *J. Virol.* 65:2220–2224). 24 h post-transfection, the recipient cells were selected with the drug G418 (500 μg/ml, 2 weeks) to enrich for stably transduced cell populations.

All of the single LTR vectors, including VLTH1 and VLTH2 were transmitted by this method, indicating that single LTR vectors can be used for promoter switching and yet revert to dual LTR vectors after a single passage. Vectors VLSNO2, VLSNO3, and VLSNOSIB were then titered on NIH 3T3 cells (using the PA317 vector producer cell lines). VLTH1 and VLTH2 vectors were titered on human HT1080 cells (PG13 cell lines). Surprisingly, all of the single LTR vectors were transmitted effectively. However the titers of stably transduced TH1 and TH2 cell lines were $5.5 \times 10^2 - 1.1 \times 10^3$ TU/ml, compared to $0.4 - 3.0 \times 10^4$ TU/ml for the VLSNO2, VLSNO3 and VLSNOSIB cell lines. Thus, switching from the NVL-3 transcriptional promoter (originally isolated from NIH 3T3 fibroblast cells) to VL30 promoters derived from T helper cells, appeared to have a negative effect on RNA expression in fibroblast cells, as determined by the transmissibility of the RNA.

In order to study the usefulness of rescued promoters as DNA transfection vectors (as opposed to retro-vectors), VLSNOSIB, VLTH1 and VLTH2 were also transfected into a number of cell lines (using Lipofectamine), including NIH 3T3, PA317, GP+E86, PG13, HT1080, SW480 and HeLa (available from ATCC). RNA expression in these cell lines is shown in Table 4, wherein gene expression from the LTR promoter (as determined by β-gal staining) is normalized to VLSNOSIB (100).

TABLE 4

| Cell line: | NIH 3T3 | PA317 | GP + E86 | PG13 | HT1080 | SW480 | HeLa |
|---|---|---|---|---|---|---|---|
| Vector: | | | | | | | |
| VLSNOSIB | 100 | 100 | 100 | 100 | 100 | 100 | 100 |
| VLTH1 | 39.3 | 18.7 | 0.1 | 21 | 25.5 | 156 | 156 |
| VLTH2 | 28.6 | 7.1 | 5.5 | 11.5 | 46.8 | 82 | 156 |

Transient expression of a β-gal marker gene by three VL30 promoters: NVL-3 (VLSNOSIB), VLTH1 and VLTH2. Cells were transfected using the Lipofectamine procedure. Total blue cells were counted from each well in 6-well plates, and the number of blue cells from VLSNOSIB was normalized to 100%.

The expression of both the VLTH1 and VLTH2 promoters was significantly reduced compared to VLSNOSIB in cell lines of fibroblastic origin, whereas in SW480 colorectal cancer cells and HeLa cells, it was comparable to or better than VLSNOSIB (the NVL-3 promoter). However, VLSNOSIB was expressed poorly in the non-fibroblastic cell lines, so a direct comparison was difficult to interpret. Unfortunately, the human T cell lines (Jurkat and MOLT4 [obtained from ATCC]) were not transfected by Lipofectamine, and they were poorly transduced by VLTH1 and VLTH2 retro-vectors. In the Jurkat and MOLT4 cells transduced with VLTH1 and VLTH2, only a small percentage (1–10%) of cells that were stably transduced by the vectors stained positively for β-gal expression. However, the marker gene (neo) continued to be expressed from an internal promoter, as evidenced by drug selection.

Taken together, the results demonstrated: 1) the ability of the promoter rescue technique to seamlessly capture functional transcriptional promoters from specialized cells; 2) the ability of single LTR vectors to introduce the rescued promoters into standard transducing vectors; 3) the ability of the rescued promoters to be expressed at differing levels in several different cell types, including T cells; and 4) screening and selection established the efficacy, or lack thereof, of individual promoter sequences.

Although the general method of promoter rescue was demonstrated by the foregoing experiments, the titers obtained from the sLTR VL30 vectors may not be useful where selection systems are not available.

Additional experimentation led to the development of a chimeric packaging signal, combining the essential packaging signal from Moloney murine leukemia virus (Ψ), and the enhanced packaging signal (Ψ+) from a mouse VL30 element. A vector embodiment of this packaging system is VLMB (SEQ ID NO:23). One advantage of the chimeric packaging system was the elimination of retroviral gag gene sequences that were present in previous high-titer MLV-based vectors (viral gag sequences contribute to the generation of replication competent retrovirus outbreaks). The titers of VLMB-based vectors ranged from approximately $1 \times 10^5$ to $4 \times 10^6$ TU/ml.

Construction of a Cloning Vector for Promoter Rescue

Using pVLSNOGMIS as a template, and primers (SEQ ID NOS:28 and 68), a 6.4 kb plasmid fragment was PCR amplified (Using Hot Start Ampliwax PCR Gems 100, Perkin Elmer). 30 cycles of PCR were performed by following the manufacturer's instructions, with the following input conditions: lower reaction, 80° C., 5 min., then add upper reaction and template, 96° C., 1 min. Each reaction vial contained 50 ng template, 0.5 μM each primer, 200 μM dNTPs and 5U (2 μl) Pfu polymerase (Stratagene, LaJolla, Calif.). 30 repeating cycles of: 96° C., 45° sec; 50° C., 45 sec; 75 C, 1 min. A final incubation of 75° C., 10 min, then hold at 4° C. After amplification, the reactions were purified using Qiaquick PCR Purification Kits (Qiagen). The PCR products were digested with Pac1, heat inactivated (65° C., 20 min) and ligated together using T4 DNA ligase (overnight at 4° C. in a 5 μl vol). The ligated DNA was transfected into SCS110 *E. coli* cells (Stratagene) with kanarnycin (50 μg/ml) antibiotic added to the agar plates. The cells were dcm⁻, dam⁻ (to prevent methylation of Bpm1 sites). The resulting plasmid, pVLBPGN (SEQ ID NO:1, FIGS. 2 & 3) has a deletion in the U3 region of the LTR. A linker containing a central Pac1 site flanked by two outwardly-digesting Bpm1 sites occupies the site of the deleted U3 sequences. The Bpm1 sites enable the plasmid to be digested with Bpm1, resulting in two 2 bp 3'-overhanging ends that are complementary to the U3-derived RT-PCR inserts described below. The digested plasmid was purified free from the intervening linker sequences from an agarose gel after digestion with Bpm1, using the Qiaquick gel purification kit (Qiagen).

Procedure for Amplification of Liver U3 Promoter Region

Purified mouse liver total tissue RNA was purchased from Ambion, Inc., (Austin, Tex.). Total liver RNA was treated with RQ1 Rnase-free (Promega, Madison, Wis.). Using Perkin Elmer Gene Amp thermostable rTth reverse transcriptase RNA PCR kit (P/N N808-0069), the following conditions for RT-PCR were used: RT-PCR A 70° (hot start); RT-PCR B, 95° C., 60 sec, then 35 cycles (95° m 10 sec, 58° C., 15 sec) then a final 58° C. incubation for 7 min, then 4° C. and hold. Additional conditions were: primer concentration 0.15 micromolar, template 100 ng/reaction, dNTPs 200 micromolar (final) and MgCL$_2$ 3.5 mM(final). The primers for insert amplification were SEQ ID NOS:28 and 68)

The amplified U3 sequences were purified using Qiaquick. The pVLBPGN plasmid was digested with Bpm1, isolated from a 1% agarose gel and purified using the Qiaquick method. The purified U3 sequences were ligated at 1:2, 1:4 and 1:6 molar ratios of VLBPGN plasmid:insert using T4 DNA ligase and a 5 microliter reaction volume overnight at 4° C. (100 ng plasmid: 16 ng insert=1:1 molar ratio). 1 microliter of each ligation reaction was transformed into E. coli SCS 110 competent cells (Stratagene). 26 colonies were recovered in total. Out of 23 clones grown overnight in the presence of kanamycin, 20 had sequences that appeared to be mouse VL30 sequences, representing 10 different VL30 species (FIG. 6, SEQ ID NOS:4–13). One of these (Hep 10, SEQ ID NO: 13) was transiently transfected into Hep G2 liver hepatocellular carcinoma cells. 48 h after transfection, intense GFP fluorescence was observed, indicating strong expression of the Hep 10 U3 promoter region.

EXAMPLE 4

Creating a Combinatorial Library of Mouse VL30 U3 Sub-regions

Figure 4A:
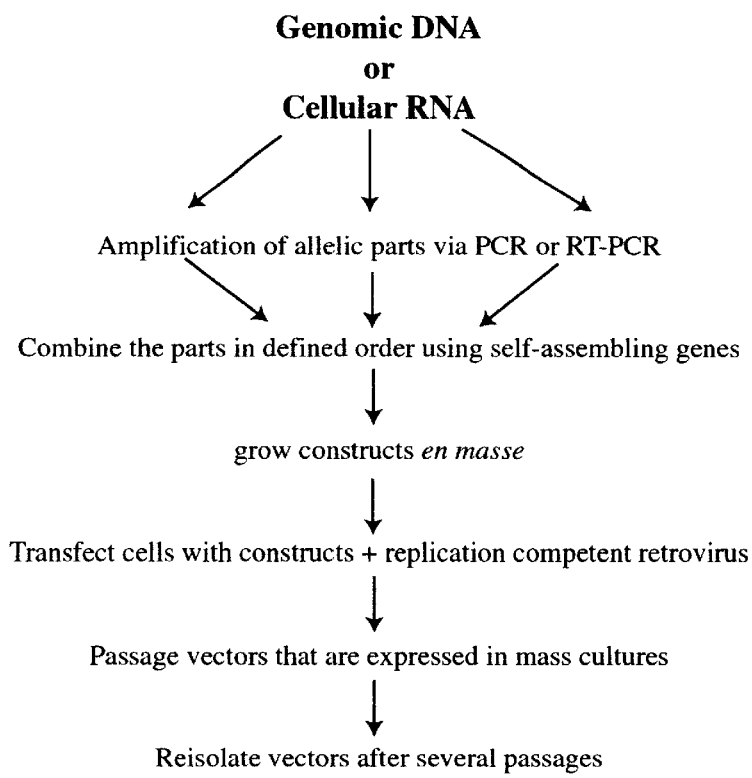
FIGS. 4A–B is a schematic illustrating steps for assembling a combinatorial library of cis- or trans-acting nucleic acid sequences for assembly and screening, useful for the rescue of biologically active species.
Figure 4B:
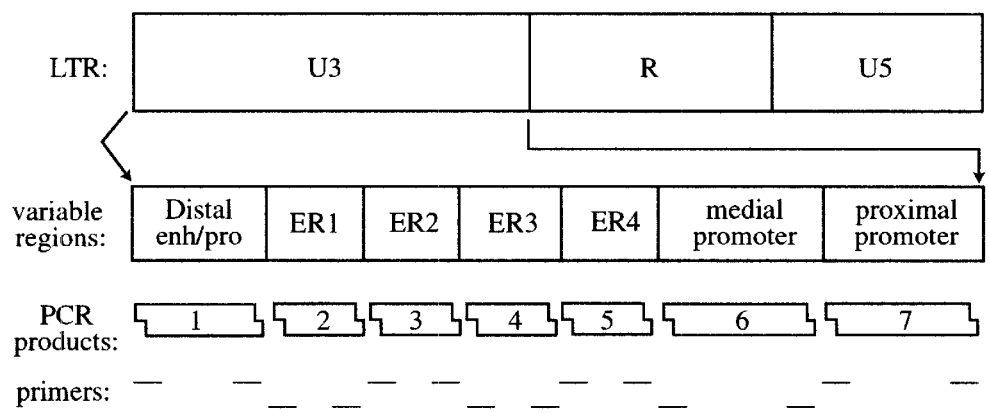

Using FIG. 7 and Hodgson, 1996, supra, FIG. 4.2 as a guide, the following three sub-regions of the VL30 U3 region were empirically established: Distal (1); medial (2); and proximal (3). Peaks of similarity were used to guide the following choice of primers: (+) primer binding site-5'-LTR boundary; ~80 bp (defines sub-region 1); ~80–210 bp (sub-region 2); ~210–430 (sub-region 3). The following primers were selected to amplify the vector VLBPGN or a similar VL30, NVL-3 LTR-containing vector:

P1 (going left from the 5'-end of the LTR to amplify the plasmid)

(SEQ ID NO:55)

GACTAACCTTGATTCCACTGGAGTTTT(CT)(CT)ATTCTTCATTCCCCACTTC TTCTT

P2 (going right from the 3'-end of the promoter region to amplify the plasmid)

(SEQ ID NO:56)

GACTAACCTTGATTCCACTG-GAGAATCTGGACCAATTCTATATAAGCCTG TGAAAAATTT

The six primers selected to amplify the inserts are as follows:

Fragment 1, primer 1 (going right from the LTR terminus into U3) (SEQ ID NO:57) GACTAACCTTGATTC-CACTGGAGAAGAAGAAGTGGGGAATGAAGAA Fragment 1, primer 2 (going left from the end of fragment 1) (SEQ ID NO:58) GACTAACCTTGATTCCACTG-GAGATCTCTAGA TGGGAGGGG(GT)(CT)GGG CTC Fragment 2, primer 1 (going right from the left end of fragment 2) (SEQ ID NO:59) GACTAACCTTGATTC-CACTGGAGCTCGGAGCCCACCCCCTCCCATCT Fragment 2, primer 2 (going left from the right end of fragment 2) (SEQ ID NO:60) GACTAACCTTGATTC-CACTGGAGGGAGGCCCTTATCTCAAAAATGTT Fragment 3, primer 1 (going right from the left end of fragment 3) (SEQ ID NO:61) GACTAACCTTGATTC-CACTGGAGTCTAAGAA-CATTTTTGAGATAAGGGCC T Fragment 3, primer 2 (going left from the right end of fragment 3) (SEQ ID NO:62) GACTAACCTTGATTC-CACTGGAGTCACAGGCT TATATAG(TG)AAA 100 ng of genomic DNA from Mus musculus is used as a template (the mouse genome bears 100–200 copies of VL30 elements). Standard PCR procedures for Pfu polymerase are used. Fragments are amplified 35 rounds of PCR to obtain single-copy genomic DNA amplification. Samples of Qiagen column purified DNA are examined on analytical agarose gels to determine the approximate size. The remainder of each reaction is digested with the appropriate enzyme and run on an acrylamide or agarose gel. The digested fragments are purified by standard gel purification procedures and are ligated to the plasmid fragment at an equimolar ratio of the four PCR fragments (three inserts and one plasmid). The ligation mix is transformed into E. coli SCS1 and is grown on kanamycin. The number of colonies is used to establish the size of the combinatorial library and the pooled colonies are grown in E. coli and the DNA is harvested en masse. A dozes or more colonies are characterized by DNA sequencing to determine the approximate fiAelity of the reaction. A library of 1,000 or more, but preferably 100,000 or more members is used for combinatorial screening procedures.

Screening the Combinatorial Libraries for Expression in Specific Cell Types Using a Replication Defective Helper Virus The U3 library DNA is transfected into the desired target cells in which expression is desired. Along with the library, approximately 25% of the total DNA should include retroviral helper sequences. The latter sequences can be a helper plasmid (such as pPAM3, Miller et al., U.S. Pat. No. 4,861,719). The virus is amphotropic, permitting it to infect most human cells. The RNA from individual clones that are transcribed in the target cells will be packaged into retroviral virions made by the helper virus, and the virions can be harvested as the cell free filtrate (0.45 mm) from the vector producer cells. This virus (containing the expressed sequences) can be transmitted to fresh target cells that do not contain helper virus. as 48 hours after passage, the DNA form of the transcriptionally active clones will be integrated in the recipient cells, and these transcriptionally active loci will produce more RNA, and protein. After G418 drug selection to increase the proportion of cells expressing the vector sequences, helper virus DNA is again transfected into the recipient cells, transforming them into vector producer cells. The virus from these cells should contain increased amounts of the RNA from clones that are transcriptionally active in those cells. Passage of the virus is continued for two or three rounds to permit recombination and mutation to take place, enhancing the effect of in vitro evolution of promoters. The actual degree of enhancement attainable at each step is illustrated in Table 2 (supra). After several passages, the actual level of RNA expressed by several clones is determined by RNA blotting, or by the amount of a reporter gene expressed as protein (determined visually or by the appropriate assay). Because human cells do not naturally contain VL30 DNA or RNA, the sequences that remain in the human cells are those with the most transcriptionally active promoters. These sequences can be amplified and re-cloned using the methods of the instant invention, or they can be rescued by virus packaging, reverse transcribed by the endogenous reverse transcriptase reaction, and grown as plasmids (due to their plasmid origin of replication and the selectable kanamycin marker gene).

In addition to using a replication defective helper virus, such as the clone pPAM3, it is also possible to use a replicatien competent retrovirus, such as Moloney murine leukemia virus to passage the library. For use in human cells, however, the virus should have a tropism that is compatible with human cells (gibbon ape leukemia virus and amphotropic [4070A] murine retroviruses are acceptable).

In addition to being useful for generating active transcriptional promoters de novo, a small variation on the above procedures may enable the isolation of hormone responsive promoters. In it, the cells are treated with the hormone (which could be a steroid, a peptide hormone known to affect the cells, a drug, a drug agonist or antagonist, etc.) during passage. After isolation of surviving VL30 vector-containing cells, individual clones of drug resistant cells are tested for reporter gene expression with and without drug treatment to determine relative protein expression. Likewise, RNA expression can be determined by blot analysis or a similar method. A useful list of known VL30 responses to pharmacological agents is listed in FIG. 4.2 of Hodgson, 1996, supra, and can be used as a guide to help assess the potential agents known to have an effect on VL30 transcription.

Once the transcriptional promoters with the known specificity have been obtained, they can be used to obtain expression of genes from a variety of types of vectors. For example, in addition to retrovirus particles, the promoters can be incorporated into all other major groups of vectors: adenoviruses herpes simplex virus vectors, DNA transfection vectors, etc. It will be apparent to persons of ordinary skill in the art that similar combinatorial libraries can also be used to screen for other characteristics than transcription activity in a particular cell. For example, combinatorial libraries of complementarity determining regions (CDRs) of antibodies or T cell receptors can be so screened using antibody screening methods, such as the phage display screening method (Pharmacia, Milwaukee, Wis.). Thus, the methods of this invention, particularly the combinatorial simplicity of this invention is a significant improvement over many in vivo recombination methods including those of (Stemmer, U.S. Pat. No. 5,605,793, 1997) that have described for the production of CDR combinatorial libraries.

EXAMPLE 5

Gene Assembly Line

From the above examples of 3 and 6 fragment gene self-assemblies, it is evident that assembly of genes by means of gene amplification, the use of offset restriction enzymes and incorporating unique, non-palindromic ends is a highly efficient process compared to conventional cloning methods, However, in addition to the considerations already discussed, it will be apparent to a person of ordinary skill in the art that the various procedures, protocols, methods and material of the instant invention become more difficult to use as the number of fragments increases. For example, if the efficiency of combining each fragment in an assemblage is 99%, then the overall efficiency of combining ten fragments will be 90%, the efficiency of combining 100 fragments will be 37%, etc. Therefore, a small drop in efficiency of any step or fragment, or a large increase in the complexity of the project, will be sufficient to reduce the overall efficiency. Fastidious procedures permit one to achieve success with more complex projects.

Foremost in its potential for inducing failure is human error in primer design where large numbers of fragments are used. Fortunately, the instant invention is suited to automation of most of the steps. This allows human input to be focused on design, analysis, and quality control. For the purposes of generating large vectors or chromosomes, it is desirable to provide an automated environment. One method to achieve this goal is a gene assembly line.

In a gene assembly line, multiple tasks are controlled by a machine or machines working together to increase speed and efficiency and to reduce human error. For example, computer aided design (CAD) and computer aided manufacturing (CAM) are incorporated and combined with the methods of this invention. The computers accept inputs in the form of template and primer sequences, together with preferences of regions to be copied and joined. The preferences include at least the sequences of the primer regions and information about the known restriction sites and maps of the sequences to be assembled, but ideally include the entire sequence. The preferences also include the number of sequences to be joined, the desired Tm for the primers, the list of potential restriction enzymes capable of offset digestion that are potential candidats for use in the assembly process, the desired end structures for each fragment terminus, a tag sequence (if any), whether circular or linear ends are desired, and additional design considerations. The computer algorithm then searches the sequences to determine the candidate enzymes and specific primers that match the criteria of the input. Candidates for selection of unique non-palindromic overlaps are selected. The computer then posts selections or preferences for the type and order of end structures, the primer binding sites, their potential for primer-dimer and intra-molecular interaction artifacts, and the potential conflicts with repeat sequences within the templates that could lead to incorrect polymerization. Based upon the selections made by the operator, the computer then determine the $T_m$ for each primer, and makes adjustments (with suitable inputs from the investigator) to achieve a suitable $T_m$ for the appropriate DNA synthesis or gene amplification reaction. Ideally, the primers should have similar $T_m$s so that all amplification reactions can be performed at once with one set of amplification instructions. In reality, it may be difficult to do this with complex projects. The output of this portion of the program, which can be in a generic format, such as a Microsoft Excel spreadsheet is then downloaded to a computerized oligonucleotide synthesizer, such as the Applied Biosystems 3928 nucleic acid synthesizer. One advantage of using a computerized synthesizer is its robotic capability to de-protect and purify the oligonucleotides automatically. In addition this synthesizer can accept computerized input.

The quantity of individual oligos recovered is then determined spectrophotometrically. It is desirable to purify the oligonucleotides by high performance liquid chromatography or by polyacrylamide gel. In a preferred embodiment, the oligonucleotides and templates are then assembled robotically using an automated nucleic acid handling system such as the Qiagen Biorobot 9600. The BioRobot is capable of accepting input from a computer and can combine the gene amplification reactions based upon the assignments of templates, primer land reagents provided in the input. The assembled reactions are then amplified for example by PCR. In a preferred embodiment, the PCR heat block is incorporated into the robotic workspace and genes are assembled robotically but with minimal human intervention to change buffers, rearrange the platform, change programs, and the like. The resulting amplified products are also purified by the BioRobot or a similar robotic device. In a preferred embodiment, the robotic device uses Qiaquick cleanup procedures, or a similar method and then assembles restriction endonuclease reactions to digest the purified gene amplification products. The gene amplification products are loaded onto a gel and electrophoresed. Human intervention may be necessary to analyze the products and excise the correct fragments from the gel. At this point, the results are assessed and missing or incorrect sized fragments are resynthesized. The robotic device is preferably used to purify the gel fragments using Qutagen or similar cleanup procedures. After spectrophotometric quantitation of the purified fragments, the robotic device is preferably used to assemble the ligation. Ideally the fragments are combined in an equimolar ratio of 1:1. However it is not necessary to use equimolar ratios in order to achieve gene self-assembly. For automated gene assembly, it may be desirable not to use equimolar ratios of input fragments, particularly if it simplified the task of quantitation. After ligation, the assemblies can be purified and ethanol precipitated or they can be added to the appropriate host cells. Automation aids in maintaining the sterility of the reaction.

Several additional considerations can assist in the construction of long genes using gene assembly. First the number of fragments and the length of constructs are limiting factors. In addition to maintaining high standards of purify of both the oligonucleotide primers and gene amplification products, it is important to keep the error rate low during copying. Thus, one can optimally start with 100 ng of template use only five rounds of gene amplification and finish with nearly 2 micrograms of product. This is more desirable for reducing errors than using a large number of amplification steps. It is also desirable to use a special copying enzyme such as Pfu DNA polymerase that has a low intrinsic error rate. Further it is desirable to use in vivo selection (in eukaryotic cells or tissues) rather than E. coli cloning to reduce the incorporation of errors into the vectors. For example, a viral vector such as an adenoviral vector or the retro-vectors of the preceding examples are auto-selecting. A single correctly-assembled adenovirus vector molecule, for example, leads to a lytic infection (the viral products of which are cloned by limiting dilution on the appropriate eukaryotic cells), even though it may be combined in a ligation mix with a large excess of incorrectly assembled molecules that are non-functional. Thus, it is not necessary to have a high efficiency, although high efficiency has been demonstrated in this system, in order to achieve success in making, for example gene therapy vectors.

For long fragments (3–30 kb), it is desirable to use enzymes and procedures that are designed or facilitate replication of long fragments, one such example is the eLONGase system (Life Technologies). This system can copy up to 30 kb on a fragment with proofreading. Considerations for long PCR are reviewed in Beck, 1998. (The Scientist, Jan. 5, 1998, pp. 16–18).

Internal restriction sites are a potential problem, particularly with large constructs and can be overcome in a number of ways. Use of alternate enzymes, methylation of internal restrictions sites (such as by using methylated DNA precursors during synthesis to leave the sites in primers unaffected, incorporation of the internal sites into the construct (if they are non-palindromic), or mutagenesis of internal sites, are exemplary ways to deal with some of these issues.

For very large constructs, it is desirable to use enzymes such as SapI (recognizing 7 nucleotides and leaving a 3 bp overhang). This enzyme digests every 16,384 bp on average. There are 64 nucleotide triplet combinations, meaning that up to 32 fragments can be ligated in a circle using SapI. Fok1 and Hga1 are other examples of class IIS enzymes that are useful for making large constructs. Hga1 has 5 bp overhangs, permitting more than 500 Hga1 fragments to be ligated. Fok1 includes a Kozak ATG start codon. In a preferred embodiment, a Fok1 site is inserted at the PuXX-ATG start site of a cDNA encoding region. The cDNA is inserted in frame, providing a site for inserting and switching coding sequences within a vector.

It will be readily understood by those skilled in the art that the foregoing description has been for purposes of illustration only and that a variety of embodiments can be envisioned without departing from the scope of the invention. Therefore, it is intended that the invention not be limited except by the claims.

What is claimed is:

1. A method for isolating and identifying promoters comprising the steps of:
   a) providing a vector comprising a portion of a promoter region from a retrovirus transposon Long Terminal Repeat (LTR) and having two non-complementary overhanging termini, said vector being generated by digesting the vector with one or more class IIS restriction enzymes, creating non-complementary termini for directional joining of promoter sequences with the vector;
   b) designing two PCR primers to amplify a region of a retrovirus transposon LTR promoter from template nucleic acid to produce a nucleic acid fragment, wherein said primers comprise at least one predetermined restriction endonuclease recognition site that recognizes a restriction endonuclease that cleaves at a distance from the recognition site and creates non-palindromic overhanging termini, a sequence complementary to the template nucleic acid, and bases positioned at the restriction endonuclease cleavage site that form non-palindromic overhanging termini after cleavage by the restriction endonuclease and are selected to be complementary to only one of the overhanging termini of the vector;
   c) combining the primers with template nucleic acid and performing a polymerase chain reaction to produce multiple copies of the template nucleic acid to form amplified template fragments incorporating the restriction endonuclease recognition site;
   d) digesting the amplified template fragments with one or more restriction endonucleases that recognize the restriction endonuclease recognition site of the primers to create digested template fragments having non-palindromic overhanging termini that are complementary to the respective termini of the vector;
   e) combining the digested template fragments in a ligation reaction with the vector to produce a gene vector with an intact LTR sequence;
   f) transforming the vector with an intact LTR sequence into at least one cell type; and
   g) selecting for expression from the LTR sequence in said cell type;
   whereby expression from the LTR sequence identifies a promoter.

2. The method of claim 1 wherein the template nucleic acid is DNA or RNA.

3. The method of claim 1 further comprising the step of sequencing the amplified template fragments to identify the promoter.

4. A promoter sequence comprising one of SEQ ID NOS:3–13 identified using the method of claim 1.

5. The method of claim 1, wherein said cell type is a retroviral vector producer cell.

6. A vector having the sequence of SEQ ID NO:1, wherein the vector is prepared for promoter insertion by digesting with the restriction enzyme BpmI, to produce a larger DNA fragment and a smaller DNA fragment, and by removing or inactivating the smaller DNA fragment.

7. A method for creating, isolating and identifying useful promoters comprising the steps of:
   a) providing a vector comprising a portion of a promoter region from a retrovirus transposon LTR and having two non-complementary, non-palindromic overhanging termini;

b) providing a pool of related but non-identical template LTR nucleic acid sequences;

c) providing two primers for amplification of each of a series of two or more contiguous regions of said template LTR sequences, wherein the primers contain class IIS restriction enzyme recognition sites that are recognized by the respective restriction enzyme, and which sites are positioned within the primers to permit digestion by said respective restriction enzyme within the LTR sequences, wherein the termini of the digested contiguous regions are non-palindromic and complementary to the termini of only the adjacent fragments when those fragments are similarly digested;

d) performing polymerase chain reactions to form amplified adjacent fragments incorporating terminal restriction endonuclease sites;

e) digesting the amplified fragments with one or more class IIS restriction endonuclease enzymes that recognize the respective sites on the fragments, creating two overhanging termini on each fragment, wherein the termini of the digested contiguous regions are non-palindromic and complementary to the termini of only the adjacent fragments when those fragments are similarly digested;

f) purifying the digested nucleic acid fragments;

g) combining the digested nucleic acid fragments with said vector in a ligation reaction to produce an intact LTR sequence;

h) transforming the assembled vector and fragments into at least one cell type; and i) selecting for expression from the LTR sequence of the vector in said cell type;

whereby expression from the LTR sequence identifies a promoter.

8. The method of claim 7, wherein said cell type is a retroviral vector producer cell.

9. The method of claim 5, wherein the retroviral producer cell is used to preferentially transmit and select for vector DNA sequences containing promoters that are actively expressed in said retroviral producer cell.

10. The method of claim 8, wherein the retroviral vector producer cell is used to preferentially transmit and select for vector DNA sequences containing promoters that are actively expressed in said retroviral producer cell.

* * * * *